(12) United States Patent
Vandehey et al.

(10) Patent No.: US 11,117,886 B2
(45) Date of Patent: Sep. 14, 2021

(54) METHODS AND INTERMEDIATES FOR PREPARING THERAPEUTIC COMPOUNDS

(71) Applicant: Gilead Sciences, Inc., Foster City, CA (US)

(72) Inventors: Amanda Lynn Vandehey, San Francisco, CA (US); Gediminas Brizgys, Menlo Park, CA (US); Vinh Xuan Ngo, Fountain Valley, CA (US); Brian Michael O'Keefe, San Francisco, CA (US); Trevor James Rainey, San Mateo, CA (US); Bing Shi, Redwood City, CA (US); Winston C. Tse, Redwood, CA (US); Anna Michelle Wagner, Hayward, CA (US); Xianghong Wang, Dublin, CA (US); Scott Alan Wolckenhauer, Redwood City, CA (US); Jennifer R. Zhang, Union City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 16/869,653

(22) Filed: May 8, 2020

(65) Prior Publication Data
US 2020/0369647 A1 Nov. 26, 2020

Related U.S. Application Data

(62) Division of application No. 16/277,552, filed on Feb. 15, 2019, now Pat. No. 10,696,657.

(60) Provisional application No. 62/710,575, filed on Feb. 16, 2018.

(51) Int. Cl.
| | |
|---|---|
| *C07D 401/14* | (2006.01) |
| *C07D 401/12* | (2006.01) |
| *C07D 495/10* | (2006.01) |
| *C07D 339/06* | (2006.01) |
| *C07C 59/50* | (2006.01) |
| *C07D 231/56* | (2006.01) |
| *C07C 45/67* | (2006.01) |
| *C07D 213/61* | (2006.01) |
| *C07D 231/54* | (2006.01) |

(52) U.S. Cl.
CPC .......... *C07D 401/14* (2013.01); *C07C 45/673* (2013.01); *C07C 59/50* (2013.01); *C07D 213/61* (2013.01); *C07D 231/54* (2013.01); *C07D 231/56* (2013.01); *C07D 339/06* (2013.01); *C07D 401/12* (2013.01); *C07D 495/10* (2013.01); *C07C 2602/18* (2017.05)

(58) Field of Classification Search
CPC .............. C07D 401/14; C07D 401/12
USPC .......................... 546/275.7, 275.4
See application file for complete search history.

(56) References Cited

U.S. PATENT DOCUMENTS

| | | | |
|---|---|---|---|
| 4,816,570 | A | 3/1989 | Farquhar |
| 4,968,788 | A | 11/1990 | Farquhar |
| 5,663,159 | A | 9/1997 | Starrett, Jr. et al. |
| 5,792,756 | A | 8/1998 | Starrett, Jr. et al. |
| 5,922,695 | A | 7/1999 | Arimilli et al. |
| 5,935,946 | A | 8/1999 | Munger, Jr. et al. |
| 5,977,089 | A | 11/1999 | Arimilli et al. |
| 7,390,791 | B2 | 6/2008 | Becker et al. |
| 7,803,788 | B2 | 9/2010 | Becker et al. |
| 8,263,627 | B2 | 9/2012 | Barrow et al. |
| 8,748,412 | B2 | 6/2014 | Liao et al. |
| 8,754,065 | B2 | 6/2014 | Liu et al. |
| 8,835,488 | B2 | 9/2014 | Yamashita et al. |
| 9,012,441 | B2 | 4/2015 | Bondy et al. |
| 9,050,344 | B2 | 6/2015 | Brizgys et al. |
| 9,216,996 | B2 | 12/2015 | Jin et al. |

(Continued)

FOREIGN PATENT DOCUMENTS

| | | |
|---|---|---|
| CN | 101910133 A | 12/2010 |
| WO | WO 1991/19721 | 12/1991 |

(Continued)

OTHER PUBLICATIONS

[No Author Listed], "2-[9-(Difluoromethyl)-5,5-difluoro-7,8-diazatricylo[4.4.0.02,4]nona-1(6),8-dien-7-yl]acetic acid," PubChem CID 71186949, Mar. 21, 2013, 18 pages.

(Continued)

*Primary Examiner* — Charanjit Aulakh
(74) *Attorney, Agent, or Firm* — Fish & Richardson P.C.

(57) ABSTRACT

The present disclosure relates to methods and intermediates useful for preparing a compound of formula I:

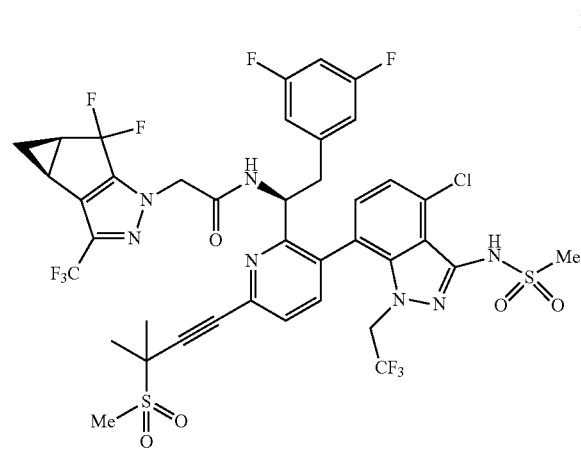

or a co-crystal, solvate, salt or combination thereof.

22 Claims, No Drawings

(56) References Cited

U.S. PATENT DOCUMENTS

| | | |
|---|---|---|
| 9,220,710 B2 | 12/2015 | Bondy et al. |
| 9,540,343 B2 | 1/2017 | Bondy et al. |
| 9,730,936 B2 | 8/2017 | Baszcynski et al. |
| 9,789,089 B2 | 10/2017 | Bondy et al. |
| 9,873,680 B2 | 1/2018 | Brizgys et al. |
| 9,944,619 B2 | 4/2018 | Bondy et al. |
| 9,951,043 B2 | 4/2018 | Brizgys et al. |
| 10,071,985 B2 | 9/2018 | Graupe et al. |
| 10,370,358 B2 | 8/2019 | Bondy et al. |
| 10,654,827 B2 | 5/2020 | Graupe et al. |
| 10,696,657 B2 | 6/2020 | Vandehey et al. |
| 10,836,746 B2 | 11/2020 | Brizgys et al. |
| 10,849,892 B2 | 12/2020 | Houston et al. |
| 2005/0282805 A1 | 12/2005 | Hangeland et al. |
| 2007/0032469 A1 | 2/2007 | Isaac et al. |
| 2007/0083045 A1 | 4/2007 | Di Francesco et al. |
| 2010/0143301 A1 | 6/2010 | Desai et al. |
| 2010/0249176 A1 | 9/2010 | Barrow et al. |
| 2012/0045761 A1 | 2/2012 | Jagannath et al. |
| 2013/0165489 A1 | 6/2013 | Cocklin et al. |
| 2014/0142085 A1 | 5/2014 | Bondy et al. |
| 2014/0221346 A1 | 8/2014 | Halcomb et al. |
| 2014/0221347 A1 | 8/2014 | Brizgys et al. |
| 2014/0221356 A1 | 8/2014 | Jin et al. |
| 2014/0221378 A1 | 8/2014 | Miyazaki et al. |
| 2014/0221380 A1 | 8/2014 | Miyazaki et al. |
| 2014/0221417 A1 | 8/2014 | Halcomb et al. |
| 2014/0221421 A1 | 8/2014 | Bondy et al. |
| 2014/0296266 A1 | 10/2014 | Hu et al. |
| 2014/0303164 A1 | 10/2014 | Brizgys et al. |
| 2016/0067224 A1 | 3/2016 | Bondy et al. |
| 2016/0083368 A1 | 3/2016 | Brizgys et al. |
| 2016/0108030 A1 | 4/2016 | Brizgys et al. |
| 2016/0250215 A1 | 9/2016 | Baszczynski et al. |
| 2016/0368881 A1 | 12/2016 | Bondy et al. |
| 2017/0137405 A1 | 5/2017 | Bondy et al. |
| 2018/0051005 A1 | 2/2018 | Graupe et al. |
| 2018/0194746 A1 | 7/2018 | Bondy et al. |
| 2018/0258097 A1 | 9/2018 | Bacon et al. |
| 2018/0273508 A1 | 9/2018 | Brizgys et al. |
| 2018/0370950 A1 | 12/2018 | Graupe et al. |
| 2019/0083478 A1 | 3/2019 | Houston et al. |
| 2019/0084963 A1 | 3/2019 | Shi |
| 2019/0300505 A1 | 10/2019 | Allan et al. |
| 2019/0345136 A1 | 11/2019 | Brizgys et al. |
| 2019/0375726 A1 | 12/2019 | Bondy et al. |
| 2020/0038389 A1 | 2/2020 | Bauer et al. |
| 2020/0262815 A1 | 8/2020 | Graupe et al. |
| 2020/0397772 A1 | 12/2020 | Houston et al. |
| 2021/0009555 A1 | 1/2021 | Brizgys et al. |

FOREIGN PATENT DOCUMENTS

| | | |
|---|---|---|
| WO | WO 2003/002530 | 1/2003 |
| WO | WO 2003/002553 | 1/2003 |
| WO | WO 2004/050643 | 6/2004 |
| WO | WO 2004/071448 | 8/2004 |
| WO | WO 2004/096286 | 11/2004 |
| WO | WO 2005/087725 | 9/2005 |
| WO | WO 2005/123680 | 12/2005 |
| WO | WO 2006/015261 | 2/2006 |
| WO | WO 2006/110157 | 10/2006 |
| WO | WO 2007/070826 | 8/2007 |
| WO | WO 2008/013622 | 1/2008 |
| WO | WO 2009/005677 | 1/2009 |
| WO | WO 2009/010804 | 1/2009 |
| WO | WO 2009/062285 | 5/2009 |
| WO | WO 2009/114677 | 9/2009 |
| WO | WO 2010/130034 | 11/2010 |
| WO | WO 2011/059887 | 5/2011 |
| WO | WO 2011/143772 | 11/2011 |
| WO | WO 2012/003497 | 1/2012 |
| WO | WO 2012/003498 | 1/2012 |
| WO | WO 2012/065062 | 5/2012 |
| WO | WO 2012/145728 | 10/2012 |
| WO | WO 2013/006738 | 1/2013 |
| WO | WO 2013/006792 | 1/2013 |
| WO | WO 2013/091096 | 6/2013 |
| WO | WO 2013/159064 | 10/2013 |
| WO | WO 2014/016358 | 1/2014 |
| WO | WO 2014/028931 | 2/2014 |
| WO | WO 2014/100323 | 6/2014 |
| WO | WO 2014/110297 | 7/2014 |
| WO | WO 2014/110298 | 7/2014 |
| WO | WO 2014/134566 | 9/2014 |
| WO | WO 2015/008097 | 1/2015 |
| WO | WO 2015/061518 | 4/2015 |
| WO | WO 2015/130966 | 9/2015 |
| WO | WO 2016/033243 | 3/2016 |
| WO | WO 2016/040084 | 3/2016 |
| WO | WO 2016/172424 | 10/2016 |
| WO | WO 2016/172425 | 10/2016 |
| WO | WO 2017/007689 | 1/2017 |
| WO | WO 2018/035359 | 2/2018 |
| WO | WO 2018/145021 | 8/2018 |
| WO | WO 2018/203235 | 11/2018 |
| WO | WO 2019/035904 | 2/2019 |
| WO | WO 2019/035973 | 2/2019 |

OTHER PUBLICATIONS

[No Author Listed], "3-Methyl-3-methylsulfonylbut-1-yne," PubChem CID 14241469, Feb. 9, 2002, 16 pages.

[No Author Listed], CAS registry No. 1620056-83-8, Aug. 6, 2014, 1 page.

Benzaria, S. et al. (Dec. 6, 1996). "Synthesis, In Vitro Antiviral Evaluation, and Stability Studies of Bis(S-Acyl-2-Thioethyl) Ester Derivatives of 9-[2-Phosphonomethoxy)Ethyl]adenine (PMEA) as Potential PMEA Prodrugs with Improved Oral Bioavailability," J. Med. Chem. 39(25):4958-4965.

Berge et al., "Pharmaceutical Salts," J. Pharma. Sci., Jan. 1977, 66(1): 1-19.

Bhattacharya et al. (2014) Structural Basis of HIV-1 Capsid Recognition by PF74 and CPSF6, PNAS; 111 (52):18625-18630.

Blair et al., (2010) "HIV Capsid is a Tractable Target for Small Molecule Therapeutic Intervention," PLoS Pathog. 6(12): e1001220.

Briggs et al., (2003) "Structural Organization of Authentic, Mature HIV-1 Virions and Cores," The EMBO Journal; vol. 22 No. 7 pp. 1707-1715.

Brown, M.K. et al. (2005) "Highly Enantioselective Cu-Catalyzed Conjugate Additions of Dialkylzinc Reagents to Unsaturated Furanones and Pyranones: Preparation of Air-Stable and Catalytically Active Cu-Peptide," Angew Chem. Int. Ed. Engl. 44(33):5306-5310.

Bundgaard, H. (1991). "Design and Application of Prodrugs," Chapter 5 in A Textbook of Drug Design and Development, Krogsgaard-Larsen, P. et al. eds., Harwood Academic Publishers, Chur, Switzerland, pp. 113-191.

Campbell et al., (2015) "HIV-1 Capsid: The Multifaceted Key Player in HIV-1 Infection," Nat Rev Microbial.; 13(8):471-483.

Carnes et al., "Inhibitors of the HIV-1 Capsid, A Target of Opportunity," Curr. Opin. HIV AIDS, 2018, 13(4):359-365.

Chin et al. (2015) "Direct Visualization of HIV-1 Replication Intermediates Shows That Capsid and CPSF6 Modulate HIV-1 Intra-Nuclear Invasion and Integration", Cell Repotis 13:1717-1731.

Cos, P. et al. (1998) "Structure-Activity Relationship and Classification of Flavonoids as Inhibitors of Xanthine Oxidase and Su peroxide Scavengers," J. Natl. Prod. 61:71-76.

Cossy, J. et al. (Oct. 23, 1995). "Ring Opening of Cyclopropylketones Induced by Photochemical Electron Transfer," Tetrahedron 51 (43):11751-11764.

Curreli et al., (2011) "Virtual Screening Based Identification of Novel Small-molecule Inhibitors Targeted to the HIV-1 Capsid," Bioorganic & Medicinal Chemistry 19:77-90.

De Lombaert, S. et al. (Feb. 18, 1994). "N-Phosphonomethyl Dipeptides and Their Phosphonate Prodrugs, A New Generation of Neutral Endopeptidase (NEP, EC 3.4.24.11) Inhibitors," J. Med. Chem. 37(4):498-511.

(56) References Cited

OTHER PUBLICATIONS

Fader et al., (2013) Optimization of a 1,5 dihydrobenzo[b][1,4]diazepine-2,4-dione Series of HIV Capsid Assembly Inhibitors 2: Structure-Activity Relationships (SAR) of the C3-Phenyl Moiety, Bioorganic & Medicinal Chemistry Letters, doi: httQ://dx.doi.org/10.1016/j.bmcl.2013.03.074>.
Farquhar, D. et al. (Mar. 1983). "Biologically Reversible Phosphate-Protective Groups," J. Pharm. Sci. 72(3):324-325.
Fields, "Methods for Removing the Fmoc Group," Methods in Molecular Biology, 1994, 35: 17-27.
Forshey et al., (2002) "Formation of a Human Immunodeficiency Virus Type 1 Core of Optimal Stability Is Crucial for Viral Replication," J. Virology, 76(11) p. 5667-5677.
Foster, "Deuterium Isotope Effects in Studies of Drug Metabolism," Trends Pharmacol. Sci., 1984, 5(12):524-527.
Ganser et al., (1999) "Assembly and Analysis of Conical Models for the HIV-1 Core," Science 283, 80-82.
Ganser-Pornillos et al., (2007) "Structure of Full-Length HIV-1 CA: A Model for the Mature Capsid Lattice," Cell, 131(1):70-9, 29 pages.
Hagmann, "The many roles for fluorine in medicinal chemistry," J. Med. Chem., 2008, 51(15):4359-4369.
Hammer, S. et al. (Aug. 6, 2008). "Antiretroviral Treatment of Adult HIV Infection. 2008 Recommendations of the International AIDS Society: USA Panel," JAMA 300(5):555-570.
Hanack et al., "cis-und trans bicyclo [3.1.0] hexano-(2)," Chemische Berichte, 1964, 97(6):1669-1672, XP055573746 (with English translation).
Hodgson, D.M. et al. (2007) "Intramolecular Cyclopropanation of Unsaturated Terminal Epoxides and Chlorohydrins," JAGS 129(14):4456-4462.
Hodgson, D.M. et al. (Jul. 21, 2004, e-pub. Jun. 24, 2004). "Intramolecular Cyclopropanation of Unsaturated Terminal Epoxides," J. Am. Chem. Soc. 126(28):8664-8665.
Hung et al. (2013) "Large-Scale Functional Purification of Recombinant HIV-1 Capsid" PLOS One, vol. 8, Issue 3, e58035, 11 pages.
Ishiyama et al., "Palladium(0)-Catalyzed Cross-Coupling Reaction of Alkoxydiboron with Haloarenes: A Direct Procedure for Arylboronic Esters," J. Org. Chem. 1995, 60(23):7508-7510.
Jeong, .J.U. (2010) "Synthesis of Tetrasubstituted Pyrazones and Pyrazone N-Oxides," Tetrahedron Letters 51 (6):974-976.
Jin et al., (2010) "SAR and Molecular Mechanism Study of Novel Acylhydrazone Compounds Targeting HIV-1 CA," Bioorganic & Medicinal Chemistry; 18: 2135-2140.
Jouvenet et al., (2006) "Plasma Membrane Is the Site of Productive HIV-1 Particle Assembly," PLoS Biol., 4(12):e435, 15 pages.
Kashima, C. et al. (Aug.-Sep. 1991). "New Peptide Synthesis Using the Ozonolysate of 2-(1-Phthalimido)alkyl-5-Phenyloxazoles," J. Heterocyclic Chem. 28: 1241-1244 (abstract only).
Kelly, et al., (2007) "Structure of the Antiviral Assembly Inhibitor CAP-1 Bound to the HIV-1 CA Protein," Journal of Molecular Biology, doi: 10.1016/j.jmb.2007.07.070, 40 pages.
Khamnei, S. et al. (Sep. 27, 1996). "Neighboring Group Catalysis in the Design of Nucleotide Prodrugs," J. Med. Chem. 39(20):4109-4115.
Kim et al., (2013) "Discovery of a New Hiv-1 Inhibitor Scaffold and Synthesis of Potential Prodrugs of Indazoles," Bioorganic & Medicinal Chemistry Letters, doi: <http://dx.doi.org/10.1016/j.bmcl.2013.03.075> 8 pages.
Kocienski, P.J. (May 1994). "Carbonyl Protecting Groups," Chapter 5 in Protecting Groups, Thieme Publishing Group: New York, NY, pp. 155-184.
Kocienski, P.J. (May 1994). "Carboxyl Protecting Groups," Chapter 4 in Protecting Groups, Thieme Publishing Group: New York, NY, pp. 118-154.
Kocienski, P.J. (May 1994). "Diol Protecting Groups," Chapter 3 in Protecting Groups, Thieme Publishing Group: New York, NY, pp. 95-117.
Kocienski, P.J. (May 1994). "Hydroxyl Protecting Groups," Chapter 2 in Protecting Groups, Thieme Publishing Group: New York, NY, pp. 21-94.
Kocienski, P.J. (May 1994). "Protecting Groups: An Overview," Chapter 1 in Protecting Groups, Thieme Publishing Group: New York, NY, pp. 1-20.
Lad et al., (2015) "Functional Label-Free Assays for Characterizing the in Vitro Mechanism of Action of Small Molecule Modulators of Capsid Assembly" Biochemistry, 54, 2240-2248.
Lamorte et al. (2015) "Discovery of Novel Small-Molecule HIV-1 Replication Inhibitors That Stabilize Capsid Complexes" Antimicrobial Agents and Chemotherapy, 57(10): 4622-4631.
Lazerwith et al., (2017) "New Antiretrovirals for HIV and Antivirals for HBV," in Comprehensive Medicinal Chemistry, 3rd Edition, 1-36.
Lee et al., (2010) "Flexible Use of Nuclear Import Pathways by HIV-1," Cell Host & Microbe; 7, 221-233.
Lemke, C.T. et al. (Jun. 2012). "Distinct Effects of Two Hiv-1 Capsid Assembly Inhibitor Families That Bind the Same Site Within the N-Terminal Domain of the Viral CA Protein," J. Viral. 86(12):6643-6655.
MacMillan et al., "Evaluation of alternative solvent in common amide coupling reactions: replacement of dicloromethane and N,N-dimethlformamide," Green Chem, 2013, 15: 596-600.
Matreyek et al., (2013) "Nucleoporin NUP153 Phenylalanine-Glycine Motifs Engage a Common Binding Pocket within the HIV-1 Capsid Protein to Mediate Lentiviral lnfectivity" PLOS Pathogens vol. 9, Issue 10, e1003693.
Mitchell, A.G. et al. (1992). "Bioreversible Protection for the Phospho Group: Bioactivation of the Di(4-Acyloxybenzyl) and Mono(4-acyloxybenzyl) Phosphoesters of Methylphosphonate and Phosphonoacetate," J. Chem. Soc. Perkin Trans. 1, pp. 2345-2353.
Miyaura and Suzuki, "Palladium-Catalyzed Cross-Coupling Reactions of Oganoboron Compounds,". Chem Rev, 1995, 95: 2457-2483.
Montalbetti and Falque, "Amide bond formation and peptide coupling," Tetrahedon, 2005, 61: 10827-10852.
Nicolaou et al., "Palladium-Catalyzed Cross-Coupling Reactions in Total Synthesis," Angew Chem Int, 2005, 44:4442-4489.
Ovais et al., "Synthesis, antiproliferative and anti-inflammatory activities of some novel 6-aryl-2-(p-(methanesulfonyl)phenyl)-4,5-dihydropyridazi-3(2H)-ones," European Journal of Medicinal Chemistry, 2013, 67:352-358.
Owen et al., "Strengths, weaknesses, opportunities and challenges for long acting injectable therapies: Insights for applications in HIV therapy," Advances Drug Delivery Reviews 103 (2016) 144-156.
Palella et al., "Declining morbidity and mortality among patients with advanced human immunodeficiency virus infection." N Engl. J Med. 1998, 338:853-860.
Patel et al., "Poloxamers: a pharmaceutical excipients with therapeutic behaviors," International Journal of PharmTech Research, Apr.-Jun. 2009, 1(2):299-303.
PCT International Search Report and Written Opinion in International Appln. No. PCT/US2019/018323, dated Feb. 4, 2019, 13 pages.
Pornillos et al., (2009) "X-ray Structures of the Hexameric Building Block of the HIV Capsid" Cell, 137(7): 1282-92.
Pornillos et al., (2009) Supplemental Data for "X-ray Structures of the Hexameric Building Block of the HIV Capsid" Cell. Jun. 26, 2009, 137(7):1282-92.
Powers et al., (2009) Synthesis of Methyl-, Fluoro-, and Chloro-substituted 6-Hydroxyisoindolin-1-1-Ones, Tetrahedron Letters 50 (12):1267-1269.
Price et al. (2012) "CPSF6 Defines a Conserved Capsid Interface That Modulates HIV-1 Replication" PLOS Pathogens, 8(8):e1002896, 14 pages.
Puech, F. et al. (Oct. 1993). "Intracellular Delivery of Nucleoside Monophosphates Through a Reductase-Mediated Activation Process," Antiviral Res. 22(2-3):155-174.
Registry (STN) [online], Mar. 22, 2010 [date of retrieval: Nov. 12, 2018], CAS registry No. 1213065-84-9.
Registry (STN) [online], Mar. 23, 2010 [date of retrieval: Nov. 12, 2018], CAS registry No. 1213495-28-3.

(56) References Cited

OTHER PUBLICATIONS

Rihn et al., (2013) "Extreme Genetic Fragility of the HIV-1 Capsid" PLOS One, vol. 9 Issue 6 e1003461, 25 pages.
Shi et al. (2011) "Small-Molecule Inhibition of Human Immunodeficiency Virus Type 1 Caps id Destabilization" Journal of Virology 85(1) 542-549.
Siddiqui, A. et al. (1999) "The Presence of Substituents on the Aryl Moiety of the Aryl Phosphoramidate Derivative of d4T Enhances Anti-HIV Efficacy in Cell Culture: A Structure-Activity Relationship" J. Med. Chem. 42:393-399.
Smith, R.J. et al. (2010) "Evolutionary Dynamis of Complex Networks of HIV Drug-Resistant Strains: The Case of San Francisco," Science 327(5966):697-701.
Sticht et al., (2005) "A peptide inhibitor of HIV-1 assembly in vitro" Nature Structural & Molecular Biology vol. 12 No. 8 671-677.
STN Registry No. 137349-29-2, Nov. 15, 1991, 1 page.
Sublocade Product Label, issued: Nov. 2017, 43 pages.
Taiwanese Office Action in TW Appln. No. 108105148, dated Jul. 2, 2020, 41 pages (with English translation).
Taiwo, B. (Sep. 2009; e-pub. Jan. 10, 2009). "Understanding Transmitted HIV Resistance Through the Experience in the USA," Intl. J. of Infectious Diseases 13(5):552-559.
Talele, "The 'Cyclopropyl Fragment' is a Versatile Player that Frequently Appears in Preclinical/Clinical Drug Molecules," Journal of Medicinal Chemistry, 2016, 59(19):8712-8756.
Tanaka, R. et al. (2005) "One-Pot Synthesis of Metalated Pyridines from Two Acetylenes, a Nitrile, and a Titanium (II) Alkoxide," J. Am. Chem. Soc. 127(21):7774-7780.
Tang et al., (2003) "Antiviral Inhibition of the HIV-1 Capsid Protein," J. Mol. Biol., 327, 1013- 1020.
Tse et al., "Discovery' of Novel Potent HIV Capsid Inhibitors with Long-Acting Potential," Presentation at the Conference on Retroviruses and Opportunistic Infections (CROI), Seattle, WA, Feb. 14, 2017, 18 pages.
Tsiang et al., (2012) "A Trimer of Dimers Is the Basic Building Block for Human Immunodeficiency Virus-1 Caosid Assembly" Biochemistry, 51, 4416-4428.
Wong et al., (2014) "SPR Assay Development to Characterize Caps id Inhibitors Binding & MOA," Poster Presented at the Developments in Protein Interaction (DiPIA), La Jolla, CA, 1 page.
Xianghui et al., "In silico virtual screening," Biotechnology in the Post-Genome Era, 2003, 20:295-309.
Yadav et al., "Co-crystals: a novel approach to modify physicochemical properties of active pharmaceutical ingredients," Indian J. Pharm. Sci., 2009, 71(4):359-370.
Yale, "The trifluoromethyl group in medicinal chemistry," J. Med. Chem., 1958, 1(2):121-133.
Yant et al., (2014) "An Improved PF74 Analog Inhibits Multiple HIV Capsid Functions Independently of Host Cyclophilin A and CPSF6" Poster Presented at the Conference on Retroviruses and Opportunistic Infections (CROI), Boston, Massachusetts, 1 page.
Yant et al., (2014) "PF74 Inhibits Multiple HIV Capsid Functions Independently of Host Cyclophilin A and CPSF6" Abstract for Poster Presented at the Conference on Retroviruses and Opportunistic Infections (CROI), Boston, Massachusetts.
Zheng et al., "GS-6207: A Novel, Potent and Selective First-In-Class Inhibitor of HIV-1 Capsid Function Displays Nonclinical Pharmacokinetics Supporting Long-Acting Potential," Poster Presented at ID Week 2018, San Francisco, CA, Oct. 3-7, 2018, 1 page.
Zhou et al. (2015) "HIV-1 Resistance to the Capsid-Targeting Inhibitor PF74 Results in Altered Dependence on Host Factors Required for Virus Nuclear Entry" Journal of Virology, doi 10.1128/JVI.00340-15. Published online Jun. 24, 2015, 37 pages.
Brittain, "Polymorphism in pharmaceutical solids," Marcel Dekker, Inc., 1999, 235-238.
Thenin-Houssier et al., "HIV-1 capsid inhibitors as antiretroviral agents," Curr. HIV Res., 2016, 14(3):270-282.
Wu et al., "Selective Inhibitors of Tumor Progression Loci-2(Tp12) Kinase with Potent Inhibition of TNF-Alpha Production in Human Whole Blood," Bioorg. Med. Chem. Lett., 2009, 19(13):3485-3488.
Australian Office Action in AU Appln. No. 2019222559, dated Feb. 3, 2021, 4 pages.
Molina et al., "On-Demand Preexposure Prophylaxis in Men at High Risk for HIV-1 Infection," N. Engl. J Med. 2015, 353:2237-2246.
AU Office Action in Australian Patent Application No. 2019222559, dated Jun. 29, 2021, 3 pages.

METHODS AND INTERMEDIATES FOR PREPARING THERAPEUTIC COMPOUNDS

CROSS REFERENCE TO RELATED APPLICATIONS

This application claims the benefit of U.S. Provisional Application 62/710,575, filed on Feb. 16, 2018, the entire content of which is hereby incorporated by reference in its entirety.

FIELD

The present disclosure relates to methods and intermediates for the synthesis of novel compounds for use in the treatment of a Retroviridae viral infection, including an infection caused by the HIV virus.

BACKGROUND

The present disclosure relates generally to the field of organic synthetic methodology for the preparation of antiviral compounds and their synthetic intermediates.

Positive-single stranded RNA viruses comprising the Retroviridae family include those of the subfamily Orthoretrovirinae and genera *Alpharetrovirus, Betaretrovirus, Gammaretrovirus, Deltaretrovirus, Epsilonretrovirus, Lentivirus*, and *Spumavirus* which cause many human and animal diseases. Among the *Lentivirus*, HIV-1 infection in humans leads to depletion of T helper cells and immune dysfunction, producing immunodeficiency and vulnerability to opportunistic infections. Treating HIV-1 infections with highly active antiretroviral therapies (HAART) has proven to be effective at reducing viral load and significantly delaying disease progression (Hammer, S. M., et al.; *JAMA* 2008, 300: 555-570). However, these treatments could lead to the emergence of HIV strains that are resistant to current therapies (Taiwo, B., International *Journal of Infectious Diseases* 2009, 13:552-559; Smith, R. J., et al., *Science* 2010, 327: 697-701). Therefore, there is a pressing need to discover and synthesize new antiretroviral agents that are active against emerging drug-resistant HIV variants.

U.S. patent application Ser. No. 15/680,041 discloses novel compounds useful for treating a Retroviridae viral infection, including an infection caused by the HIV virus. One specific compound identified therein is a compound of formula I:

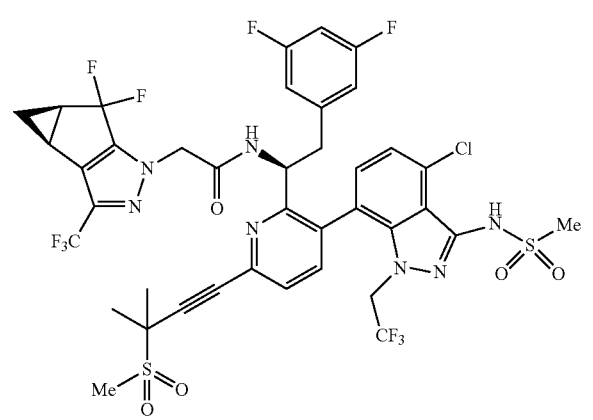

There is currently a need for improved synthetic methods and intermediates that can be used to prepare the compound of formula I and co-crystals, solvates, salts, and combinations thereof. There is also a need for improved methods for preparing intermediate compounds that can be used to prepare the compound of formula I and its co-crystals, solvates, salts, and combinations thereof. The improved methods and intermediates may reduce the cost, time, and/or the amount of waste associated with the existing methods for preparing the compound of formula I and co-crystals, solvates, salts, and combinations thereof.

SUMMARY

In some embodiments, the present disclosure provides a process for making a compound of formula I:

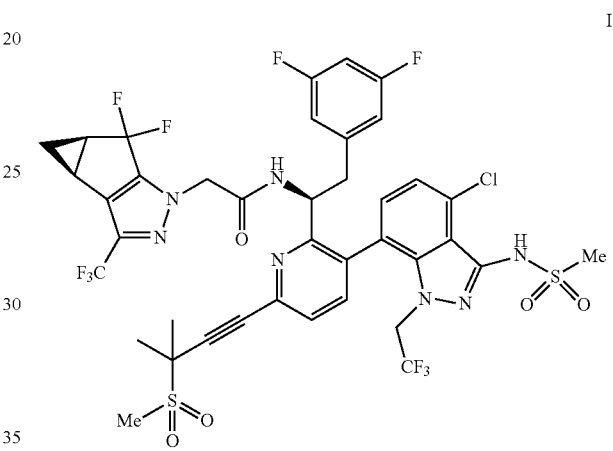

or a co-crystal, solvate, salt or combination thereof. The compound of formula I may also be named or identified as: N—((S)-1-(3-(4-chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide.

In some embodiments, disclosed herein is a process for preparing a compound of formula I:

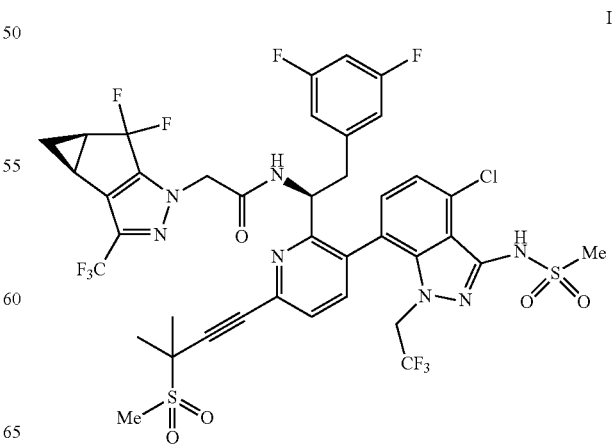

or a co-crystal, solvate, salt, or combination thereof, comprising:

(a) combining a compound of formula VIII:

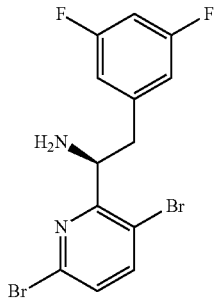

or a co-crystal, solvate, salt, or combination thereof, with a compound of formula IX:

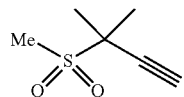

or a co-crystal, solvate, or combination thereof, under alkynylation conditions to provide the compound of formula VI:

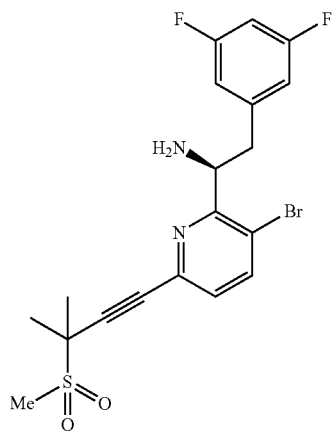

or a co-crystal, solvate, salt, or combination thereof;

(b) combining the compound of formula VI or a co-crystal, solvate, salt, or combination thereof, with a compound of formula VII:

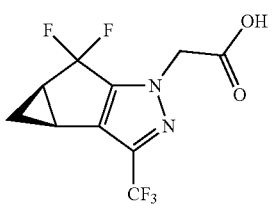

or a co-crystal, solvate, salt, or combination thereof, under amide coupling conditions to provide a compound of formula IV:

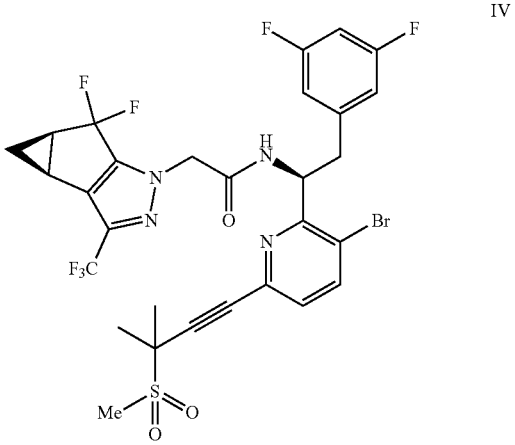 [SMILES: CC(C)(C#Cc1ccc(Br)c([C@H](Cc2cc(F)cc(F)c2)NC(=O)Cn2nc(C(F)(F)F)c3c2C(F)(F)[C@@H]2C[C@H]32)n1)S(C)(=O)=O]

or a co-crystal, solvate, salt, or combination thereof;

(c) combining the compound of formula IV or a co-crystal, solvate, salt, or combination thereof, with a compound of formula V:

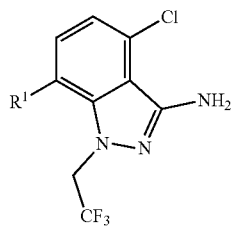

or a co-crystal, solvate, salt, or combination thereof, wherein IV is $B(OH)_2$, $B(OCH(Me)CH_2C(Me)_2O)$, $B((1,2-di-O)C_6H_4)$, $B(OCH_2C(Me)_2CH_2O)$, $BF_4K$, $B(O_2CCH_2N(Me)CH_2CO_2)$, or $B(OC(Me)_2C(Me)_2O)$, under palladium-catalyzed cross-coupling conditions to provide a compound of formula III:

or a co-crystal, solvate, salt, or combination thereof and (d) combining the compound of formula III or a co-crystal, solvate, salt, or combination thereof, with a mesylating reagent under mesylating conditions to provide the compound of formula I or a co-crystal, solvate, salt, or combination thereof.

In some embodiments, provided herein are novel intermediates (e.g., intermediates of formulae II, III, IV, VI, and VIII, identified below) for the formation of the compound of formula I or a co-crystal, solvate, salt, or combination thereof.

Accordingly, in one embodiment, a compound of formula II:

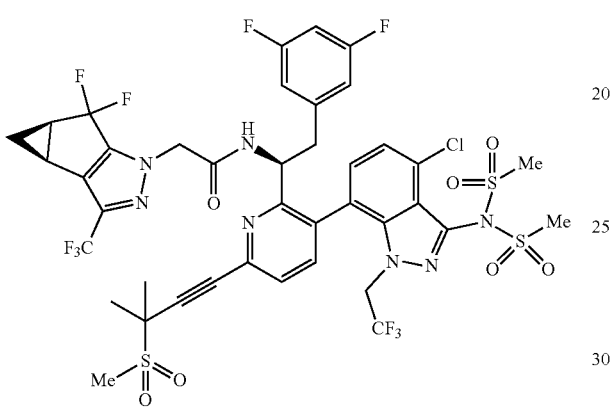

II or a co-crystal, solvate, salt, or combination thereof is provided.

In another embodiment, a compound of formula III:

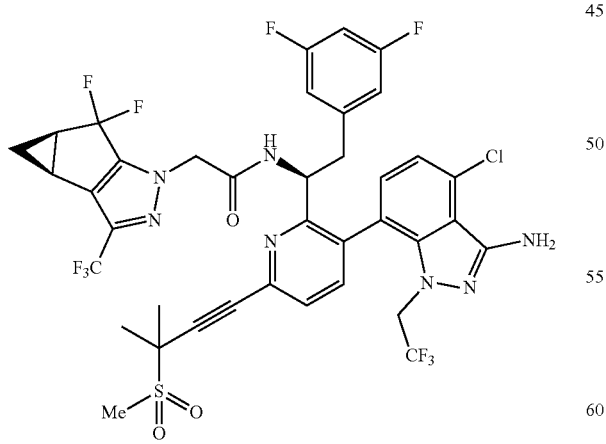

III or a co-crystal, solvate, salt, or combination thereof is provided.

In another embodiment, a compound of formula IV:

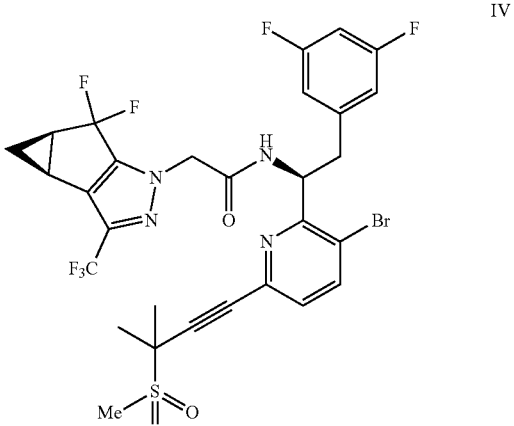

IV or a co-crystal, solvate, salt, or combination thereof is provided.

In another embodiment, a compound of formula VI:

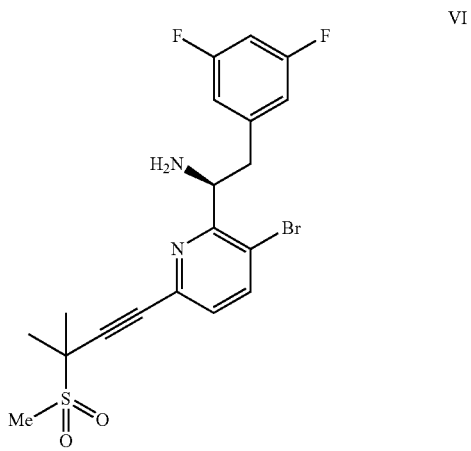 [SMILES: CC(C)(C#Cc1ccc(Br)c([C@@H](N)Cc2cc(F)cc(F)c2)n1)S(C)(=O)=O]

VI or a co-crystal, solvate, salt, or combination thereof is provided.

In another embodiment, a compound of formula VIII:

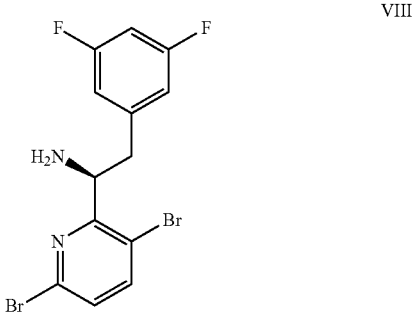

VIII or a co-crystal, solvate, salt, or combination thereof is provided.

The synthetic routes and intermediates disclosed herein reduce the cost, time, and amount of waste associated with the preparation of the compound of formula I and its co-crystals, solvates, and salts, and combinations thereof.

Additionally, the synthetic methods disclosed herein provide the compound of formula I in fewer steps (for example, carbamate protection and deprotection of amino groups is avoided) than in previous synthetic methods, and atropisomers are introduced later in the sequence than in previous synthetic methods.

Additional embodiments of the disclosure, including additional novel synthetic intermediates and methods for preparing such intermediates, are provided herein.

DETAILED DESCRIPTION

The description below is made with the understanding that the present disclosure is to be considered as an exemplification of the claimed subject matter, and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading. Unless defined otherwise, all technical and scientific terms used herein have the same meaning as commonly understood by one of ordinary skill in the art.

When trade names are used herein, it is intended to independently include the tradename product and the active pharmaceutical ingredient(s) of the tradename product.

As used herein and in the appended claims, the singular forms "a" and "an", and "the" include plural referents unless the context clearly dictates otherwise. Thus, e.g., reference to "the compound" includes a plurality of such compounds and reference to "the assay" includes reference to one or more assays, and so forth.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. A mixture of enantiomers at a ratio other than 1:1 is a "scalemic" mixture.

"Diastereoisomers" are stereoisomers that have at least two asymmetric atoms, but which are not mirror-images of each other.

The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and/or hindered rotation about a bond axis and may thus give rise to enantiomers, diastereomers, and other stereoisomeric forms that may be defined, in terms of absolute stereochemistry, as (R)- or (S)-. The present disclosure is meant to include all such possible isomers, including racemic mixtures, scalemic mixtures, diastereomeric mixtures, optically pure forms and intermediate mixtures. Optically active (R)- and (S)-isomers may be prepared using chiral synthons or chiral reagents, or resolved using conventional techniques.

Except as expressly defined otherwise, the present disclosure includes all tautomers of compounds detailed herein, even if only one tautomer is expressly represented (e.g., both tautomeric forms are intended and described by the presentation of one tautomeric form where a pair of two tautomers may exist). For example, if reference is made to a compound containing an amide (e.g., by structure or chemical name), it is understood that the corresponding imidic acid tautomer is included by this disclosure and described the same as if the amide were expressly recited either alone or together with the imidic acid. Where more than two tautomers may exist, the present disclosure includes all such tautomers even if only a single tautomeric form is depicted by chemical name and/or structure.

Compounds described herein may have chiral centers and/or geometric isomeric centers (E- and Z-isomers), and it is to be understood that all such optical, enantiomeric, diastereoisomeric and geometric isomers are encompassed. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

The terms "amine transaminase" and "ATA" as used herein refer to a polypeptide having an enzymatic capability of exchanging an amino group of a donor amine with a carbonyl group of an acceptor molecule. The transamination reaction is carried out in presence of pyridoxal-phosphate (PLP), which acts as a cofactor. In transamination reactions using transaminase enzymes, the amine group of the amino donor is transferred to the coenzyme to produce a ketone as a by-product, while pyridoxal-5'-phosphate is converted to pyridoxamine phosphate. The transfer of the amine group from pyridoxamine phosphate to the ketone substrate produces a chiral amine and regenerates the coenzyme. S-selective transaminases include, but are not limited to ATA-1, ATA-2, ATA-007, ATA-013, ATA-025, ATA-113, ATA-117, ATA-200, ATA-217, ATA-234, ATA-237, ATA-238, ATA-251, ATA-254, ATA-256, ATA-260, ATA-301, ATA-303, ATA-412, ATA-415, ATA-P1-B04, ATA-P1-F03, ATA-P1-G05, ATA-P2-A01, ATA-P2-A07, ATA-P2-B01, and mixtures thereof.

The term "asymmetric catalyst" as used herein refers to a catalyst that promotes the enantioselective and/or diastereoselective transformation of an achiral center or molecule into a chiral center or molecule, respectively. For example, an asymmetric catalyst may generate an enantiomeric excess of a product. Exemplary asymmetric catalysts comprise a transition metal and a chiral ligand. Non-limiting examples of chiral ligands include BINAP/SEGPHOS®, salens, bisoxazolines, tartrate ligands, cinchona alkaloids, DuPhos phospholanes, BPE phospholanes, DSM phosphoramidites, Solvias® Josiphos families, phosphine-oxazolines, the Reetz and Trost ligands, and ChiralQuest phosphines.

Also provided are pharmaceutically acceptable hydrates, solvates, co-crystals, tautomeric forms, polymorphs, and prodrugs of the compounds described herein.

The term "hydrate" refers to the complex formed by the combining of a compound of Formula I, or any Formula disclosed herein, and water.

The term "solvate" refers to a complex formed by the combining of a compound of Formula I, or any other Formula as disclosed herein, and a solvent or a crystalline solid containing amounts of a solvent incorporated within the crystal structure. As used herein, the term "solvate" includes hydrates.

The term "co-crystal" refers to a crystalline material formed by combining a compound of Formula I, or any Formula disclosed herein and one or more co-crystal formers (i.e., a molecule, ion or atom). In certain instances, co-crystals may have improved properties as compared to the parent form (i.e., the free molecule, zwitterion, etc.) or a salt of the parent compound. Improved properties can be increased solubility, increased dissolution, increased bioavailability, increased dose response, decreased hygroscopicity, a crystalline form of a normally amorphous compound, a crystalline form of a difficult to salt or unsaltable compound, decreased form diversity, more desired morphology, and the like. Methods for making and characterizing co-crystals are known to those of skill in the art.

Any formula or structure given herein, including Formula I, or any Formula disclosed herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$F, $^{32}$F, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes compounds of Formula I, or any Formula disclosed herein, in which from 1 to "n" hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal. See, for example, Foster, "Deuterium Isotope Effects in Studies of Drug Metabolism", *Trends Pharmacol. Sci.* 5(12): 524-527 (1984). Such compounds are synthesized by means well known in the art, for example by employing starting materials in which one or more hydrogen atoms have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the Formula I, or any Formula disclosed herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

The modifier "about" used in connection with a quantity is inclusive of the stated value and has the meaning dictated by the context (e.g., includes the degree of error associated with measurement of the particular quantity).

The term "chiral" refers to molecules which have the property of non-superimposability of the mirror image partner, and the term "achiral" refers to molecules which are superimposable on their mirror image partner.

"Alkyl" is a straight or branched saturated hydrocarbon. For example, an alkyl group can have 1 to 8 carbon atoms (i.e., ($C_1$-$C_8$)alkyl) or 1 to 6 carbon atoms (i.e., ($C_1$-$C_6$ alkyl) or 1 to 4 carbon atoms (i.e., ($C_1$-$C_4$)alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

"Alkenyl" is a straight or branched hydrocarbon with at least one carbon-carbon, sp$^2$ double bond. For example, an alkenyl group can have 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2$CH=$CH_2$) and 5-hexenyl (—$CH_2CH_2CH_2CH_2$CH=$CH_2$).

"Alkynyl" is a straight or branched hydrocarbon with at least one carbon-carbon, sp triple bond. For example, an alkynyl group can have 2 to 8 carbon atoms (i.e., $C_2$-$C_8$ alkyne,) or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

The term "halo" or "halogen" as used herein refers to fluoro, chloro, bromo and iodo.

The term "haloalkyl" as used herein refers to an alkyl as defined herein, wherein one or more hydrogen atoms of the alkyl are each independently replaced by a halo substituent. For example, ($C_1$-$C_6$)haloalkyl is a ($C_1$-$C_6$)alkyl wherein one or more of the hydrogen atoms of the $(C_1-C_6)$alkyl have been replaced by a halo substituent. Examples of haloalkyls include but are not limited to fluoromethyl, fluorochloromethyl, difluoromethyl, difluorochloromethyl, trifluoromethyl, 1,1,1, trifluoroethyl and pentafluoroethyl.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. It is also to be understood that when reference is made to a certain atom-range membered aryl (e.g., 6-12 membered aryl), the atom range is for the total ring atoms of the aryl. For example, a 6-membered aryl would include phenyl and a 10-membered aryl would include naphthyl and 1, 2, 3, 4-tetrahydronaphthyl. Non-limiting examples of aryl groups include, but are not limited to, phenyl, indenyl, naphthyl, 1, 2, 3, 4-tetrahydronaphthyl, anthracenyl, and the like.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example 1,8-naphthyridinyl), heterocycles, (to form for example 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system. It is also to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). It also to be understood that when a reference is made to a certain atom-range membered heteroaryl (e.g., a 5-14 membered heteroaryl), the atom range is for the total ring atoms of the heteroaryl and includes carbon atoms and heteroatoms. For example, a 5-membered heteroaryl would include a thiazolyl and a 10-membered heteroaryl would include a quinolinyl. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5,6,7-tetrahydro-1H-indazole and 3b,4,4a,5-tetrahydro-1H-cyclopropa[3,4]cyclopenta[1,2-c]pyrazole.

The term "heterocyclyl" or "heterocycle" as used herein refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from heterocycles (to form for example a 1,8-decahydronapthyridinyl), carbocycles (to form for example a decahydroquinolyl) and aryls to form the multiple condensed ring system. Thus, a heterocycle (a single saturated or single partially unsaturated ring or multiple condensed ring system) has about 2-20 carbon atoms and 1-6 heteroatoms within the heterocycle ring. Such multiple condensed ring systems may be optionally substituted with one or more (e.g., 1, 2, 3 or 4) oxo groups on the carbocycle or heterocycle portions of the multiple condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring. It is also to be understood that the point of attachment for a heterocycle or heterocycle multiple condensed ring system can be at any suitable atom of the heterocycle or heterocycle multiple condensed ring system including a carbon atom and a heteroatom (e.g., a nitrogen). It is also to be understood that when reference is made to a certain atom-range membered heterocycle (e.g., a 3-14 membered heterocycle), the atom range is for the total ring atoms of the heterocycle and includes carbon atoms and heteroatoms. For example, a 3-membered heterocycle would include an aziridinyl and a 10-membered heterocycle would include a 1,2,3,4-tetrahydroquinolyl. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one and pyrrolidin-2-one.

The term "cycloalkyl" refers to a cyclic alkyl and alkenyl groups. A cycloalkyl group can have one or more cyclic rings and includes fused and bridged groups that are fully saturated or partially unsaturated. Examples include, but are not limited to, cyclopropyl, cyclobutyl, cyclopentyl, cyclohexyl, adamantyl, methylcycloproyl (cyclopropylmethyl), ethylcyclopropyl, cyclohexenyl and the like.

The term "fused" refers to a ring which is bound to an adjacent ring.

"Bridged" refers to a ring fusion wherein non-adjacent atoms on a ring are joined by a divalent substituent, such as an alkylenyl or heteroalkylenyl group or a single heteroatom. Quinuclidinyl and admantanyl are examples of bridged ring systems.

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents.

The term "azido" refers to a group

The term "keto" or "oxo" refers to a group =O.
The term "carboxyl" refers to a group —C(O)—OH.
The term "hydroxy" or "hydroxyl" refers to a group —OH.

The term "amine protecting group" is well understood by the person skilled in synthetic organic chemistry as a moiety that can be selectively installed onto and removed from, and masks or alters the properties of, a suitable amine functional group. The field of protecting group methodology is advanced, and many amine protecting groups, and methods for using them, are well known in the art, such as those described in the authoritative treatise on the subject, P. G. M. Wuts and T. W. Greene, Greene's *Protective Groups in Organic Synthesis,* 4th Edition (Wiley, 2006).

The term "borylation agent" also is well understood in the field of organic synthesis as a reagent that is useful for installing any one of a wide range of boronate moieties onto a suitable substrate to provide an organoboron reagent. Non-limiting examples of borylation agents and related synthetic methodology are set forth in T. Ishiyama et al., *J. Org. Chem.* 1995, 60, 7508-7510 and N. Miyaura and A. Suzuki, *Chem. Rev.* 1995, 95, 2457-2483.

As used herein, the term "alkynylation conditions" refers to the reaction conditions under which a terminal alkyne is coupled to another compound (e.g., a suitable aryl or heteroaryl halide substrate) in the presence of a catalyst, solvent, and optionally a base, to form an alkyne (e.g., an internal alkyne). Non-limiting examples of catalysts for "alkynylation conditions" include palladium catalysts such as [(π-allyl)PdCl]$_2$, Pd(acac)$_2$, (SIPr)PdCl$_2$, PdCl$_2$(PPh$_3$)$_2$, PdCl$_2$, Pd(OAc)$_2$, PdCl$_2$(CH$_3$CN)$_2$, Pd$_2$(dba)$_3$, and the like, in combination with a tertiary phosphine, e.g., triphenylphosphine, tri-cyclohexylphosphine, tri-tert-butylphosphine, 1,2-bis(diphenylphosphino)ethane, 1,3-bis(diphenylphosphino)propane, and 1,1'-bis(diphenylphosphino)ferrocene), such as dichlorobis(triphenylphosphine)palladium(II); copper catalysts such as copper(I) iodide, copper(I) bromide, copper(I) chloride, and the like; and combinations thereof. In some embodiments, the catalyst is PdCl$_2$(PPh$_3$)$_2$.

The "alkynylation conditions" as disclosed herein typically comprise a base. Non-limiting examples of the base include amines (e.g., triethylamine, diisopropylamine, ethyldiisopropylamine, pyrrolidine, 1,4-diazabicylo[2.2.2]-octane, 1,8-diazabicyclo[5.4.0]undec-7-ene, 1,5-diazabicyclo-4.3.0]non-5-ene, pyridine, piperidine, etc.), carbonates (e.g., cesium carbonate, potassium carbonate, etc.), phosphates (e.g., potassium phosphate, etc.), and tetra alkyl ammonium salts (e.g., tetrabutylammonium fluoride), and the like. In some embodiments, the base is triethylamine.

The alkynylation conditions further comprise a solvent. Non-limiting examples of the solvent include ethers (e.g., diethyl ether, methyl tert-butyl ether, tetrahydrofuran, 2-methyltetrahydrofuran, 1,4-dioxane, etc.), aromatic solvents (e.g., benzene, xylenes, etc.), polar protic solvents (e.g., N,N-dimethylformamide, N,N-dimethylacetamide, N-methylpyrrolidinone, etc.), water, and combinations thereof. In some embodiments, the solvent is 2-methyltetrahydrofuran.

In some embodiments, the alkynylation conditions comprise a temperature range of about 120° C. or less. In some embodiments, the alkynylation conditions comprise a temperature range of from about 0° C. to about 120° C. In certain embodiments, the alkynylation conditions comprise a temperature range of from about 50° C. to about 80° C.

The term "amide coupling conditions" refers to the reaction conditions under which an amine and a carboxylic acid couple to form an amide, using a coupling reagent and, optionally, a coupling additive, in the presence of a base. Non-limiting examples of coupling reagents include n-propyl phosphonic anhydride, oxalyl chloride, thionyl chloride, dicyclohexylcarbodiimide, diisopropylcarbodiimide, 1-ethyl-3-(3-dimethylaminopropyl)carbodiimide (EDC), carbonyl diimidazole, isobutyl chloroformate, 2-(7-aza-1H-benzotriazole-1-yl)-1,1,3,3-tetramethyluronium hexafluorophosphate, O-benzotriazole-N,N,N',N'-tetramethyluronium-hexafluoro-phosphate, O-(7-azabenzotriazole-1-yl)-N,N,N',N'-tetramethyluronium tetrafluoroborate, O-(benzotriazol-1-yl)-N,N,N',N'-tetramethyluronium tetrafluoroborate, O-(6-chlorobenzotriazol-1-yl)-N,N,N',N'-tetramethyluronium hexafluorophosphate, (benzotriazol-1-yloxy)tris(dimethylamino)phosphonium hexafluorophosphate, (benzotriazol-1-yloxy)tripyrrolidinophosphonium hexafluorophosphate, (1-cyano-2-ethoxy-2-oxoethylidenaminooxy)dimethylamino-morpholino-carbenium hexafluorophosphate, and the like. In some embodiments, the coupling reagent is n-propyl phosphonic anhydride. Non-limiting examples of coupling additives include 4-(dimethylamino)pyridine, 1-hydroxybenzotriazole, 1-hydroxy-7-azabenzotriazole, and the like.

Non-limiting examples of the base used for the "amide coupling conditions" include aliphatic amines (e.g., triethylamine, tributylamine, ethyldiisopropylamine, N-methylmorpholine, etc.), aromatic amines (e.g., pyridine, 2,6-lutidine, N-methylimidazole, etc.), and the like. In some embodiments, the base is triethylamine.

The amide coupling conditions further comprise a solvent. Non-limiting examples of the solvent include nitriles (e.g., propionitrile, butyronitrile, acetonitrile, etc.), esters (e.g., ethyl acetate, butyl acetate, isobutyl acetate, etc.), ethers (e.g., diethyl ether, methyl tert-butyl ether, tetrahydrofuran, 2-methyltetrahydrofuran, 1,4-dioxane, etc.), aromatic hydrocarbon solevents (e.g., toluene, benzene, xylenes, etc.), polar aprotic solvents (e.g., N,N-dimethylformamide, N,N-dimethylacetamide, N-methylpyrrolidinone, dimethylsulfoxide, etc.), chlorinated solvents (e.g., dichloromethane, dichloroethane, chloroform, etc.), and combinations thereof. In some embodiments, the solvent is acetonitrile.

In some embodiments, the amide coupling conditions comprise a temperature range of from about 120° C. or less. In some embodiments, the amide coupling conditions comprise a temperature range of from about −20° C. to about 120° C. In certain embodiments, the amide coupling conditions comprise a temperature range of from about 0° C. to about 40° C.

As used herein, the term "palladium-catalyzed cross-coupling conditions" refers to the reaction conditions under which an aryl halide or an aryl sulfonate (e.g., a triflate, mesylate, tosylate) couples with an organoboron reagent to form a compound, such as a biaryl compound, in the presence of a palladium catalyst and a base. In some embodiments, the organoboron reagent is aryl-R', wherein R' is B(OH)$_2$, B(OR)$_2$ wherein R is unsubstituted or substituted alkyl, BF$_4$K, and the like. Non-limiting examples of organoboron reagents include aryl boronic acids (aryl-B(OH)$_2$), arylboronic esters (e.g., aryl-B(OR)$_2$, e.g., aryl-B(OC(Me)$_2$C(Me)$_2$O), aryl-B(OCH(Me)CH$_2$C(Me)$_2$O), aryl-B((1,2-di-O)C$_6$H$_4$), and aryl-B(OCH$_2$C(Me)$_2$CH$_2$O)), and aryl trifluoroborate salts (e.g., aryl-BF$_3$K). In some embodiments, the organoboron reagent is aryl-B(OC(Me)$_2$C(Me)$_2$O).

In some embodiments, non-limiting examples of palladium catalysts for the "palladium-catalyzed cross-coupling conditions" include dichlorobis(tricyclohexylphosphine)palladium(II), bis(di-tert-butyl(4-dimethylaminophenyl)phosphine)dichloropalladium(II), bis[(dicyclohexyl)(4-dimethylaminophenyl)phosphine]palladium(II) chloride, dichlorobis(triphenylphosphine)palladium(II), [1,1'-bis(diphenylphosphino)ferrocene]dichloropalladium(II), [1,2-bis(diphenylphosphino)ethane]dichloropalladium(II), dichloro[9,9-dimethyl-4,5-bis(diphenylphosphino)xanthene]palladium(II), palladium(II) precatalyst (palladium(II) chloride, palladium(II) acetate, palladium(II) trifluoroacetate) or palladium(0) precatalyst (tetrakis(triphenylphosphine)palladium(0), bis(dibenzylideneacetone)palladium(0), in combination with a phosphine ligand such as tricyclohexylphosphine, triphenylphosphine, cyclohexyldiphenylphosphine, dicyclohexylphenylphosphine, and the like. In some embodiments, the palladium catalyst is dichlorobis(tricyclohexylphosphine)palladium(II).

In some embodiments, non-limiting examples of the base for the "palladium-catalyzed cross-coupling conditions" include carbonates (e.g., potassium bicarbonate, sodium bicarbonate, sodium carbonate, potassium carbonate, cesium carbonate, etc.), inorganic bases (e.g., potassium fluoride, potassium phosphate dibasic, potassium phosphate tribasic, sodium hydroxide, potassium hydroxide, etc.), aliphatic amines (e.g., dicyclohexylamine, N-methylmorpholine, triethylamine, etc.), and the like. In some embodiments, the base is potassium bicarbonate.

In some embodiments, the "palladium-catalyzed cross-coupling conditions" further comprise a solvent. In some embodiments, non-limiting examples of the solvent include ethers (e.g., diethyl ether, 1,4-dioxane, 2-methyltetrahydrofuran, dimethoxyethane, etc.), aromatic hydrocarbon solvents (e.g., toluene, xylenes, etc.), esters (ethyl acetate, isopropyl acetate, propyl acetate, isobutyl acetate, etc.), alcohols (ethanol, isopropanol, etc.), polar aprotic solvents (N,N-dimethylformamide, N,N-dimethylacetamide, N-methyl-2-pyrrolidine, etc.), water, and combinations thereof. In some embodiments, the solvent is a mixture of n-butyl acetate and water.

In some embodiments, the palladium-catalyzed cross-coupling conditions comprise a temperature range of from 120° C. or less. In some embodiments, the palladium-catalyzed cross-coupling conditions comprise a temperature range of from about 20° C. to about 120° C. In some embodiments, the palladium-catalyzed cross-coupling conditions comprise a temperature range of from about 75° C. to about 95° C.

As used herein, the term "mesylating reagent" refers to a reagent used to install a mesyl, or methanesulfonyl (i.e., CH$_3$SO$_2$—), group onto a suitable hydroxy group or a suitable amino group. In some embodiments, non-limiting examples of mesylating reagents include methanesulfonyl chloride, methanesulfonic anhydride, and methanesulfonic acid in combination with an activating agent such as oxalyl chloride, thionyl chloride, or cyanuric chloride. In some embodiments, the mesylating reagent is methanesulfonic anhydride. In some embodiments, the mesylating reagent is methanesulfonyl chloride.

As used, herein the term "mesylation conditions" refers to the reaction conditions under which a mesyl, or methanesulfonyl (i.e., CH$_3$SO$_2$—), group is installed onto a suitable hydroxy group or a suitable amino group. When installing a methanesulfonyl group onto a suitable hydroxy group, the mesylation conditions as disclosed herein typically comprise a base, a catalyst and a solvent.

In some embodiments, when installing a methanesulfonyl group onto a suitable hydroxy group, non-limiting examples of the base for the mesylation conditions include aliphatic amines (e.g., triethylamine, diisopropylethylamine, N,N-dicyclohexylmethylamine, etc.) and aromatic amines (e.g., pyridine, 2,3,5-collidine, 2,4,6-collidine, N-methylimidazole, etc.). In some embodiments, the base is triethylamine.

In some embodiments, when installing a methanesulfonyl group onto a suitable hydroxy group, non-limiting examples of suitable catalysts for the "mesylation conditions" include 4-dimethylaminopyridine (DMAP), and the like.

In some embodiments, when installing a methanesulfonyl group onto a suitable hydroxy group, non-limiting examples of solvents for the mesylation conditions include ethers (e.g., diethyl ether, 1,4-dioxane, cyclopentyl methyl ether, tetrahydrofuran, 2-methyltetrahydrofuran, dimethoxyethane, etc.), aromatic hydrocarbon solvents (e.g., toluene, xylenes, etc.), esters (e.g., ethyl acetate, isopropyl acetate, isobutyl acetate, etc.), chlorinated solvents (e.g., dichloromethane, chloroform, dichloroethane, etc.), nitriles (e.g., acetonitrile, etc.), polar aprotic solvents (e.g, N,N-dimethylformamide, N,N-dimethylacetamide, and N-methylpyrrolidinone, etc.), and combinations thereof. In some embodiments, the solvent is tetrahydrofuran. In some embodiments, the solvent is tetrahydrofuran and the catalyst is DMAP.

In some embodiments, when installing a methanesulfonyl group onto a suitable hydroxy group, the mesylating conditions comprise a temperature range of from about 60° C. or less. In some embodiments, the mesylating conditions comprise a temperature range of from about −80° C. to about 60° C. In some embodiments, the mesylating conditions comprise a temperature range of from about 0° C. to about 40° C.

When installing a methanesulfonyl group onto a suitable amino group, the mesylation conditions as disclosed herein typically comprise a solvent, and optionally, a base.

In some embodiments, when installing a methanesulfonyl group onto a suitable amino group, non-limiting examples of the base for the mesylation conditions include alkyl amines (e.g., triethylamine, N-methylmorpholine, tri-n-propylamine, ethyl diisopropylamine, tri-n-butylamine, etc.), aromatic amines (e.g., pyridine, 2,6-lutidine, collidine, etc.), carbonates (e.g, sodium bicarbonate, sodium carbonate, potassium bicarbonate, potassium carbonate, inorganic bases (e.g., sodium phosphate monobasic, sodium phosphate dibasic, potassium phosphate monobasic, potassium phosphate dibasic, etc.), and alkoxide bases (e.g., sodium tert-amylate, sodium tert-butoxide, etc.). In some embodiments, the base is triethylamine.

In some embodiments, when installing a methanesulfonyl group onto a suitable amino group, non-limiting examples of solvents for the mesylation conditions include ethers (e.g., diethyl ether, 1,4-dioxane, cyclopentyl methyl ether, tetrahydrofuran, 2-methyltetrahydrofuran, dimethoxyethane, etc.), aromatic hydrocarbon solvents (e.g., toluene, xylenes, etc.), esters (e.g., ethyl acetate, isopropyl acetate, isobutyl acetate, etc.), chlorinated solvents (e.g., dichloromethane, chloroform, dichloroethane, etc.), nitriles (e.g., acetonitrile, etc.), polar aprotic solvents (e.g., N,N-dimethylformamide, N,N-dimethylacetamide, N-methylpyrrolidinone, etc.), and combinations thereof. In some embodiments, the solvent is 2-methyltetrahydrofuran. In some embodiments, the solvent is cyclopentyl methyl ether.

In some embodiments, when installing a methanesulfonyl group onto a suitable amino group, the mesylating conditions comprise a temperature range of from about 100° C. or less. In some embodiments, the mesylating conditions comprise a temperature range of from about −20° C. to about 100° C. In some embodiments, the mesylating conditions comprise a temperature range of from about −10° C. to about 20° C. In some embodiments, the mesylating conditions comprise a temperature range of from about 20° C. to about 120° C. In some embodiments, the mesylating conditions comprise a temperature range of from about 70° C. to about 90° C.

The term "borylation conditions" refers to the reaction conditions under which a compound such as an aryl halide is converted into an organoboron reagent (e.g., an arylboron derivative such as compound of formula V). The borylation conditions as disclosed herein typically comprise a borylation agent and either an organometallic reagent or a catalyst. When the borylation conditions comprise a borylation agent and an organometallic reagent, non-limiting examples of borylation agents include trimethyl borate, triethyl borate, pinacolborane, 2-methoxy-4,4,5,5-tetramethyl-1,3,2-dioxaboralane, B-catecholborane, 2-bromo-1,3, 2-benzodioxaborole, and 2-isopropoxy-4,4,5,5-tetramethyl-1,3,2-dioxaborolane. In some embodiments, the borylation agent is 2-isopropoxy-4,4,5,5-tetramethyl-1,3,2-dioxaborolane or isopropoxyboronic acid pinacol ester. Non-limiting examples of organometallic reagents include lithium metal, magnesium metal, n-butyllithium, s-butylmagnesium chloride lithium chloride complex, tert-butylmagnesium chloride, isopropylmagnesium chloride lithium chloride complex, and isopropylmagnesium chloride. In some embodiments, the organometallic reagent is isopropylmagnesium chloride. In some embodiments, the organometallic reagent is isopropylmagnesium chloride lithium chloride complex.

In some embodiments, the borylation conditions further comprise a solvent. Non-limiting examples of solvents include ethers (e.g, diethyl ether, 1,4-dioxane, 2-methyltetrahydrofuran, dimethoxyethane, etc.), hydrocarbons (e.g., n-hexane, n-heptane, etc.), aromatic hydrocarbons (e.g., toluene, xylenes, etc.), and combinations thereof. In some embodiments, the solvent is tetrahydrofuran.

In some embodiments, the borylation conditions comprise a temperature range of from about 40° C. or less. In some embodiments, the borylation conditions comprise a temperature range of from about −80° C. to about 40° C. In some embodiments, the borylation conditions comprise a temperature range of from about −40° C. to about 20° C. In some embodiments, the borylation conditions comprise a temperature range of from about −20° C. to about 20° C.

In some embodiments, when the borylation conditions comprise a borylation agent and a catalyst, non-limiting examples of borylation agents include bis(neopentyl glycolato)diboron, tetrahydroxydiboron, bis(hexylene glycolato) diboron, and bis(pinacolato)diboron. In some embodiments, the borylation reagent is bis(pinacolato)diboron. Non-limiting examples of catalysts include bis(di-tert-butyl(4-dimethylaminophenyl)phosphine)dichloropalladium(II), bis[(dicyclohexyl)(4-dimethylaminophenyl)phosphine]palladium(II) chloride, dichlorobis(triphenylphosphine)palladium(II), and [1,1'-bis(diphenylphosphino)ferrocene]dichloropalladium (II). In one embodiment, the catalyst is [1,1'-bis(diphenylphosphino)ferrocene]dichloropalladium(II).

In some embodiments, non limiting examples of solvents for the borylation conditions include ethers (e.g., diethyl ether, methyl tert-butyl ether, dioxane, tetrahydrofuran, 2-methyltetrahydrofuran, etc.), polar aprotic solvents (N,N-dimethylacetamide, N,N-dimethylformamide, N-methylpyrrolidinone, etc.), aromatic hydrocarbon solvents (e.g., benzene, toluene, xylenes, etc.), chlorinated solvents (dichloromethane, etc.), alcohols (e.g., methanol, ethanol, isopropanol, etc.), esters (e.g., ethyl acetate, isopropyl acetate, etc.), and combinations thereof. In some embodiments, the solvent is a mixture of dioxane and N,N-dimethylformamide.

In some embodiments, the borylation conditions comprise a temperature range of from about 130° C. or less. In some embodiments, the borylation conditions comprise a temperature range of from about 10° C. to about 130° C. In some embodiments, the alkynylation conditions comprise a temperature range of from about 80° C. to about 110° C.

In addition, abbreviations as used herein have respective meanings as follows:

ACN or MeCN acetonitrile
acac acetyl acetonate
AcOH or HOAc acetic acid
Ac$_2$O acetic anhydride
aq. aqueous
ATA amine transaminase
BEMP 2-tert-butylimino-2-diethylamino-1,3-dimethylperhydro-1,3,2-diazaphosphorine
BINAP (1,1'-binaphthalene-2,2'-diyl)bis(diphenylphosphine)
Bn benzyl
Boc or BOC tert-butoxycarbonyl
BOP (benzotriazol-1-yloxy)tris(dimethylamino)phosphonium hexafluorophosphate
BPD bis(pinacolato)diboron
Bu butyl n-BuOAc n-butyl acetate
CBS Corey-Bakshi-Shibata (oxazaborolidine)
CDI carbonyldiimidazole
cod 1,5-cyclooctadiene
COMU or COMU® (1-cyano-2-ethoxy-2-oxoethylide-naminooxy)dimethylamino-morpholino-carbenium hexafluorophosphate
CPME cyclopentyl methyl ether
Cy cyclohexyl
DABCO 1,4-diazabicyclo[2.2.2]octane
dba dibenzylideneacetone
DBDMH 1,3-dibromo-5,5-dimethylhydantoin
DBMP 3,6-dibromo-2-methylpyridine
DBN 1,5-diazabicyclo[4.3.0]non-5-ene
2,5-DBP 2,5-dibromopyridine
DBU 1,8-diazabicyclo[5.4.0]undec-7-ene
DCC N,N-dicyclohexylcarbodiimide
DCE dichloroethane
DCM dichloromethane
dd doublet of doublets
ddd doublet of doublet of doublets
dddd doublet of doublet of doublets of doublets
DDQ 2,3-dichloro-5,6-dicyano-1,4-benzoquinone
DFBZ (3,5-difluorobenzyl)zinc(II)bromide
DIC N,N'-diisopropylcarbodiimide
DIPEA N,N-diisopropylethylamine
DMAC N,N-dimethylacetamide
DMAP 4-(dimethylamino)pyridine
DMF dimethylformamide
DMS dimethyl sulfide
DMSO dimethylsulfoxide
DPEN 1,2-diphenylethylenediamine
dppf 1,1'-bis(diphenylphosphino)ferrocene
DuPhos 1-[2-(2,5-dialkylphospholan-1-yl)phenyl]-2,5-dimethylphospholane
dq doublet of quartets
dt doublet of triplets
EDC 1-ethyl-3-(3-dimethylaminopropyl) carbodiimide
EDCI 1-ethyl-3-(3-dimethylaminopropyl) carbodiimide
EDTA ethylenediaminetetraacetic acid
EHA ethyl hydrazinoacetate
Et ethyl
$Et_3N$ triethylamine
EtOAc ethyl acetate
EtOH ethanol
h hour(s)
HATU 2-(7-aza-1H-benzotriazole-1-yl)-1,1,3,3-tetramethyluronium hexafluorophosphate
HBTU O-benzotriazole-N,N,N',N'-tetramethyluronium-hexafluoro-phosphate
HCTU O-(6-chlorobenzotriazol-1-yl)-N,N,N',N'-tetramethyluronium hexafluorophosphate
HOAt 1-hydroxy-7-azabenzotriazole
HOBt 1-hydroxybenzotriazole
HOSA hydroxylamine-O-sulfonic acid
HPLC high pressure liquid chromatography
Hz hertz
IPA isopropyl alcohol
iPAc isopropyl acetate
J coupling constant
Josiphos a [2-(diphenylphosphino)ferrocenyl]ethyldialkyl or diarylphosphine
KHMDS potassium hexamethyldisilazane
LDA lithium diisopropylamide
LHMDS lithium hexamethyldisilazane
LiHMDS lithium hexamethyldisilazane
m multiplet
M Molar
MTBE methyl tert-butyl ether
mCPBA 3-chloroperbenzoic acid
Me methyl
MeOH methanol
MeCN acetonitrile
MeTHF 2-methyltetrahydrofuran
MHz megahertz
min. minute(s)
mmol millimole
mL milliliter
mol mole
MP Melting point
MS mass spectroscopy
MMSB 3-methyl-3-(methylsulfonyl)but-1-yne
Monophos a (2,6-dimethyl-3,5-dioxa-4-phospha-cyclohepta[2,1-a;3,4a']-dinaphthalen-4-yl)dialkylamine
Ms mesyl or methanesulfonyl
MsO or OMs mesylate or methanesulfonate
MsOH methanesulfonic acid
MTBE methyl-tert-butyl ether
m/z Mass to charge
NaHMDS sodium hexamethyldisilazane
NCS N-chlorosuccinimide
NIS N-iodosuccinimide
NLT no later than
NMM N-methylmorpholine
NMP N-methylpyrrolidine
NMR nuclear magnetic resonance
NMT not more than
OAc acetate
Ph phenyl
PhMe toluene
PhOH phenol
PMB p-methoxybenzyl
PPA polyphosphoric acid
$PPh_3$ triphenylphosphine
ppm parts per million
Pr propyl
py pyridine
PyBOP (benzotriazol-1-yloxy)tripyrrolidinophosphonium hexafluorophosphate
pyr pyridine
q quartet
qNMR quantitative nuclear magnetic resonance
RT room temperature
(R)—RuCY-XylBINAP or (R)—RuCY®-XylBINAP RuCl[(R)-daipena][(R)-xylbinap] or [1-[2-bis(3,5-dimethylphenyl)phosphanylnaphthalen-1-yl]naphthalen-2-yl]-bis(3,5-dimethylphenyl)phosphane; (2R)-1,1-bis(4-methoxyphenyl)-3-methylbutane-1,2-diamine; ruthenium(1+) chloride
s singlet
segphos (+)-5,5'-bis(diphenylphosphino)-4,4'-bi-1,3-benzodioxole
SIPr 1,3-bis(2,6-diisopropylphenyl)-2-imidazolidinylidene
SMB simulated moving bed
SMPS (S)-(−)-2-methyl-2-propanesulfinamide
t triplet
T3P propylphosphonic anhydride or propanephosphonic acid anhydride
TATU O-(7-azabenzotriazole-1-yl)-N,N,N',N'-tetramethyluronium tetrafluoroborate
TBTU O-(benzotriazol-1-yl)-N,N,N',N'-tetramethyluronium tetrafluoroborate
td Triplet of doublets TEA triethylamine
TEMPO 2,2,6,6-tetramethyl-1-piperidinyloxy, free radical
TFA trifluoroacetic acid
Tf triflyl or trifluoromethanesulfonyl
TfO or OTf triflate or trifluoromethanesulfonate
TfOH triflic acid or trifluoromethanesulfonic acid
THF tetrahydrofuran
TMS trimethylsilyl
TMP 2,2,6,6-tetramethylpiperidinyl
TPP triphenylphosphine
Ts tosyl or p-toluenesulfonyl
TsO or OTs tosylate or p-toluenesulfonate
TsOH or p-TsOH p-toluenesulfonic acid
tt Triplet of triplets
UPLC ultra performance liquid chromatography Except as otherwise noted, the methods and techniques of the present disclosure are generally performed according to conventional methods well known in the art and as described in various general and more specific references that are cited and discussed throughout the present specification. See, e.g., Loudon, *Organic Chemistry*, 5th edition, New York: Oxford University Press, 2009; Smith, *March's Advanced Organic Chemistry: Reactions, Mechanisms, and Structure*, 7th edition, Wiley-Interscience, 2013.

In certain instances, the processes disclosed herein involve a step of forming a salt of a compound of the present disclosure.

Compounds as described herein can be purified by any of the means known in the art, including chromatographic means, such as high performance liquid chromatography (HPLC), preparative thin layer chromatography, flash column chromatography, supercritical fluid chromatography (SFC), and ion exchange chromatography. Any suitable stationary phase can be used, including normal and reversed phases as well as ionic resins. Most typically the disclosed compounds are purified via silica gel and/or alumina chromatography. See, e.g., *Introduction to Modern Liquid Chromatography*, 2nd ed., ed. L. R. Snyder and J. J. Kirkland, John Wiley and Sons, 1979; and *Thin Layer Chromatography*, E. Stahl (ed.), Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as T. W. Greene and P. G. M. Wuts, *Protective Groups in Organic Synthesis*, 4th ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. One of skill in the art will recognize that the transformations shown in the schemes below may be performed in any order that is compatible with the functionality of the particular pendant groups. In some embodiments, each of the reactions depicted in the general schemes is run at a temperature from about −80° C. to the reflux temperature of the organic solvent used.

The compounds disclosed herein may display atropisomerism resulting from steric hindrance affecting the axial rotation rate around a single bond. The resultant conformational isomers may each be observed as distinct entities by characterization techniques such as NMR and HPLC. The compounds disclosed herein may exist as a mixture of atropisomers. However, the detection of atropisomers is dependent on factors such as temperature, solvent, conditions of purification, and timescale of spectroscopic technique. The interconversion rate at room temperature has a half-life of minutes to hours, hours to days, or days to years.

The ratio of atropisomers at equilibrium may not be unity. Characterization data presented herein may not represent the equilibrium state depending on the conditions of isolation and characterization which may include but not limited to handling, solvents used, and temperature.

The present disclosure provides in some embodiments processes and intermediates for preparing the compound of formula I and co-crystals, solvates, salts and combinations thereof. In other embodiments, the disclosure provides processes for preparing intermediates that can be used to prepare the compound of formula I and co-crystals, solvates, salts and combinations thereof.

In some embodiments, a process for preparing a compound of formula VI:

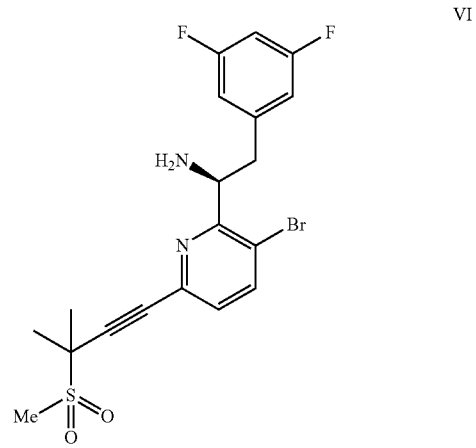 [SMILES: CC(C)(C#Cc1ccc(Br)c([C@@H](N)Cc2cc(F)cc(F)c2)n1)S(C)(=O)=O]

VI or a co-crystal, solvate, salt, or combination thereof is provided, comprising combining a compound of formula VIII:

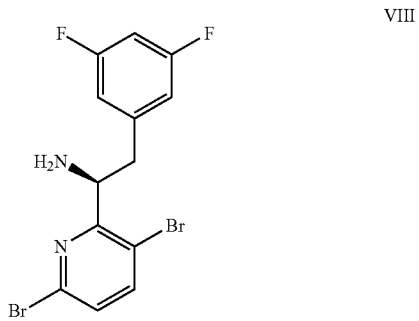

VIII or a co-crystal, solvate, salt, or combination thereof, with a compound of formula IX:

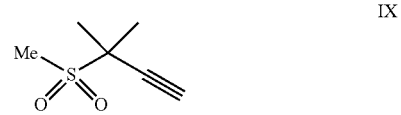

IX or a co-crystal, solvate, or combination thereof,
a base,
a solvent, and
a catalyst, to provide the compound of formula VI or a co-crystal, solvate, salt, or combination thereof.

In certain embodiments, the compound of formula VIII is a compound of formula VIII-02:

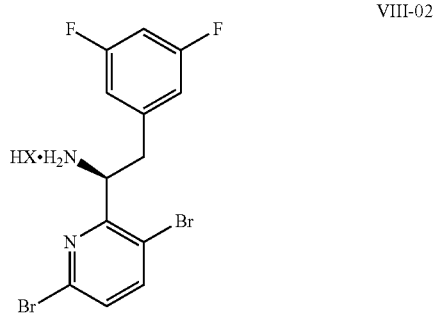

VIII-02 or a co-crystal, solvate, or combination thereof, wherein HX is a chiral or achiral acid.

In particular embodiments, HX is selected from the group consisting of L-lactic acid, L-(+)-tartaric acid, L-aspartic acid, L-glutamic acid, L-(−)-malic acid, D-glucuronic acid, (1R, 3S)-(+)-camphoric acid, (1S)-(+)-camphor-10-sulfonic acid, (R)-(+)-N-(1-phenylethyl)succinamic acid, carbobenzyloxy-L-proline, dibenzoyl-L-tartaric acid, (R)-(+)-3-methyladipic acid, (+)-menthyloxyacetic acid, (−)-pyroglutamic acid, (−)—N-acetyl-L-leucine, (−)-N-acetyl-D-leucine, N-Boc-D-leucine, N-(+)-BOC-phenylalanine, (−)-quinic acid, (+)-n-acetyl-L-phenylalanine, (+)-N-BOC-isoleucine, L-(−)-acetyl glutamic acid, (−)-acetyl mandelic acid, (R)-(−)-citramalic acid, (−)-camphanic acid, and (R)-mandelic acid.

In certain embodiments, HX is a chiral acid. In particular embodiments, HX is selected from the group consisting of L-lactic acid, L-(+)-tartaric acid, L-aspartic acid, L-glutamic acid, L-(−)-malic acid, D-glucuronic acid, (1R, 3S)-(+)-camphoric acid, (1S)-(+)-camphor-10-sulfonic acid, (R)-(+)-N-(1-phenylethyl)succinamic acid, carbobenzyloxy-L-proline, dibenzoyl-L-tartaric acid, (R)-(+)-3-methyladipic acid, (+)-menthyloxyacetic acid, (−)-pyroglutamic acid, (−)—N-acetyl-L-leucine, N-Boc-D-leucine, N-(+)-BOC-phenylalanine, (−)-quinic acid, (+)-n-acetyl-L-phenylalanine, (+)-N-BOC-isoleucine, L-(−)-acetyl glutamic acid, (−)-acetyl mandelic acid, (R)-(−)-citramalic acid, (−)-camphanic acid, and (R)-mandelic acid. In some embodiments, HX is (R)-mandelic acid. In some embodiments, HX is N-Boc-D-leucine.

In some embodiments, HX is (−)-N-acetyl-D-leucine.

In certain embodiments, HX is an achiral acid. In particular embodiments, HX is selected from the group consisting of hydrochloric acid, sulfuric acid, methanesulfonic acid, p-toluenesulfonic acid, and phosphoric acid. In some embodiments, HX is methanesulfonic acid.

In certain embodiments, the catalyst comprises a palladium catalyst and a copper catalyst. In particular embodiments, the palladium catalyst is selected from the group consisting of [(π-allyl)PdCl]$_2$, Pd(acac)$_2$, (SIPr)PdCl$_2$, PdCl$_2$(PPh$_3$)$_2$, PdCl$_2$, Pd(OAc)$_2$, PdCl$_2$(CH$_3$CN)$_2$, and Pd$_2$(dba)$_3$, optionally, in combination with a tertiary phosphine. In some embodiments, the tertiary phosphine is selected from the group consisting of triphenylphosphine, tri-cyclohexylphosphine, tri-tert-butylphosphine, 1,2-bis(diphenylphosphino)ethane, 1,3-bis(diphenylphosphino)propane, and 1,1'-bis(diphenylphosphino)ferrocene. In particular embodiments, the copper catalyst is selected from the group consisting of copper(I) iodide, copper(I) bromide, copper(I) chloride, and combinations thereof. In particular embodiments, the catalyst comprises PdCl$_2$(PPh$_3$)$_2$ and copper(I) iodide.

In certain embodiments, the catalyst is a palladium catalyst. In particular embodiments, the palladium catalyst is selected from the group consisting of [(π-allyl)PdCl]$_2$, Pd(acac)$_2$, (SIPr)PdCl$_2$, PdCl$_2$(PPh$_3$)$_2$, PdCl$_2$, Pd(OAc)$_2$, PdCl$_2$(CH$_3$CN)$_2$, and Pd$_2$(dba)$_3$, optionally, in combination with a tertiary phosphine. In some embodiments, the tertiary phosphine is selected from the group consisting of triphenylphosphine, tri-cyclohexylphosphine, tri-tert-butylphosphine, 1,2-bis(diphenylphosphino)ethane, 1,3-bis(diphenylphosphino)propane, and 1,1'-bis(diphenylphosphino)ferrocene. In some embodiments, the palladium catalyst is PdCl$_2$(PPh$_3$)$_2$.

In particular embodiments, the copper catalyst is selected from the group consisting of copper(I) iodide, copper(I) bromide, copper(I) chloride, and combinations thereof.

In certain embodiments, the catalyst is a copper catalyst. In particular embodiments, the copper catalyst is selected from the group consisting of copper(I) iodide, copper(I) bromide, and copper(I) chloride.

In certain embodiments, the base is selected from the group consisting of triethylamine, diisopropylamine, ethyldiisopropylamine, pyrrolidine, 1,4-diazabicylo[2.2.2]-octane, 1,8-diazabicyclo[5.4.0]undec-7-ene, 1,5-diazabicyclo-4.3.0]non-5-ene, pyridine, cesium carbonate, potassium carbonate, sodium carbonate, piperidine, potassium phosphate, and tetrabutylammonium fluoride. In certain embodiments, the base is triethylamine.

In certain embodiments, the solvent is selected from the group consisting of an ether (e.g., diethyl ether, methyl tert-butyl ether, tetrahydrofuran, 2-methyltetrahydrofuran, 1,4-dioxane), aromatic solvents (e.g., benzene, toluene, xylenes), a polar aprotic solvent (e.g., N,N-dimethylformamide, N,N-dimethylacetamide, N-methylpyrrolidinone), water, acetonitrile, and a combination thereof.

In certain embodiments, the solvent is selected from the group consisting of an ether (e.g., diethyl ether, methyl tert-butyl ether, tetrahydrofuran, 2-methyltetrahydrofuran, 1,4-dioxane), aromatic solvents (e.g., benzene, toluene, xylenes), a polar aprotic solvent (e.g., N,N-dimethylformamide, N,N-dimethylacetamide, N-methylpyrrolidinone), water, and a combination thereof. In some embodiments, the solvent is 2-methyltetrahydrofuran.

In some embodiments, the process is carried out in the temperature range of about 120° C. or less. In certain embodiments, the process is carried out in the temperature range of from about 0° C. to about 120° C. In particular embodiments, the process is carried out in the temperature range of from about 50° C. to about 80° C.

In some embodiments, a process for preparing a compound of formula IV:

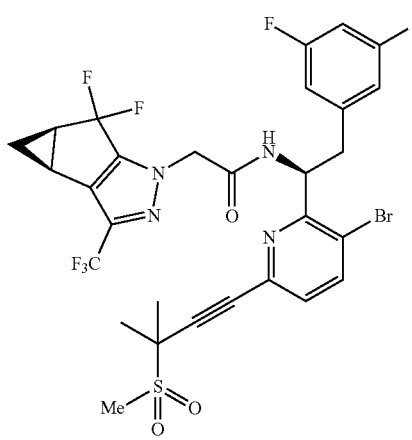

IV

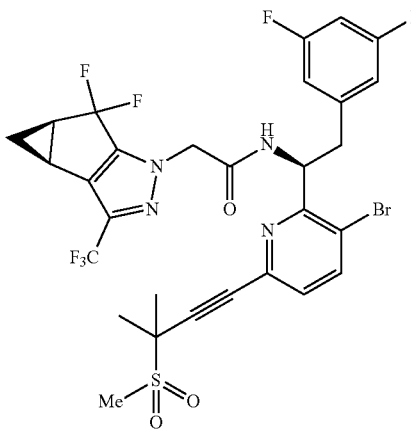

IV or a co-crystal, solvate, salt, or combination thereof is provided, comprising combining a compound of formula VI:

or a co-crystal, solvate, salt, or combination thereof is provided, comprising combining a compound of formula VI:

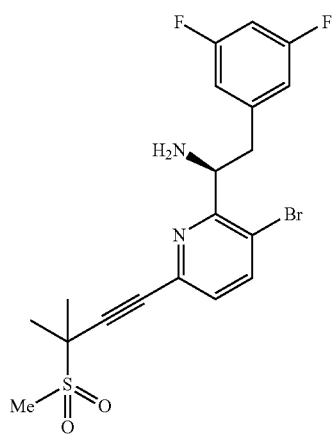

VI

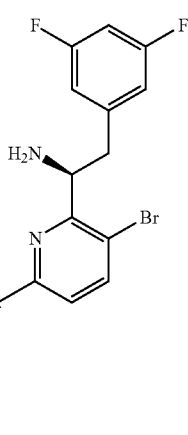

VI or a co-crystal, solvate, salt, or combination thereof, with a compound of formula VII:

or a co-crystal, solvate, salt, or combination thereof, with a compound of formula VII:

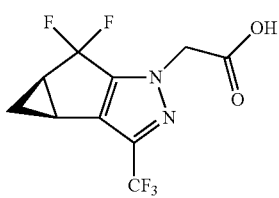

VII

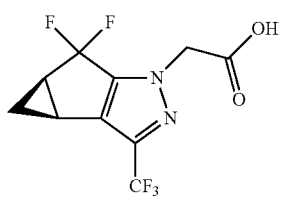

VII or a co-crystal, solvate, salt, or combination thereof,
   a base,
   a solvent,
   optionally a coupling agent; and
   optionally an activating agent.

In some embodiments, a process for preparing a compound of formula IV:

or a co-crystal, solvate, salt, or combination thereof,
   a coupling reagent or an activating agent,
   a base, and
   a solvent,
to provide the compound of formula IV or a co-crystal, solvate, salt, or combination thereof.

In certain embodiments, the coupling reagent is an aryl boronic acid. Non-limiting examples of aryl boronic acids include phenylboronic acid, 3,5-bis(trifluoromethyl)phenylboronic acid, 3-nitrophenylboronic acid, and 2-iodophenylboronic acid.

In certain embodiments, the coupling reagent is selected from the group consisting of n-propyl phosphonic cyclic anhydride, n-propyl phosphonic anhydride, 2-chloro-4,6-dimethoxy-1,3,5-triazine, 4-(4,6-dimethoxy-1,3,5-triazin-2-yl)-4-methylmorpholinium chloride, 2-chloro-1-methylpyridinium iodide, dicyclohexylcarbodiimide, diisopropylcarbodiimide, 1-ethyl-3-(3-dimethylaminopropyl)carbodiimide, carbonyl diimidazole, isobutyl chloroformate, 2-(7-aza-1H-benzotriazole-1-yl)-1,1,3,3-tetramethyluronium hexafluorophosphate, O-benzotriazole-N,N,N',N'-tetramethyluronium-hexafluoro-phosphate, O-(7-azabenzotriazole-1-yl)-N,N,N',N'-tetramethyluronium tetrafluoroborate, O-(benzotriazol-1-yl)-N,N,N',N'-tetramethyluronium tetrafluoroborate, O-(6-chlorobenzotriazol-1-yl)-N,N,N',N'-tetramethyluronium hexafluorophosphate, (benzotriazol-1-yloxy)tris(dimethylamino)phosphonium hexafluorophosphate, (benzotriazol-1-yloxy)tripyrrolidino-phosphonium hexafluorophosphate, (1-cyano-2-ethoxy-2-oxoethylidenaminooxy)dimethylamino-morpholino-carbenium hexafluorophosphate, 4-(4,6-dimethoxy-1,3,5-triazin-2-yl)-4-methylmorphonium chloride, boric acid, tetramethyl orthosilicate, trimethyoxysilane, diphenylphosphinic chloride, chloro-N, N, N', N'-tetramethylformamidinium hexafluorophosphate, triisopropyl borate, phenylboronic acid, 3,5-bis(trifluoromethyl)phenylboronic acid, 3-nitrophenylboronic acid, and 2-iodophenylboronic acid.

In certain embodiments, the coupling reagent is selected from the group consisting of n-propyl phosphonic anhydride, 2-chloro-4,6-dimethoxy-1,3,5-triazine, 4-(4,6-dimethoxy-1,3,5-triazin-2-yl)-4-methylmorpholinium chloride, 2-chloro-1-methylpyridinium iodide, dicyclohexylcarbodiimide, diisopropylcarbodiimide, 1-ethyl-3-(3-dimethylaminopropyl)carbodiimide, carbonyl diimidazole, isobutyl chloroformate, 2-(7-aza-1H-benzotriazole-1-yl)-1,1,3,3-tetramethyluronium hexafluorophosphate, O-benzotriazole-N,N,N',N'-tetramethyluronium-hexafluoro-phosphate, O-(7-azabenzotriazole-1-yl)-N,N,N',N'-tetramethyluronium tetrafluoroborate, O-(benzotriazol-1-yl)-N,N,N',N'-tetramethyluronium tetrafluoroborate, O-(6-chlorobenzotriazol-1-yl)-N,N,N',N'-tetramethyluronium hexafluorophosphate, (benzotriazol-1-yloxy)tris(dimethylamino)phosphonium hexafluorophosphate, (benzotriazol-1-yloxy)tripyrrolidino-phosphonium hexafluorophosphate, and (1-cyano-2-ethoxy-2-oxoethylidenaminooxy)dimethylamino-morpholino-carbenium hexafluorophosphate. In particular embodiments, the coupling reagent is n-propyl phosphonic anhydride. In particular embodiments, the coupling reagent is n-propyl phosphonic cyclic anhydride.

In certain embodiments, the activating agent is selected from the group consisting of oxalyl chloride, thionyl chloride, diphenylphosphinic chloride, pivaloyl chloride, cyanuric chloride, and methanesulfonyl chloride, wherein a compound of formula VII-B:

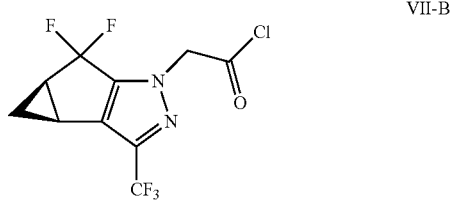 [SMILES: O=C(Cl)Cn1nc(C(F)(F)F)c2c1C(F)(F)[C@@H]1C[C@H]21]

or a or a co-crystal, solvate, salt, or combination thereof, is produced from the compound of formula VII, or a co-crystal, solvate, salt, or combination thereof.

In certain embodiments, the activating agent is selected from the group consisting of oxalyl chloride, thionyl chloride, and diphenylphosphinic chloride, wherein a compound of formula VII-B:

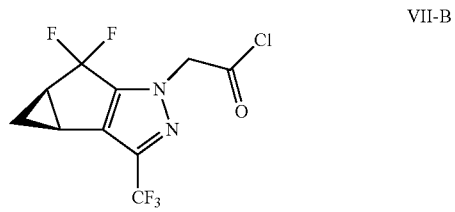 [SMILES: O=C(Cl)Cn1nc(C(F)(F)F)c2c1C(F)(F)[C@@H]1C[C@H]21]

or a co-crystal, solvate, salt, or combination thereof, is produced from the compound of formula VII, or a co-crystal, solvate, salt, or combination thereof.

In certain embodiments, the base is selected from the group consisting of triethylamine, tributylamine, ethyldiisopropylamine, N-methylmorpholine, pyridine, 2,6-lutidine, and N-methylimidazole. In particular embodiments, the base is triethylamine.

In certain embodiments, the solvent is selected from the group consisting of an ester (e.g., ethyl acetate, butyl acetate, isobutyl acetate, isopropyl acetate), an ether (e.g., diethyl ether, methyl tert-butyl ether, tetrahydrofuran, 2-methyltetrahydrofuran, 1,4-dioxane), an aromatic hydrocarbon solvent (e.g., toluene, benzene, xylenes), a polar aprotic solvent (e.g., N,N-dimethylformamide, N,N-dimethylacetamide, N-methylpyrrolidinone, dimethylsulfoxide), a chlorinated solvent (e.g., dichloromethane, dichloroethane, chloroform), a nitrile (e.g., propionitrile, butyronitrile, acetonitrile), and a combination thereof. In particular embodiments, the solvent is acetonitrile.

In some embodiments, the process is carried out in the temperature range of from about 120° C. or less. In certain embodiments, the process is carried out in the temperature range of from about −20° C. to about 120° C. In particular embodiments, the process is carried out in the temperature range of from about 0° C. to about 40° C.

In some embodiments, the process further comprises a coupling additive. In certain embodiments, the coupling additive is selected from the group consisting of 4-(dimethylamino)pyridine, N-hydroxysuccinimide, ethyl cyanohydroxyiminoacetate, 1-hydroxybenzotriazole, 1-hydroxy-7-azabenzotriazole, and N-methylimidazole. In certain embodiments, the coupling additive is selected from the group consisting of 4-(dimethylamino)pyridine, N-hydroxysuccinimide, ethyl cyanohydroxyiminoacetate, 1-hydroxybenzotriazole, and 1-hydroxy-7-azabenzotriazole.

In some embodiments, a process for preparing a compound of formula III:

III

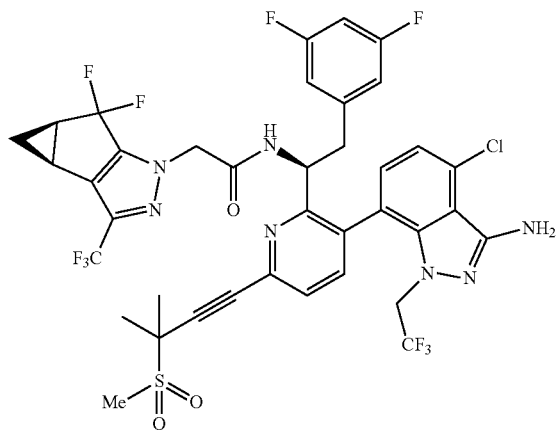

or a co-crystal, solvate, salt, or combination thereof is provided, comprising combining a compound of formula IV:

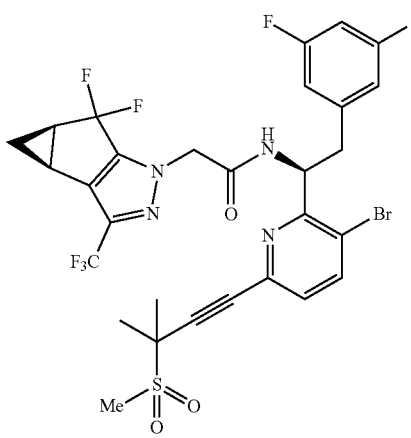

or a co-crystal, solvate, salt, or combination thereof, with a compound of formula V:

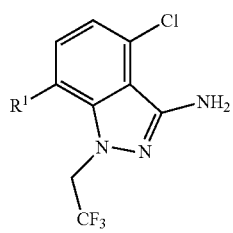

or a co-crystal, solvate, salt, or combination thereof, wherein $R^1$ is $B(OH)_2$, $B(OCH(Me)CH_2C(Me)_2O)$, $B((1,2\text{-di-O})C_6H_4)$, $B(OCH_2C(Me)_2CH_2O)$, $BF_3K$, $B(O_2CCH_2N(Me)CH_2CO_2)$, or $B(OC(Me)_2C(Me)_2O)$,
    a palladium catalyst,
    a base, and
    a solvent,
to provide the compound of formula III or a co-crystal, solvate, salt, or combination thereof.

In some embodiments, a process for preparing a compound of formula III:

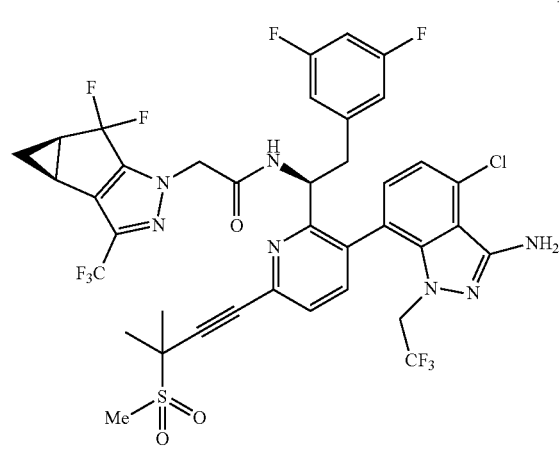

or a co-crystal, solvate, salt, or combination thereof is provided, comprising combining a compound of formula IV:

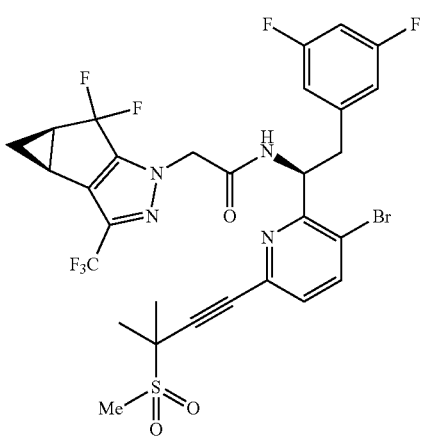

or a co-crystal, solvate, salt, or combination thereof, with a compound of formula V:

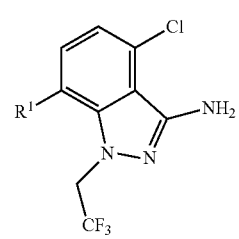

or a co-crystal, solvate, salt, or combination thereof, wherein $R^1$ is $B(OH)_2$, $B(OCH(Me)CH_2C(Me)_2O)$, $B((1,2\text{-di-O})C_6H_4)$, $B(OCH_2C(Me)_2CH_2O)$, $BF_4K$, $B(O_2CCH_2N(Me)CH_2CO_2)$, or $B(OC(Me)_2C(Me)_2O)$,
    a palladium catalyst,
    a base, and
    a solvent, to provide the compound of formula III or a co-crystal, solvate, salt, or combination thereof.

In certain embodiments, $R^1$ is $B(OC(Me)_2C(Me)_2O)$.

In certain embodiments, the palladium catalyst is selected from the group consisting of dichlorobis(tricyclohexylphosphine)palladium(II), bis(di-tert-butyl(4-dimethylaminophenyl)phosphine)dichloropalladium(II), bis[(dicyclohexyl)(4-dimethylaminophenyl)phosphine]palladium(II) chloride, dichlorobis(triphenylphosphine)palladium(II), [1,1'-bis(diphenylphosphino)ferrocene]dichloropalladium(II), [1,2-bis(diphenylphosphino)ethane]dichloropalladium(II), dichloro[9,9-dimethyl-4,5-bis(diphenylphosphino)xanthene] palladium(II), chloro[(tricyclohexylphosphine)-2-(2'-aminobiphenyl)]palladium(II), [(tricyclohexylphosphine)-2-(2'-aminobiphenyl)]palladium(II) methanesulfonate, $PCy_3$ Pd G4, palladium chloride, palladium acetate, and palladium trifluoroacetate. In certain embodiments, the palladium catalyst further comprises a phosphine ligand, wherein the palladium catalyst is selected from the group consisting of palladium chloride, palladium acetate, palladium trifluoroacetate, dichloro(1,5-cyclooctadiene)palladium(II), allylpalladium(II) chloride dimer, palladium(II) acetylacetonate, (tetrakis(triphenylphosphine)palladium(0) and bis(dibenzylideneacetone)palladium(0). In particular embodiments, the phosphine ligand is selected from the group consisting of di-tert-butyl(4-dimethylaminophenyl)phosphine, dicyclohexyl(4-dimethylaminophenyl)phosphine, 1,2-bis(diphenylphosphino)ethane, 2-dicyclohexylphosphino-2',4',6'-triisopropylbiphenyl, 2-dicyclohexylphosphino-2',6'-dimethoxybiphenyl, 2,2'-bis(diphenylphosphino)-1,1'-binaphthalene, 1,3-bis(diphenylphosphino)propane, ethylenebis(diphenylphosphine), 1,1'-ferrocenediyl-bis(diphenylphosphine, 4,5-bis(diphenylphosphino)-9,9-dimethylxanthene, tricyclohexylphosphine, triphenylphosphine, cyclohexyldiphenylphosphine, dicyclohexylphenylphosphine, tritertbutylphosphine, cyclohexylditertbutylphosphine, and dicyclohexyltertbutylphosphine. In some embodiments, the palladium catalyst is dichlorobis(tricyclohexylphosphine)palladium(II).

In certain embodiments, the base is selected from the group consisting of potassium bicarbonate, sodium bicarbonate, sodium carbonate, potassium carbonate, cesium carbonate, potassium fluoride, potassium phosphate dibasic, potassium phosphate tribasic, sodium hydroxide, potassium hydroxide, dicyclohexylamine, N-methylmorpholine, and triethylamine. In particular embodiments, the base is potassium bicarbonate.

In certain embodiments, the solvent is selected from the group consisting of an ether (e.g., diethyl ether, 2-methyltetrahydrofuran, 1,4-dioxane, dimethoxyethane), an aromatic hydrocarbon solvent (e.g., toluene, xylenes), an ester (e.g., ethyl acetate, n-butyl acetate, isobutyl acetate, isopropyl acetate, propyl acetate), an alcohol (e.g., ethanol, isopropanol), a polar aprotic solvent (e.g., N,N-dimethylformamide, N,N-dimethylacetamide, N-methylpyrrolidinone), water, and a combination thereof. In particular embodiments, the solvent is a mixture of n-butyl acetate and water.

In some embodiments, the process is carried out in the temperature range of from about 120° C. or less. In certain embodiments, the process is carried out in the temperature range of from about 20° C. to about 120° C. In particular embodiments, the process is carried out in the temperature range of from about 75° C. to about 95° C.

In some embodiments, the process of making the compound of formula III:

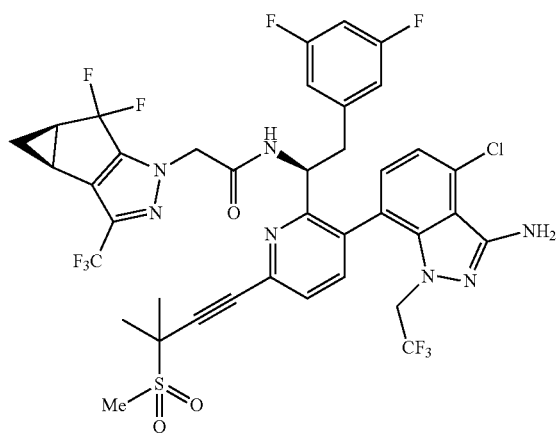

or a co-crystal, solvate, salt, or combination thereof, further comprises:

(a) combining the compound of formula III, or a co-crystal, solvate, salt, or combination thereof, with a second solvent and an acid to provide a compound of formula III-02:

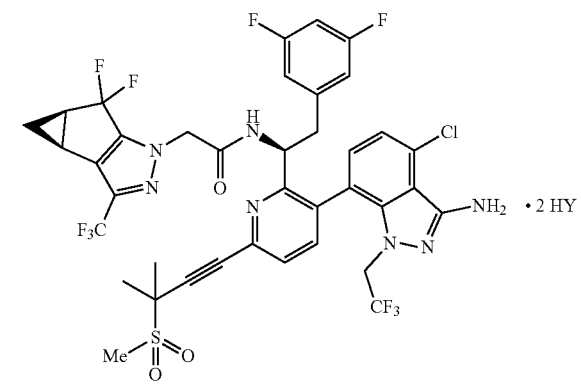

or a co-crystal, solvate, or combination thereof, wherein HY is selected from the group consisting of acetic acid, oxalic acid, sulfuric acid, hydrochloric acid, phosphoric acid, chloroacetic acid, citric acid, nitric acid, formic acid, lactic acid, ascorbic acid, benzoic acid, propionic acid, ethanesulfonic acid, p-toluenesulfonic acid, benzenesulfonic acid, and methanesulfonic acid; and (b) free-basing the compound of formula III-02, or a co-crystal, solvate, or combination thereof, by combining it with a second base and a third solvent to provide the compound of formula III or a co-crystal, solvate, salt, or combination thereof.

In certain embodiments, HY is methanesulfonic acid.

In certain embodiments, the second solvent is selected from the group consisting of an alcohol (e.g., methanol, ethanol, 1-propanol, isopropanol, tert-amyl alcohol), a nitrile (e.g., acetonitrile), a ketone (e.g., methyl isobutyl ketone), a chlorinated solvent (e.g., dichloromethane), an ester (e.g., ethyl acetate, isopropyl acetate), an aromatic hydrocarbon solvent (e.g., toluene), an ether (e.g., methyl tert-butyl ether, cyclopentyl methyl ether, 2-methyltetrahydrofuran), and a combination thereof.

In certain embodiments, the compound of formula III-02 is produced as a bis-methanesulfonic acid.

In certain embodiments, the compound of formula III-02 is produced as a solvate. In particular embodiments, the compound of formula III-02 is produced as a 1-propanol, isopropanol, ethanol, methanol, tert-amyl alcohol, acetonitrile, methyl isobutyl ketone, dichloromethane, 2-methyl tetrahydrofuran, ethyl acetate, isopropyl acetate, methyl tert-butyl ether, toluene, or cyclopentyl methyl ether solvate. In some embodiments, the compound of formula III-02 is produced as an ethanol solvate. In other embodiments, the compound of formula III-02 is produced as a 1-propanol solvate. In other embodiments, the compound of formula III-02 is produced as an isopropanol solvate. In other embodiments, the compound of formula III-02 is produced as a methanol solvate. In other embodiments, the compound of formula III-02 is produced as a tert-amyl alcohol solvate. In other embodiments, the compound of formula III-02 is produced as an acetonitrile solvate. In other embodiments, the compound of formula III-02 is produced as a methyl isobutyl ketone solvate. In other embodiments, the compound of formula III-02 is produced as a dichloromethane solvate. In other embodiments, the compound of formula III-02 is produced as a 2-methyl tetrahydrofuran solvate. In other embodiments, the compound of formula III-02 is produced as an ethyl acetate solvate. In other embodiments, the compound of formula III-02 is produced as an isopropyl acetate solvate. In other embodiments, the compound of formula III-02 is produced as a methyl tert-butyl ether solvate. In other embodiments, the compound of formula III-02 is produced as a toluene solvate. In other embodiments, the compound of formula III-02 is produced as a cyclopentyl methyl ether solvate.

In some embodiments, the compound of formula III-02 is produced in the temperature range of from about 20° C. or less. In certain embodiments, the compound of formula III-02 is produced in the temperature range of from about −20° C. to about 20° C.

In certain embodiments, the second base is selected from the group consisting of sodium hydroxide, lithium hydroxide, potassium hydroxide, sodium carbonate, potassium carbonate, sodium bicarbonate, potassium bicarbonate, benzyltrimethylammonium hydroxide, choline hydroxide, sodium or potassium methoxide, sodium or potassium ethoxide, triethylamine, 1,4-diazabicyclo[2.2.2]octane, 1,8-diazabicyclo[5.4.0]undec-7-ene, ammonium hydroxide, and diethylamine. In particular embodiments, the second base is sodium hydroxide.

In certain embodiments, the third solvent is selected from the group consisting of an ether (e.g., diethyl ether, methyl tert-butyl ether, 2-methyltetrahydrofuran, 1,4-dioxane, dimethoxyethane), an aromatic hydrocarbon solvent (e.g., toluene, xylenes), an ester (e.g., ethyl acetate, isopropyl acetate), water, and a combination thereof. In particular embodiments, the third solvent is a mixture of 2-methyltetrahydrofuran and water.

In some embodiments, the free-basing step is carried out in the temperature range of from about 80° C. or less. In certain embodiments, the free-basing step is carried out in the temperature range of from about −20° C. to about 80° C. In particular embodiments, free-basing step is carried out in the temperature range of from about 0° C. to about 50° C.

In some embodiments, the process of making the compound of formula III:

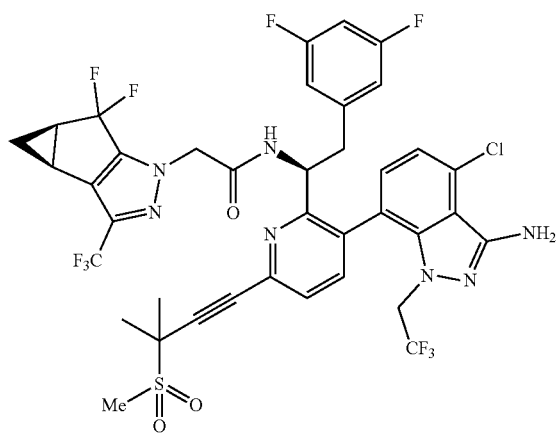

III or a co-crystal, solvate, salt, or combination thereof, further comprises:

(a) combining the compound of formula III, or a co-crystal, solvate, salt, or combination thereof, with a second solvent and an acid to provide a compound of formula III-02:

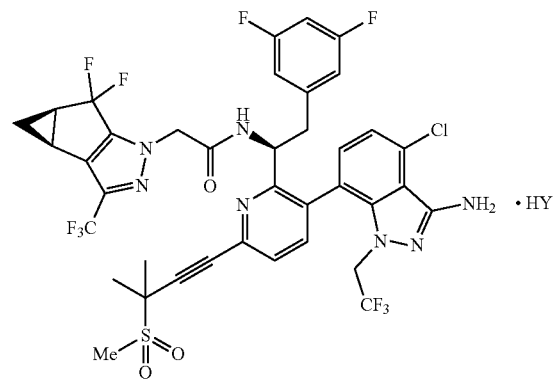

III-02 or a co-crystal, solvate, or combination thereof, wherein HY is selected from the group consisting of acetic acid, oxalic acid, sulfuric acid, hydrochloric acid, phosphoric acid, chloroacetic acid, citric acid, nitric acid, formic acid, lactic acid, ascorbic acid, benzoic acid, propionic acid, ethanesulfonic acid, p-toluenesulfonic acid, benzenesulfonic acid, and methanesulfonic acid; and (b) free-basing the compound of formula III-02, or a co-crystal, solvate, or combination thereof, by combining it with a second base and a third solvent to provide the compound of formula III or a co-crystal, solvate, salt, or combination thereof.

In certain embodiments, HY is methanesulfonic acid.

In certain embodiments, the second solvent is selected from the group consisting of an alcohol (e.g., methanol, ethanol, 1-propanol, isopropanol, tert-amyl alcohol), a nitrile (e.g., acetonitrile), a ketone (e.g., methyl isobutyl ketone), a chlorinated solvent (e.g., dichloromethane), an ester (e.g., ethyl acetate, isopropyl acetate), an aromatic hydrocarbon solvent (e.g., toluene), an ether (e.g., methyl tert-butyl ether, cyclopentyl methyl ether, 2-methyltetrahydrofuran), and a combination thereof.

In certain embodiments, the compound of formula III-02 is produced as a solvate. In particular embodiments, the compound of formula III-02 is produced as a 1-propanol, isopropanol, ethanol, methanol, tert-amyl alcohol, acetonitrile, methyl isobutyl ketone, dichloromethane, 2-methyl tetrahydrofuran, ethyl acetate, isopropyl acetate, methyl tert-butyl ether, toluene, or cyclopentyl methyl ether solvate. In some embodiments, the compound of formula III-02 is produced as an ethanol solvate. In other embodiments, the compound of formula III-02 is produced as a 1-propanol solvate. In other embodiments, the compound of formula III-02 is produced as an isopropanol solvate. In other embodiments, the compound of formula III-02 is produced as a methanol solvate. In other embodiments, the compound of formula III-02 is produced as a tert-amyl alcohol solvate. In other embodiments, the compound of formula III-02 is produced as an acetonitrile solvate. In other embodiments, the compound of formula III-02 is produced as a methyl isobutyl ketone solvate. In other embodiments, the compound of formula III-02 is produced as a dichloromethane solvate. In other embodiments, the compound of formula III-02 is produced as a 2-methyl tetrahydrofuran solvate. In other embodiments, the compound of formula III-02 is produced as an ethyl acetate solvate. In other embodiments, the compound of formula III-02 is produced as an isopropyl acetate solvate. In other embodiments, the compound of formula III-02 is produced as a methyl tert-butyl ether solvate. In other embodiments, the compound of formula III-02 is produced as a toluene solvate. In other embodiments, the compound of formula III-02 is produced as a cyclopentyl methyl ether solvate.

In some embodiments, the compound of formula III-02 is produced in the temperature range of from about 20° C. or less. In certain embodiments, the compound of formula III-02 is produced in the temperature range of from about −20° C. to about 20° C.

In certain embodiments, the second base is selected from the group consisting of sodium hydroxide, lithium hydroxide, potassium hydroxide, sodium carbonate, potassium carbonate, sodium bicarbonate, potassium bicarbonate, benzyltrimethylammonium hydroxide, choline hydroxide, sodium or potassium methoxide, sodium or potassium ethoxide, triethylamine, 1,4-diazabicyclo[2.2.2]octane, 1,8-diazabicyclo[5.4.0]undec-7-ene, ammonium hydroxide, and diethylamine. In particular embodiments, the second base is sodium hydroxide.

In certain embodiments, the third solvent is selected from the group consisting of an ether (e.g., diethyl ether, methyl tert-butyl ether, 2-methyltetrahydrofuran, 1,4-dioxane, dimethoxyethane), an aromatic hydrocarbon solvent (e.g., toluene, xylenes), an ester (e.g., ethyl acetate, isopropyl acetate), water, and a combination thereof. In particular embodiments, the third solvent is a mixture of 2-methyltetrahydrofuran and water.

In some embodiments, the free-basing step is carried out in the temperature range of from about 80° C. or less. In certain embodiments, the free-basing step is carried out in the temperature range of from about −20° C. to about 80° C. In particular embodiments, free-basing step is carried out in the temperature range of from about 0° C. to about 50° C.

In some embodiments, a process for preparing a compound of formula I:

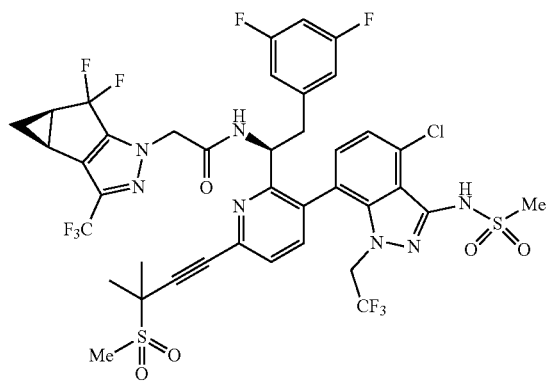

I or a co-crystal, solvate, salt, or combination thereof is provided, comprising combining a compound of formula III:

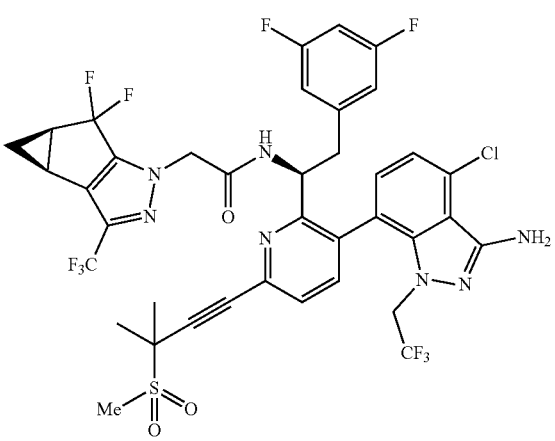

III or a co-crystal, solvate, salt, or combination thereof, with
  a mesylating reagent, and
  a solvent,
to provide the compound of formula I or a co-crystal, solvate, salt, or combination thereof.

In certain embodiments, the mesylating reagent is selected from the group consisting of methanesulfonyl chloride and methanesulfonic anhydride. In particular embodiments, the mesylating reagent is methanesulfonic anhydride.

In certain embodiments, the solvent is selected from the group consisting of an ester (e.g., ethyl acetate, isopropyl acetate), an ether (e.g., cyclopentyl methyl ether, tetrahydrofuran, 2-methyltetrahydrofuran, 1,4-dioxane), a nitrile (e.g., acetonitrile), a polar aprotic solvent (e.g., N,N-dimethylformamide, N,N-dimethylacetamide, N-methylpyrrolidinone), an aromatic hydrocarbon solvent (e.g., toluene, xylenes), a chlorinated solvent (e.g., dichloromethane, dichloroethane, chloroform), and a combination thereof. In particular embodiments, the solvent for the mesylating step is cyclopentyl methyl ether.

In some embodiments, the process is carried out in the temperature range of from about 120° C. or less. In certain embodiments, the process is carried out in the temperature range of from about 20° C. to about 120° C. In particular embodiments, the process is carried out in the temperature range of from about 70° C. to about 90° C.

In some embodiments, a process for preparing a compound of formula I:

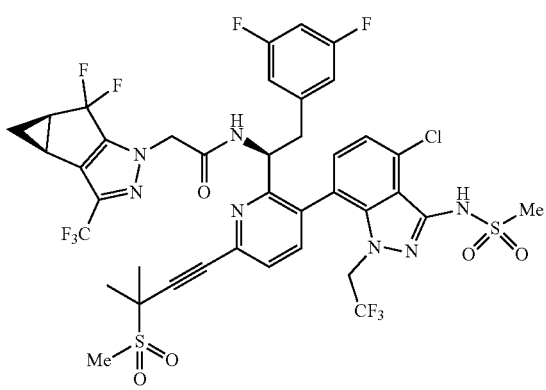

or a co-crystal, solvate, salt, or combination thereof is provided, comprising:
(a) combining a compound of formula III:

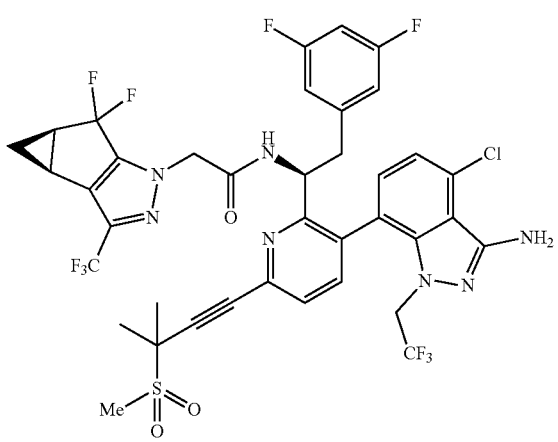

or a co-crystal, solvate, salt, or combination thereof with a mesylating reagent, a base, and a solvent to provide a compound of formula II:

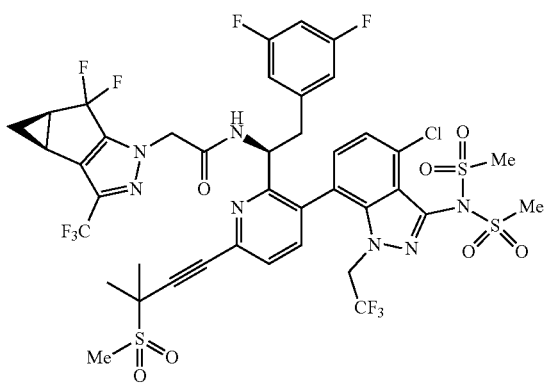

or a co-crystal, solvate, salt, or combination thereof; and
(b) hydrolyzing the compound of formula II or a co-crystal, solvate, salt, or combination thereof, with a nucleophilic reagent, and optionally, a phase transfer catalyst, in a solvent, to provide the compound of formula I or a co-crystal, solvate, salt, or combination thereof.

In certain embodiments, the mesylating reagent is selected from the group consisting of methanesulfonyl chloride and methanesulfonic anhydride. In particular embodiments, the mesylating reagent is methanesulfonyl chloride.

In certain embodiments, a phase transfer catalyst is used in step (b). In certain embodiments, the phase transfer catalyst used in step (b) is an ammonium or phosphonium salt. In certain embodiments, the phase transfer catalyst is selected from the group consisting of tetra-n-butylammonium chloride, benzyltri-n-butylammonium bromide, 1-methylimidazolium hydrogen sulfate, tetra-n-butylammonium hydrogen sulfate, and tetra-n-butylphosphonium chloride. In particular embodiments, the phase transfer catalyst is tetra-n-butylammonium hydrogen sulfate.

In certain embodiments, the base is selected from the group consisting of N-methylmorpholine, tri-n-propylamine, ethyl diisopropylamine, tri-n-butylamine, triethylamine, pyridine, 2,6-lutidine, collidine, sodium bicarbonate, sodium carbonate, sodium phosphate monobasic, sodium phosphate dibasic, potassium bicarbonate, potassium carbonate, potassium phosphate monobasic, potassium phosphate dibasic, sodium tert-amylate, and sodium tert-butoxide. In particular embodiments, the base is triethylamine.

In certain embodiments, the solvent for the mesylating step is selected from the group consisting of an ether (e.g., diethyl ether, 2-methyltetrahydrofuran, 1,4-dioxane, dimethoxyethane), an aromatic hydrocarbon solvent (e.g., toluene, xylenes), an ester (e.g., isobutyl acetate, isopropyl acetate), a chlorinated solvent (e.g., dichloromethane), a nitrile (e.g., acetonitrile), and a combination thereof. In particular embodiments, the solvent for the mesylating step is 2-methyltetrahydrofuran.

In certain embodiments, the mesylating step is carried out in the temperature range of from about 100° C. or less. In certain embodiments, the mesylating step is carried out in the temperature range of from about −20° C. to about 100° C. In particular embodiments, the mesylating step is carried out in the temperature range of from about −10° C. to about 20° C.

In certain embodiments, the nucleophilic reagent for the hydrolyzing step is selected from the group consisting of sodium hydroxide, lithium hydroxide, potassium hydroxide, sodium ethanethiolate, N-acetylcysteine, sodium thiophenolate, choline, sodium methoxide, sodium ethoxide, potassium ethoxide, sodium n-propoxide, sodium isopropoxide, sodium t-butoxide, methylamine, ethylamine, n-propylamine, dimethylamine, diethylamine, and hydroxylamine. In particular embodiments, the nucleophilic reagent for the hydrolyzing step is sodium hydroxide.

In certain embodiments, the solvent for the hydrolyzing step is selected from the group consisting of an alcohol (e.g., methanol, ethanol, 1-propanol, isopropanol, n-butanol, sec-butanol), an ether (e.g., diethyl ether, 2-methyltetrahydrofuran, 1,4-dioxane, dimethoxyethane), an aromatic hydrocarbon solvent (e.g., toluene, xylenes), an ester (e.g., isobutyl acetate, isopropyl acetate), a chlorinated solvent (e.g., dichloromethane), a nitrile (e.g., acetonitrile), a polar aprotic solvent (e.g., N,N-dimethylformamide, N,N-dimethylacetamide, N-methylpyrrolidinone), water, and a combination thereof. In particular embodiments, the solvent for the hydrolyzing step is water and 2-methyltetrahydrofuran.

In some embodiments, the hydrolyzing step is carried out in the temperature range of from about 100° C. or less. In certain embodiments, the hydrolyzing step is carried out in the temperature range of from about −20° C. to about 100° C. In particular embodiments, the hydrolyzing step is carried out in the temperature range of from about 10° C. to about 60° C.

In some embodiments, a process for preparing a compound of formula I:

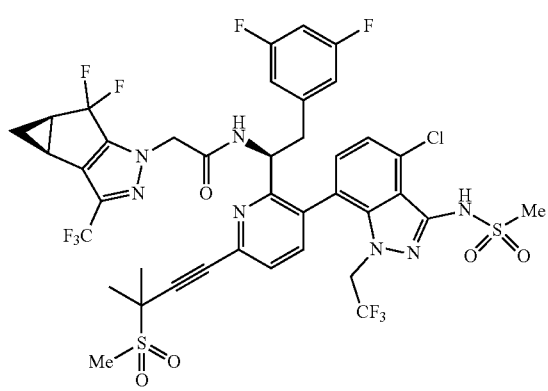

or a co-crystal, solvate, salt, or combination thereof is provided, comprising:

(a) combining a compound of formula VIII:

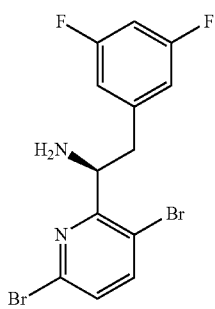

or a co-crystal, solvate, salt, or combination thereof, with a compound of formula IX:

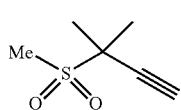

or a co-crystal, solvate, or combination thereof, under alkynylation conditions to provide the compound of formula VI:

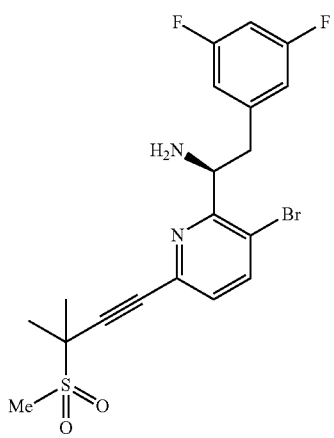

or a co-crystal, solvate, salt, or combination thereof;

(b) combining the compound of formula VI or a co-crystal, solvate, salt, or combination thereof, with a compound of formula VII:

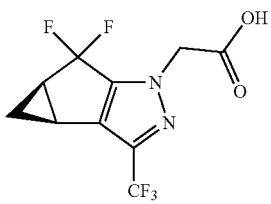

or a co-crystal, solvate, salt, or combination thereof, under amide coupling conditions to provide a compound of formula IV:

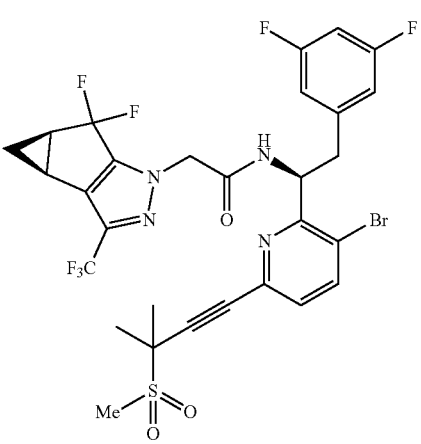

or a co-crystal, solvate, salt, or combination thereof;

(c) combining the compound of formula IV or a co-crystal, solvate, salt, or combination thereof, with a compound of formula V:

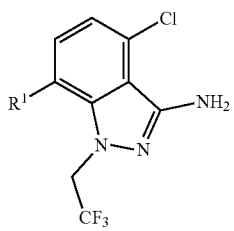
V or a co-crystal, solvate, salt, or combination thereof, wherein IV is B(OH)₂, B(OCH(Me)CH₂C(Me)₂O), B((1,2-di-O)C₆H₄), B(OCH₂C(Me)₂CH₂O), BF₃K, B(O₂CCH₂N(Me)CH₂CO₂), or B(OC(Me)₂C(Me)₂O), under palladium-catalyzed cross-coupling conditions to provide a compound of formula III:

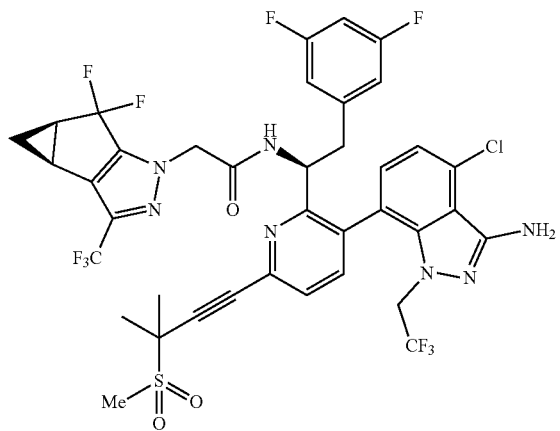
III or a co-crystal, solvate, salt, or combination thereof; and
(d) combining the compound of formula III or a co-crystal, solvate, salt, or combination thereof, with a mesylating reagent under mesylating conditions to provide the compound of formula I or a co-crystal, solvate, salt, or combination thereof.

In some embodiments, a process for preparing a compound of formula I:

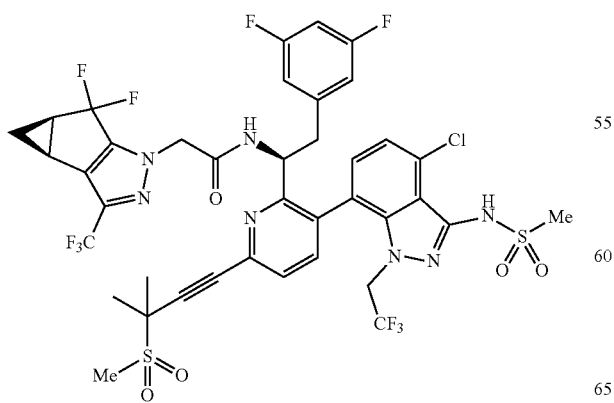
I or a co-crystal, solvate, salt, or combination thereof is provided, comprising:
(a) combining a compound of formula VIII:

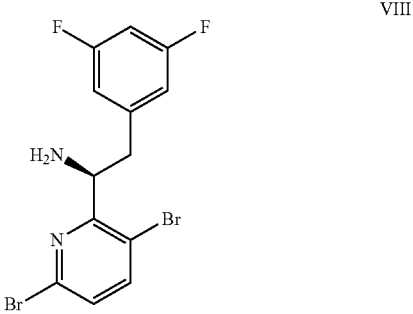 [SMILES: N[C@@H](Cc1cc(F)cc(F)c1)c1nc(Br)ccc1Br]
VIII or a co-crystal, solvate, salt, or combination thereof, with a compound of formula IX:

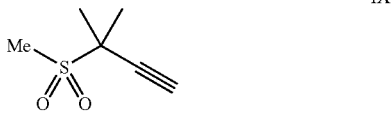
IX or a co-crystal, solvate, or combination thereof, under alkynylation conditions to provide the compound of formula VI:

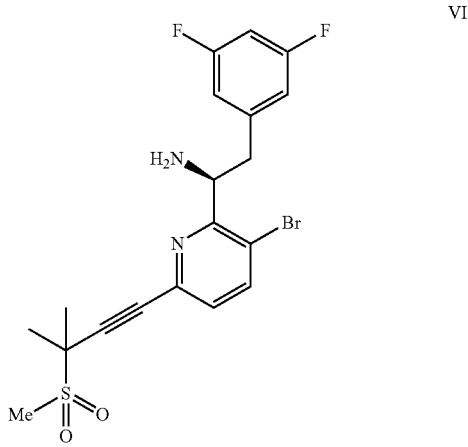 [SMILES: CC(C)(C#Cc1ccc(Br)c([C@@H](N)Cc2cc(F)cc(F)c2)n1)S(C)(=O)=O]
VI or a co-crystal, solvate, salt, or combination thereof;
(b) combining the compound of formula VI or a co-crystal, solvate, salt, or combination thereof, with a compound of formula VII:

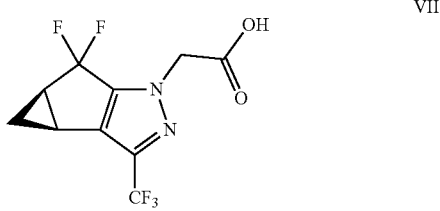 [SMILES: O=C(O)Cn1nc(C(F)(F)F)c2c1C(F)(F)[C@@H]1C[C@H]21]
VII or a co-crystal, solvate, salt, or combination thereof, under amide coupling conditions to provide a compound of formula IV:

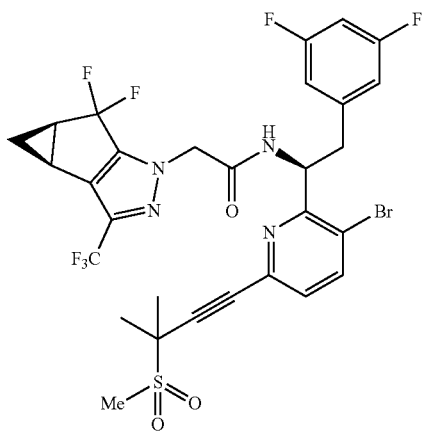

or a co-crystal, solvate, salt, or combination thereof;

(c) combining the compound of formula IV or a co-crystal, solvate, salt, or combination thereof, with a compound of formula V:

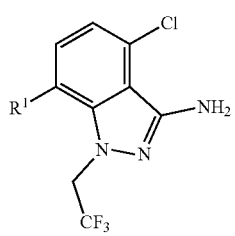

or a co-crystal, solvate, salt, or combination thereof, wherein IV is $B(OH)_2$, $B(OCH(Me)CH_2C(Me)_2O)$, $B((1,2-di-O)C_6H_4)$, $B(OCH_2C(Me)_2CH_2O)$, $BF_4K$, $B(O_2CCH_2N(Me)CH_2CO_2)$, or $B(OC(Me)_2C(Me)_2O)$, under palladium-catalyzed cross-coupling conditions to provide a compound of formula III:

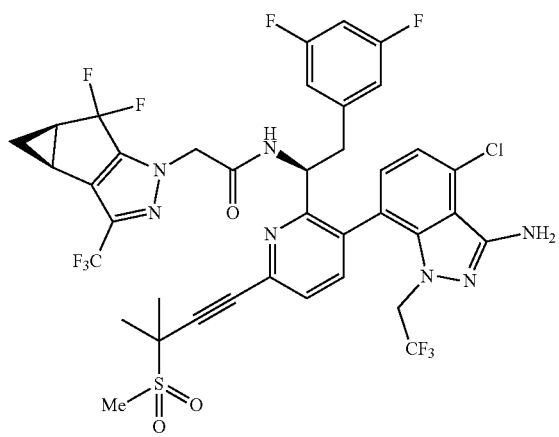

or a co-crystal, solvate, salt, or combination thereof and (d) combining the compound of formula III or a co-crystal, solvate, salt, or combination thereof, with a mesylating reagent under mesylating conditions to provide the compound of formula I or a co-crystal, solvate, salt, or combination thereof.

In some embodiments, the process for preparing a compound of formula I:

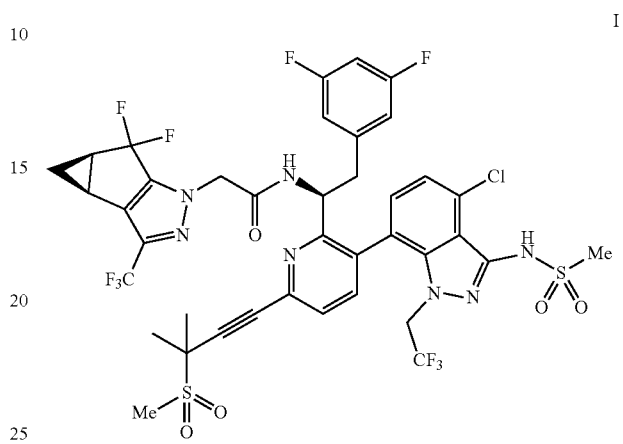

or a co-crystal, solvate, salt, or combination thereof, further comprises:

(a) forming the sodium salt of the compound of formula I to provide a compound of formula I-02:

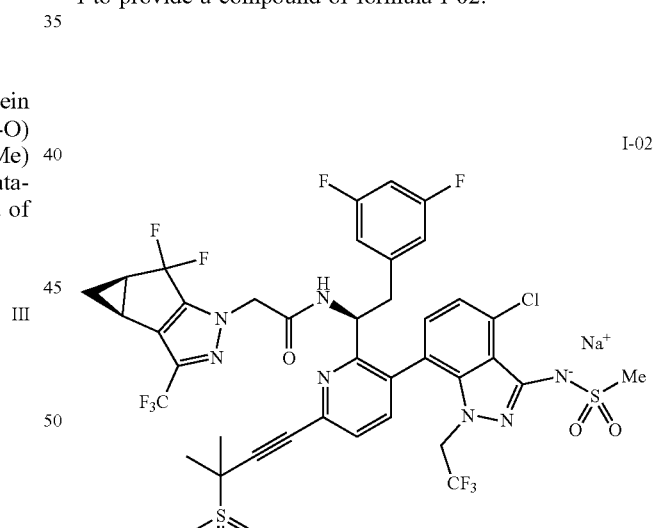

by combining the compound of formula I with a sodium source and a solvent; and (b) neutralizing the compound of formula I-02 with an acid, in a solvent, to provide the compound of formula I.

In some embodiments, the process for preparing a compound of formula I:

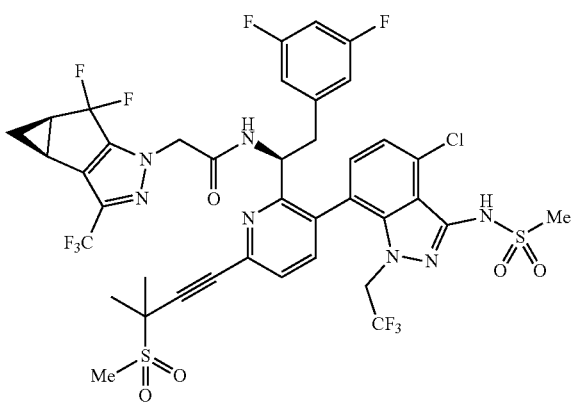

or a co-crystal, solvate, salt, or combination thereof, further comprises:

(a) forming the sodium salt of the compound of formula I to provide a compound of formula I-02:

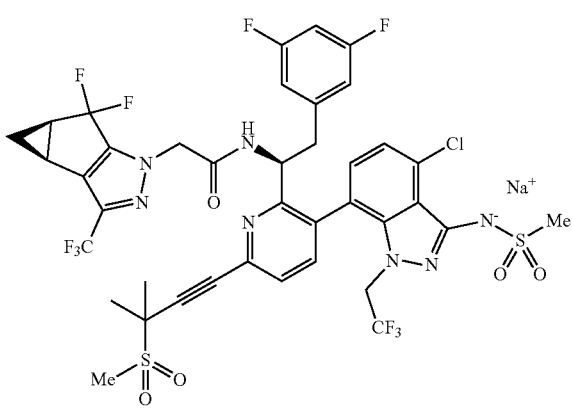

by combining the compound of formula I with a sodium source and a solvent; and (b) neutralizing the compound of formula I-02 with an acid to provide the compound of formula I.

In certain embodiments, the sodium source for the sodium salt forming step (a) is selected from the group consisting of sodium hydroxide, sodium bicarbonate, sodium carbonate, sodium phosphate, sodium methoxide, sodium ethoxide, sodium n-propoxide, sodium t-butoxide, sodium hexamethyldisilazide, and sodium metal and an alcohol selected from the group consisting of methanol, ethanol, isopropanol, 1-propanol, n-butanol, and sec-butanol. In particular embodiments, the sodium source is sodium ethoxide. In particular embodiments, the sodium source is sodium hydroxide.

In certain embodiments, the solvent for the sodium salt forming step (a) is selected from the group consisting of of an ether (e.g., diethyl ether, 2-methyltetrahydrofuran, 1,4-dioxane, dimethoxyethane), a hydrocarbon solvent (e.g., n-heptane), an aromatic hydrocarbon solvent (e.g., toluene, xylenes), an ester (e.g., ethyl acetate, isobutyl acetate, isopropyl acetate), a chlorinated solvent (e.g., dichloromethane), a nitrile (e.g., acetonitrile), a ketone (e.g., acetone, methyl ethyl ketone, methyl isobutylketone), an alcohol (e.g., methanol, ethanol, 1-propanol, isopropanol, n-butanol, sec-butanol), and a combination thereof. In particular embodiments, the solvent for the sodium salt forming step is ethanol and n-heptane.

In certain embodiments, the sodium salt forming step (a) is carried out in the temperature range of from about 100° C. or less. In certain embodiments, the sodium salt forming step is carried out in the temperature range of from about −20° C. to about 100° C. In particular embodiments, the sodium salt forming step is carried out in the temperature range of from about 0° C. to about 50° C.

In certain embodiments, the acid for the neutralizing step (b) is selected from the group consisting of acetic acid, oxalic acid, sulfuric acid, hydrochloric acid, phosphoric acid, chloroacetic acid, citric acid, nitric acid, formic acid, lactic acid, ascorbic acid, benzoic acid, and propionic acid. In particular embodiments, the acid for the neutralizing step is acetic acid.

In certain embodiments, the solvent for the neutralizing step (b) is selected from water, ethers (e.g., diethyl ether, 1,4-dioxane, 2-methyltetrahydrofuran, dimethoxyethane, methyl tert-butyl ether), hydrocarbon solvents (e.g., n-hexane, n-heptane, toluene, xylenes), esters (e.g., ethyl acetate, isopropyl acetate, isobutyl acetate), dichloromethane, acetonitrile, ketones (e.g., acetone, methyl ethyl ketone, methyl isobutylketone), alcohols (e.g., methanol, ethanol, isopropyl alcohol, tert-butyl alcohol), and a combination thereof. In particular embodiments, the solvent for the neutralizing step (b) is water and alcohol (e.g., methanol, ethanol, isopropyl alcohol, tert-butyl alcohol). In particular embodiments, the solvent for the neutralizing step (b) is water and ethanol. In particular embodiments, the solvent for the neutralizing step (b) is water. In particular embodiments, the ratio of the acid to water is from 2:5 to 2:30. In particular embodiments, the ratio of the acetic acid to water is from 2:5 to 2:30.

In certain embodiments, the neutralizing step (b) is carried out in the temperature range of from about 100° C. or less. In certain embodiments, the neutralizing step is carried out in the temperature range of from about −20° C. to about 100° C. In particular embodiments, the neutralizing step is carried out in the temperature range of from about 0° C. to about 50° C.

In some embodiments, a process for preparing a compound of formula I:

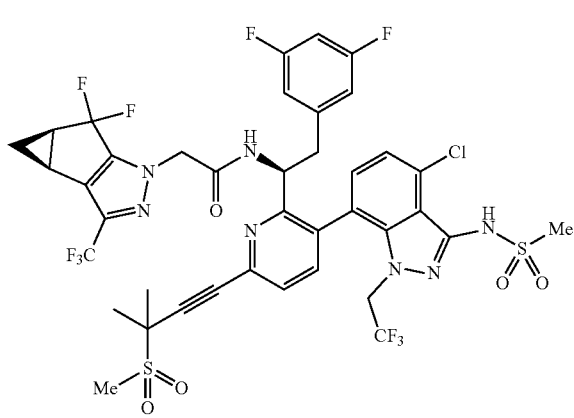

or a co-crystal, solvate, salt, or combination thereof is provided, comprising:

(a) combining a compound of formula IV:

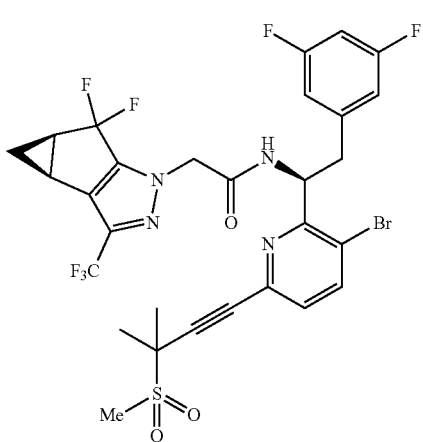

or a co-crystal, solvate, salt, or combination thereof, with
a base,
a solvent,
a catalyst, and
a compound of formula V-04-A:

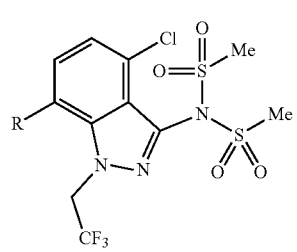

or a co-crystal, solvate, salt, or combination thereof,
wherein R is $B(OH)_2$, $B(OCH(Me)CH_2C(Me)_2O)$, $B((1,2-di-O)C_6H_4)$, $B(OCH_2C(Me)_2CH_2O)$, $BF_3K$, $B(O_2CCH_2N(Me)CH_2CO_2)$, or $B(OC(Me)_2C(Me)_2O)$, to provide a compound of II:

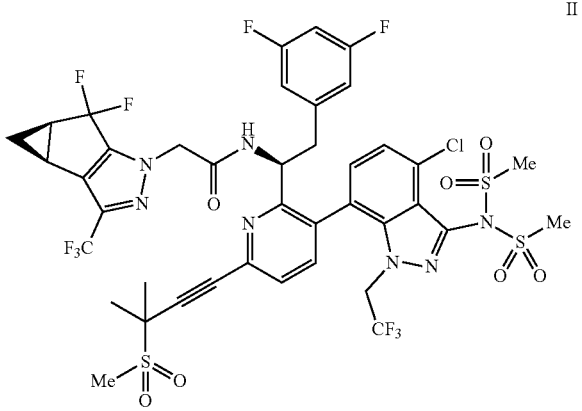 [SMILES: CC(C)(C#Cc1ccc(-c2ccc(Cl)c3c(N(S(C)(=O)=O)S(C)(=O)=O)nn(CC(F)(F)F)c23)c([C@H](Cc2cc(F)cc(F)c2)NC(=O)Cn2nc(C(F)(F)F)c3c2C(F)(F)[C@@H]2C[C@H]32)n1)S(C)(=O)=O]

or a co-crystal, solvate, salt, or combination thereof and
(b) hydrolyzing the compound of formula II or a co-crystal, solvate, salt, or combination thereof, with a base, a solvent, and optionally a phase transfer catalyst, to provide the compound of formula I or a co-crystal, solvate, salt, or combination thereof.

In certain embodiments, R is $B(OC(Me)_2C(Me)_2O)$.

In certain embodiments, the catalyst used in step (a) is selected from the group consisting of bis(di-tert-butyl(4-dimethylaminophenyl)phosphine)dichloropalladium(II), bis[(dicyclohexyl)(4-dimethylaminophenyl)phosphine]palladium(II) chloride, dichlorobis(triphenylphosphine)palladium(II), [1,1'-bis(diphenylphosphino)ferrocene]dichloropalladium(II), [1,2-bis(diphenylphosphino)ethane]dichloropalladium(II), and dichloro[9,9-dimethyl-4,5-bis(diphenylphosphino)xanthene]palladium(II). In certain embodiments, the catalyst used in step (a) is palladium(II) precatalyst (e.g., palladium(II) chloride, palladium(II) acetate, palladium (II) trifluoroacetate) or palladium(0) precatalyst (e.g., tetrakis(triphenylphosphine)palladium(0), bis(dibenzylideneacetone)palladium(0)) and the catalyst used in step (a) further comprises a phosphine ligand (e.g., tricyclohexylphosphine, triphenylphosphine, cyclohexyldiphenylphosphine, dicyclohexylphenylphosphine). In certain embodiments, the catalyst used in step (a) is selected from the group consisting of palladium(II) chloride, palladium(II) acetate, palladium(II) trifluoroacetate, tetrakis(triphenylphosphine)palladium(0), and bis(dibenzylideneacetone)palladium(0). In some embodiments, the palladium catalyst used in step (a) is palladium (II) chloride and cyclohexyldiphenylphosphine.

In certain embodiments, the base used in step (a) is selected from the group consisting of sodium hydroxide, potassium acetate, sodium acetate, cesium acetate, potassium propionate, sodium propionate, potassium carbonate, sodium carbonate, cesium carbonate, potassium bicarbonate, sodium bicarbonate, sodium phosphate, sodium hydroxide, potassium hydroxide, potassium fluoride, potassium phosphate dibasic, potassium phosphate tribasic, sodium hydroxide, potassium hydroxide, dicyclohexylamine, N-methylmorpholine, triethylamine, and diisopropylethylamine. In particular embodiments, the base used in step (a) is potassium bicarbonate.

In certain embodiments, the solvent used in step (a) is selected from the group consisting of water, ethers (e.g., 1,4-dioxane, 2-methyltetrahydrofuran, dimethoxyethane), aromatic hydrocarbon solvents (e.g., toluene, xylenes), esters (e.g., ethyl acetate, isopropyl acetate, propyl acetate, isobutyl acetate), alcohols (e.g., ethanol, isopropanol,), and polar aprotic solvents (e.g., N,N-dimethylformamide, N,N-dimethylacetamide, N-methyl-2-pyrrolidine), and a combination thereof. In certain embodiments, the solvent used in step (a) is selected from the group consisting of water, 1,4-dioxane, 2-methyltetrahydrofuran, dimethoxyethane, toluene, xylenes, ethyl acetate, isopropyl acetate, propyl acetate, isobutyl acetate, ethanol, isopropanol, N,N-dimethylformamide, N,N-dimethylacetamide, N-methyl-2-pyrrolidine, and a combination thereof. In particular embodiments, the solvent used in step (a) is 2-methyltetrahydrofuran and water.

In some embodiments, step (a) is carried out in the temperature range of from about 120° C. or less. In certain embodiments, step (a) is carried out in the temperature range of from about 20° C. to about 120° C. In particular embodiments, step (a) is carried out in the temperature range of from about 65° C. to about 75° C.

In some embodiments, the base used in step (b) is selected from the group consisting of hydroxide bases (e.g., sodium hydroxide, lithium hydroxide, potassium hydroxide), carbonate bases (sodium carbonate, potassium carbonate), bicarbonate bases (e.g., sodium bicarbonate potassium bicarbonate), tetraalkylammonium hydroxides (e.g., benzyltrimethylammonium hydroxide, choline hydroxide), alkoxide bases (e.g., sodium or potassium methoxide, sodium or potassium ethoxide), and amine bases (e.g., triethylamine, 1,4-diazabicyclo[2.2.2]octane (DABCO), 1,8-Diazabicyclo[5.4.0]undec-7-ene (DBU), diethylamine). In some embodiments, the base used in step (b) is selected from the group consisting of sodium hydroxide, lithium hydroxide, potassium hydroxide, sodium carbonate, potassium carbonate, bicarbonate bases, sodium bicarbonate, potassium bicarbonate, benzyltrimethylammonium hydroxide, choline hydroxide, sodium or potassium methoxide, sodium or potassium ethoxide, triethylamine, DABCO, DBU, and diethylamine. In particular embodiments, the base used in step (b) is sodium hydroxide.

In some embodiments, the solvent used in step (b) is selected from the group consisting of ethers (e.g., diethyl ether, 1,4-dioxane, 2-methyltetrahydrofuran, dimethoxyethane), hydrocarbon solvents (e.g., toluene, xylenes), esters (e.g., isopropyl acetate, isobutyl acetate), dichloromethane, acetonitrile, polar aprotic solvents (e.g., N,N-dimethylformamide, N-methyl-2-pyrrolidone, N,N-dimethylacetamide), and a combination thereof. In some embodiments, the solvent used in step (b) is selected from the group consisting of diethyl ether, 1,4-dioxane, 2-methyltetrahydrofuran, dimethoxyethane, toluene, xylenes, isopropyl acetate, isobutyl acetate, dichloromethane, acetonitrile, N,N-dimethylformamide, N-methyl-2-pyrrolidone, N,N-dimethylacetamide, and a combination thereof. In particular embodiments, the solvent used in step (b) is 2-methyltetrahydrofuran.

In some embodiments, a phase transfer catalyst is used in step (b). In some embodiments, the phase transfer catalyst used in step (b) is selected from the group consisting of ammonium salts (e.g., tetrabutylammonium chloride, benzyltributylammonium bromide, 1-methylimidazolium hydrogen sulfate), and phosphonium salts (e.g., tetrabutylphosphonium chloride). In particular embodiments, the phase transfer catalyst used in step (b) is selected from the group consisting of tetrabutylammonium chloride, benzyltributylammonium bromide, 1-methylimidazolium hydrogen sulfate, and tetrabutylphosphonium chloride In some embodiments, step (b) is carried out in the temperature range of from about 100° C. or less. In certain embodiments, step (b) is carried out in the temperature range of from about −20° C. to about 100° C. In particular embodiments, step (b) is carried out in the temperature range of from about 10° C. to about 60° C.

In some embodiments, a process for preparing a compound of formula I:

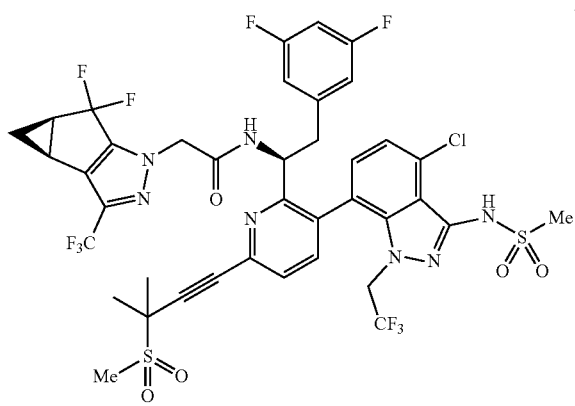

or a co-crystal, solvate, salt, or combination thereof is provided, comprising combining a compound of formula IV:

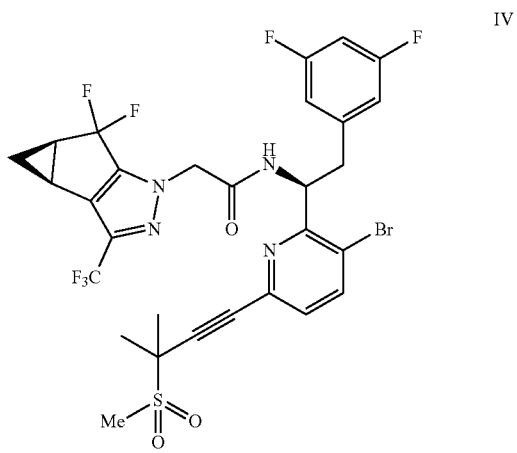 [SMILES: CC(C)(C#Cc1ccc(Br)c([C@H](Cc2cc(F)cc(F)c2)NC(=O)Cn2nc(C(F)(F)F)c3c2C(F)(F)[C@@H]2C[C@H]32)n1)S(C)(=O)=O]

or a co-crystal, solvate, salt, or combination thereof, with
a base,
a solvent,
a catalyst, and
a compound of formula V-03-A:

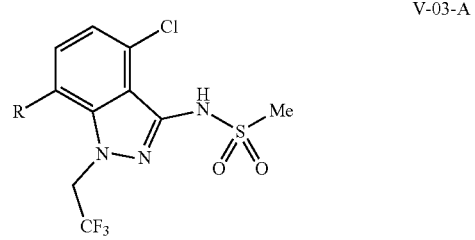

or a co-crystal, solvate, salt, or combination thereof,
wherein R is B(OH)$_2$, B(OCH(Me)CH$_2$C(Me)$_2$O), B((1,2-di-O)C$_6$H$_4$), B(OCH$_2$C(Me)$_2$CH$_2$O), BF$_3$K, B(O$_2$CCH$_2$N(Me)CH$_2$CO$_2$), or B(OC(Me)$_2$C(Me)$_2$O),
to provide the compound of formula I, or a co-crystal, solvate, salt, or combination thereof.

In certain embodiments, R is B(OC(Me)$_2$C(Me)$_2$O).

In certain embodiments, the catalyst is selected from the group consisting of bis(di-tert-butyl(4-dimethylaminophenyl)phosphine)dichloropalladium(II), bis[(dicyclohexyl)(4-dimethylaminophenyl)phosphine]palladium(II) chloride, dichlorobis(triphenylphosphine)palladium(II), [1,1'-bis(diphenylphosphino)ferrocene]dichloropalladium(II), [1,2-bis(diphenylphosphino)ethane]dichloropalladium(II), and dichloro[9,9-dimethyl-4,5-bis(diphenylphosphino)xanthene]palladium(II). In certain embodiments, the catalyst is palladium(II) precatalyst (e.g., palladium(II) chloride, palladium(II) acetate, palladium(II) trifluoroacetate) or palladium(0) precatalyst (e.g., tetrakis(triphenylphosphine)palladium(0), bis(dibenzylideneacetone)palladium(0)) and the catalyst further comprises a phosphine ligand (e.g., tricyclohexylphosphine, triphenylphosphine, cyclohexyldiphenylphosphine, dicyclohexylphenylphosphine). In some embodiments, the catalyst is selected from the group consisting of palladium(II) chloride, palladium(II) acetate, palladium(II) trifluoroacetate, tetrakis(triphenylphosphine)palladium(0), and bis(dibenzylideneacetone)palladium(0)) and the catalyst further comprises a phosphine ligand selected from the group consisting of tricyclohexylphosphine, triphenylphosphine, cyclohexyldiphenylphosphine, and dicyclohexylphenylphosphine. In some embodiments, the palladium catalyst is palladium (II) chloride and cyclohexyldiphenylphosphine.

In certain embodiments, the base is selected from the group consisting of potassium acetate, sodium acetate, cesium acetate, potassium propionate, sodium propionate, potassium carbonate, sodium carbonate, cesium carbonate, potassium bicarbonate, sodium bicarbonate, sodium phosphate, sodium hydroxide, potassium hydroxide, potassium fluoride, potassium phosphate dibasic, potassium phosphate tribasic, sodium hydroxide, potassium hydroxide, dicyclohexylamine, N-methylmorpholine, triethylamine, and diisopropylethylamine. In particular embodiments, the base is potassium bicarbonate.

In certain embodiments, the solvent is selected from the group consisting of water, ethers (e.g., 1,4-dioxane, 2-methyltetrahydrofuran, dimethoxyethane), aromatic hydrocarbon solvents (e.g., toluene, xylenes), esters (e.g., ethyl acetate, isopropyl acetate, propyl acetate, isobutyl acetate), alcohols (e.g., ethanol, isopropanol,), and polar aprotic solvents (e.g., N,N-dimethylformamide, N,N-dimethylacetamide, N-methyl-2-pyrrolidine), and a combination thereof. In certain embodiments, the solvent is selected from the group consisting of water, 1,4-dioxane, 2-methyltetrahydrofuran, dimethoxyethane, toluene, xylenes, ethyl acetate, isopropyl acetate, propyl acetate, isobutyl acetate, ethanol, isopropanol, N,N-dimethylformamide, N,N-dimethylacetamide, N-methyl-2-pyrrolidine, and a combination thereof. In particular embodiments, the solvent is 2-methyltetrahydrofuran and water.

In some embodiments, the process is carried out in the temperature range of from about 120° C. or less. In certain embodiments, the process is carried out in the temperature range of from about 20° C. to about 120° C. In particular embodiments, the process is carried out in the temperature range of from about 65° C. to about 75° C.

In some embodiments, a process for preparing a compound of formula V-03-A:

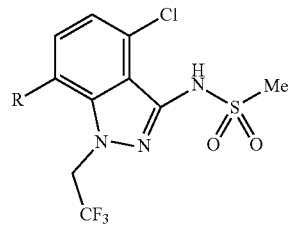

or a co-crystal, solvate, salt, or combination thereof is provided, comprising:
(a) combining a compound of formula V:

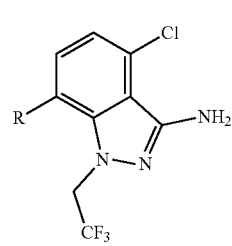

or a co-crystal, solvate, salt, or combination thereof, wherein R is $B(OH)_2$, $B(OCH(Me)CH_2C(Me)_2O)$, $B((1,2-di-O)C_6H_4)$, $B(OCH_2C(Me)_2CH_2O)$, $BF_3K$, $B(O_2CCH_2N(Me)CH_2CO_2)$, or $B(OC(Me)_2C(Me)_2O)$, with a mesylating reagent, a base and a solvent to provide a compound of V-04-A:

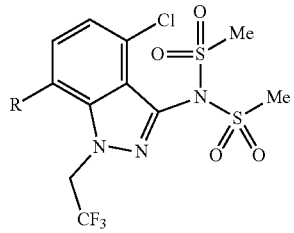

or a co-crystal, solvate, salt, or combination thereof and
(b) hydrolyzing the compound of formula V-04-A or a co-crystal, solvate, salt, or combination thereof, with a nucleophilic reagent, a solvent, and optionally, a phase transfer catalyst to provide the compound of formula V-03-A or a co-crystal, solvate, salt, or combination thereof.

In certain embodiments, R is $B(OC(Me)_2C(Me)_2O)$.

In certain embodiments, the mesylating reagent used in step (a) is methanesulfonic anhydride. In some embodiments, the mesylating reagent used in step (a) is methanesulfonyl chloride.

In certain embodiments, the base used in step (a) is selected from the group consisting of tertiary amines (e.g., triethylamine, N-methylmorpholine, tri-n-propylamine, ethyl diisopropylamine, tri-n-butylamine), aromatic amines (e.g., pyridine, 2,6-lutidine, collidine), inorganic bases (e.g., sodium bicarbonate, sodium carbonate, sodium phosphate monobasic, sodium phosphate dibasic, potassium bicarbonate, potassium carbonate, potassium phosphate monobasic, potassium phosphate dibasic), and alkoxide bases (e.g., sodium tert-amylate, sodium tert-butoxide). In certain embodiments, the base used in step (a) is selected from the group consisting of triethylamine, N-methylmorpholine, tri-n-propylamine, ethyl diisopropylamine, tri-n-butylamine, pyridine, 2,6-lutidine, collidine, sodium bicarbonate, sodium carbonate, sodium phosphate monobasic, sodium phosphate dibasic, potassium bicarbonate, potassium carbonate, potassium phosphate monobasic, potassium phosphate dibasic, sodium tert-amylate, and sodium tert-butoxide. In particular embodiments, the base used in step (a) is triethylamine.

In certain embodiments, the solvent used in step (a) is selected from the group consisting of ethers (e.g., diethyl ether, 1,4-dioxane, 2-methyltetrahydrofuran, dimethoxyethane,), hydrocarbon solvents (e.g., toluene, xylenes), esters (e.g., isopropyl acetate, isobutyl acetate), dichloromethane, acetonitrile, and a combination thereof. In certain embodiments, the solvent used in step (a) is selected from the group consisting of diethyl ether, 1,4-dioxane, 2-methyltetrahydrofuran, dimethoxyethane, toluene, xylenes, isopropyl acetate, isobutyl acetate, dichloromethane, acetonitrile, and a combination thereof. In particular embodiments, the solvent used in step (a) is 2-methyltetrahydrofuran.

In certain embodiments, step (a) is carried out in the temperature range of from about 100° C. or less. In certain embodiments, step (a) is carried out in the temperature range of from about −20° C. to about 100° C. In particular embodiments, step (a) is carried out in the temperature range of from about −10° C. to about 20° C.

In certain embodiments, the nucleophilic reagent used in step (b) is selected from the group consisting of hydroxide bases (e.g., sodium hydroxide, lithium hydroxide, potassium hydroxide), sulfur nucleophiles (e.g., sodium ethanethiolate, N-acetylcysteine, sodium thiophenolate), choline, alkoxide bases (e.g., sodium methoxide, sodium ethoxide, potassium ethoxide, sodium n-propoxide, sodium i-propoxide, sodium t-butoxide), and amines (e.g., methylamine, ethylamine, n-propylamine, dimethylamine, diethylamine, hydroxylamine). In certain embodiments, the nucleophilic reagent used in step (b) is selected from the group consisting of sodium hydroxide, lithium hydroxide, potassium hydroxide, sodium ethanethiolate, N-acetylcysteine, sodium thiophenolate, choline, sodium methoxide, sodium ethoxide, potassium ethoxide, sodium n-propoxide, sodium i-propoxide, sodium t-butoxide, methylamine, ethylamine, n-propylamine, dimethylamine, diethylamine, and hydroxylamine. In particular embodiments, the base used in step (b) is sodium hydroxide.

In certain embodiments, the solvent used in step (b) is selected from the group consisting of ethers (e.g., diethyl ether, 1,4-dioxane, 2-methyltetrahydrofuran, dimethoxyethane), hydrocarbon solvents (e.g., toluene, xylenes), esters (e.g., isopropyl acetate, isobutyl acetate), dichloromethane, acetonitrile, polar aprotic solvents (e.g., N,N-dimethylformamide, N-methyl-2-pyrrolidone, N,N-dimethylacetamide), and a combination thereof. In certain embodiments, the solvent used in step (b) is selected from the group consisting of diethyl ether, 1,4-dioxane, 2-methyltetrahydrofuran, dimethoxyethane, toluene, xylenes, isopropyl acetate, isobutyl acetate, dichloromethane, acetonitrile, N,N-dimethylformamide, N-methyl-2-pyrrolidone, N,N-dimethylacetamide, and a combination thereof. In particular embodiments, the solvent used in step (b) is 2-methyltetrahydrofuran and water.

In certain embodiments, a phase transfer catalyst is used in step (b). In certain embodiments, the phase transfer catalyst used in step (b) is selected from the group consisting of ammonium salts (e.g., tetrabutylammonium hydrogen sulfate, tetrabutylammonium chloride, benzyltributylammonium bromide, 1-methylimidazolium hydrogen sulfate), and phosphonium salts (e.g., tetrabutylphosphonium chloride). In certain embodiments, the phase transfer catalyst used in step (b) is selected from the group consisting of tetrabutylammonium hydrogen sulfate, tetrabutylammonium chloride, benzyltributylammonium bromide, 1-methylimidazolium hydrogen sulfate, and tetrabutylphosphonium chloride. In particular embodiments, the phase transfer catalyst used in step (b) is tetrabutylammonium hydrogen sulfate.

In certain embodiments, step (b) is carried out in the temperature range of from about 100° C. or less. In certain embodiments, step (b) is carried out in the temperature range of from about −20° C. to about 100° C. In particular embodiments, step (b) is carried out in the temperature range of from about 10° C. to about 60° C.

In some embodiments, a process for preparing a compound of formula V-5:

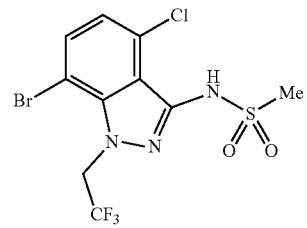

V-5 or a co-crystal, solvate, salt, or combination thereof is provided, comprising:
(a) combining a compound of formula V-A:

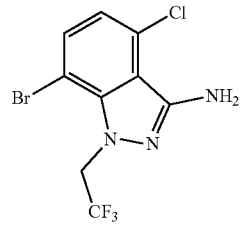

V-A or a co-crystal, solvate, salt, or combination thereof, with a mesylating reagent, a base and a solvent to provide a compound of V-6:

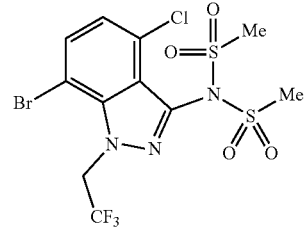

V-6 or a co-crystal, solvate, salt, or combination thereof and
(b) hydrolyzing the compound of formula V-6 or a co-crystal, solvate, salt, or combination thereof, with a nucleophilic reagent, a solvent, and optionally, a phase transfer catalyst to provide the compound of formula V-5 or a co-crystal, solvate, salt, or combination thereof.

In certain embodiments, the mesylating reagent used in step (a) is methanesulfonic anhydride or methanesulfonyl chloride. In certain embodiments, the mesylating reagent used in step (a) is methanesulfonic anhydride. In certain embodiments, the mesylating reagent used in step (a) is methanesulfonyl chloride.

In certain embodiments, the base used in step (a) is selected from the group consisting of tertiary amines (triethylamine, N-methylmorpholine, tri-n-propylamine, ethyl diisopropylamine, tri-n-butylamine, etc.), aromatic amines (pyridine, 2,6-lutidine, collidine, etc.), inorganic bases (sodium bicarbonate, sodium carbonate, sodium phosphate monobasic, sodium phosphate dibasic, potassium bicarbonate, potassium carbonate, potassium phosphate monobasic, potassium phosphate dibasic, etc.), and alkoxide bases (sodium tert-amylate, sodium tert-butoxide, etc). In certain embodiments, the base used in step (a) is selected from the group consisting of triethylamine, N-methylmorpholine, tri-n-propylamine, ethyl diisopropylamine, tri-n-butylamine, pyridine, 2,6-lutidine, collidine, sodium bicarbonate, sodium carbonate, sodium phosphate monobasic, sodium phosphate dibasic, potassium bicarbonate, potassium carbonate, potassium phosphate monobasic, potassium phosphate dibasic, sodium tert-amylate, and sodium tert-butoxide. In particular embodiments, the base used in step (a) is triethylamine.

In certain embodiments, the solvent used in step (a) is selected from the group consisting of ethers (diethyl ether, 1,4-dioxane, 2-methyltetrahydrofuran, dimethoxyethane, etc.), hydrocarbon solvents (toluene, xylenes, etc.), esters (isopropyl acetate, isobutyl acetate, etc.), dichloromethane, acetonitrile, and a combination thereof. In certain embodiments, the solvent used in step (a) is selected from the group of consisting of diethyl ether, 1,4-dioxane, 2-methyltetrahydrofuran, dimethoxyethane, toluene, xylenes, isopropyl acetate, isobutyl acetate, dichloromethane, acetonitrile, and a combination thereof. In particular embodiments, the solvent used in step (a) is 2-methyltetrahydrofuran.

In certain embodiments, step (a) is carried out in the temperature range of from about 100° C. or less. In certain embodiments, step (a) is carried out in the temperature range of from about −20° C. to about 100° C. In particular embodiments, step (a) is carried out in the temperature range of from about −10° C. to about 20° C.

In certain embodiments, the nucleophilic reagent used in step (b) is selected from the group consisting of hydroxide bases (sodium hydroxide, lithium hydroxide, potassium hydroxide, etc.), sulfur nucleophiles (sodium ethanethiolate, N-acetylcysteine, sodium thiophenolate, etc.), choline, alkoxide bases (sodium methoxide, sodium ethoxide, potassium ethoxide, sodium n-propoxide, sodium i-propoxide, sodium t-butoxide, etc.), and amines (methylamine, ethylamine, n-propylamine, dimethylamine, diethylamine, hydroxylamine, etc.). In particular embodiments, the base used in step (b) is sodium hydroxide.

In certain embodiments, the solvent used in step (b) is selected from the group consisting of ethers (diethyl ether, 1,4-dioxane, 2-methyltetrahydrofuran, dimethoxyethane, etc.), hydrocarbon solvents (toluene, xylenes, etc.), esters (isopropyl acetate, isobutyl acetate, etc.), dichloromethane, acetonitrile, polar aprotic solvents (N,N-dimethylformamide, N-methyl-2-pyrrolidone, N,N-dimethylacetamide, etc), and a combination thereof. In particular embodiments, the solvent used in step (b) is 2-methyltetrahydrofuran and water.

In certain embodiments, the phase transfer catalyst used in step (b) is selected from the group consisting of ammonium salts (tetrabutylammonium hydrogen sulfate, tetrabutylammonium chloride, benzyltributylammonium bromide, 1-methylimidazolium hydrogen sulfate, etc), and phosphonium salts (tetrabutylphosphonium chloride, etc). In particular embodiments, the phase transfer catalyst used in step (b) is tetrabutylammonium hydrogen sulfate.

In certain embodiments, step (b) is carried out in the temperature range of from about 100° C. or less. In certain embodiments, step (b) is carried out in the temperature range of from about −20° C. to about 100° C. In particular embodiments, step (b) is carried out in the temperature range of from about 10° C. to about 60° C.

In some embodiments, a process for preparing a compound of formula V-04-A:

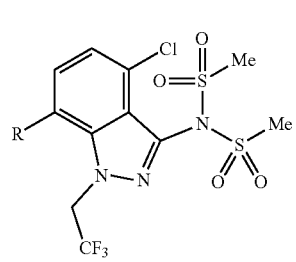

V-04-A or a co-crystal, solvate, salt, or combination thereof, wherein R is $B(OH)_2$, $B(OCH(Me)CH_2C(Me)_2O)$, $B((1,2\text{-di-O})C_6H_4)$, $B(OCH_2C(Me)_2CH_2O)$, $BF_3K$, $B(O_2CCH_2N(Me)CH_2CO_2)$, or $B(OC(Me)_2C(Me)_2O)$, is provided, comprising combining a compound of formula V-6:

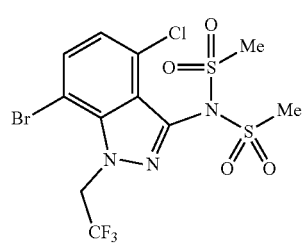

V-6 or a co-crystal, solvate, salt, or combination thereof, with a boron coupling agent, a base and a solvent, and a catalyst, to provide the compound of V-04-A, or a co-crystal, solvate, salt, or combination thereof.

In certain embodiments, R is $B(OC(Me)_2C(Me)_2O)$.

In certain embodiments, the boron coupling agent is selected from the group consisting of bis(pinacolato)diboron, bis(neopentyl glycolato)diboron, bisboronic acid, and bis(ethylene glycolato diboron). In particular embodiments, the boron coupling agent is bis(pinacolato)diboron.

In certain embodiments, the base is selected from the group consisting of cesium acetate, potassium propionate, sodium propionate, potassium acetate, sodium acetate, cesium acetate, potassium propionate, sodium propionate, potassium carbonate, sodium carbonate, cesium carbonate, potassium bicarbonate, sodium bicarbonate, sodium phosphate, sodium hydroxide, potassium hydroxide, potassium fluoride, potassium phosphate dibasic, potassium phosphate tribasic, sodium hydroxide, potassium hydroxide, dicyclohexylamine, N-methylmorpholine, triethylamine, and diisopropylethylamine. In particular embodiments, the base is potassium acetate.

In certain embodiments, the solvent is selected from the group of consisting of ethers (e.g., 1,4-dioxane, 2-methyltetrahydrofuran, dimethoxyethane), aromatic hydrocarbon solvents (e.g., toluene, xylenes), esters (e.g., ethyl acetate, isopropyl acetate, propyl acetate, isobutyl acetate), alcohols (e.g., ethanol, isopropanol), and polar aprotic solvents (e.g., N,N-dimethylformamide, N,N-dimethylacetamide, N-methyl-2-pyrrolidine,), and a combination thereof. In certain embodiments, the solvent is selected from the group of consisting of 1,4-dioxane, 2-methyltetrahydrofuran, dimethoxyethane, toluene, xylenes, ethyl acetate, isopropyl acetate, propyl acetate, isobutyl acetate, ethanol, isopropanol, N,N-dimethylformamide, N,N-dimethylacetamide, N-methyl-2-pyrrolidine, and a combination thereof. In particular embodiments, the solvent is toluene and N,N-dimethylformamide.

In certain embodiments, the catalyst is selected from the group consisting of bis(di-tert-butyl(4-dimethylaminophenyl)phosphine)dichloropalladium(II), bis[(dicyclohexyl)(4-dimethylaminophenyl)phosphine]palladium(II) chloride, bis(triphenylphosphine)palladium (II) dichloride, [1,1'-bis(diphenylphosphino)ferrocene]dichloropalladium(II), [1,2-bis(diphenylphosphino)ethane]dichloropalladium(II), dichloro[9,9-dimethyl-4,5-bis(diphenylphosphino)xanthene]palladium(II). In certain embodiments, the palladium catalyst is palladium(II) precatalyst (e.g., palladium(II) chloride, palladium(II) acetate, palladium(II) trifluoroacetate) or palladium(0) precatalyst (e.g., tetrakis(triphenylphosphine)palladium(0), bis(dibenzylideneacetone)palladium(0)) and optionally further comprises a phosphine ligand (e.g., tricyclohexylphosphine, triphenylphosphine, cyclohexyldiphenylphosphine, dicyclohexylphenylphosphine). In certain embodiments, the catalyst is palladium(II) chloride, palladium(II) acetate, palladium(II) trifluoroacetate, tetrakis(triphenylphosphine)palladium(0), or bis(dibenzylideneacetone)palladium(0); and the catalyst optionally further comprises a phosphine ligand selected from the group consisting of tricyclohexylphosphine, triphenylphosphine, cyclohexyldiphenylphosphine, and dicyclohexylphenylphosphine. In particular embodiments, the palladium catalyst is bis(triphenylphosphine)palladium (II) dichloride.

In certain embodiments, the process is carried out in the temperature range of from about 120° C. or less. In certain embodiments, the process is carried out in the temperature range of from about 20° C. to about 120° C. In particular embodiments, the process is carried out in the temperature range of from about 95° C. to about 105° C.

In some embodiments, a process for preparing a compound of formula V-5:

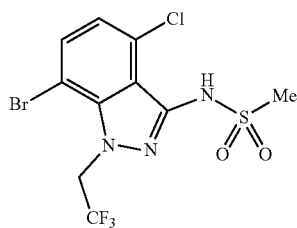

V-5 or a co-crystal, solvate, salt, or combination thereof is provided, comprising hydrolyzing a compound of formula V-6:

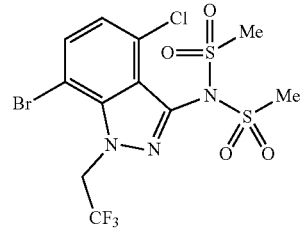

V-6 or a co-crystal, solvate, salt, or combination thereof, with a base, a solvent, and optionally, a phase transfer catalyst, to provide the compound of formula V5 or a co-crystal, solvate, salt, or combination thereof.

In certain embodiments, the base is selected from the group consisting of hydroxide bases (e.g., sodium hydroxide, lithium hydroxide, potassium hydroxide), sulfur nucleophiles (e.g., sodium ethanethiolate, N-acetylcysteine, sodium thiophenolate), choline, alkoxide bases (e.g., sodium methoxide, sodium ethoxide, potassium ethoxide, sodium n-propoxide, sodium i-propoxide, sodium t-butoxide), and amines (e.g., methylamine, ethylamine, n-propylamine, dimethylamine, diethylamine, hydroxylamine). In certain embodiments, the base is selected from the group consisting of sodium hydroxide, lithium hydroxide, potassium hydroxide, sodium ethanethiolate, N-acetylcysteine, sodium thiophenolate, choline, sodium methoxide, sodium ethoxide, potassium ethoxide, sodium n-propoxide, sodium i-propoxide, sodium t-butoxide, methylamine, ethylamine, n-propylamine, dimethylamine, diethylamine, and hydroxylamine. In particular embodiments, the base is sodium hydroxide.

In certain embodiments, the solvent is selected from the group consisting of ethers (e.g., diethyl ether, 1,4-dioxane, 2-methyltetrahydrofuran, dimethoxyethane,), hydrocarbon solvents (e.g., toluene, xylenes,), esters (e.g., isopropyl acetate, isobutyl acetate), dichloromethane, acetonitrile, polar aprotic solvents (e.g., N,N-dimethylformamide, N-methyl-2-pyrrolidone, N,N-dimethylacetamide), water, and a combination thereof. In certain embodiments, the solvent is selected from the group consisting of diethyl ether, 1,4-dioxane, 2-methyltetrahydrofuran, dimethoxyethane, toluene, xylenes, isopropyl acetate, isobutyl acetate, dichloromethane, acetonitrile, N,N-dimethylformamide, N-methyl-2-pyrrolidone, N,N-dimethylacetamide, water, and a combination thereof. In particular embodiments, the solvent is 2-methyltetrahydrofuran and water.

In some embodiments, the process comprises a phase transfer catalyst. In some embodiments, the phase transfer catalyst is selected from the group consisting of ammonium salts (e.g., tetrabutylammonium hydrogen sulfate, tetrabutylammonium chloride, benzyltributylammonium bromide, 1-methylimidazolium hydrogen sulfate), and phosphonium salts (e.g., tetrabutylphosphonium chloride). In some embodiments, the phase transfer catalyst is selected from the group consisting of tetrabutylammonium hydrogen sulfate, tetrabutylammonium chloride, benzyltributylammonium bromide, 1-methylimidazolium hydrogen sulfate, phosphonium salts, and tetrabutylphosphonium chloride. In particular embodiments, the phase transfer catalyst is tetrabutylammonium hydrogen sulfate.

In some embodiments, the process is carried out in the temperature range of from about 100° C. or less. In certain embodiments, the process is carried out in the temperature range of from about −20° C. to about 100° C. In particular embodiments, the process is carried out in the temperature range of from about 10° C. to about 60° C.

In some embodiments, a process for preparing a compound of formula V-03-A:

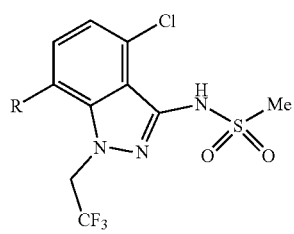

or a co-crystal, solvate, salt, or combination thereof, wherein R is B(OH)$_2$, B(OCH(Me)CH$_2$C(Me)$_2$O), B((1,2-di-O)C$_6$H$_4$), B(OCH$_2$C(Me)$_2$CH$_2$O), BF$_3$K, B(O$_2$CCH$_2$N(Me)CH$_2$CO$_2$), or B(OC(Me)$_2$C(Me)$_2$O), is provided, comprising combining a compound of formula V-5:

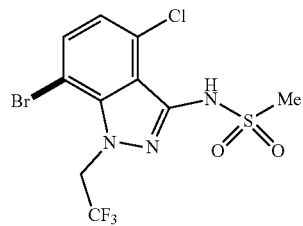

or a co-crystal, solvate, salt, or combination thereof, with a boron coupling agent, a base, a solvent, and a catalyst, to provide the compound of V-03-A, or a co-crystal, solvate, salt, or combination thereof.

In certain embodiments, R is B(OC(Me)$_2$C(Me)$_2$O).

In certain embodiments, the boron coupling agent is selected from the group consisting of bis(pinacolato)diboron, bis(neopentyl glycolato)diboron, bisboronic acid, and bis(ethylene glycolato diboron). In particular embodiments, the boron coupling agent is bis(pinacolato)diboron.

In certain embodiments, the base is selected from the group consisting of cesium acetate, potassium propionate, sodium propionate, potassium acetate, sodium acetate, cesium acetate, potassium propionate, sodium propionate, potassium carbonate, sodium carbonate, cesium carbonate, potassium bicarbonate, sodium bicarbonate, sodium phosphate, sodium hydroxide, potassium hydroxide, potassium fluoride, potassium phosphate dibasic, potassium phosphate tribasic, sodium hydroxide, potassium hydroxide, dicyclohexylamine, N-methylmorpholine, triethylamine, and diisopropylethylamine. In particular embodiments, the base is potassium acetate.

In certain embodiments, the solvent is selected from the group consisting of ethers (e.g., 1,4-dioxane, 2-methyltetrahydrofuran, dimethoxyethane), aromatic hydrocarbon solvents (e.g., toluene, xylenes), esters (e.g., ethyl acetate, isopropyl acetate, propyl acetate, isobutyl acetate), alcohols (e.g., ethanol, isopropanol), and polar aprotic solvents (e.g., N,N-dimethylformamide, N,N-dimethylacetamide, N-methyl-2-pyrrolidine, etc.), and a combination thereof. In certain embodiments, the solvent is selected from the group of consisting of 1,4-dioxane, 2-methyltetrahydrofuran, dimethoxyethane, toluene, xylenes, ethyl acetate, isopropyl acetate, propyl acetate, isobutyl acetate, ethanol, isopropanol, N,N-dimethylformamide, N,N-dimethylacetamide, N-methyl-2-pyrrolidine, and a combination thereof. In particular embodiments, the solvent is toluene and N,N-dimethylformamide.

In certain embodiments, the catalyst is selected from the group consisting of bis(di-tert-butyl(4-dimethylaminophenyl)phosphine)dichloropalladium(II), bis[(dicyclohexyl)(4-dimethylaminophenyl)phosphine]palladium(II) chloride, bis(triphenylphosphine)palladium (II) dichloride, [1,1'-bis(diphenylphosphino)ferrocene]dichloropalladium(II), [1,2-bis(diphenylphosphino)ethane]dichloropalladium(II), and dichloro[9,9-dimethyl-4,5-bis(diphenylphosphino)xanthene]palladium(II). In certain embodiments, the catalyst is palladium(II) precatalyst (e.g., palladium(II) chloride, palladium(II) acetate, palladium(II) trifluoroacetate) or palladium(0) precatalyst (e.g., tetrakis(triphenylphosphine)palladium(0), bis(dibenzylideneacetone)palladium(0)) and further comprises a phosphine ligand (e.g., tricyclohexylphosphine, triphenylphosphine, cyclohexyldiphenylphosphine, dicyclohexylphenylphosphine). In certain embodiments, the catalyst comprises palladium(II) chloride, palladium(II) acetate, palladium(II) trifluoroacetate, tetrakis(triphenylphosphine)palladium(0), or bis(dibenzylideneacetone)palladium(0), and the catalyst optionally further comprises a phosphine ligand selected from the group consisting of tricyclohexylphosphine, triphenylphosphine, cyclohexyldiphenylphosphine, and dicyclohexylphenylphosphine. In particular embodiments, the palladium catalyst is bis(triphenylphosphine)palladium (II) dichloride.

In certain embodiments, the process is carried out in the temperature range of from about 120° C. or less. In certain embodiments, the process is carried out in the temperature range of from about 20° C. to about 120° C. In particular embodiments, the process is carried out in the temperature range of from about 95° C. to about 105° C.

In some embodiments, a process for preparing a compound of formula VIII:

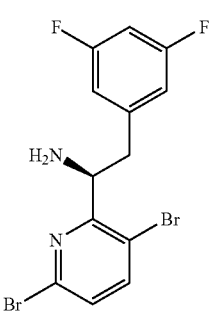

or a co-crystal, solvate, salt, or combination thereof is provided, comprising resolving a compound of formula X:

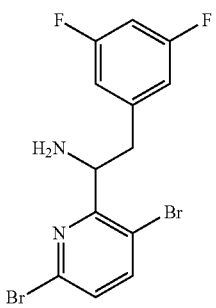

X or a co-crystal, solvate, salt, or combination thereof, with a chiral acid in a solvent and optionally in the presence of an aldehyde catalyst and/or optionally a metal catalyst, to provide the compound of formula VIII or a co-crystal, solvate, salt, or combination thereof.

In some embodiments, a process for preparing a compound of formula VIII:

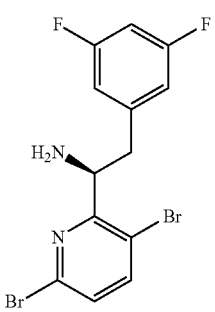

VIII or a co-crystal, solvate, salt, or combination thereof is provided, comprising resolving a compound of formula X:

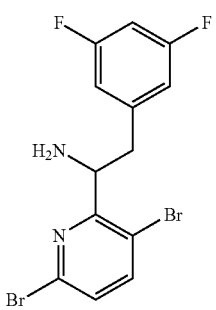

X or a co-crystal, solvate, salt, or combination thereof, with a chiral acid in a solvent, to provide the compound of formula VIII or a co-crystal, solvate, salt, or combination thereof.

In some embodiments, the compound of formula VIII is a compound of formula VIII-02:

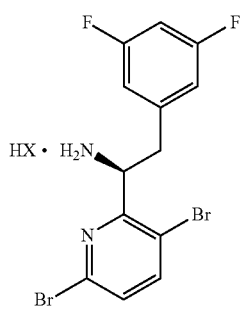

VIII-02 or a co-crystal, solvate, or combination thereof, wherein HX is a chiral acid selected from the group consisting of lactic acid, L-lactic acid, L-(+)-tartaric acid, L-aspartic acid, L-glutamic acid, L-(−)-malic acid, D-glucuronic acid, (1R, 3S)-(+)-camphoric acid, (1S)-(+)-camphor-10-sulfonic acid, (R)-(+)-N-(1-phenylethyl)succinamic acid, carbobenzyloxy-L-proline, dibenzoyl-L-tartaric acid, (R)-(+)-3-methyladipic acid, (+)-menthyloxyacetic acid, (−)-pyroglutamic acid, (−)-N-acetyl-L-leucine, (−)-N-acetyl-D-leucine, N-Boc-D-leucine, N-(+)-BOC-phenylalanine, (−)-quinic acid, (+)-n-acetyl-L-phenylalanine, (+)-N-BOC-isoleucine, L-(−)-acetyl glutamic acid, (−)-acetyl mandelic acid, (R)-(−)-citramalic acid, (−)-camphanic acid, and (R)-mandelic acid.

In some embodiments, the compound of formula VIII is a compound of formula VIII-02:

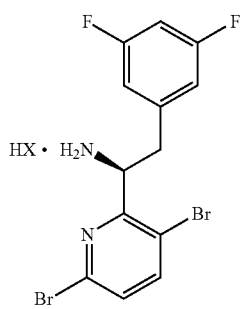

VIII-02 or a co-crystal, solvate, or combination thereof, wherein HX is a chiral acid selected from the group consisting of lactic acid, L-(+)-tartaric acid, L-aspartic acid, L-glutamic acid, L-(−)-malic acid, D-glucuronic acid, (1R, 3S)-(+)-camphoric acid, (1S)-(+)-camphor-10-sulfonic acid, (R)-(+)-N-(1-phenylethyl)succinamic acid, carbobenzyloxy-L-proline, dibenzoyl-L-tartaric acid, (R)-(+)-3-methyladipic acid, (+)-menthyloxyacetic acid, (−)-pyroglutamic acid, (−)—N-acetyl-L-leucine, N-Boc-D-leucine, N-(+)-BOC-phenylalanine, (−)-quinic acid, (+)-n-acetyl-L-phenylalanine, (+)-N-BOC-isoleucine, L-(−)-acetyl glutamic acid, (−)-acetyl mandelic acid, (R)-(−)-citramalic acid, (−)-camphanic acid, and (R)-mandelic acid. In some embodiments, HX is N-Boc-D-leucine or (−)-N-acetyl-D-leucine. In some embodiments, HX is (R)-mandelic acid. In some embodiments, HX is N-Boc-D-leucine.

In some embodiments, HX is (−)-N-acetyl-D-leucine.

In certain embodiments, the solvent is selected from the group consisting of a hydrocarbon solvent (e.g., n-heptane), an ether (e.g., diethyl ether, methyl tert-butyl ether, tetrahydrofuran, 2-methyltetrahydrofuran, 1,4-dioxane), an aromatic hydrocarbon solvent (e.g., toluene, benzene, xylenes), a chlorinated solvent (e.g., dichloromethane), an alcohol (e.g., methanol, ethanol, 1-propanol, isopropanol), a ketone (e.g., acetone, methyl ethyl ketone, methyl isobutylketone), water, an ester (e.g., ethyl acetate, butyl acetate, isobutyl acetate,), dichloroethane, chloroform, polar aprotic solvents (e.g., N,N-dimethylformamide, N,N-dimethylacetamide, N-methylpyrrolidinone, dimethylsulfoxide), nitriles (e.g., acetonitrile, propionitrile, butyronitrile), and a combination thereof.

In certain embodiments, the solvent is selected from the group consisting of a hydrocarbon solvent (e.g., n-heptane), an ether (e.g., diethyl ether, methyl tert-butyl ether, tetrahydrofuran, 2-methyltetrahydrofuran, 1,4-dioxane), an aromatic hydrocarbon solvent (e.g., toluene, benzene, xylenes), a chlorinated solvent (e.g., dichloromethane), an alcohol (e.g., methanol, ethanol, 1-propanol, isopropanol), a ketone (e.g., acetone, methyl ethyl ketone, methyl isobutylketone), water, and a combination thereof. In particular embodiments, the solvent is methyl tert-butyl ether and toluene.

In particular embodiments, the solvent is toluene.

In certain embodiments, the process is carried out in the presence of an aldehyde catalyst and/or a metal catalyst. In certain embodiments, the aldehyde catalyst is selected from the group consisting of aromatic aldehydes (e.g., benzaldehyde, 2,4-dichlorobenzaldehyde, 2-methoxybenzaldehyde, 4-(dimethylamino)benzaldehyde, 2-(dimethylamino)benzaldehyde, 2-hydroxy-5-methoxybenzaldehyde, 2-hydroxy-5-nitrobenzaldehyde, 5-chloro-2-hydroxybenzaldehyde, 4-hydroxybenzaldehyde, 2-hydroxybenzaldehyde, 3,5-dichloro-2-hydroxybenzaldehyde, 3-hydroxybenzaldehyde, 2-hydroxy-3-nitrobenzaldehyde,), heteroaromatic aldehydes (e.g., 2-formylpyridine, 3-(trifluoromethyl)picolinaldehyde, 4-chloropicolinaldehyde, nicotinaldehyde, quinolone-4-carbaldehyde, quinolone-2-carbaldehyde, etc.), and aliphatic aldehydes (e.g., formaldehyde, ethylglyoxylate, glyoxylic acid). In certain embodiments, the metal catalyst is selected from the group consisting of zinc salts (e.g., zinc(II) oxide, zinc(II) acetate, zinc(II) trifluoromethanesulfonate, zinc(II) trifluoroacetate, zinc(II) chloride, zinc (II) stearate, zinc (II) neodecanoate, zinc (II) tetrafluoroborate); nickel salts (e.g., nickel(II) acetate, nickel(II) chloride, nickel(II) triflate); indium salts (e.g., indium (III) acetate); copper salts (e.g., copper(II) acetate); cobalt salts (e.g., cobalt(II) acetate); and manganese salts (e.g., manganese(II) acetate). In certain embodiments, the process is carried out in the presence of an aldehyde catalyst and/or a metal catalyst. In particular embodiments, the process is carried out in the presence of an aldehyde catalyst and a metal catalyst. In particular embodiments, the aldehyde catalyst is 2-formylpyridine and the metal catalyst is zinc(II) oxide.

In some embodiments, the process is carried out in the temperature range of from about 120° C. or less. In certain embodiments, the process is carried out in the temperature range of from about −20° C. to about 120° C. In particular embodiments, the process is carried out in the temperature range of from about −20° C. to about 50° C. In some embodiments, the process is carried out at a temperature of about 35° C.

In some embodiments, the process is carried out in the temperature range of from about 100° C. or less. In certain embodiments, the process is carried out in the temperature range of from about −20° C. to about 100° C. In particular embodiments, the process is carried out in the temperature range of from about −20° C. to about 20° C. In particular embodiments, the process is carried out at a temperature of about 35° C.

In certain embodiments, the compound of formula X may be treated with a base in a first solvent before the resolving. In certain embodiments, the base is selected from the group consisting of potassium hydroxide, potassium carbonate, potassium bicarbonate, sodium carbonate, sodium bicarbonate, triethylamine, ammonium hydroxide, potassium phosphate dibasic, potassium phosphate tribasic, sodium phosphate dibasic, and sodium phosphate tribasic. In particular embodiments, the base is sodium hydroxide. In certain embodiments, the first solvent is selected from the group consisting of ethers (e.g., diethyl ether, methyl tert-butyl ether, 2-methyltetrahydrofuran, tetrahydrofuran, 1,4-dioxane), aromatic solvents (e.g., benzene, xylenes), chlorinated solvents (e.g., dichloromethane), and a combination thereof. In certain embodiments, the first solvent is selected from the group consisting of diethyl ether, methyl tert-butyl ether, 2-methyltetrahydrofuran, tetrahydrofuran, 1,4-dioxane, aromatic solvents, dichloromethane, and a combination thereof. In particular embodiments, the solvent is 2-methyltetrahydrofuran. In certain embodiments, the compound of formula X is treated with a base in a first solvent at the temperature range of from about 0° C. to about 100° C. In certain embodiments, the compound of formula X is treated with a base in a first solvent at the temperature range of from about 10° C. to about 50° C.

In some embodiments, a process for preparing a compound of formula 1a:

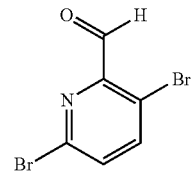

or a co-crystal, solvate, salt, or combination thereof is provided, comprising combining 2,5-dibromopyridine:

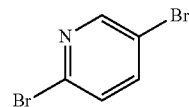

with an electrophile, a base and a solvent to provide a compound of formula 1a or a co-crystal, solvate, salt, or combination thereof.

In some embodiments, the electrophile is selected from the group consisting of formylated amines (e.g., N,N-diethylformamide, 1-formylpyrrolidine, 4-formylmorpholine, N-methylformanilide); formate esters (e.g., cyanomethyl formate, phenyl formate, ethyl formate, trifluoroethyl formate); ortho esters (e.g., triethyl orthoformate, diethyl phenyl orthoformate); formamide acetals (e.g., N,N-dimethylformamide dipropyl acetal, N,N-dimethylformamide dimethylacetal); and (chloromethylene)dimethyliminium chloride. In particular embodiments, the electrophile is N,N-dimethylformamide.

In some embodiments, the base is selected from the group consisting of 2,2,6,6-tetramethylpiperidinylmagnesium chloride lithium chloride complex, n-butyllithium, isopropylmagnesium chloride lithium chloride complex, sec-butylmagnesium chloride lithium chloride complex, phenyllithium, phenylmagnesium chloride, n-butyllithium lithium N,N-dimethylaminoethanol complex, mesityllithium, lithium di-isopropylamide, phenyllithium, lithium 2,2,6,6-tetramethylpiperidide, lithium dichloro(2,2,6,6-tetramethylpiperidinato)zincate, and lithium di-tert-butyl-(2,2,6,6-tetramethylpiperidino)zincate. In particular embodiments, the base is 2,2,6,6-tetramethylpiperidinylmagnesium chloride lithium chloride complex.

In some embodiments, the solvent is selected from the group consisting of ethers (e.g., diethyl ether, methyl tert-butyl ether, tetrahydrofuran, 2-methyltetrahydrofuran, 1,4-dioxane, dimethoxyethane), aromatic solvents (e.g., benzene, toluene, xylenes) amines (e.g., triethylamine, ethyldiisopropylamine), cyclic amides (e.g., N-ethyl-2-pyrrolidone, N-methyl-2-pyrrolidone, N-butyl-2-pyrrolidone), urea derivatives (e.g., N,N-dimethylpropylene urea) and a combination thereof. In particular embodiments, the solvent is tetrahydrofuran.

In some embodiments, the process is carried out in the temperature range of from about 50° C. or less. In certain embodiments, the process is carried out in the temperature range of from about −80° C. to about 50° C. In particular embodiments, the process is carried out in the temperature range of from about −40° C. to about 0° C.

In some embodiments, a process for preparing a compound of formula X:

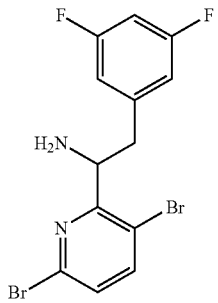

X or a co-crystal, solvate, salt, or combination thereof is provided, comprising:

(a) condensing a compound of formula 1a:

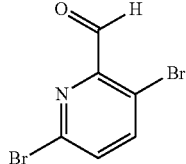

1a or a co-crystal, solvate, salt, or combination thereof, with a suitable amine (e.g., aminodiphenylmethane) in a solvent, and optionally in the presence of an additive, to provide a compound of formula 1b:

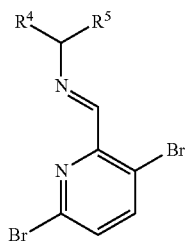

1b or a co-crystal, solvate, salt, or combination thereof, wherein $R^4$ and $R^5$ are each independently hydrogen, methyl, phenyl, benzyl, 4-nitrobenzyl, 4-chlorobenzyl, 4-bromobenzylamine, or 4-methoxybenzyl;

(b) alkylating the compound of formula 1b, or a co-crystal, solvate, salt, or combination thereof, with a compound of formula 1c:

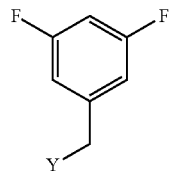

1c wherein Y is Br, Cl, I, OMs, OTs, or $OSO_2CF_3$, in the presence of a base and optionally a phase transfer catalyst, in a solvent to provide a compound of formula 1d:

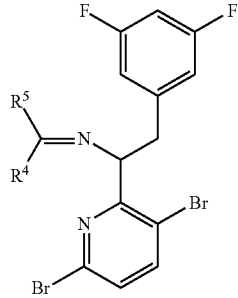

1d or a co-crystal, solvate, salt, or combination thereof and (c) deprotecting the compound of formula 1d with an acid in a solvent to provide a compound of formula X:

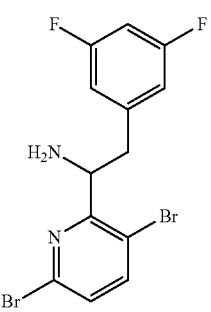

X or a co-crystal, solvate, salt, or combination thereof.

In some embodiments, a process for preparing a compound of formula X:

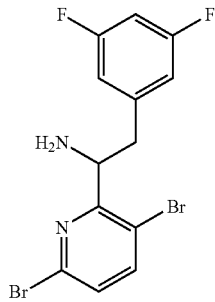

or a co-crystal, solvate, salt, or combination thereof is provided, comprising:

(a) condensing a compound of formula 1a:

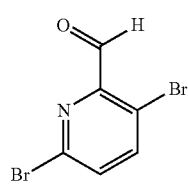

or a co-crystal, solvate, salt, or combination thereof, with a suitable amine (e.g., aminodiphenylmethane) in a solvent to provide a compound of formula 1b:

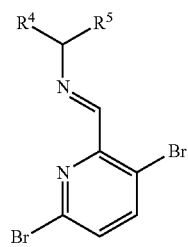

or a co-crystal, solvate, salt, or combination thereof, wherein $R^4$ and $R^5$ are each independently hydrogen, methyl, phenyl, benzyl, 4-nitrobenzyl, 4-chlorobenzyl, 4-bromobenzylamine, or 4-methoxybenzyl;

(b) alkylating the compound of formula 1b, or a co-crystal, solvate, salt, or combination thereof, with a compound of formula 1c:

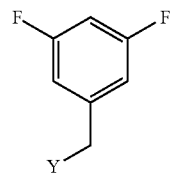

wherein Y is Br, Cl, I, OMs, OTs, or $OSO_2CF_3$, in the presence of a base and optionally, a phase transfer catalyst, in a solvent to provide a compound of formula 1d:

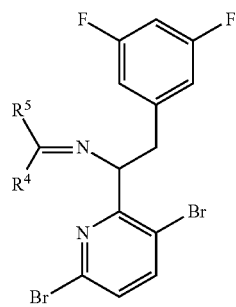

or a co-crystal, solvate, salt, or combination thereof; and (c) deprotecting the compound of formula 1d with an acid in a solvent to provide a compound of formula X:

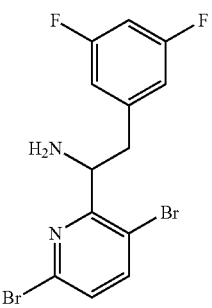

or a co-crystal, solvate, salt, or combination thereof.

In some embodiments, the suitable amine for forming the compound of formula 1b, or a co-crystal, solvate, salt, or combination thereof, is aminodiphenylamine, benzylamine, 4-nitrobenzylamine, 4-chlorobenzylamine, 4-bromobenzylamine, 4-methoxybenzylamine, or a-methylbenzylamine. In some embodiments, the suitable amine for forming the compound of formula 1b, or a co-crystal, solvate, salt, or combination thereof, is aminodiphenylamine.

In some embodiments, the compound of formula 1b, or a co-crystal, solvate, salt, or combination thereof, is a compound of formula 1b-02:

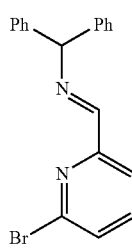

or a co-crystal, solvate, salt, or combination thereof.

In some embodiments, the compound of formula 1d, or a co-crystal, solvate, salt, or combination thereof, is a compound of formula 1d-02:

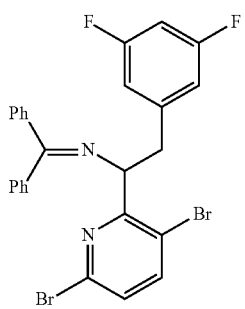

1d-02 or a co-crystal, solvate, salt, or combination thereof.

In certain embodiments, the solvent for the condensing step (a) is selected from the group consisting of an ether (e.g., diethyl ether, methyl tert-butyl ether, tetrahydrofuran, 2-methyltetrahydrofuran, 1,4-dioxane), an ester (e.g., ethyl acetate, isopropyl acetate), a polar aprotic solvent (e.g., N,N-dimethylformamide, N,N-dimethylacetamide, N-methylpyrrolidinone), a nitrile (e.g., acetonitrile), an aromatic hydrocarbon solvent (e.g., toluene, benzene, xylenes), a chlorinated solvent (e.g., dichloromethane), and a combination thereof. In particular embodiments, the solvent for the condensing step (a) is toluene.

In some embodiments, the condensing step (a) is performed in the presence of an additive. In certain embodiments, the additive used in the condensation step (a) is a dehydrating reagent (e.g., magnesium sulfate).

In certain embodiments, the condensing step (a) is carried out in the temperature range of from about 120° C. or less. In certain embodiments, the condensing step (a) is carried out in the temperature range of from about −20° C. to about 120° C. In particular embodiments, the condensing step (a) is carried out in the temperature range of from about 20° C. to about 90° C. In particular embodiments, the condensing step (a) is carried out in the temperature range of from about 20° C. to about 80° C.

In certain embodiments, Y is Br, Cl, or I. In particular embodiments, Y is Br.

In certain embodiments, the base for the alkylating step (b) is selected from the group consisting of potassium hydroxide, sodium hydroxide, lithium hydroxide, sodium ethoxide, sodium tert-butoxide, sodium tert-pentoxide, potassium tert-butoxide, triethylamine, diisopropylethylamine, 1,8-diazabicyclo[5.4.0]undec-7-ene, 1,5-diazabicyclo[4.3.0]non-5-ene, 1,4-diazabicyclo[2.2.2]octane, isopropylmagnesium chloride lithium chloride complex, sec-butylmagnesium chloride, lithium chloride complex, n-butyllithium, lithium N,N-dimethylaminoethanol complex, mesityllithium, lithium di-isopropylamide, and phenyllithium. In particular embodiments, the base for the alkylating step (b) is potassium hydroxide.

In certain embodiments, a phase transfer catalyst is used in the alkylating step (b).

In certain embodiments, the phase transfer catalyst for the alkylating step (b) is selected from the group consisting of tetramethylammonium chloride, tetramethylammonium bromide, tetramethylammonium iodide, tetramethylammonium hydrogen sulfate, tetraethylammonium chloride, tetraethylammonium bromide, tetra-n-butyl-ammonium bromide, tetraethylammonium iodide, tetraethylammonium hydrogen sulfate, and benzyltrimethylammonium. In particular embodiments, the phase transfer catalyst for the alkylating step (b) is tetra-n-butyl-ammonium bromide.

In certain embodiments, the solvent for the alkylating step (b) is selected from the group consisting of diethyl ether, methyl tert-butyl ether, tetrahydrofuran, 2-methyltetrahydrofuran, 1,4-dioxane, N,N-dimethylformamide, N,N-dimethylacetamide, N-methylpyrrolidinone, benzene, xylenes, toluene, dichloromethane, water, and combinations thereof. In particular embodiments, the solvent for the alkylating step (b) is a mixture of toluene and water.

In certain embodiments, the compound of formula 1c is selected from the group consisting of 3,5-difluorobenzyl bromide, 3,5-difluorobenzyl chloride, 3,5-difluorobenzyl mesylate, 3,5-difluorobenzyl iodide, 3,5-difluorobenzyl triflate, and 3,5-difluorobenzyl tosylate. In particular embodiments, the compound of formula 1c is 3,5-difluorobenzyl bromide.

In certain embodiments, the alkylating step (b) is carried out in the temperature range of from about 120° C. or less. In certain embodiments, the alkylating step (b) is carried out in the temperature range of from about −20° C. to about 120° C. In particular embodiments, the alkylating step (b) is carried out in the temperature range of from about 10° C. to about 80° C.

In certain embodiments, the acid for the deprotecting step (c) is selected from the group consisting of hydrochloric acid, hydrobromic acid, methanesulfonic acid, p-toluenesulfonic acid, benzenesulfonic acid, trifluoroacetic acid, phosphoric acid, formic acid, and oxalic acid. In particular embodiments, the acid for the deprotecting step (c) is methanesulfonic acid.

In particular embodiments, the acid equivalent is 1 to 10. In particular embodiments, the acid equivalent is 1 to 3.

In certain embodiments, the solvent for the deprotecting step (c) is selected from the group consisting of an ether (e.g., diethyl ether, methyl tert-butyl ether, tetrahydrofuran, 2-methyltetrahydrofuran, 1,4-dioxane), an aromatic hydrocarbon solvent (e.g., toluene, benzene, xylenes), a chlorinated solvent (e.g., dichloromethane), and a combination thereof. In particular embodiments, the solvent for the deprotecting step (c) is 2-methyltetrahydrofuran.

In certain embodiments, the deprotecting step (c) is carried out in the temperature range of from about 120° C. or less. In certain embodiments, the deprotecting step (c) is carried out in the temperature range of from about −40° C. to about 120° C. In particular embodiments, the deprotecting step (c) is carried out in the temperature range of from about 10° C. to about 40° C.

In some embodiments, a process for forming the compound of formula X:

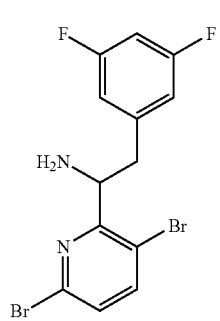

X or a co-crystal, solvate, salt, or combination thereof is provided, comprising:

(a) combining a compound of formula XIII:

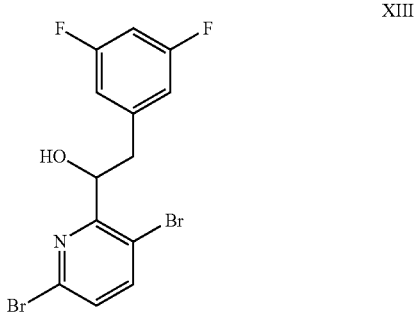 [SMILES: OC(Cc1cc(F)cc(F)c1)c1nc(Br)ccc1Br]

XIII or a co-crystal, solvate, salt, or combination thereof, with a mesylating reagent, a base, a solvent, and optionally an additive, to provide a compound of formula XIII-A:

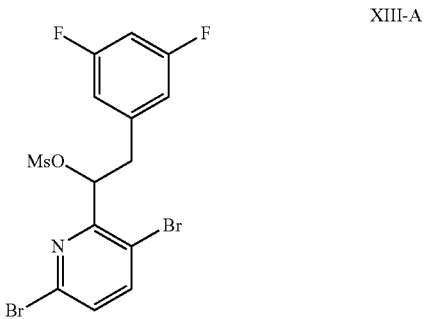 [SMILES: CS(=O)(=O)OC(Cc1cc(F)cc(F)c1)c1nc(Br)ccc1Br]

XIII-A or a co-crystal, solvate, salt, or combination thereof; and (b) combining the compound of formula XIII-A or a co-crystal, solvate, salt, or combination thereof, with an amination reagent and optionally a solvent, to provide the compound of formula X:

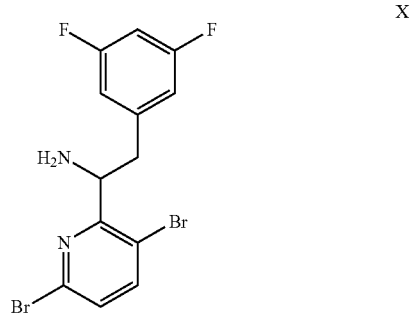 [SMILES: NC(Cc1cc(F)cc(F)c1)c1nc(Br)ccc1Br]

X or a co-crystal, solvate, salt, or combination thereof.

In certain embodiments, the mesylating reagent for mesylating step (a) is selected from the group consisting of methanesulfonyl chloride and methanesulfonic anhydride. In particular embodiments, the mesylating reagent is methanesulfonyl chloride.

In certain embodiments, the base for mesylating step (a) is selected from the group consisting of triethylamine, diisopropylethylamine, pyridine, 2,3,5-collidine, 2,4,6-collidine, N,N-dicyclohexylmethylamine, and N-methylimidazole. In particular embodiments, the base for the mesylating step is triethylamine.

In certain embodiments, mesylating step (a) uses an additive. In particular embodiments, the additive for step (a) is selected from the group consisting of 4-(dimethylamino) pyridine (DMAP), N-methylimidazole, pyridine N-oxide, diphenylcyclopropenone, and antimony pentachloride. In some embodiments, the additive for step (a) is 4-(dimethylamino)pyridine (DMAP).

In certain embodiments, the solvent for mesylating step (a) is selected from the group consisting of an ether (e.g., diethyl ether, methyl tert-butyl ether, tetrahydrofuran, 2-methyltetrahydrofuran, 1,4-dioxane), an aromatic hydrocarbon solvent (e.g., toluene, benzene, xylenes), a polar aprotic solvent (e.g., N,N-dimethylformamide, N,N-dimethylacetamide, N-methylpyrrolidinone), a chlorinated solvent (e.g., dichloromethane), and a combination thereof. In particular embodiments, the solvent for mesylating step (a) is tetrahydrofuran.

In certain embodiments, the mesylating step (a) is carried out in the temperature range of from about 60° C. or less. In certain embodiments, the mesylating step (a) is carried out in the temperature range of from about −80° C. to about 60° C. In particular embodiments, the mesylating step (a) is carried out in the temperature range of from about 0° C. to about 40° C.

In certain embodiments, the amination reagent for the aminating step (b) is ammonia.

In certain embodiments, the aminating step (b) comprises a solvent.

In certain embodiments, the solvent for the aminating step (b) is selected from the group consisting of an alcohol (e.g., methanol, ethanol, 1-propanol, isopropanol), an ether (e.g., diethyl ether, methyl tert-butyl ether, tetrahydrofuran, 2-methyltetrahydrofuran, 1,4-dioxane), an aromatic hydrocarbon solvent (e.g., toluene, benzene, xylenes), water, and a combination thereof. In particular embodiments, the solvent for the aminating step (b) is methanol and water.

In certain embodiments, the aminating step (b) is carried out in the temperature range of from about 100° C. or less. In certain embodiments, the aminating step (b) is carried out in the temperature range of from about 0° C. to about 100° C. In particular embodiments, the aminating step (b) is carried out in the temperature range of from about 40° C. to about 80° C.

In alternative embodiments, the compound of formula XIII-A:

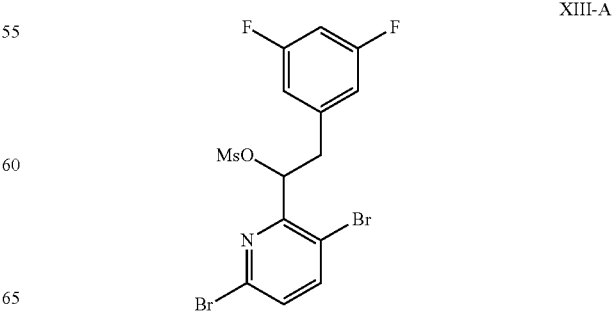

XIII-A or a co-crystal, solvate, salt, or combination thereof may be combined with an amine equivalent (e.g., di-tert-butyl-iminodicarboxylate, phthalimide, benzylamine, dibenzylamine, hexamethyldisilazane) followed by deprotection (using, e.g., hydrochloric acid, hydrazine, hydrogen, Pd/C) to provide the compound of formula X:

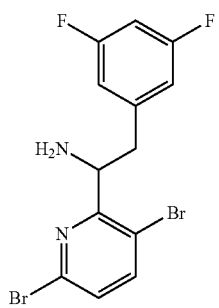

X or a co-crystal, solvate, salt, or combination thereof.

In some embodiments, a process for preparing a compound of formula VIII:

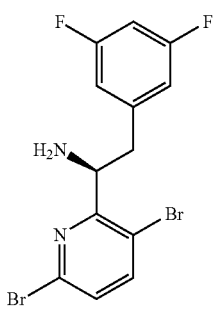

VIII or a co-crystal, solvate, salt, or combination thereof is provided, comprising:

(a) hydrogenating a compound of formula XI:

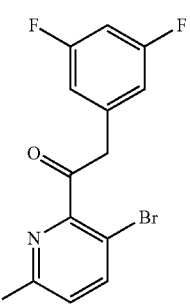

XI or a co-crystal, solvate, salt, or combination thereof, in the presence of an asymmetric catalyst and a solvent to provide a compound of formula XII:

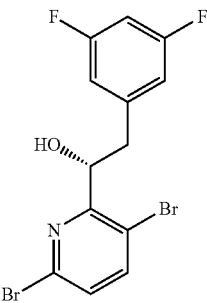

XII or a co-crystal, solvate, salt, or combination thereof;

(b) forming the azide of the compound of formula XII or a co-crystal, solvate, salt, or combination thereof with an azidification reagent in the presence of a base and a solvent to produce a compound of formula XVI:

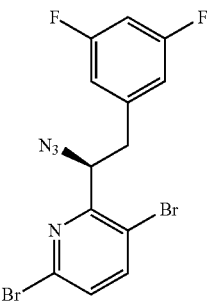

XVI or a co-crystal, solvate, salt, or combination thereof and (c) reducing the compound of formula XVI using a reducing agent, to provide the compound of formula VIII or a co-crystal, solvate, salt, or combination thereof.

In certain embodiments, the asymmetric catalyst for hydrogenating step (a) is selected from the group consisting of [Rh(cod)((S)-segphos]BF$_4$, IrCl(cod)((S)-segphos), [RuCl(p-cymene)(segphos)]Cl, Ru(OAc)$_2$(segphos), (Me$_2$NH$_2$)[RuCl((S)-segphos)]$_2$($\mu$-Cl)$_3$, and (R)—RuCY-XylBINAP. In particular embodiments, the asymmetric catalyst is (R)—RuCY-XylBINAP.

In certain embodiments, wherein the solvent for the hydrogenating step (a) is selected from the group consisting of an ester (e.g., isopropyl acetate, n-propyl acetate), an alcohol (e.g., ethanol, 1-propanol, isopropanol), an ether (e.g., diethyl ether, methyl tert-butyl ether, tetrahydrofuran, 2-methyltetrahydrofuran, 1,4-dioxane), an aromatic hydrocarbon solvent (e.g., toluene, benzene, xylenes), a chlorinated solvent (e.g., dichloromethane, 1,2-dichloroethane, chloroform), and a combination thereof. In particular embodiments, the solvent for the hydrogenating step is ethanol and isopropanol.

In certain embodiments, the hydrogenating step (a) is carried out in the temperature range of from about 150° C. or less. In certain embodiments, the hydrogenating step (a) is carried out in the temperature range of from about −20° C. to about 150° C. In particular embodiments, the hydrogenating step (a) is carried out in the temperature range of from about 0° C. to about 60° C.

In certain embodiments, the azidification reagent for step (b) is methanesulfonyl chloride and sodium azide or diphenylphosphoryl azide. In particular embodiments, the azidification reagent is diphenylphosphoryl azide.

In certain embodiments, the base for step (b) is selected from the group consisting of triethylamine, diisopropylethylamine, N,N-dimethylaminopyridine, and 1,8-diazabicyclo[5.4.0]undec-7-ene. In particular embodiments, the base is 1,8-diazabicyclo[5.4.0]undec-7-ene.

In certain embodiments, the solvent for steps (b) and (c) is selected from the group consisting of an ether (e.g., diethyl ether, methyl tert-butyl ether, tetrahydrofuran, 2-methyltetrahydrofuran, 1,4-dioxane), an aromatic hydrocarbon solvent (e.g., toluene, benzene, xylenes), a polar aprotic solvent (e.g., N,N-dimethylformamide, N,N-dimethylacetamide, N-methylpyrrolidinone), a chlorinated solvent (e.g., dichloromethane), and a combination thereof. In particular embodiments, the solvent for steps (b) and (c) is tetrahydrofuran.

In certain embodiments, steps (b) and (c) are carried out in the temperature range of from about 60° C. or less. In certain embodiments, steps (b) and (c) are carried out in the temperature range of from about −10° C. to about 60° C. In particular embodiments, steps (b) and (c) are carried out in the temperature range of from about 0° C. to about 40° C. In certain embodiments, the reducing agent for reducing step (c) is selected from the group consisting of trimethylphosphine, triethylphosphine, trimethylphosphite, triethylphosphite, tributylphosphine, trifurylphosphine, tris(hydroxymethyl)phosphine, and triphenylphosphine. In particular embodiments, the reducing agent is triphenylphosphine.

In certain embodiments, the reducing step (c) is carried out in the temperature range of from about 60° C. or less. In certain embodiments, the reducing step (c) is carried out in the temperature range of from about −10° C. to about 60° C. In particular embodiments, the reducing step (c) is carried out in the temperature range of from about 0° C. to about 40° C.

In some embodiments, a process for preparing a compound of formula VIII:

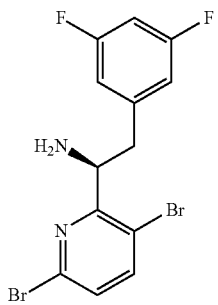

or a co-crystal, solvate, salt, or combination thereof is provided, comprising:

(a) combining a compound of formula XI:

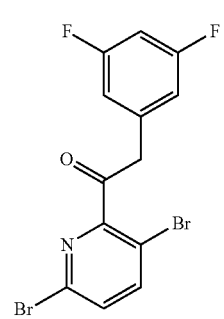

or a co-crystal, solvate, salt, or combination thereof, with a hydroxylamine source, a base and a solvent to provide a compound of formula 1e:

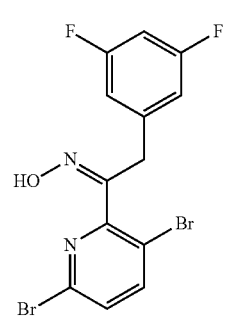

or a co-crystal, solvate, salt, or combination thereof;

(b) combining the compound of formula 1e with a reducing agent, an acylating reagent, and a solvent to provide a compound of formula 1f-1:

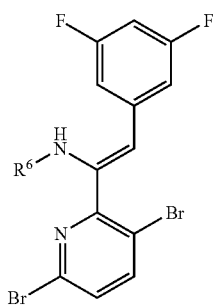

or a co-crystal, solvate, salt, or combination thereof, wherein $R^6$ is selected from the group consisting of acetyl, benzyl, trichloroacetyl, trifluoroacetyl, and propionyl; and (c) hydrogenating the compound of formula 1f-1 with a catalyst and a solvent to provide a compound of formula 1g-1:

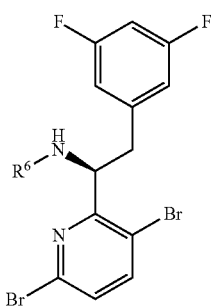

1g-1 or a co-crystal, solvate, salt, or combination thereof and (d) deprotecting the compound of 1g-1 with an acid and a solvent to provide the compound of formula VIII or a co-crystal, solvate, salt, or combination thereof.

In certain embodiments, $R^6$ is selected from the group consisting of acetyl, benzyl, trichloroacetyl, trifluoroacetyl, and propionyl. In particular embodiments, $R^6$ is acetyl.

In certain embodiments, the hydroxylamine source for step (a) is selected from hydroxylamine hydroxide.

In certain embodiments, the solvent for step (a) is selected from the group consisting of esters (e.g., n-propyl acetate, isopropyl acetate), alcohols (e.g., methanol, 1- or 2-propanol, ethanol), ethers (e.g., diethyl ether, methyl tert-butyl ether, tetrahydrofuran, 2-methyltetrahydrofuran, 1,4-dioxane), aromatic solvents (e.g., toluene, benzene, xylenes), chlorinated solvents (e.g., dichloromethane, chloroform, 1,2-dichloroethane) and a combination thereof. In certain embodiments, the solvent for step (a) is selected from the group consisting of n-propyl acetate, isopropyl acetate, methanol, 1- or 2-propanol, diethyl ether, methyl tert-butyl ether, tetrahydrofuran, 2-methyltetrahydrofuran, 1,4-dioxane, toluene, benzene, xylenes, dichloromethane, chloroform, 1,2-dichloroethane, and a combination thereof. In particular embodiments, the solvent for step (a) is ethanol.

In certain embodiments, the base for step (a) is selected from the group consisting of tertiary amines (e.g., pyridine, triethylamine, tri-n-propylamine, tri-n-butylamine, N-methylmorpholine, N-methylpyrrolidine, N-methylpiperidine), carbonate bases (e.g., sodium carbonate, potassium carbonate, cesium carbonate), carboxylate bases (e.g., sodium acetate, lithium pivalate), alkoxide bases (e.g., sodium ethoxide, potassium ethoxide, sodium tert-butoxide), sodium hydride, and disilazide bases (e.g., lithium hexamethyldisilazide, sodium hexamethyldisilazide, potassium hexamethyldisilazide). In certain embodiments, the base for step (a) is selected from the group consisting of pyridine, triethylamine, tri-n-propylamine, tri-n-butylamine, N-methylmorpholine, N-methylpyrrolidine, N-methylpiperidine, sodium carbonate, potassium carbonate, cesium carbonate, sodium acetate, lithium pivalate, sodium ethoxide, potassium ethoxide, sodium tert-butoxide, sodium hydride, lithium hexamethyldisilazide, sodium hexamethyldisilazide, and potassium hexamethyldisilazide. In particular embodiments, the base for step (a) is pyridine.

In certain embodiments, step (a) is carried out in the temperature range of from about 150° C. or less. In certain embodiments, step (a) is carried out in the temperature range of from about 0° C. to about 150° C. In particular embodiments, step (a) is carried out in the temperature range of from about 10° C. to about 60° C. In particular embodiments, step (a) is carried out in the temperature range of about 20° C.

In certain embodiments, the reducing agent for step (b) is selected from the group consisting of hydrogenation agents (e.g., palladium on carbon, hydrogen), iron(II)acetate, samarium diiodide, titanium(IV) tetrachloride/tin(II) chloride, and metallic zinc. In certain embodiments, the reducing agent for step (b) is selected from the group consisting of palladium on carbon, hydrogen, iron(II)acetate, samarium diiodide, titanium(IV) tetrachloride/tin(II) chloride, and metallic zinc. In particular embodiments, the reducing agent is iron(II)acetate. In some embodiments, the reducing agent is iron(II)acetate prepared in situ.

In certain embodiments, the acylating reagent for step (b) is selected from the group consisting of acid chlorides (e.g., acetyl chloride, trichloroacetyl chloride), anhydrides (e.g., acetic anhydride, trichloroacetic anhydride, trifluoroacetic anhydride), and alkyl halides (e.g., benzyl chloride, benzyl bromide). In certain embodiments, the acylating reagent for step (b) is selected from the group consisting of acetyl chloride, trichloroacetyl chloride, acetic anhydride, trichloroacetic anhydride, trifluoroacetic anhydride, benzyl chloride, and benzyl bromide. In particular embodiments, th acylating reagent is acetic anhydride.

In certain embodiments, the solvent for step (b) is selected from the group consisting of acetic acid, esters (e.g., n-propyl acetate, isopropyl acetate, acetate), alcohols (e.g., methanol, 1-propanol, 2-propanol), ethers (e.g., diethyl ether, methyl tert-butyl ether, tetrahydrofuran, 2-methyltetrahydrofuran, 1,4-dioxane), aromatic solvents (e.g., toluene, benzene, xylenes), chlorinated solvents (e.g., dichloromethane, chloroform, 1,2-dichloroethane) and a combination thereof. In certain embodiments, the solvent for step (b) is selected from the group consisting of acetic acid, n-propyl acetate, isopropyl acetate, acetate, methanol, 1- or 2-propanol, diethyl ether, methyl tert-butyl ether, tetrahydrofuran, 2-methyltetrahydrofuran, 1,4-dioxane, toluene, benzene, xylenes, dichloromethane, chloroform, 1,2-dichloroethane and a combination thereof. In particular embodiments, the solvent for the step (b) is isopropyl acetate and acetic acid.

In certain embodiments, step (b) is carried out in the temperature range of from about 150° C. or less. In certain embodiments, step (b) is carried out in the temperature range of from about 0° C. to about 150° C. In particular embodiments, step (b) is carried out in the temperature range of from about 30° C. to about 70° C. In particular embodiments, step (b) is carried out in the temperature range of about 50° C.

In certain embodiments, the catalyst for step (c) is selected from the group consisting of IrCl(cod)((S)-segphos), Rh(cod)((S)-segphos]BF$_4$, and (Me$_2$NH$_2$)[RuCl((S)-segphos)]$_2$(µ-Cl)$_3$. In particular embodiments, the catalyst is (IrCl(cod)((S)-segphos).

In certain embodiments, the solvent for step (c) and step (d) is selected from the group consisting of esters (e.g., ethyl acetate, n-propyl acetate, isopropyl acetate), alcohols (e.g., ethanol, 1-propanol, 2-propanol), ethers (e.g., diethyl ether, methyl tert-butyl ether, tetrahydrofuran, 2-methyltetrahydrofuran, 1,4-dioxane,), aromatic solvents (e.g., toluene, benzene, xylenes), chlorinated solvents (e.g., dichloromethane, chloroform, 1,2-dichloroethane) and a combination thereof. In certain embodiments, the solvent for step (c) and step (d) is selected from the group consisting of ethyl acetate, n-propyl acetate, isopropyl acetate, ethanol, 1- or 2-propanol, diethyl ether, methyl tert-butyl ether, tetrahydrofuran, 2-methyltetrahydrofuran, 1,4-dioxane, toluene, benzene, xylenes, dichloromethane, chloroform, 1,2-dichloroethane and a combination thereof. In particular embodiments, the solvent for step (c) and step (d) is ethyl acetate.

In certain embodiments, step (c) is carried out in the temperature range of from about 150° C. or less. In certain embodiments, step (c) is carried out in the temperature range of from about 0° C. to about 150° C. In particular embodiments, step (c) is carried out in the temperature range of from about 80° C. to about 150° C.

In certain embodiments, the acid for step (d) is selected from the group consisting of hydrochloric acid, hydrobromic acid, nitric acid, methanesulfonic acid, and p-toluenesulfonic acid. In particular embodiments, the acid for step (d) is hydrochloric acid.

In certain embodiments, step (d) is carried out in the temperature range of from about 100° C. or less. In certain embodiments, step (d) is carried out in the temperature range of from about 20° C. to about 100° C. In particular embodiments, step (d) is carried out in the temperature range of from about 20° C. to about 80° C.

In some embodiments, a process for preparing a compound of formula VIII:

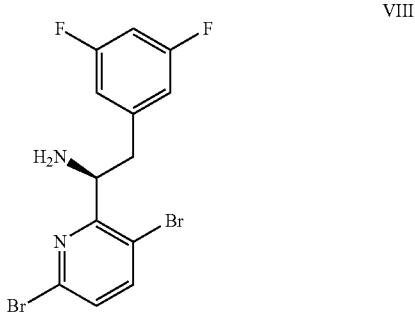 [SMILES: N[C@@H](Cc1cc(F)cc(F)c1)c1nc(Br)ccc1Br]

VIII or a co-crystal, solvate, salt, or combination thereof is provided, comprising reductively aminating a compound of formula XI:

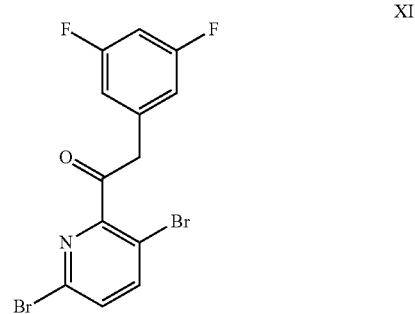 [SMILES: O=C(Cc1cc(F)cc(F)c1)c1nc(Br)ccc1Br]

XI or a co-crystal, solvate, salt, or combination thereof, with:
a hydrogen source,
a catalyst,
an amine,
an acid, and
a solvent,
to provide the compound of formula VIII or a co-crystal, solvate, salt, or combination thereof.

In certain embodiments, the hydrogen source is selected from the group consisting of hydrogen gas, ammonium formate, and formic acid triethylamine complex. In particular embodiments, the hydrogen source is hydrogen gas.

In certain embodiments, the solvent is selected from the group consisting of an ether (e.g., diethyl ether, methyl tert-butyl ether, tetrahydrofuran, 2-methyltetrahydrofuran, 1,4-dioxane), an aromatic hydrocarbon solvent (e.g., benzene, xylenes), a polar aprotic solvent (e.g., N,N-dimethylformamide, N,N-dimethylacetamide, N-methylpyrrolidinone, dimethylsulfoxide), an alcohol (e.g., methanol, isopropanol, tert-amyl alcohol), water, and a combination thereof. In particular embodiments, the solvent is methanol.

In certain embodiments, the water is at pH 6-10.

In certain embodiments, the catalyst is an asymmetric catalyst or an enzymatic catalyst.

In certain embodiments, the catalyst is an asymmetric catalyst. In some embodiments, the asymmetric catalyst is a ruthenium or iridium catalyst with a chiral ligand (e.g., SegPhos, DM-SegPhos, tert-butyl-Josiphos, DuPhos, MonoPhos, or BINAP). In particular embodiments, the catalyst is a ruthenium or iridium catalyst selected from the group consisting of $RuCl_3$, ruthenium(III) acetylacetonate, chlorocyclopentadienylbis(triphenylphosphine)ruthernium (II), chlorohydridotris(triphenylphosphine) ruthenium(II) toluene adduct, chlorotris(triphenylphosphine)ruthenium(II) acetate, [Ru(Cl)H(CO)(PPh$_3$)$_3$], [Ir(COD)Cl]$_2$, (acetylacetonato)(1,5-cyclooctadiene)iridium(I), and (acetylacetonato) dicarbonyliridium(I). In some embodiments, the catalyst is $Ru(OAc)_2((R)$-SegPhos).

In certain embodiments, the catalyst is an enzymatic catalyst. In some embodiments, the enzymatic catalyst is an amine transaminase and a cofactor in a buffer. In particular embodiments, the amine transaminase is a ω-transaminase selected from the group consisting of ATA-1, ATA-2, ATA-007, ATA-013, ATA-025, ATA-113, ATA-117, ATA-200, ATA-217, ATA-234, ATA-237, ATA-238, ATA-251, ATA-254, ATA-256, ATA-260, ATA-301, ATA-303, ATA-412, ATA-415, ATA-P1-B04, ATA-P1-F03, ATA-P1-G05, ATA-P2-A01, ATA-P2-A07, and ATA-P2-B01.

In certain embodiments, the buffer is selected from the group consisting of triethanolamine, tris, tricine, BES, MOPS, HEPES, sodium phosphate, and potassium phosphate.

In certain embodiments, the cofactor is pyridoxal phosphate.

In certain embodiments, the amine is selected from the group consisting of ammonia, ammonium acetate, ammonium salicylate, ammonium formate, a-methylbenzylamine, isopropylamine, benzhydrylamine, DL-alanine, and aspartame. In particular embodiments, the amine is ammonia.

In certain embodiments, the acid is selected from the group consisting of p-toluenesulfonic acid, hydrochloric acid, and phosphoric acid. In particular embodiments, the acid is p-toluenesulfonic acid.

In certain embodiments, the catalyst is an asymmetric catalyst and the process is carried out at a pressure of from about 100 to about 1000 psi. In certain embodiments, the catalyst is an asymmetric catalyst and the process is carried out at a pressure of from about 200 to about 600 psi.

In some embodiments, the catalyst is an asymmetric catalyst and the process is carried out in the temperature range of from 120° C. or less. In certain embodiments, the catalyst is an asymmetric catalyst and the process is carried out in the temperature range of from about 0° C. to about 120° C. In certain embodiments, the catalyst is an asymmetric catalyst and the process is carried out in the temperature range of from about 55° C. to about 65° C.

In certain embodiments, the catalyst is an enzymatic catalyst and the process is carried out in the temperature range of from about 100° C. or less. In certain embodiments, the catalyst is an enzymatic catalyst and the process is carried out in the temperature range of from about 5° C. to about 100° C.

In some embodiments, disclosed herein is a process for preparing a compound of formula V:

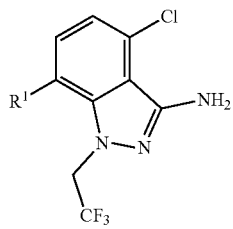

or a co-crystal, solvate, salt, or combination thereof, wherein R$^1$ is B(OH)$_2$, B(OCH(Me)CH$_2$C(Me)$_2$O), B((1,2-di-O) C$_6$H$_4$), B(OCH$_2$C(Me)$_2$CH$_2$O), BF$_3$K, B(O$_2$CCH$_2$N(Me) CH$_2$CO$_2$), or B(OC(Me)$_2$C(Me)$_2$O), comprising:
(a) combining a compound of formula V-A:

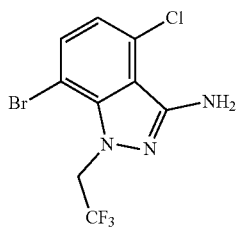

or a co-crystal, solvate, salt, or combination thereof, with
a silylating agent,
a base, and
a solvent to provide a compound of formula 7a:

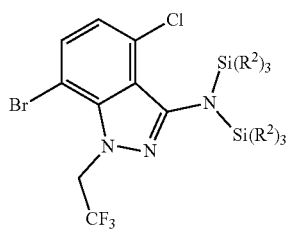

or a co-crystal, solvate, salt, or combination thereof, wherein
each R$^2$ is independently C$_1$-6 alkyl or C$_6$ aryl, wherein the C$_1$-6 alkyl and C$_6$ aryl are
independently unsubstituted or substituted with one to five C$_1$-6 alkyl groups; and
(b) combining the compound of formula 7a with
an organometallic reagent, and
a borylation reagent,
to provide the compound of formula V, or a co-crystal, solvate, salt, or combination thereof.

In some embodiments, disclosed herein is a process for preparing a compound of formula V:

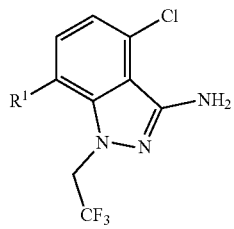

or a co-crystal, solvate, salt, or combination thereof, wherein R$^1$ is B(OH)$_2$, B(OCH(Me)CH$_2$C(Me)$_2$O), B((1,2-di-O) C$_6$H$_4$), B(OCH$_2$C(Me)$_2$CH$_2$O), BF$_3$K, B(O$_2$CCH$_2$N(Me) CH$_2$CO$_2$), or B(OC(Me)$_2$C(Me)$_2$O), comprising:
(a) combining a compound of formula V-A:

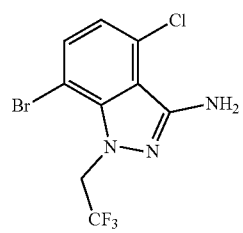

or a co-crystal, solvate, salt, or combination thereof, with
a silylating agent,
a base, and
a solvent to provide a compound of formula 7a:

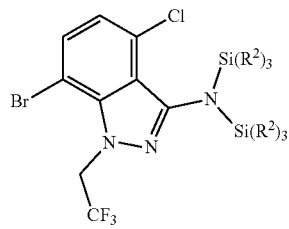

or a co-crystal, solvate, salt, or combination thereof,
wherein each R$^2$ is independently C$_1$-6 alkyl that is unsubstituted or substituted with one to five C$_1$-6 alkyl groups; and
(b) combining the compound of formula 7a with
an organometallic reagent, and
a borylation reagent,
to provide the compound of formula V, or a co-crystal, solvate, salt, or combination thereof.

In certain embodiments, the base for step (a) is selected from the group consisting of sodium hydride, potassium hydride, methylmagnesium bromide, phenylmagnesium bromide, sodium hexamethyldisilazide, potassium hexamethyl disilazide, and lithium hexamethyldisilazide. In particular embodiments, the base for step (a) is lithium hexamethyldisilazide.

In certain embodiments, the silylating agent for step (a) is selected from the group consisting of trimethylsilyl bromide, N,O-bis(trimethylsilyl)acetamide, trimethylsilyl chloride, chloro(dimethyl)phenylsilane, chloro(methyl)diphenylsilane, and 1,2-bis(chlorodimethylsilyl)ethane.

In certain embodiments, the silylating agent for step (a) is selected from the group consisting of trimethylsilyl bromide, N,O-bis(trimethylsilyl)acetamide, and trimethylsilyl chloride. In particular embodiments, the silylating agent for step (a) is trimethylsilyl chloride.

In certain embodiments, the solvent is selected from the group consisting of an ether (e.g., diethyl ether, tetrahydrofuran, 2-methyltetrahydrofuran, 1,4-dioxane, dimethoxyethane), a hydrocarbon solvent (e.g., n-hexane), an aromatic hydrocarbon solvent (e.g., toluene, xylenes), and a combination thereof. In particular embodiments, the solvent is tetrahydrofuran.

In certain embodiments, the organometallic reagent for step (b) is selected from the group consisting of n-butyllithium, s-butylmagnesium chloride lithium chloride complex, tert-butylmagnesium chloride, isopropylmagnesium chloride, and isopropylmagnesium chloride lithium chloride complex.

In certain embodiments, the organometallic reagent for step (b) is selected from the group consisting of n-butyllithium, s-butylmagnesium chloride lithium chloride complex, tert-butylmagnesium chloride, and isopropylmagnesium chloride lithium chloride complex. In particular embodiments, the organometallic reagent is isopropylmagnesium chloride lithium chloride complex.

In certain embodiments, the borylation reagent for step (b) is selected from the group consisting of trimethyl borate, triethyl borate, pinacolborane, 2-methoxy-4,4,5,5-tetramethyl-1,3,2-dioxaboralane, 2-isopropoxy-4,4,5,5-tetramethyl-1,3,2-dioxaborolane, B-catecholborane, and 2-bromo-1,3,2-benzodioxaborole. In particular embodiments, the borylation reagent is 2-isopropoxy-4,4,5,5-tetramethyl-1,3,2-dioxaborolane.

In certain embodiments, the process for preparing a compound of formula V, or a co-crystal, solvate, salt, or combination, thereof is carried out in the temperature range of from about 40° C. or less. In certain embodiments, the process is carried out in the temperature range of from about −80° C. to about 40° C. In particular embodiments, the process is carried out in the temperature range of from about −40° C. to about 20° C.

In certain embodiments, IV is B(OC(Me)$_2$C(Me)$_2$O).

In some embodiments, a process for preparing a compound of formula VII:

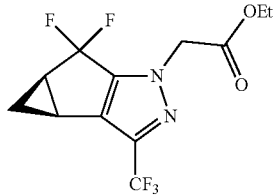

VII or a co-crystal, solvate, salt, or combination thereof is provided, comprising hydrolyzing a compound of formula VII-A:

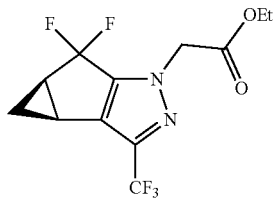

VII-A or a co-crystal, solvate, salt, or combination thereof in the presence of a base and a solvent to provide a compound of formula VII.

In certain embodiments, the base is selected from the group consisting of potassium hydroxide, sodium hydroxide, lithium hydroxide, and potassium trimethylsilanoate. In particular embodiments, the base is potassium hydroxide.

In certain embodiments, the solvent is selected from the group consisting of a chlorinated solvent (e.g., dichloromethane), an alcohol (e.g., ethanol, methanol, 1-propanol, 2-propanol), an ether (e.g., diethyl ether, methyl tert butyl ether, tetrahydrofuran, 2-methyltetrahydrofuran, 1,4-dioxane), an aromatic hydrocarbon solvent (e.g., benzene, toluene, xylene), water, and a combination thereof.

In certain embodiments, the solvent is selected from the group consisting of a chlorinated solvent (e.g., dichloromethane), an alcohol (e.g., ethanol), an ether (e.g., tetrahydrofuran, 2-methyltetrahydrofuran), an aromatic hydrocarbon solvent (e.g., toluene), water, and a combination thereof. In particular embodiments, the solvent is a mixture of dichloromethane and ethanol.

In particular embodiments, the solvent is a mixture of dichloromethane, water, and, ethanol. In particular embodiments, the solvent is a mixture of water and ethanol.

In certain embodiments, the process is carried out in the temperature range of from about 100° C. or less. In certain embodiments, the process is carried out in the temperature range of from about 10° C. to about 100° C. In particular embodiments, the process is carried out in the temperature range of from about 10° C. to about 60° C.

In some embodiments, a process for preparing a compound of formula VII-A:

VII-A or a co-crystal, solvate, salt, or combination thereof is provided, comprising fluorinating a compound of formula 5h-1:

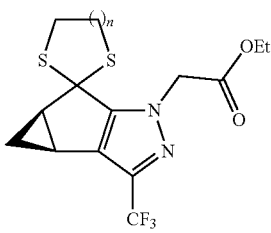

5h-1 or a co-crystal, solvate, salt, or combination thereof, wherein n is 1 or 2, with a fluorinating reagent, in a solvent, and in the presence of an activator, to provide the compound of formula VII-A or a co-crystal, solvate, salt, or combination thereof.

In certain embodiments, n is 1. In certain embodiments, n is 2.

In certain embodiments, the fluorinating reagent is selected from the group consisting of hydrogen fluoride pyridine, calcium fluoride, potassium hydrogenfluoride, triethylamine trihydrofluoride, elemental fluorine, bromine trifluoride, iodine pentafluoride, tetra-N-butylammonium dihydrogen trifluoride, 4-iodotoluene difluoride, and hydrogen fluoride melamine. In particular embodiments, the fluorinating reagent is hydrogen fluoride pyridine.

In certain embodiments, the solvent is selected from the group consisting of ethers (e.g., diethyl ether, methyl tert-butyl ether, tetrahydrofuran, 2-methyltetrahydrofuran, 1,4-dioxane), polar aprotic solvents (e.g., acetone, N,N-dimethylformamide, N,N-dimethylacetamide, N-methylpyrrolidinone), aromatic solvents (e.g., benzene, toluene, xylenes), chlorinated solvents (e.g., dichloromethane), and a combination thereof. In certain embodiments, the solvent is selected from the group consisting of diethyl ether, methyl tert-butyl ether, tetrahydrofuran, 2-methyltetrahydrofuran, 1,4-dioxane, acetone, N,N-dimethylformamide, N,N-dimethylacetamide, N-methylpyrrolidinone, benzene, toluene, xylenes, dichloromethane, and a combination thereof. In particular embodiments, the solvent is dichloromethane.

In certain embodiments, the activator is selected from the group consisting of 1,3-dibromo-5,5-dimethylhydantoin, N-bromosuccinimide, N-iodosuccinimide, nitrosonium tetrafluoroborate, sulfuryl chloride fluoride, triflic acid, and mercuric fluoride. In particular embodiments, the activator is 1,3-dibromo-5,5-dimethylhydantoin.

In certain embodiments, the process is carried out in the temperature range of from about 100° C. or less. In certain embodiments, the process is carried out in the temperature range of from about −70° C. to about 100° C. In particular embodiments, the process is carried out in the temperature range of from about −30° C. to about 20° C.

In some embodiments, a process for preparing a compound of formula 5h-1:

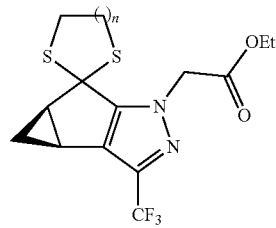

5h-1 or a co-crystal, solvate, salt, or combination thereof, wherein n is 1 or 2, is provided, comprising combining a compound of formula XIV:

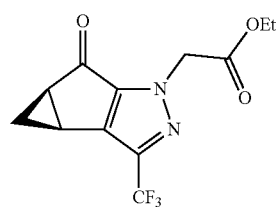

XIV or a co-crystal, solvate, salt, or combination thereof, with a dithiol reagent and a promoter, in a solvent, to provide the compound of formula 5h-1 or a co-crystal, solvate, salt, or combination thereof.

In certain embodiments, n is 1. In certain embodiments, n is 2.

In certain embodiments, the dithiol reagent is 1,2-ethanedithiol or 1,2-propanedithiol. In particular embodiments, the reagent is 1,2-ethanedithiol.

In certain embodiments, the solvent is selected from the group consisting of ethers (e.g., diethyl ether, methyl tert-butyl ether, tetrahydrofuran, 2-methyltetrahydrofuran, 1,4-dioxane), polar aprotic solvents (e.g., acetone, N,N-dimethylformamide, N,N-dimethylacetamide, N-methylpyrrolidinone), aromatic solvents (e.g., benzene, toluene, xylenes), chlorinated solvents (e.g., dichloromethane), and a combination thereof. In certain embodiments, the solvent is selected from the group consisting of diethyl ether, methyl tert-butyl ether, tetrahydrofuran, 2-methyltetrahydrofuran, 1,4-dioxaneacetone, N,N-dimethylformamide, N,N-dimethylacetamide, N-methylpyrrolidinone, benzene, toluene, xylenes, dichloromethane, and a combination thereof. In particular embodiments, the solvent is dichloromethane.

In certain embodiments, the promoter is selected from the group consisting of boron trifluoride acetic acid complex, p-toluenesulfonic acid, iodine, 1,3-dibromo-5,5-dimethylhydantoin, copper(II) dodecyl sulfate, ytterbium(III) triflate, yttrium(III) triflate, bismuth(III) triflate, bismuth(III) chloride, tungstophosphoric acid, perchloric acid, praseodymium triflate, hafnium(IV) triflate, iron(III) chloride, hydrogen chloride, p-dodecyl benzenesulfonic acid, $BF_3.OEt_2$, $BF_3.OMe_2$, $BF_3.THF$, $BF_3.OBu_2$, $BF_3.MeOH$, $BF_3.Me_2S$, and $BF_3.PhOHBF_3.2H_2O$. In particular embodiments, the promotor is boron trifluoride acetic acid complex.

In certain embodiments, the process is carried out in the temperature range of from about 100° C. or less. In certain embodiments, the process is carried out in the temperature range of from about −20° C. to about 100° C. In particular embodiments, the process is carried out in the temperature range of from about 0° C. to about 40° C.

In some embodiments, a process for preparing a compound of formula XIV:

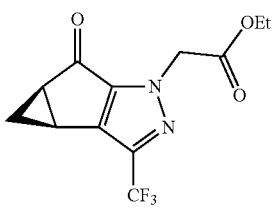

XIV or a co-crystal, solvate, salt, or combination thereof is provided, comprising alkylating a compound of formula XIV-A:

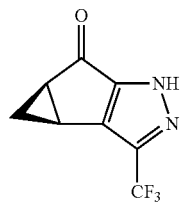

XIV-A or a co-crystal, solvate, salt, or combination thereof, with an alkylating agent in the presence of a base, a solvent, and optionally a phase transfer catalyst, to provide the compound of formula XIV or a co-crystal, solvate, salt, or combination thereof.

In certain embodiments, the alkylating agent is selected from the group consisting of ethyl chloroacetate, ethyl iodoacetate, ethyl (methanesulfonyloxy)acetate, ethyl (p-tosyloxy)acetate, ethyl(((trifluoromethyl)sulfonyl)oxy)acetate, and ethyl bromoacetate. In particular embodiments, the alkylating agent is ethyl bromoacetate.

In certain embodiments, the base is selected from the group consisting of ethyl diisopropylamine, triethylamine, tri-n-propylamine, tri-n-butylamine, N-methylmorpholine, N-methylpyrrolidine, N-methylpiperidine, sodium carbonate, potassium carbonate, cesium carbonate, sodium ethoxide, potassium ethoxide, sodium tert-butoxide, sodium hydride, lithium hexamethyldisilazide, sodium hexamethylsilazide, and potassium hexamethyldisilazide. In particular embodiments, the base is ethyl diisopropylamine.

In certain embodiments, the process comprises a phase transfer catalyst.

In certain embodiments, the phase transfer catalyst is selected from the group consisting of tetra-N-butylammonium hydrogensulfate and tetra-N-butylammonium iodide.

In certain embodiments, the solvent is selected from the group consisting of an ether (e.g., diethyl ether, methyl tert-butyl ether, tetrahydrofuran, 2-methyltetrahydrofuran, 1,4-dioxane), a polar aprotic solvent (e.g., N,N-dimethylformamide, N,N-dimethylacetamide, N-methylpyrrolidinone), an aromatic hydrocarbon solvent (e.g., toluene, benzene, xylenes), a chlorinated solvent (e.g., dichloromethane), an ester (e.g., ethyl acetate, n-butyl acetate, isopropyl acetate), a ketone (e.g., acetone, methyl ethyl ketone, methyl isobutylketone), a nitrile (e.g., acetonitrile), water, and a combination thereof. In particular embodiments, the solvent is acetonitrile.

In certain embodiments, the process is carried out in the temperature range of from about 100° C. or less. In certain embodiments, the process is carried out in the temperature range of from about −20° C. to about 100° C. In particular embodiments, the process is carried out in the temperature range of from about −20° C. to about 30° C.

In some embodiments, a process for preparing a compound of formula XIV-A:

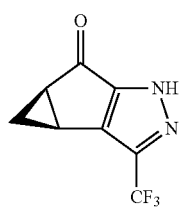

XIV-A or a co-crystal, solvate, salt, or combination thereof is provided, comprising oxidizing a compound of formula 3c:

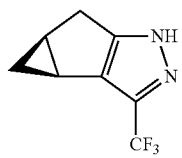

3c or a co-crystal, solvate, salt, or combination thereof, with an oxidant, a promoter, a solvent, and a catalyst, to provide the compound of formula XIV-A or a co-crystal, solvate, salt, or combination thereof.

In certain embodiments, the oxidant is selected from the group consisting of tert-butyl hydroperoxide, peracetic acid, hydrogen peroxide, molecular oxygen, air, sodium hypochlorite, sodium chlorite, sodium periodate, potassium peroxymonosulfate, 2,3-dichloro-5,6-dicyano-1,4-benzoquinone, 1,4-benzoquinone, periodic acid, potassium bromate, meta-chloroperoxybenzoic acid (mCPBA or m-CPBA), and magnesium monoperoxypthalate. In particular embodiments, the oxidant is tert-butyl hydroperoxide.

In certain embodiments, the promoter is selected from the group consisting of pyridine, bipyridine, neocuproine, 1,10-phenanthroline, 2,6-lutidine, 4-picoline, 2-picoline, 3-methylpyridine, Isonicotinamide, nicotinamide, nicotinic acid, (2,2,6,6-tetramethylpiperidin-1-yl)oxyl, and didecyldimethylammonium bromide. In particular embodiments, the promoter is pyridine.

In certain embodiments, the solvent is selected from the group consisting of acetic acid, acetonitrile, n-butyl acetate, isopropyl acetate, ethyl acetate, acetaone, dichloromethane, dimethyl carbonate, tetrahydrofuran, methanol, tert-butanol, dichloromethane, sulfolane, water, and a combination thereof. In particular embodiments, the solvent is water.

In certain embodiments, the catalyst is selected from the group consisting of manganese(II) triflate, copper(II) chloride, (2S,2'S-(−)-[N,N'-Bis(2-pyridylmethyl)]-2,2'-bipyrrolidinebis(acetonitrile)iron(II) hexafluoroantimonate, bismuth, cobalt(II) acetate, manganese(M) acetate, ruthenium (III) chloride, N-hydroxyphthalimide, bis(cyclopentadienyl)

vanadium(W) dichloride, and manganese dioxide. In particular embodiments, the catalyst is copper(II) chloride.

In certain embodiments, the process is carried out in the temperature range of from about 100° C. or less. In certain embodiments, the process is carried out in the temperature range of from about −40° C. to about 100° C. In particular embodiments, the process is carried out in the temperature range of from about 10° C. to about 50° C.

In some embodiments, disclosed herein is a process for preparing a compound of formula 3c:

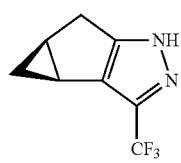

3c or a co-crystal, solvate, salt, or combination thereof, comprising:
(a) cyclizing a compound of formula 3a:

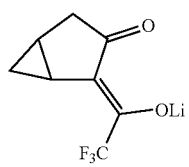

3a or a co-crystal, solvate, or combination thereof, with a hydrazine derivative and a promoter, in a solvent, to provide a compound of formula 3b:

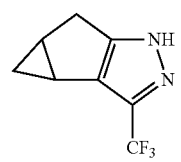

3b or a co-crystal, solvate, salt or combination thereof; and
(b) separating the compound of formula 3b, or a co-crystal, solvate, salt or combination thereof, to provide the compound of formula 3c, or a co-crystal, solvate, salt, or combination thereof.

In certain embodiments, the hydrazine derivative in step (a) is selected from the group consisting of anhydrous hydrazine, hydrazine monohydrate, aqueous hydrazine, hydrazine acetate, hydrazine dihydrochloride, hydrazine monohydrochloride, hydrazine sulfate, hydrazine hemisulfate, and hydrazine monohydrobromide. In particular embodiments, the hydrazine derivative in step (a) is hydrazine hydrate.

In certain embodiments, the solvent in step (a) is selected from the group consisting of water, alcohols (e.g., methanol, ethanol, 1-propanol, 2-propanol, etc.), ethers (e.g., diethyl ether, methyl tert-butyl ether, tetrahydrofuran, 2-methyltetrahydrofuran, 1,4-dioxane), polar aprotic solvents (e.g., N,N-dimethylformamide, N,N-dimethylacetamide, N-methylpyrrolidinone), aromatic solvents (e.g., benzene, toluene, xylenes), carboxylic acids (e.g., acetic acid, formic acid, propionic acid, butanoic acid) and a combination thereof. In certain embodiments, the solvent in step (a) is selected from the group consisting of water, methanol, ethanol, 1- or 2-propanoldiethyl ether, methyl tert-butyl ether, tetrahydrofuran, 2-methyltetrahydrofuran, 1,4-dioxane, N,N-dimethylformamide, N,N-dimethylacetamide, N-methylpyrrolidinone, benzene, toluene, xylenes, carboxylic acids, acetic acid, formic acid, propionic acid, butanoic acid, and a combination thereof. In particular embodiments, the solvent used in step (a) is acetic acid.

In certain embodiments, the promoter in step (a) is selected from the group consisting of Brønsted acids (e.g., hydrogen chloride, hydrogen bromide, sulfuric acid, methanesulfonic acid, toluenesulfonic acid,), and Lewis acids (e.g., zinc chloride, magnesium chloride, titanium tetrachloride). In certain embodiments, the promoter in step (a) is selected from the group consisting of hydrogen chloride, hydrogen bromide, sulfuric acid, methanesulfonic acid, toluenesulfonic acid, zinc chloride, magnesium chloride, and titanium tetrachloride.

In some embodiments, step (a) is carried out at a temperature range of from about 120° C. or less. In certain embodiments, step (a) is carried out at a temperature range of from about −40 to about 120° C. In particular embodiments, step (a) is carried out at a temperature range of from about 30 to about 70° C.

In some embodiments, disclosed herein is a process for preparing a compound of formula 3c:

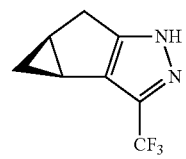

3c or a co-crystal, solvate, salt, or combination thereof, comprising:
(b) cyclizing a compound of formula 3a:

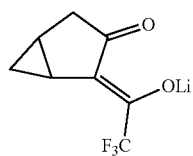

3a or a co-crystal, solvate, or combination thereof, with a hydrazine derivative and a promoter, in a solvent, to provide a compound of formula 3b:

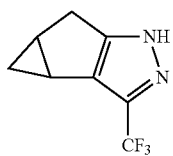

3b or a co-crystal, solvate, salt or combination thereof and
(b) chromatographically separating the compound of formula 3b, or a co-crystal, solvate, salt or combination thereof, with a chiral stationary phase and a solvent to provide the compound of formula 3c, or a co-crystal, solvate, salt, or combination thereof.

In certain embodiments, the hydrazine derivative in step (a) is selected from the group consisting of anhydrous hydrazine, hydrazine monohydrate, aqueous hydrazine, hydrazine acetate, hydrazine dihydrochloride, hydrazine monohydrochloride, hydrazine sulfate, hydrazine hemisulfate, and hydrazine monohydrobromide. In particular embodiments, the hydrazine derivative in step (a) is hydrazine hydrate.

In certain embodiments, the solvent in step (a) is selected from the group consisting of water, alcohols (e.g., methanol, ethanol, 1-propanol, 2-propanol, etc.), ethers (e.g., diethyl ether, methyl tert-butyl ether, tetrahydrofuran, 2-methyltetrahydrofuran, 1,4-dioxane), polar aprotic solvents (e.g., N,N-dimethylformamide, N,N-dimethylacetamide, N-methylpyrrolidinone), aromatic solvents (e.g., benzene, toluene, xylenes), carboxylic acids (e.g., acetic acid, formic acid, propionic acid, butanoic acid) and a combination thereof. In certain embodiments, the solvent in step (a) is selected from the group consisting of water, methanol, ethanol, 1- or 2-propanoldiethyl ether, methyl tert-butyl ether, tetrahydrofuran, 2-methyltetrahydrofuran, 1,4-dioxane, N,N-dimethylformamide, N,N-dimethylacetamide, N-methylpyrrolidinone, benzene, toluene, xylenes, carboxylic acids, acetic acid, formic acid, propionic acid, butanoic acid, and a combination thereof. In particular embodiments, the solvent used in step (a) is acetic acid.

In certain embodiments, the promoter in step (a) is selected from the group consisting of Brønsted acids (e.g., hydrogen chloride, hydrogen bromide, sulfuric acid, methanesulfonic acid, toluenesulfonic acid,), and Lewis acids (e.g., zinc chloride, magnesium chloride, titanium tetrachloride). In certain embodiments, the promoter in step (a) is selected from the group consisting of hydrogen chloride, hydrogen bromide, sulfuric acid, methanesulfonic acid, toluenesulfonic acid, zinc chloride, magnesium chloride, and titanium tetrachloride.

In some embodiments, step (a) is carried out at a temperature range of from about 120° C. or less. In certain embodiments, step (a) is carried out at a temperature range of from about −40 to about 120° C. In particular embodiments, step (a) is carried out at a temperature range of from about 30 to about 70° C.

In certain embodiments, the chiral stationary phase used in step (b) is selected from the group consisting of Chiralpaks AD, AS, AY, AZ, T101, OD, IA, IB, IC, ID, IE, IF, IG (Chiral Technologies); Lux Celluloses 2, 3, 4 (Phenomenex); and (R,R) Whelk-O, (R,R) ULMO, (S,S) Dach DNB (Regis Technologies). In certain embodiments, the chiral stationary phase used in step (b) is selected from the group consisting of Chiralpaks AD, AS, AY, AZ, T101, OD, IA, IB, IC, ID, IE, IF, IG; Lux Celluloses 2, 3, 4; and (R,R) Whelk-O, (R,R) ULMO, and (S,S) Dach DNB. In particular embodiments, the chiral stationary phase is Chiralpak IG.

In certain embodiments, the solvent used in step (b) is selected from the group consisting of hydrocarbons (e.g., hexanes, heptanes, octanes), esters (e.g., ethyl acetate, n-propyl acetate, isopropyl acetate), alcohols (e.g., methanol, ethanol, 1- or 2-propanol), ethers (e.g., diethyl ether, methyl tert-butyl ether, tetrahydrofuran, 2-methyltetrahydrofuran, 1,4-dioxane), aromatic solvents (e.g., benzene, toluene, xylenes), chlorinated solvents (e.g., dichloromethane, chloroform, 1,2-dichloroethane,), acetonitrile, and a combination thereof. In certain embodiments, the solvent used in step (b) is selected from the group consisting of hexanes, heptanes, octanes, esters, ethyl acetate, n-propyl acetate, isopropyl acetate, methanol, ethanol, 1- or 2-propanol, diethyl ether, methyl tert-butyl ether, tetrahydrofuran, 2-methyltetrahydrofuran, 1,4-dioxane, benzene, toluene, xylenes, dichloromethane, chloroform, 1,2-dichloroethane, acetonitrile, and a combination thereof. In particular embodiments, the solvent is acetontrile.

In certain embodiments, step (b) is carried out at a temperature range of from about 50° C. or less. In particular embodiments, step (b) is carried out at a temperature range of from about 10 to about 50° C.

In some embodiments, a process for preparing a compound of formula XIV:

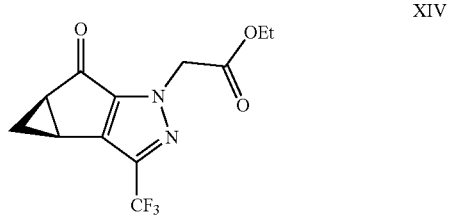 [SMILES: CCOC(=O)Cn1nc(C(F)(F)F)c2c1C(=O)[C@@H]1C[C@H]21]

or a co-crystal, solvate, salt, or combination thereof is provided, comprising kinetically resolving a compound of formula XVII:

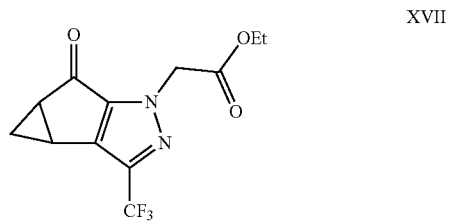 [SMILES: CCOC(=O)Cn1nc(C(F)(F)F)c2c1C(=O)C1CC21]

or a co-crystal, solvate, or combination thereof, with:
a catalyst,
a reducing agent, and
a solvent,
to provide a compound of formula XIV or a co-crystal, solvate, salt or combination thereof.

In certain embodiments, the catalyst for resolving a compound of formula XVII, or a co-crystal, solvate, or combination thereof, is selected from the group consisting of (R)-(+)-o-tolyl-CBS-oxazaborolidine, (R)-(+)-2-butyl-CBS-oxazaborolidine, (R)-(−)-2-methyl-CBS-oxazoborolidine trans-RuCl$_2$[(R)-xylbinap]-[(R)-diapen], RuBr$_2$[(R)-BINAP], [RuCl(PhH)(R)-BINAP)]Cl, RuCl(p-cymene)[(S,S)-Ts-DPEN], RuCl(mesitylene)[(S,S)-Ts-DPEN], RuBF$_4$(p-cymene)[(S,S)-Ts-DPEN], RuCl(p-cymene)[(S,S)-Fs-DPEN], RuCl(p-cymene)[(R,R)-Teth-Ts-DPEN], and Baker's yeast. In particular embodiments, the catalyst is (R)-(−)-2-methyl-CBS-oxazoborolidine.

In certain embodiments, the reducing agent is selected from the group consisting of borane.dimethylsulfide complex, borane tetrahydrofuran complex, borane trimethylamine complex, borane triethylamine complex, borane N,N-diethylaniline complex, catecholborane, hydrogen gas, formic acid/triethylamine, and 2-propanol. In particular embodiments, the reducing agent is borane.dimethylsulfide complex.

In certain embodiments, the solvent is selected from the group consisting of an ether (e.g., diethyl ether, methyl tert-butyl ether, tetrahydrofuran, 2-methyltetrahydrofuran, 1,4-dioxane, dimethoxyethane), a hydrocarbon solvent (e.g., n-hexane, n-heptane), an aromatic hydrocarbon solvent (e.g., toluene, xylenes), an ester (e.g., ethyl acetate, isobutyl acetate, isopropyl acetate), a chlorinated solvent (e.g., dichloromethane), a nitrile (e.g., acetonitrile), and a combination thereof. In particular embodiments, the solvent is tetrahydrofuran.

In certain embodiments, the process is carried out at a temperature range of from about 100° C. or less. In certain embodiments, the process is carried out at a temperature range of from about −20° C. to about 100° C. In particular embodiments, the process is carried out at a temperature range of from about 0° C. to about 10° C.

In some embodiments, disclosed herein is a process for preparing a compound of formula XIV:

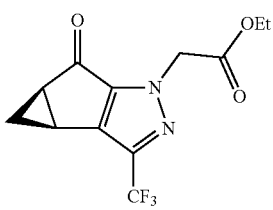

XIV or a co-crystal, solvate, salt, or combination thereof, comprising:

(c) kinetically resolving a compound of formula XVII:

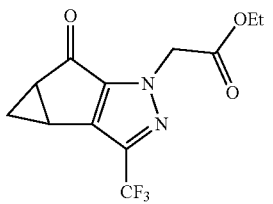

XVII or a co-crystal, solvate, or combination thereof, with:
a catalyst,
a reducing agent, and
a solvent,
to provide a first mixture comprising the compound of formula XIV, or a co-crystal, solvate, or combination thereof, and a compound of formula XVIII:

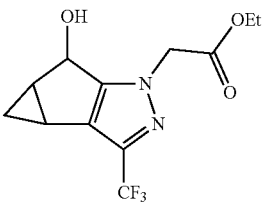

XVIII or a co-crystal, solvate, salt or combination thereof;

(b) combining the first mixture with an alcohol derivatizing agent (e.g., succinic anhydride), a catalyst (e.g., DMAP), and a solvent to produce a second mixture; and (c) extracting the second mixture with a base and solvent to provide the compound of formula XIV, or a co-crystal, solvate, salt, or combination thereof.

In some embodiments, step (c) provides the compound of formula XIV, or a co-crystal, solvate, salt, or combination thereof, substantially free of the compound of formula XVIII, or a co-crystal, solvate, or combination thereof. In some embodiments, step (c) removes 99-95% of the compound of formula XVIII, or a co-crystal, solvate, salt, or combination thereof. In some embodiments, step (c) removes 95-85% of the compound of formula XVIII, or a co-crystal, solvate, salt, or combination thereof. In some embodiments, step (c) removes 85-75% of the compound of formula XVIII, or a co-crystal, solvate, salt, or combination thereof.

In certain embodiments, the solvent used in the resolving step step (a) is selected from the group consisting of an ether (e.g., diethyl ether, methyl tert-butyl ether, tetrahydrofuran, 2-methyltetrahydrofuran, 1,4-dioxane, dimethoxyethane), a hydrocarbon solvent (e.g., n-hexane, n-heptane), an aromatic hydrocarbon solvent (e.g., toluene, xylenes), an ester (e.g., ethyl acetate, isobutyl acetate, isopropyl acetate), a chlorinated solvent (e.g., dichloromethane), a nitrile (e.g., acetonitrile), a ketone (e.g., acetone), a polar aprotic solvent (e.g., N,N-dimethylformamide, N,N-dimethylacetamide, N-methylpyrrolidinone), and a combination thereof. In particular embodiments, the solvent is tetrahydrofuran.

In certain embodiments, the catalyst for the resolving step (a) is selected from the group consisting of (R)-(+)-o-tolyl-CBS-oxazaborolidine, (R)-(+)-2-butyl-CBS-oxazaborolidine, (R)-(−)-2-methyl-CBS-oxazoborolidine trans-RuCl$_2$[(R)-xylbinap]-[(R)-diapen], RuBr$_2$[(R)-BINAP], [RuCl(PhH)(R)-BINAP)]Cl, RuChp-cymene)[(S,S)-Ts-DPEN], RuChmesitylene)[(S,S)-Ts-DPEN], RuBF$_4$(p-cymene)[(S,S)-Ts-DPEN], RuChp-cymene)[(S,S)-Fs-DPEN], RuCl(p-cymene)[(R,R)-Teth-Ts-DPEN], and Baker's yeast. In particular embodiments, the catalyst is (R)-(−)-2-methyl-CBS-oxazoborolidine.

In certain embodiments, the reducing agent for the resolving step (a) is selected from the group consisting of borane.dimethylsulfide complex, borane tetrahydrofuran complex, borane trimethylamine complex, borane triethylamine complex, borane N,N-diethylaniline complex, catecholborane, hydrogen gas, formic acid/triethylamine, and 2-propanol. In particular embodiments, the reducing agent is borane.dimethylsulfide complex.

In some embodiments, the process of the resolving step (a) is carried out at a temperature range of from about 100° C. or less. In certain embodiments, the process of step (a) is carried out at a temperature range of from about −40° C. to about 100° C. In particular embodiments, the process of step (a) is carried out at a temperature range of from about 10° C. to about 60° C.

In certain embodiments, the process of step (a) is carried out at a temperature range of from about −20° C. to about 100° C. In particular embodiments, the process of step (a) is carried out at a temperature range of from about 0° C. to about 10° C.

In certain embodiments, the alcohol derivatizing agent used in step (b) is selected from the group consisting of succinic anhydride, maleic anhydride, phthalic anhydride, glutaric anhydride, and diglycolic anhydride. In particular embodiments, the alcohol derivatizing agent is succinic anhydride.

In certain embodiments, the catalyst used in step (b) is selected from the group consisting of 4-(dimethylamino)pyridine, diethylaniline, scandium triflate, silica sulfuric acid, and N-methylimidazole. In particular embodiments, the catalyst is 4-(dimethylamino)pyridine (DMAP).

In certain embodiments, the extraction base used in step (c) is selected from the group consisting of potassium carbonate, potassium hydrogen carbonate, potassium hydroxide, sodium carbonate, sodium hydrogen carbonate, sodium hydroxide, and ammonium hydroxide. In particular embodiments, the extraction base is potassium carbonate.

In certain embodiments, the extraction solvent in step (c) is selected from the group consisting of an ether (e.g., diethyl ether, methyl tert-butyl ether, tetrahydrofuran, 2-methyltetrahydrofuran, 1,4-dioxane, dimethoxyethane), a hydrocarbon solvent (e.g., n-hexane, n-heptane), an aromatic hydrocarbon solvent (e.g., toluene, xylenes), an ester (e.g., ethyl acetate, isobutyl acetate, isopropyl acetate), a chlorinated solvent (e.g., dichloromethane), water and a combination thereof. In particular embodiments, the extraction solvent is tetrahydrofuran, methyl tert-butyl ether, and water.

In certain embodiments, step (b) and step (c) are carried out at a temperature range of from about 100° C. or less. In certain embodiments, step (b) and step (c) are carried out at a temperature range of from about −40° C. to about 100° C. In particular embodiments, step (b) and step (c) are carried out at a temperature range of from about −10° C. to about 60° C.

In some embodiments, a process for preparing a compound of formula XIV:

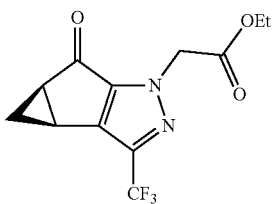

XIV or a co-crystal, solvate, or combination thereof is provided, comprising:
(a) oxidizing a compound of formula 5a:

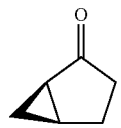

5a or a co-crystal, solvate, or combination thereof, with an oxidant, a base, and a solvent to provide a compound of formula 5b:

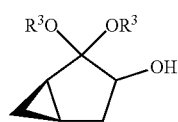

5b or a co-crystal, solvate, or combination thereof, wherein each $R^3$ is independently $C_{1-6}$ alkyl that is unsubstituted or substituted with one to five $C_{1-6}$ alkyl groups;

(b) further oxidizing the compound of formula 5b or a co-crystal, solvate, or combination thereof, with an oxidant, a base, and a solvent, to provide a compound of formula 5c:

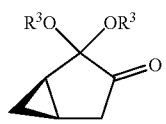

5c or a co-crystal, solvate, or combination thereof.
(c) combining the compound of formula 5c or a co-crystal, solvate, or combination thereof with a trifluoroacetylating agent and a lithium base in a solvent, to provide a compound of formula 3d:

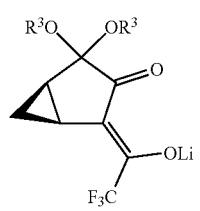

3d or a co-crystal, solvate, or combination thereof and
(d) combining the compound of formula 3d or a co-crystal, solvate, or combination thereof with ethyl hydrazinoacetate hydrochloride, an acid and optionally, an additive, to provide the compound of formula XIV, or a co-crystal, solvate, salt, or combination thereof.

In certain embodiments, the oxidant used in step (a) is selected from the group consisting of iodine, thianthrenium tetrafluoroborate, diacetoxyiodobenzene, and potassium iodide/platinum electrode. In particular embodiments, the oxidant used in step (a) is diacetoxyiodobenzene.

In certain embodiments, the base used in step (a) is selected from the group consisting of sodium hydroxide, lithium hydroxide, and potassium hydroxide. In particular embodiments, the base used in step (a) is potassium hydroxide.

In certain embodiments, the solvent used in step (a) is an alcohol (e.g., methanol, ethanol, 1-propanol, ethylene glycol). In particular embodiments, the solvent used in step (a) is methanol.

In certain embodiments, step (a) is carried out in the temperature range of from about 100° C. or less. In certain embodiments, step (a) is carried out in the temperature range of from about −20° C. to about 100° C. In particular embodiments, step (a) is carried out in the temperature range of from about −15° C. to about 30° C.

In certain embodiments, the oxidant used in step (b) is selected from the group consisting of dimethyl sulfoxide and an activating agent selected from the group consisting of cyanuric chloride, oxalyl chloride, dicyclohexylcarbodiimide, N,N'-diisopropylcarbodiimide, N-chlorosuccinimide, benzoic anhydride, methanesulfonic anhydride, tosic anhydride, triflic anhydride, methyl chloroglyoxylate, thionyl chloride, diphosgene, triphosgene, methanesulfonyl chloride, tosyl chloride, benzenesulfonyl chloride, trichloroacetonitrile, 2-chloro-1,2-dimethylimidazolinium chloride, polyphosphoric acid, $PCl_3$, triphenylphosphine dichloride, triphenylphosphine dibromide, $POCl_3$, phosphorous pentoxide, acetyl chloride, benzoyl chloride, acetyl bromide, phenyl dichlorophosphate, diphenyl chlorophosphate, diethyl chlorophosphate, and ethoxyacetylene, TEMPO and bleach, chromium trioxide, Dess-Martin periodinane, 2-iodoxybenzoic acid, and sulfur trioxide pyridine complex. In particular embodiments, the oxidant used in step (b) is dimethyl sulfoxide and oxalyl chloride.

In certain embodiments, the base used in step (b) is selected from the group consisting of diisopropylethylamine, tri-n-propylamine, triethylamine, pyridine, and 2,6-lutidine. In particular embodiments, the base used in step (b) is triethylamine.

In certain embodiments, the solvent used in step (b) is selected from the group consisting of a chlorinated solvent (e.g., dichloromethane, 1,2-dichloroethane), an aromatic hydrocarbon solvent (e.g., toluene), and a combination thereof. In particular embodiments, the solvent used in step (b) is dichloromethane.

In certain embodiments, step (b) is carried out in the temperature range of from about 50° C. or less. In certain embodiments, step (b) is carried out in the temperature range of from about −80° C. to about 50° C. In particular embodiments, step (b) is carried out in the temperature range of from about −60° C. to about −10° C.

In certain embodiments, $R^3$ is methyl, ethyl, or propyl. In some embodiments, $R^3$ is methyl.

In certain embodiments, the trifluoroacetylating agent used in step (c) is selected from the group consisting of trifluoroacetic anhydride, phenyltrifluoroacetate, methyl trifluoroacetate, ethyl trifluoroacetate, and trifluoroethyl trifluoroacetate. In particular embodiments, the trifluoroacetylating agent is ethyl trifluoroacetate.

In certain embodiments, the lithium base used in step (c) is selected from the group consisting of lithium hexamethyldisilazide, lithium diisopropylamine, lithium tetramethylpiperidide, lithium methoxide, lithium ethoxide, and lithium tert-butoxide. In particular embodiments, the lithium base is lithium hexamethyldisilazide.

In certain embodiments, the solvent used in step (c) is selected from the group consisting of an ether (e.g., diethyl ether, methyl tert-butyl ether, tetrahydrofuran, 2-methyltetrahydrofuran, 1,4-dioxane, dimethoxyethane), a hydrocarbon solvent (e.g., n-hexane, n-heptane), an aromatic hydrocarbon solvent (e.g., toluene, xylenes), a chlorinated solvent (e.g., dichloromethane), a polar aprotic solvent (e.g., N,N-dimethylformamide, N,N-dimethylacetamide, N-methylpyrrolidinone), a nitrile (e.g., acetonitrile), and a combination thereof. In particular embodiments, the solvent used in step (c) is tetrahydrofuran.

In certain embodiments, step (c) is carried out in the temperature range of from about 30° C. or less. In certain embodiments, step (c) is carried out in the temperature range of from about −30° C. to about 30° C. In particular embodiments, step (c) is carried out in the temperature range of from about −80° C. to about 60° C. In particular embodiments, step (c) is carried out in the temperature range of from about −80° C. to about 30° C.

In certain embodiments, step (c) is carried out in the temperature range of from about 60° C. or less. In certain embodiments, step (c) is carried out in the temperature range of from about −80° C. to about 60° C. In particular embodiments, step (c) is carried out in the temperature range of from about −30° C. to about 30° C.

In certain embodiments, the acid used in step (d) is selected from the group consisting of hydrochloric acid, sulfuric acid, trifluoroacetic acid, hydrogen bromide, methanesulfonic acid, p-toluenesulfonic acid, magnesium chloride, zinc chloride, scandium triflate, and bismuth chloride. In particular embodiments, the acid is sulfuric acid.

In certain embodiments, step (d) comprises an additive.

In certain embodiments, the additive used in step (d) is selected from the group consisting of ethyl orthoacetate, ethyl orthoformate, molecular sieves, and Dean-Stark distillation. In particular embodiments, the additive is ethyl orthoformate.

In certain embodiments, the solvent used in step (d) is selected from the group consisting of an ether (e.g., diethyl ether, methyl tert-butyl ether, tetrahydrofuran, 2-methyltetrahydrofuran, 1,4-dioxane), a ketone (e.g., acetone), a polar aprotic solvent (e.g., N,N-dimethylformamide, N,N-dimethylacetamide, N-methylpyrrolidinone), an aromatic hydrocarbon solvent (e.g., toluene, benzene, xylenes), an ester (e.g., ethyl acetate, isopropyl acetate), an alcohol (e.g., methanol, ethanol, isopropanol, ethylene glycol, propylene glycol), a chlorinated solvent (e.g., dichloromethane), and a combination thereof. In particular embodiments, the solvent used in step (d) is ethanol.

In certain embodiments, step (d) is carried out in the temperature range of from about 60° C. or less. In certain embodiments, step (d) is carried out in the temperature range of from about −20° C. to about 60° C. In particular embodiments, step (d) is carried out in the temperature range of from about −20° C. to about 20° C.

In some embodiments, a process for preparing a compound of formula XV:

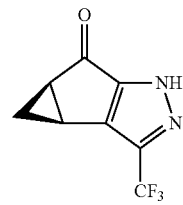

XV or a co-crystal, solvate, salt, or combination thereof is provided, comprising combining a compound of formula 3d-02:

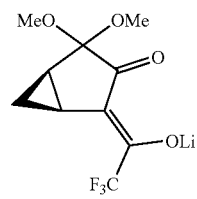

3d-02 or a co-crystal, solvate, or combination thereof, with a hydrazine source and a solvent to provide a compound of formula XV or a co-crystal, solvate, salt, or combination thereof.

In certain embodiments, the hydrazine source is selected from the group consisting of hydrazine sulfate, hydrazine hemisulfate, hydrazine hydrochloride, hydrazine dihydrochloride, hydrazine acetate, hydrazine hydrobromide, hydrazine hydrate, and anhydrous hydrazine. In particular embodiments, the hydrazine source is hydrazine sulfate.

In certain embodiments, the solvent is selected from the group consisting of alcohols (e.g., methanol, ethanol, ethylene glycol), ethers (e.g., diethyl ether, methyl tert-butyl ether, tetrahydrofuran, 2-methyltetrahydrofuran, 1,4-dioxane), polar aprotic solvents (e.g., acetone, N,N-dimethylformamide, N,N-dimethylacetamide, N-methylpyrrolidinone), aromatic solvents (e.g., benzene, toluene, xylenes), chlorinated solvents (e.g., dichloromethane), and a combination thereof. In particular embodiments, the solvent is ethylene glycol.

In certain embodiments, the process is carried out at a temperature range of from about 80° C. or less. In certain embodiments, the process is carried out at a temperature range of from about 0° C. to about 80° C. In particular embodiments, the process is carried out at a temperature range of from about 20° C. to about 60° C. In particular embodiments, the process is carried out at a temperature of about 40° C.

In some embodiments, a process for preparing a compound of formula XV:

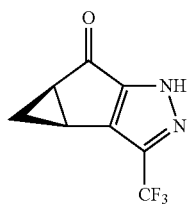

XV or a co-crystal, solvate, salt, or combination thereof is provided, comprising combining a compound of formula 3k:

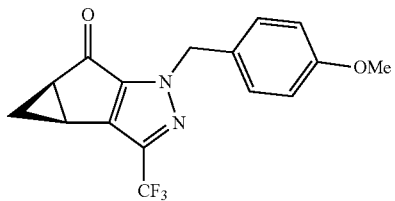

3k or a co-crystal, solvate, salt, or combination thereof, with a reagent to provide the compound of formula XV, or a co-crystal, solvate, salt, or combination thereof.

In certain embodiments, the reagent is selected from the group consisting of 2,3-dichloro-5,6-dicyano-1,4-benzoquinone (DDQ), ceric ammonium nitrate, hydrogen chloride, hydrogen bromide, methanesulfonic acid (MsOH), triflic acid (TfOH), trifluoroacetic acid (TFA), Pd/C (with H$_2$, NH$_4$HCO$_2$, or Et$_3$SiH), BCl$_3$, BBr$_3$, and lithium naphthalenide. In particular embodiments, the reagent is trifluoroacetic acid.

In certain embodiments, the process is carried out at a temperature range of from about 120° C. or less. In certain embodiments, the process is carried out at a temperature range of from about 0° C. to about 120° C. In particular embodiments, the process is carried out at a temperature range of from about 40° C. to about 80° C.

In some embodiments, a process for preparing a compound of formula 3k:

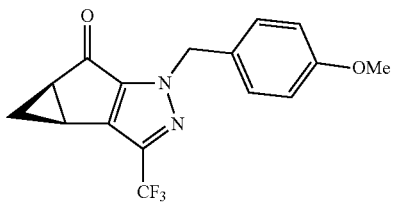

3k or a co-crystal, solvate, salt, or combination thereof is provided, comprising combining a compound of formula 3j:

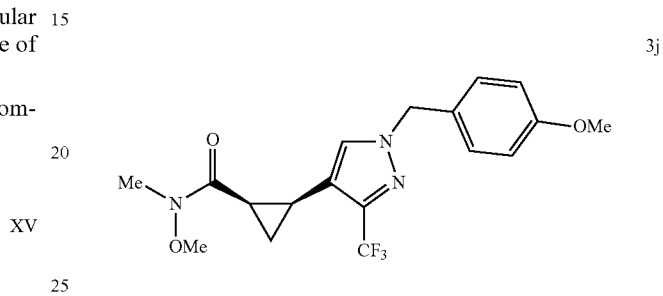

3j or a co-crystal, solvate, salt, or combination thereof, with a base and a solvent, to provide the compound of formula 3k, or a co-crystal, solvate, salt, or combination thereof.

In certain embodiments, the base is selected from the group consisting of lithium diisopropylamide, 2,2,6,6-tetramethylpiperidinylmagnesium chloride lithium chloride complex, n-butyllithium, phenyllithium, phenylmagnesium chloride, isopropylmagnesium chloride lithium chloride complex, sec-butylmagnesium chloride lithium chloride complex, n-butyllithium lithium N,N-dimethylaminoethanol complex, and mesityllithium disilazide bases (e.g., lithium hexamethyldisilazide, sodium hexamethyldisilazide, potassium hexamethyldisilazide). In particular embodiments, the base is lithium diisopropylamide.

In certain embodiments, the solvent is selected from the group consisting of ethers (e.g., diethyl ether, methyl tert-butyl ether, tetrahydrofuran, 2-methyltetrahydrofuran, 1,4-dioxane), aromatic solvents (e.g., benzene, toluene, xylenes), and a combination thereof. In particular embodiments, the solvent is tetrahydrofuran.

In certain embodiments, the process is carried out at a temperature range of from about 50° C. or less. In certain embodiments, the process is carried out at a temperature range of from about −80° C. to about 50° C. In particular embodiments, the process is carried out at a temperature range of from about −80° C. to about −20° C.

In some embodiments, a process for preparing a compound of formula 3j:

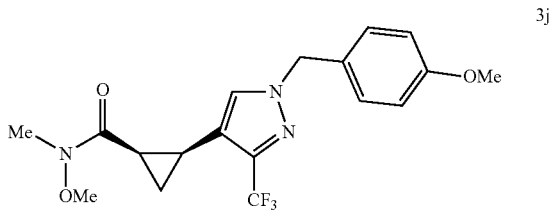 [SMILES: COc1ccc(Cn2cc([C@H]3C[C@H]3C(=O)N(C)OC)c(C(F)(F)F)n2)cc1]

3j or a co-crystal, solvate, salt, or combination thereof is provided, comprising combining a compound of formula 3f:

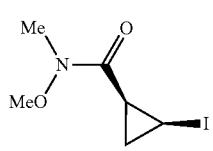

3f or a co-crystal, solvate, salt, or combination thereof, with a compound of formula 3i:

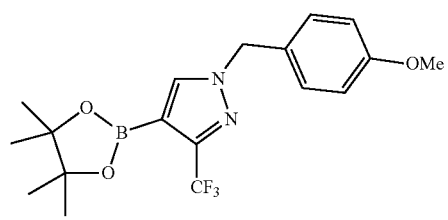

3i or a co-crystal, solvate, salt, or combination thereof, a base, a solvent, and a catalyst, to provide the compound of formula 3j, or a co-crystal, solvate, salt, or combination thereof.

In certain embodiments, the base is selected from the group consisting of cesium fluoride, sodium bicarbonate, potassium phosphate dibasic, sodium carbonate, potassium carbonate, potassium phosphate tribasic, sodium hydroxide, and potassium hydroxide. In particular embodiments, the base is cesium fluoride.

In certain embodiments, the solvent is selected from the group consisting of combinations of water and ethers (e.g., diethyl ether, 1,4-dioxane, 2-methyltetrahydrofuran, dimethoxyethane), hydrocarbon solvents (e.g., toluene, xylenes), dimethylformamide, esters (e.g., isopropyl acetate, isobutyl acetate), and a combination thereof. In particular embodiments, the solvent is dimethylformamide.

In certain embodiments, the catalyst is selected from the group consisting of palladium catalysts (e.g., palladium(II) acetate/triphenylphosphine, bis(di-tert-butyl(4-dimethylaminophenyl)phosphine) dichloropalladium(II), bis[(dicyclohexyl)(4-dimethylaminophenyl)phosphine]palladium(II) chloride, dichlorobis(triphenylphosphine)palladium(II), [1,1'-bis(diphenylphosphino) ferrocene]dichloropalladium (II)). In particular embodiments, the catalyst is palladium(II) acetate/triphenylphosphine.

In certain embodiments, the process is carried out at a temperature range of from about 120° C. or less. In certain embodiments, the process is carried out at a temperature range of from about 20° C. to about 120° C. In particular embodiments, the process is carried out at a temperature range of from about 40° C. to about 100° C.

In some embodiments, a process for preparing a compound of formula 3i-1:

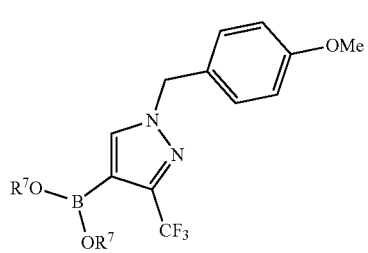

3i-1 or a co-crystal, solvate, salt, or combination thereof, is provided, comprising combining a compound of formula 3h:

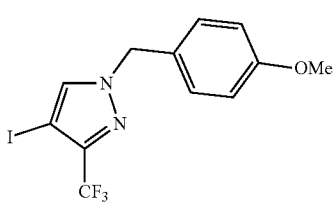

3h or a co-crystal, solvate, salt, or combination thereof, with a borylating reagent, a solvent and, a catalyst, to provide the compound of formula 3i-1, or a co-crystal, solvate, salt, or combination thereof, wherein each $R^7$ is independently H, alkyl, or aryl, or both $R^7$ and the atoms to which they are attached form a 5-6 membered heterocyclyl, wherein the 5-6 membered heterocyclyl is optionally substituted with 1-5 $C_{1-3}$ alkyl.

In certain embodiments, both $R^7$ and the atoms to which they are attached form a 5-membered heterocyclyl optionally substituted with 1-5 $C_{1-3}$ alkyl. In certain embodiments, both $R^7$ and the atoms to which they are attached form a 5-membered heterocyclyl substituted with 1-4 $C_{1-3}$ alkyl. In certain embodiments, both $R^7$ and the atoms to which they are attached form a 5-membered heterocyclyl substituted with four methyl groups. In particular embodiments, both $R^7$ and the atoms to which they are attached form pinacolboranyl.

In certain embodiments, the compound of formula 3i-1 is a compound of formula 3i:

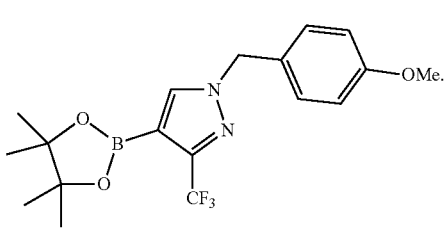

3i

In certain embodiments, the borylating reagent is selected from the group consisting of Bis(pinacolato)diboron, Bis (neopentyl glycolato)diboron, tetrahydroxydiboron, bis (hexylene glycolato)diboron, and bis(catecholato)diboron. In particular embodiments, the borylating reagent is Bis (pinacolato)diboron.

In certain embodiments, the solvent is selected from the group consisting of ethers (e.g., diethyl ether, methyl tert-butyl ether, tetrahydrofuran, 2-methyltetrahydrofuran), polar aprotic solvents (e.g., N,N-dimethylacetamide, N-methylpyrrolidinone), aromatic solvents (e.g., benzene, toluene, xylenes), chlorinated solvents (e.g., dichloromethane), alcohols (e.g., methanol, ethanol, isopropanol), esters (e.g., ethyl acetate, isopropyl acetate), and a combination thereof. In particular embodiments, the solvent is dioxane and N,N-dimethylformamide.

In certain embodiments, the catalyst is selected from the group consisting of palladium catalysts (e.g., [1,1'-bis(diphenylphosphino)ferrocene]dichloropalladium(11), bis(di-tert-butyl(4-dimethylaminophenyl)phosphine) dichloropalladium(II), bis[(dicyclohexyl)(4-dimethylaminophenyl)phosphine]palladium(II) chloride, dichlorobis(triphenylphosphine)palladium(II), [1,1'-bis(diphenylphosphino)ferrocene]dichloropalladium(II)). In particular embodiments, the catalyst is [1 P-bis(diphenyphosphino)ferrocene]dichloropalladium(II).

In certain embodiments, the process is carried out at a temperature range of from about 130° C. or less. In certain embodiments, the process is carried out at a temperature range of from about 10° C. to about 130° C. In particular embodiments, the process is carried out at a temperature range of from about 80° C. to about 110° C.

In some embodiments, a process for preparing a compound of formula 3i-1:

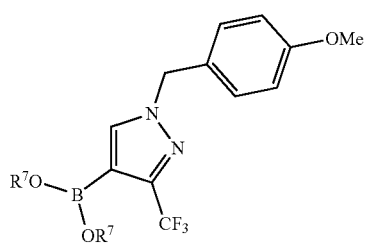

3i-1 or a co-crystal, solvate, salt, or combination thereof, is provided, comprising combining a compound of formula 3h:

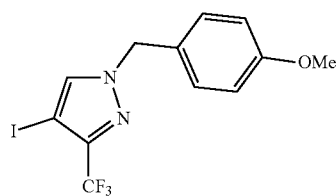

3h or a co-crystal, solvate, salt, or combination thereof, with a borylating reagent, an organometallic reagent and a solvent, to provide the compound of formula 3i-1, or a co-crystal, solvate, salt, or combination thereof, wherein each $R^7$ is independently H, alkyl, or aryl, or both $R^7$ and the atoms to which they are attached form a 5-6 membered heterocyclyl, wherein the 5-6 membered heterocyclyl is optionally substituted with 1-5 $C_{1-3}$ alkyl.

In certain embodiments, both $R^7$ and the atoms to which they are attached form a 5-membered heterocyclyl optionally substituted with 1-5 $C_{1-3}$ alkyl. In certain embodiments, both $R^7$ and the atoms to which they are attached form a 5-membered heterocyclyl substituted with 1-4 $C_{1-3}$ alkyl. In certain embodiments, both $R^7$ and the atoms to which they are attached form a 5-membered heterocyclyl substituted with four methyl groups. In particular embodiments, both both $R^7$ and the atoms to which they are attached form pinacolboranyl.

In certain embodiments, the compound of formula 3i-1 is a compound of formula 3i:

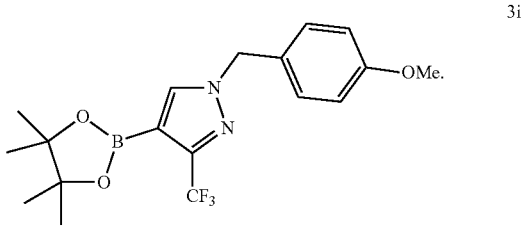 [SMILES: COc1ccc(Cn2cc(B3OC(C)(C)C(C)(C)O3)c(C(F)(F)F)n2)cc1]

3i

In certain embodiments, the borylating reagent is selected from the group consisting of trialkyl borates (e.g., trimethyl borate, triethyl borate), pinacolborane, 2-isopropoxy-4,4,5,5-tetramethyl-1,3,2-dioxaborolane, 2-methoxy-4,4,5,5-tetramethyl-1,3,2-dioxaboralane, B-catecholborane, and 2-bromo-1,3,2-benzodioxaborole. In particular embodiments, the borylating reagent is 2-isopropoxy-4,4,5,5-tetramethyl-1,3,2-dioxaborolane.

In certain embodiments, the organometallic reagent is selected from the group consisting of lithium metal, magnesium metal, isopropylmagnesium chloride, n-butyllithium, s-butylmagnesium chloride lithium chloride complex, tert-butylmagnesium chloride, and isopropylmagnesium chloride lithium chloride complex. In particular embodiments, the organometallic reagent is isopropylmagnesium chloride.

In certain embodiments, the solvent is selected from the group consisting of ethers (e.g., diethyl ether, 1,4-dioxane, tetrahydrofuran, 2-methyltetrahydrofuran, dimethoxyethane), hydrocarbon solvents (e.g., n-hexane, n-heptane, toluene, xylenes), and a combination thereof. In particular embodiments, the solvent is tetrahydrofuran.

In certain embodiments, the process is carried out at a temperature range of from about 40° C. or less. In certain embodiments, the process is carried out at a temperature range of from about −80° C. to about 40° C. In particular embodiments, the process is carried out at a temperature range of from about −20° C. to about 20° C.

In some embodiments, a process for preparing a compound of formula 3h:

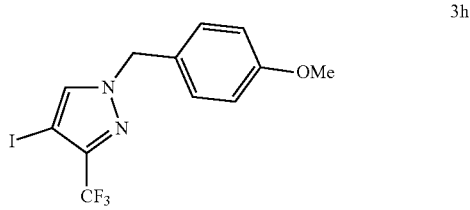 [SMILES: COc1ccc(Cn2cc(I)c(C(F)(F)F)n2)cc1]

3h or a co-crystal, solvate, salt, or combination thereof, is provided, comprising combining a compound of formula 3h:

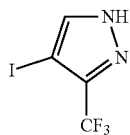

3g or a co-crystal, solvate, salt, or combination thereof, with an alkylating agent, a base and a solvent, to provide the compound of formula 3h, or a co-crystal, solvate, salt, or combination thereof.

In certain embodiments, the alkylating agent is selected from the group consisting of 4-methoxybenzyl chloride, 4-methoxybenzyl bromide, 4-methoxybenzyl-2,2,2-trichloroacetimidate, and (4-methoxybenzyloxy)-4-methylquinoline. In particular embodiments, the alkylating agent is 4-methoxybenzyl chloride.

In certain embodiments, the base is selected from the group consisting of tertiary amines (e.g., triethylamine, tri-n-propylamine, tri-n-butylamine, N-methylmorpholine, N-methylpyrrolidine, N-methylpiperidine), carbonate bases (e.g., sodium carbonate, potassium carbonate, cesium carbonate), alkoxide bases (e.g., sodium ethoxide, potassium ethoxide, sodium tert-butoxide), sodium hydride, and disilazide bases (e.g., lithium hexamethyldisilazide, sodium hexamethyldisilazide, potassium hexamethyldisilazide). In particular embodiments, the base is sodium hydride.

In certain embodiments, the solvent is selected from the group consisting of ethers (e.g., diethyl ether, methyl tert-butyl ether, tetrahydrofuran, 2-methyltetrahydrofuran, 1,4-dioxane), polar aprotic solvents (e.g., acetone, N,N-dimethylformamide, N,N-dimethylacetamide, N-methylpyrrolidinone), aromatic solvents (e.g., benzene, toluene, xylenes,), chlorinated solvents (e.g., dichloromethane), and a combination thereof. In particular embodiments, the solvent is dimethylformamide.

In certain embodiments, the process is carried out at a temperature range of from about 100° C. or less. In certain embodiments, the process is carried out at a temperature range of from about −20° C. to about 100° C. In particular embodiments, the process is carried out at a temperature range of from about 0° C. to about 40° C.

In some embodiments, a process for preparing a compound of formula 3f:

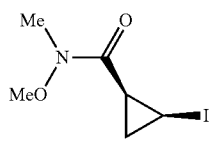

3f or a co-crystal, solvate, salt, or combination thereof, is provided, comprising amidating a compound of formula 3e:

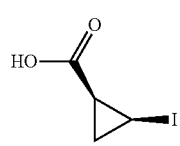

3e or a co-crystal, solvate, salt, or combination thereof, with a coupling agent and a solvent, to provide the compound of formula 3f, or a co-crystal, solvate, salt, or combination thereof.

In certain embodiments, the coupling agent is selected from the group consisting of carbonyl diimidazole, oxalyl chloride, thionyl chloride, dicyclohexylcarbodiimide, diisopropylcarbodiimide, 1-ethyl-3-(3-dimethylaminopropyl) carbodiimide, isobutyl chloroformate, hexafluorophosphate azabenzotriazole tetramethyl uronium (HATU), hexafluorophosphate benzotriazole tetramethyl uronium (HBTU), (benzotriazol-1-yloxy)tris(dimethylamino)phosphonium hexafluorophosphate (BOP), (Benzotriazol-1-yloxy)tripyrrolidinophosphonium hexafluorophosphate (PyBOP), tri-n-propylphosphonic anhydride, and 2-chloro-4,6-dimethoxy-1,3,5-triazine. In particular embodiments, the coupling agent is carbonyl diimidazole.

In certain embodiments, the solvent is selected from the group consisting of ethers (e.g., diethyl ether, methyl tert-butyl ether, tetrahydrofuran, 2-methyltetrahydrofuran, 1,4-dioxane), aromatic solvents (e.g., benzene, xylenes), polar aprotic solvents (e.g., N,N-dimethylformamide, N,N-dimethylacetamide, N-methylpyrrolidinone), dichloromethane, and a combination thereof. In particular embodiments, the solvent is tetrahydrofuran.

In certain embodiments, the process is carried out at a temperature range of from about 120° C. or less. In certain embodiments, the process is carried out at a temperature range of from about −20° C. to about 120° C. In particular embodiments, the process is carried out at a temperature range of from about 0° C. to about 40° C.

In some embodiments, a process for preparing a compound of formula 3n-1:

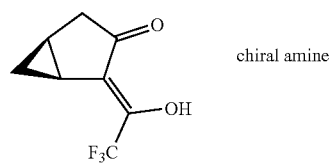

3n-1 chiral amine is provided, comprising
(a) combining a compound of formula 3a:

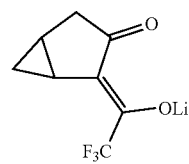

3a or a co-crystal, solvate, or combination thereof, with an acid to to provide a compound of formula 3l

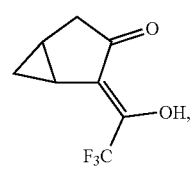

3l or a co-crystal, solvate, or combination thereof; and
(b) combining the compound of formula 3l or a co-crystal, solvate, or combination thereof, with a chiral amine and a solvent, to provide the compound of formula 3n-1.

In certain embodiments, the acid used in step (a) is selected from the group consisting of hydrochloric acid, sulfuric acid, hydrobromic acid, methanesulfonic acid, toluenesulfonic acid, benzenesulfonic acid, and trifluoroacetic acid. In particular embodiments, the acid used in step (a) is hydrochloric acid or sulfuric acid. In particular embodiments, the acid used in step (a) is hydrochloric acid. In particular embodiments, the acid used in step (a) is sulfuric acid.

In certain embodiments, the chiral amine used in step (b) is selected from the group consisting of quinine, (S)-(−)-α-methylbenzylamine, (R)-(+)-α-methylbenzylamine, (S)-(+)-2-phenylglycinol, (R)-(−)-2-phenylglycinol, (S)-valinol, (R)-valinol, quinidine, quinine, brucine, cinchonine, cinchonidine, (+)-dehydroabietylamine, (1R,2S)-(−)-ephedrine, (1 S,2R)-(+)-ephedrine hemihydrate, (1 S,2R)-(−)-cis-1-amino-2-indanol, (1R,2S)-(−)-cis-1-amino-2-indanol, (S)-(+)-1-cyclohexylethylamine, (R)-(−)-1-cyclohexylethylamine, (S)-(−)-1-(1-naphthyl)ethylamine, (R)-(+)-1-(1-napthyl)ethylamine, (S)-(+)-2-amino-1-butanol, (R)-(−)-2-amino-1-butanol, (S)-2-aminohexane, (R)-2-aminohexane, (R)-phenylglycine, and (R)-(1-napthyl)ethylamine. In particular embodiments, the chiral amine is quinine.

In certain embodiments, the solvent used in step (b) is selected from the group consisting of ethers (e.g., diethyl ether, methyl tert-butyl ether, tetrahydrofuran, 2-methyltetrahydrofuran, 1,4-dioxane), polar aprotic solvents (e.g., acetone, N,N-dimethylformamide, N,N-dimethylacetamide, N-methylpyrrolidinone), aromatic solvents (e.g., benzene, toluene, xylenes), chlorinated solvents (e.g., dichloromethane), alcohols (e.g., methanol, ethanol, isopropanol), esters (e.g., ethyl acetate, isopropyl acetate), and a combination thereof. In particular embodiments, the solvent used in e.g., step (b) is acetone.

In certain embodiments, the process is carried out at a temperature range of from about 80° C. or less. In certain embodiments, the process is carried out at a temperature range of from about −30° C. to about 80° C. In particular embodiments, the process is carried out at a temperature range of from about −20° C. to about 60° C.

In some embodiments, a process for preparing a compound of formula 5h:

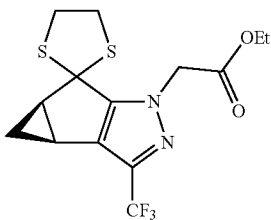

5h or a co-crystal, solvate, or combination thereof is provided, comprising:
(a) combining a compound of formula 5b-02:

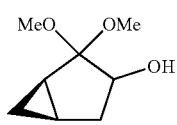

5b-02 or a co-crystal, solvate, or combination thereof, with 1,2-ethanedithiol, a solvent, and a promoter, to provide a compound of formula 5d-01:

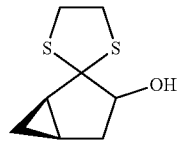

5d-01 or a co-crystal, solvate, or combination thereof;
(b) oxidizing the compound of formula 5d-01 or a co-crystal, solvate, or combination thereof, with an oxidant, a base, and a solvent, to provide a compound of formula 5e:

5e or a co-crystal, solvate, or combination thereof;
(c) combining the compound of formula 5e or a co-crystal, solvate, or combination thereof with a trifluoroacetylating agent, a base, and a solvent, to provide a compound of formula 5f-1:

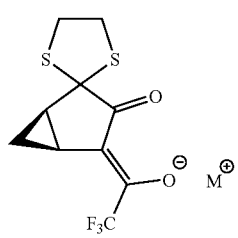

5f-1 or a co-crystal, solvate, or combination thereof, wherein M is selected from the group consisting of alkali metals (e.g., Li, Na, K, Mg, Ca), transition metals (e.g., Zn, Sr), aliphatic ammoniums (e.g., diisopropylammonium, dicyclohexylammonium, diethylammonium, triethylammonium), and aromatic ammoniums (e.g., pyridinium); and
(d) combining the compound of formula 5f-1 or a co-crystal, solvate, or combination thereof with ethyl hydrazinoacetate hydrochloride and an acid to provide the compound of formula 5h or a co-crystal, solvate, salt, or combination thereof.

In certain embodiments, the promoter used in step (a) is selected from the group consisting of p-toluenesulfonic acid, copper(II) dodecyl sulfate, ytterbium(III) triflate, yttrium (III) triflate, bismuth(III) triflate, bismuth(III) chloride, tungstophosphoric acid, perchloric acid, praseodymium triflate, hafnium(IV) triflate, iron(III) chloride, hydrogen chloride, p-dodecyl benzenesulfonic acid, $BiCl_3$, $BF_3$—HOAc, $BF_3.OEt_2$, $BF_3.OMe_2$, $BF_3.THF$, $BF_3.OBu_2$, $BF_3.MeOH$, $BF_3.Me_2S$, $BF_3.PhOH$, and $BF_3.2H_2O$. In particular embodiments, the promoter used in step (a) is $BiCl_3$.

In certain embodiments, the solvent used in step (a) is ethers (e.g., diethyl ether, methyl tert-butyl ether, tetrahydrofuran, 2-methyltetrahydrofuran, 1,4-dioxane,), polar aprotic solvents (e.g., acetone, N,N-dimethylformamide, N,N-dimethylacetamide, N-methylpyrrolidinone), aromatic solvents (e.g., benzene, toluene, xylenes), chlorinated solvents (e.g., dichloromethane), esters (e.g., ethyl acetate, isopropyl acetate), a nitrile (e.g., acetonitrile) and a combination thereof. In particular embodiments, the solvent used in step (a) is acetonitrile.

In certain embodiments, step (a) is carried out in the temperature range of from about 100° C. or less. In certain embodiments, step (a) is carried out in the temperature range of from about −20° C. to about 100° C. In particular embodiments, step (a) is carried out in the temperature range of from about 0° C. to about 80° C.

In certain embodiments, the oxidant used in step (b) is selected from the group consisting of dimethyl sulfoxide (DMSO) and an activating agent (e.g., $SO_3$.pyridine complex, oxalyl chloride, cyanuric chloride, dicyclohexylcarbodiimide (DCC), N, N'-Diisopropylcarbodiimide (DIC), N-chlorosuccinimide (NCS), benzoic anhydride, methanesulfonic anhydride, tosic anhydride, triflic anhydride, methyl chloroglyoxylate, thionyl chloride, diphosgene, triphosgene, methanesulfonyl chloride, tosyl chloride, benzenesulfonyl chloride, trichloroacetonitrile, 2-chloro-1,2-dimethylimidazolinium chloride, polyphosphoric acid (PPA), $PCl_3$, $P_2O_5$, triphenylphosphine dichloride ($TPP.Cl_2$), triphenylphosphine dibromide ($TPP.Br_2$), $POCl_3$, acetyl chloride, benzoyl chloride, acetyl bromide, phenyl dichlorophosphate, diphenyl chlorophosphate, diethyl chlorophosphate, and ethoxyacetylene), (2,2,6,6-tetramethylpiperidin-1-yl)oxyl/bleach (TEMPO/bleach), chromium trioxide, Dess-Martin periodinane, and 2-iodoxybenzoic acid. In particular embodiments, the oxidant used in step (b) is DMSO and $SO_3$.pyridine complex.

In certain embodiments, the base used in step (b) is selected from the group consisting of aliphatic amines (e.g., triethylamine, diisopropylethylamine, tri-n-propylamine), and aromatic amines (e.g., pyridine, 2,6-lutidine). In particular embodiments, the base used in step (b) is triethylamine.

In certain embodiments, the solvent used in step (b) is dichloromethane, dichloroethane, toluene, DMSO, ethyl acetate, and a combination thereof. In particular embodiments, the solvent used in step (b) is dichloromethane.

In certain embodiments, step (b) is carried out in the temperature range of from about 80° C. or less. In certain embodiments, step (b) is carried out in the temperature range of from about −80° C. to about 80° C. In particular embodiments, step (a) is carried out in the temperature range of from about −60° C. to about 60° C.

In certain embodiments, M is selected from the group consisting of alkali metals (e.g., Li, Na, K, Mg, Ca), transition metals (e.g., Zn), aliphatic ammonium (e.g., diisopropylammonium, dicyclohexylammonium, diethylammonium, triethylammonium), aromatic ammonium (e.g., pyridinium). In certain embodiments, M is an aliphatic ammonium. In particular embodiments, M is diisopropylammonium.

In certain embodiments, the trifluoroacetylating agent used in step (c) is selected from the group consisting of ethyl trifluoroacetate, trifluoroacetic anhydride, phenyltrifluoroacetate, alkyl trifluoroacetates, and 1-(trifluoroacetyl)imidazole. In particular embodiments, the trifluoroacetylating agent is ethyl trifluoroacetate.

In certain embodiments, the base used in step (c) is selected from the group consisting of lithium hexamethyldisilazide, lithium diisopropylamine, lithium tetramethylpiperidide, lithium methoxide, lithium ethoxide, lithium tert-butoxide, alkali metal alkoxides, and alkali metal amides. In particular embodiments, the lithium base is lithium hexamethyldisilazide.

In certain embodiments, the salt used in step (c) is selected from the group consisting of alkali metals (e.g., Na, K, Mg, Ca), transition metals (e.g., Zn, aliphatic ammoniums (e.g., diisopropylammonium, dicyclohexylammonium, diethylammonium, triethylammonium), and aromatic ammoniums (e.g., pyridinium). In particular embodiments, the salt is diisopropylammonium.

In certain embodiments, the solvent used in step (c) is selected from the group consisting of ethers (e.g., diethyl ether, 1,4-dioxane, tetrahydrofuran, 2-methyltetrahydrofuran, dimethoxyethane, methyl tert-butyl ether), hydrocarbon solvents (e.g., n-hexane, n-heptane, toluene, xylenes), dichloromethane, acetonitrile, and a combination thereof. In particular embodiments, the solvent used in step (c) is tetrahydrofuran.

In certain embodiments, the acid used in step (d) is selected from the group consisting of hydrochloric acid, sulfuric acid, trifluoroacetic acid, hydrogen bromide, methanesulfonic acid, p-toluenesulfonic acid, benzenesulfonic acid, trifluoromethanesulfonic acid, and $BF_3.2HOAc$. In particular embodiments, the acid is sulfuric acid. In particular embodiments, the acid is hydrochloric acid.

In certain embodiments, the solvent used in step (d) is selected from the group consisting of ethanol, esters (e.g., ethyl acetate, isopropyl acetate), ether (e.g., tetrahydrofuran, 2-methyl tetrahydrofuran, 1,4-dioxane), aprotic solvent (e.g., acetonitrile, N,N-dimethylformamide, N,N-dimethylacetamide, N-methylpyrrolidinone), aromatic solvent (e.g., benzene, toluene, xylenes), chlorinated solvents (e.g., dichloromethane) and a combination thereof. In particular embodiments, the solvent used in step (d) is ethanol.

In certain embodiments, step (d) is carried out in the temperature range of from about 100° C. or less. In certain embodiments, step (d) is carried out in the temperature range of from about −20° C. to about 100° C. In particular embodiments, step (d) is carried out in the temperature range of from about 0° C. to about 40° C.

In some embodiments, a process for preparing a compound of formula 5h:

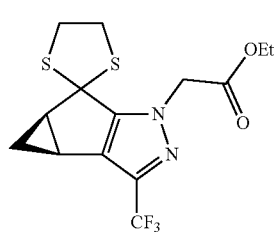

5h or a co-crystal, solvate, or combination thereof is provided, comprising:

(a) condensing a compound of formula 5f-1a:

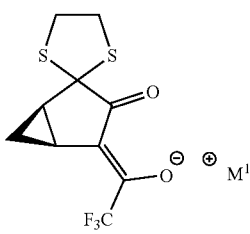

5f-1a or a co-crystal, solvate, or combination thereof, wherein $M^1$ is selected from the group consisting alkali metals (e.g., Li, Na, K, Mg, Ca), transition metals (e.g., Zn, Sr), aliphatic ammonium (e.g., diisopropylammonium, dicyclohexylammonium, diethylammonium, triethylammonium), aromatic ammonium (e.g., pyridinium), with a hydrazine derivative, a solvent, and a promoter, to provide a compound of formula 5g:

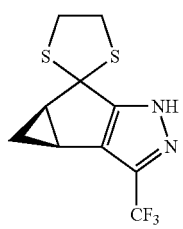

5g or a co-crystal, solvate, or combination thereof;

(b) alkylating the compound of formula 5g or a co-crystal, solvate, or combination thereof, with an alkylating agent, a base, a solvent, and optionally a phase transfer catalyst, to provide the compound of formula 5h or a co-crystal, solvate, salt, or combination thereof.

In certain embodiments, $M^1$ is selected from the group consisting of alkali metals (e.g., Li, Na, K, Mg, Ca), transition metals (e.g., Zn, Sr), aliphatic amines (e.g., diisopropylammonium, dicyclohexylamine, diethylamine, triethylamine), and aromatic ammonium (e.g., pyridinium). In particular embodiments, $M^1$ is an alkali metal. In particular embodiments, $M^1$ is Lithium.

In certain embodiments, the hydrazine derivative used in step (a) is selected from the group consisting of anhydrous hydrazine, hydrazine monohydrate, hydrazine acetate, hydrazine dihydrochloride, hydrazine hydrate (e.g., hydrazine monohydrochloride), hydrazine sulfate, hydrazine hemisulfate, and hydrazine monohydrobromide. In particular embodiments, the hydrazine derivative used in step (a) is hydrazine hydrate.

In certain embodiments, the promoter used in step (a) is selected from the group consisting of carboxylic acids (e.g., formic acid, propionic acid, butanoic acid, acetic acid), Brønsted acids (e.g., hydrogen chloride, hydrogen bromide, sulfuric acid, methanesulfonic acid, toluenesulfonic acid), and Lewis acids (e.g., zinc chloride, magnesium chloride, titanium tetrachloride). In certain embodiments, the promoter used in step (a) is a carboxylic acid. In particular embodiments, the promoter used in step (a) is acetic acid.

In certain embodiments, the solvent used in step (a) is selected from the group consisting of water, alcohols (e.g., methanol, ethanol, 1- or 2-propanol), ethers (e.g., diethyl ether, methyl tert-butyl ether, tetrahydrofuran, 2-methyltetrahydrofuran, 1,4-dioxane), polar aprotic solvents (e.g., N,N-dimethylformamide, N,N-dimethylacetamide, N-methylpyrrolidinone), aromatic solvents (e.g., benzene, toluene, xylenes), alkyl carboxylic acid (e.g., formic acid, acetic acid, propanic acid, butanoic acid) and a combination thereof. In particular embodiments, the solvent used in step (a) is water.

In certain embodiments, step (a) is carried out in the temperature range of from about 120° C. or less. In certain embodiments, step (a) is carried out in the temperature range of from about 0° C. to about 120° C. In particular embodiments, step (a) is carried out in the temperature range of from about 20° C. to about 100° C.

In certain embodiments, the alkylating agent used in step (b) is selected from the group consisting of ethyl bromoacetate, ethyl chloroacetate, ethyl iodoacetate, ethyl (methanesulfonyloxy)acetate, ethyl (p-tosyloxy)acetate, and ethyl (((trifluoromethyl)sulfonyl)oxy)acetate. In particular embodiments, the alkylating agent used in step (b) is ethyl bromoacetate.

In certain embodiments, the base used in step (b) is selected from the group consisting of tertiary amines (e.g., triethylamine, tri-n-propylamine, tri-n-butylamine, N-methylmorpholine, N-methylpyrrolidine, N-methylpiperidine), carbonate bases (e.g., sodium carbonate, potassium carbonate, cesium carbonate), alkoxide bases (e.g., sodium ethoxide, potassium ethoxide, sodium tert-butoxide, potassium tert-butoxide, lithium tert-butoxide), sodium hydride, disilazide bases (e.g., sodium hexamethyldisilazide, lithium hexamethyldisilazide, sodium hexamethylsilazide, potassium hexamethyldisilazide), and a combination thereof. In particular embodiments, the base used in step (b) is sodium hexamethyldisilazide.

In certain embodiments, the solvent used in step (b) is selected from the group consisting of ethers (e.g., diethyl ether, methyl tert-butyl ether, tetrahydrofuran, 2-methyltetrahydrofuran, 1,4-dioxane), polar aprotic solvents (e.g., N,N-dimethylformamide, N,N-dimethylacetamide, N-methylpyrrolidinone, acetonitrile), aromatic solvents (e.g., benzene, toluene, xylenes), chlorinated solvents (e.g., dichloromethane), esters (e.g., ethyl acetate, isopropyl acetate, n-butyl acetate), ketones (e.g., acetone, methyl ethyl ketone, methyl isobutyl ketone), alcohols (e.g., methanol, ethanol), water, and a combination thereof. In particular embodiments, the solvent used in step (b) is tetrahydrofuran.

In certain embodiments, step (b) comprises a phase transfer catalyst. In certain embodiments, the phase transfer catalyst used in step (b) is selected from the group consisting of tetra-alkylammonium salts. In particular embodiments, the tetra-alkylammonium salt is tetra-N-butylammonium hydrogensulfate and/or tetra-N-butylammonium iodide.

In certain embodiments, step (b) is carried out in the temperature range of from about 100° C. or less. In certain embodiments, step (b) is carried out in the temperature range of from about −20° C. to about 100° C. In particular embodiments, step (b) is carried out in the temperature range of from about −20° C. to about 50° C.

In some embodiments, a process for preparing a compound of formula 5e:

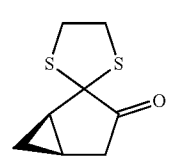

5e or a co-crystal, solvate, or combination thereof is provided, comprising:

(a) oxidizing a compound of formula 5a:

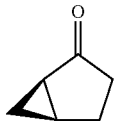

5a or a co-crystal, solvate, or combination thereof, with an oxidant, a base, and a solvent to provide a compound of formula 4a

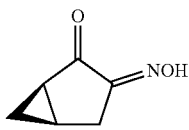

4a or a co-crystal, solvate, or combination thereof;

(b) combining the compound of formula 4a or a co-crystal, solvate, or combination thereof, with 1,2-ethanedithiol, a solvent, and a catalyst, to provide a compound of formula 5i:

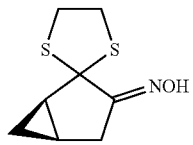

5i or a co-crystal, solvate, or combination thereof and (c) hydrolyzing the compound of formula 5i or a co-crystal, solvate, or combination thereof, with an acid, a solvent, and a promoter, to provide the compound of formula 5e or a co-crystal, solvate, salt, or combination thereof.

In certain embodiments, the oxidant used in step (a) is selected from the group consisting of alkyl nitrites (e.g., isopentyl nitrite, n-butyl nitrite, tert-butyl nitrite, ethyl nitrite), nitrite salts (e.g., sodium nitrite, potassium nitrite), nitrosyl chloride, nitrosyl sulfate, and nitrosonium salts (e.g., tetrafluoroborate, hydrogen sulfate). In certain embodiments, the oxidant used in step (a) is selected from the group consisting of isopentyl nitrite, n-butyl nitrite, tert-butyl nitrite, ethyl nitrite, sodium nitrite, potassium nitrite, nitrosyl chloride, nitrosyl sulfate, tetrafluoroborate, and hydrogen sulfate. In particular embodiments, the oxidant used in step (a) is tert-butyl nitrite.

In certain embodiments, the base used in step (a) is selected from the group consisting of alkali metal alkoxides (e.g., potassium tert-butoxide, sodium tert-butoxide, lithium tert-butoxide, sodium isopropoxide, sodium ethoxide, sodium methoxide), alkali metal hydrides (e.g., sodium hydride), amide bases (e.g., lithium tetramethylpiperidide, lithium hexamethyldisilazide), and phosphazenes. In certain embodiments, the base used in step (a) is selected from the group consisting of potassium tert-butoxide, sodium tert-butoxide, lithium tert-butoxide, sodium isopropoxide, sodium ethoxide, sodium methoxide, sodium hydride, lithium tetramethylpiperidide, lithium hexamethyldisilazide, and phosphazenes. In particular embodiments, the base used in step (a) is potassium tert-butoxide.

In certain embodiments, the solvent used in step (a) is selected from the group consisting of tetrahydrofuran, ethers (e.g., diethyl ether, methyl tert-butyl ether, cyclopentyl methyl ether, 2-methyltetrahydrofuran, 1,4-dioxane), polar aprotic solvents (e.g., N,N-dimethylformamide, N,N-dimethylacetamide, N-methylpyrrolidinone), halogenated solvents (e.g., dichloromethane), alcohols (methanol, ethanol, isopropanol), sulfolane, and a combination thereof. In certain embodiments, the solvent used in step (a) is selected from the group consisting of tetrahydrofuran, diethyl ether, methyl tert-butyl ether, cyclopentyl methyl ether, 2-methyltetrahydrofuran, 1,4-dioxane, N,N-dimethylformamide, N,N-dimethylacetamide, N-methylpyrrolidinone, dichloromethane, methanol, ethanol, isopropanol, sulfolane, and a combination thereof. In particular embodiments, the solvent used in step (a) is tetrahydrofuran.

In certain embodiments, step (a) is carried out in the temperature range of from about 70° C. or less. In certain embodiments, step (a) is carried out in the temperature range of from about −78° C. to about 70° C. In particular embodiments, step (a) is carried out in the temperature range of from about −10° C. to about 10° C.

In certain embodiments, the catalyst used in step (b) is selected from the group consisting of mineral acids (e.g., hydrochloric acid, hydrobromic acid, sulfuric acid), sulfonic acids (e.g., para-toluenesulfonic acid monohydrate, methanesulfonic acid, benzenesulfonic acid), trifluoroacetic acid, phosphoric acid, iodine, 1,3-dibromo-5,5-dimethylhydantoin, copper(II) dodecyl sulfate, ytterbium(III) triflate, yttrium(III) triflate, bismuth(111) bismuth(III) chloride, tungstophosphoric acid, perchloric acid, praseodymium triflate, hafnium(IV) triflate, iron(III) chloride, hydrogen chloride, p-dodecyl benzenesulfonic acid, $BF_3.OEt_2$, $BF_3.OMe_2$, $BF_3.THF$, $BF_3.OBu_2$, $BF_3.MeOH$, $BF_3.Me_2S$, $BF_3.PhOH$, and $BF_3.2H_2O$. In certain embodiments, the catalyst used in step (b) is selected from the group consisting of hydrochloric acid, hydrobromic acid, sulfuric acid, para-toluenesulfonic acid monohydrate, methanesulfonic acid, benzenesulfonic acid, trifluoroacetic acid, phosphoric acid, iodine, 1,3-dibromo-5,5-dimethylhydantoin, copper(II) dodecyl sulfate, ytterbium(III) triflate, yttrium(III) triflate, bismuth(III) triflate, bismuth(III) chloride, tungstophosphoric acid, perchloric acid, praseodymium triflate, hafnium(IV) triflate, iron(III) chloride, hydrogen chloride, p-dodecyl benzenesulfonic acid, $BF_3.OEt_2$, $BF_3.OMe_2$, $BF_3.THF$, $BF_3.OBu_2$, $BF_3.MeOH$, $BF_3.Me_2S$, $BF_3.PhOH$, and $BF_3.2H_2O$. In particular embodiments, the catalyst used in step (b) is para-toluenesulfonic acid monohydrate.

In certain embodiments, the solvent used in step (b) is selected from the group consisting of ethers (e.g., diethyl ether, methyl tert-butyl ether, cyclopentyl methyl ether, tetrahydrofuran, 2-methyltetrahydrofuran, 1,4-dioxane,), aromatic solvents (e.g., benzene, xylenes), polar aprotic solvents (e.g., N,N-dimethylformamide, N,N-dimethylacetamide, N-methylpyrrolidinone), acetonitrile, halogenated solvents (e.g., dichloromethane, dichloroethane), carboxylic acids (e.g., acetic acid, propionic acid), sulfolane and a combination thereof. In particular embodiments, the solvent used in step (b) is a carboxylic acid. In certain embodiments, the solvent used in step (b) is selected from the group consisting of diethyl ether, methyl tert-butyl ether, cyclopentyl methyl ether, tetrahydrofuran, 2-methyltetrahydrofuran, 1,4-dioxane, benzene, xylenes, N,N-dimethylformamide, N,N-dimethylacetamide, N-methylpyrrolidinone, acetonitrile, dichloromethane, dichloroethane, acetic acid, propionic acid, sulfolane, and a combination thereof. In particular embodiments, the solvent used in step (b) is acetic acid.

In certain embodiments, step (b) is carried out in the temperature range of from about 80° C. or less. In particular embodiments, step (b) is carried out in the temperature range of from about 0° C. to about 80° C.

In certain embodiments, the acid used in step (c) is selected from the group consisting of mineral acids (e.g., hydrochloric acid, hydrobromic acid, sulfuric acid), sulfonic acids (e.g., methanesulfonic acid, benzenesulfonic acid, para-toluenesulfonic acid monohydrate), trifluoroacetic acid, phosphoric acid, levulinic acid, glyoxylic acid, alkali metal bisulfites (e.g., sodium bisulfite, sodium metabisulfite, potassium bisulfite), and sodium dithionite. In certain embodiments, the acid used in step (c) is selected from the group consisting of hydrochloric acid, hydrobromic acid, sulfuric acid, methanesulfonic acid, benzenesulfonic acid, para-toluenesulfonic acid monohydrate, trifluoroacetic acid, phosphoric acid, levulinic acid, glyoxylic acid, sodium bisulfite, sodium metabisulfite, potassium bisulfite, and sodium dithionite. In certain embodiments, the acid used in step (c) is a sulfonic acid. In particular embodiments, the acid used in step (c) is para-toluenesulfonic acid monohydrate.

In certain embodiments, the solvent used in step (c) is selected from the group consisting of ethers (e.g., diethyl ether, methyl tert-butyl ether, tetrahydrofuran, 2-methyltetrahydrofuran, 1,4-dioxane), aromatic solvents (e.g., benzene, xylenes), polar aprotic solvents (e.g., N,N-dimethylformamide, N,N-dimethylacetamide, N-methylpyrrolidinone), acetonitrile, halogenated solvents (e.g., dichloromethane, dichloroethane), ketones (e.g., methyl ethyl ketone, acetone, methyl isobutyl ketone), aldehydes (e.g., formaldehyde/formalin, acetaldehyde, isobutyraldehyde), water, and a combination thereof. In certain embodiments, the solvent used in step (c) is selected from the group consisting of diethyl ether, methyl tert-butyl ether, tetrahydrofuran, 2-methyltetrahydrofuran, 1,4-dioxane, benzene, xylenesN,N-dimethylformamide, N,N-dimethylacetamide, N-methylpyrrolidinone, acetonitrile, dichloromethane, dichloroethane, methyl ethyl ketone, acetone, methyl isobutyl ketone, formaldehyde/formalin, acetaldehyde, isobutyraldehyde, water, and a combination thereof. In particular embodiments, the solvent used in step (c) is methyl ethyl ketone and water.

In certain embodiments, step (c) is carried out in the temperature range of from about 100° C. or less. In particular embodiments, step (c) is carried out in the temperature range of from about 20° C. to about 100° C.

In some embodiments, a process for preparing a compound of formula 5a:

5a or a co-crystal, solvate, or combination thereof is provided, comprising combining a compound of formula 4e:

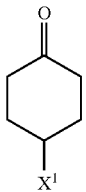

4e or a co-crystal, solvate, salt, or combination thereof, with a catalyst, an acid, a base, a solvent, and optionally an additive to provide the compound of formula 5a, or a co-crystal, solvate, or combination thereof, wherein $X^1$ is selected from the group consisting of tosyloxy, chloro, bromo, iodo, mesyloxy, 2,4,6-trimethylbenzenesulfonyloxy, 2,4,6-triisopropylbenzenesufonyloxy, acetoxy, trichloroacetoxy, and trifluoroacetoxy.

In certain embodiments, $X^1$ is tosyloxy.

In certain embodiments, the catalyst is selected from the group consisting of (8a,9S)-6'-methoxycinchonan-9-amine trihydrochloride, cinchona alkaloid derivatives, amino acids (e.g. D- or L-phenylglycine, D- or L-cyclopentylglycine, D- or L-proline) primary amines (e.g., 1-phenylethylamine), secondary amines (e.g., 2-methylpyrrolidine, 2,5-dimethylpyrrolidine), and aldolase. In certain embodiments, the catalyst is selected from the group consisting of (8a,9S)-6'-methoxycinchonan-9-amine trihydrochloride, cinchona alkaloid derivatives, D- or L-phenylglycine, D- or L-cyclopentylglycine, D- or L-proline, 1-phenylethylamine, 2-methylpyrrolidine, 2,5-dimethylpyrrolidine, and aldolase. In particular embodiments, the catalyst is (8a,9S)-6'-methoxycinchonan-9-amine trihydrochloride.

In certain embodiments, the acid is selected from the group consisting of carboxylic acids (e.g., acetic acid, trifluoroacetic acid, trichloroacetic acid, tartaric acid), sulfonic acids (e.g., camphorsulfonic acid), sulfuric acid, phosphonic acids, phosphoric acid, and triflic acid. In certain embodiments, the acid is selected from the group consisting of acetic acid, trifluoroacetic acid, trichloroacetic acid, tartaric acid, camphorsulfonic acid, sulfuric acid, phosphonic acids, phosphoric acid, and triflic acid. In particular embodiments, the acid is trifluoroacetic acid.

In certain embodiments, the base is selected from the group consisting of carboxylates (e.g., lithium acetate, sodium acetate, potassium acetate, lithium benzoate, sodium benzoate), carbonates (e.g., lithium bicarbonate, lithium carbonate, sodium bicarbonate, sodium carbonate), sulfates (e.g., lithium sulfate, sodium sulfate), phosphates (e.g., sodium phosphates, potassium phosphate), and organic amines (e.g., imidazole, triethylamine, DABCO). In certain embodiments, the base is selected from the group consisting of lithium acetate, sodium acetate, potassium acetate, lithium benzoate, sodium benzoate, lithium bicarbonate, lithium carbonate, sodium bicarbonate, sodium carbonate, lithium sulfate, sodium sulfate, sodium phosphates, potassium phosphate, imidazole, triethylamine, and DABCO. In particular embodiments, the base is lithium acetate.

In certain embodiments, the solvent is selected from the group consisting of alcohols (e.g., methanol, ethanol, 2-propanol), esters (e.g., ethyl acetate, butyl acetate, isobutyl acetate), ethers (e.g., diethyl ether, methyl tert-butyl ether, 2-methyltetrahydrofuran, tetrahydrofuran, 1,4-dioxane), aromatic solvents (e.g., toluene, benzene, xylenes), polar aprotic solvents (e.g., N,N-dimethylformamide, N,N-dimethylacetamide, N-methylpyrrolidinone, dimethylsulfoxide), chlorinated solvents (e.g., dichloromethane, dichloroethane, chloroform), nitriles (e.g., acetonitrile, propionitrile, butyronitrile), water, and a combination thereof. In certain embodiments, the solvent is selected from the group consisting of methanol, ethanol, 2-propanol, ethyl acetate, butyl acetate, isobutyl acetate, diethyl ether, methyl tert-butyl ether, 2-methyltetrahydrofuran, tetrahydrofuran, 1,4-dioxane, toluene, benzene, xylenes, N,N-dimethylformamide, N,N-dimethylacetamide, N-methylpyrrolidinone, dimethylsulfoxide, dichloromethane, dichloroethane, chloroform, acetonitrile, propionitrile, butyronitrile, water, and a combination thereof. In particular embodiments, the solvent is 2-methyltetrahydrofuran and water. In particular embodiments, the solvent is 2-methyltetrahydrofuran.

In certain embodiments, the process comprises an additive. In certain embodiments, the additive is an alcohol. In certain embodiments, the additive is selected from the group consisting of methanol, ethanol, 1-propanol, 2-propanol, and water. In particular embodiments, the additive is water.

In certain embodiments, the process is carried out in the temperature range of from about 120° C. or less. In certain embodiments, the process is carried out in the temperature range of from about –40° C. to about 120° C. In particular embodiments, the process is carried out in the temperature range of from about 0° C. to about 40° C. In particular embodiments, the process is carried out at about 20° C.

In some embodiments, a process for preparing a compound of formula V-02:

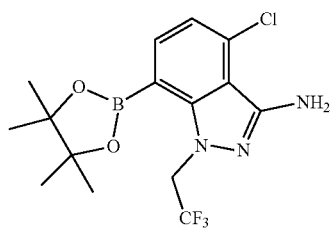

V-02 or a co-crystal, solvate, salt, or combination thereof is provided, comprising
(a) combining a compound of formula 6d:

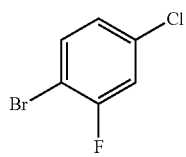

6d or a co-crystal, solvate, salt, or combination thereof, with a formyl source, a base and a solvent to provide a compound of formula 6a:

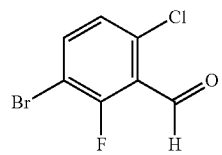

6a or a co-crystal, solvate, salt, or combination thereof;
(b) combining the compound of formula 6a or a co-crystal, solvate, salt, or combination thereof, with a reagent, a dehydrating reagent, and a solvent to provide a compound of formula 6b:

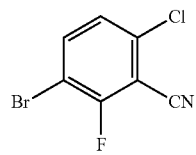

6b or a co-crystal, solvate, salt, or combination thereof;
(c) combining the compound of formula 6b or a co-crystal, solvate, salt, or combination thereof, with a hydrazine source and a solvent to provide a compound of formula 6c:

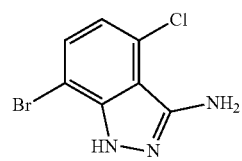

6c or a co-crystal, solvate, salt, or combination thereof;
(d) combining the compound of formula 6c or a co-crystal, solvate, salt, or combination thereof, with an alkylating reagent, a base, a solvent, and, optionally an alkylating additive, to provide a compound of formula V-A:

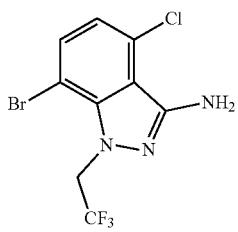

V-A or a co-crystal, solvate, salt, or combination thereof; and
(e) combining the compound of formula V-A or a co-crystal, solvate, salt, or combination thereof, with a boron coupling agent, a base, a palladium catalyst and a solvent to provide the compound of formula V-02, or a co-crystal, solvate, salt, or combination thereof.

In certain embodiments, the formyl source used in step (a) is selected from the group consisting of carbon monoxide and hydrogen chloride; hydrogen cyanide and hydrogen chloride; metal cyanide and hydrogen chloride; phosphorus oxychloride; N,N-dimethylformamide; hexamine acetic acid; dichloromethyl methyl ether; and formamide. In particular embodiments, the formyl source used in step (a) is N,N-dimethylformamide.

In certain embodiments, the base used in step (a) is selected from the group consisting of sodium, lithium, or potassium bis(trimethylsilyl)amide, sodium or potassium diisopropylamide, lithium tetramethylpiperidide, and lithium or sodium amide. In particular embodiments, the base used in step (a) is lithium diisopropyl amide. In particular embodiments, the based used in step (a) is lithium diisopropyl amide that is prepared in situ from diisopropylamine and n-butyl lithium.

In certain embodiments, the solvent used in step (a) is selected from the group consisting of ethers (e.g., diethyl ether, methyl tert-butyl ether, tetrahydrofuran, 2-methyltetrahydrofuran, 1,4-dioxane), aromatic solvents (e.g., toluene, benzene, xylenes), chlorinated solvents (e.g., dichloromethane, dichloroethane, chloroform,), non-polar solvents (e.g., hexanes, heptane, cyclohexane), and a combination thereof. In particular embodiments, the solvent used in step (a) is tetrahydrofuran.

In certain embodiments, step (a) is carried out in the temperature range of from about 60° C. or less. In certain embodiments, step (a) is carried out in the temperature range of from about −80° C. to about 60° C. In particular embodiments, step (a) is carried out in the temperature range of from about −30° C. to about 40° C.

In certain embodiments, the reagent used in step (b) is selected from the group consisting of hydroxylamine hydrochloride, hydroxylamine-O-sulfonic acid, sodium azide, trifluoromethanesulfonic acid, and propylphosphonic anhydride. In particular embodiments, the reagent used in step (b) is hydroxylamine hydrochloride.

In certain embodiments, the dehydrating reagent used in step (b) is selected from the group consisting of acetic anhydride, acids (e.g., formic acid, hydrochloric acid, sulfuric acids, citric acids, phosphoric acids), copper(II) acetate, and cyanuric chloride/dimethylformamide. In particular embodiments, the base used in step (b) is acetic anhydride.

In certain embodiments, the solvent used in step (b) is selected from the group consisting of acids (e.g., acetic acid, formic acid), polar solvents (e.g., dimethyl sulfoxide, N,N-dimethylformamide, N,N-dimethylacetamide, N-methyl-2-pyrrolidone, acetonitrile, water, tert-butyl alcohol), non-polar solvents (e.g., toluene), and a combination thereof. In particular embodiments, the solvent used in step (b) is acetic acid.

In certain embodiments, step (b) is carried out in the temperature range of from about 95° C. or less. In certain embodiments, step (b) is carried out in the temperature range of from about 20° C. to about 95° C. In particular embodiments, step (b) is carried out in the temperature range of from about 40° C. to about 70° C.

In certain embodiments, the hydrazine source used in step (c) is selected from the group consisting of hydrazine, hydrazine hydrochloride, hydrazine hydrobromide, hydrazine sulfate, and hydrazine acetate. In particular embodiments, the hydrazine source used in step (c) is hydrazine hydrate.

In certain embodiments, the solvent used in step (c) is selected from the group consisting of alcohols (e.g., ethanol, methanol, isopropanol), water and a combination thereof. In particular embodiments, the solvent used in step (c) is water and isopropanol.

In certain embodiments, step (c) is carried out in the temperature range of from about 85° C. or less. In particular embodiments, step (c) is carried out in the temperature range of from about 75° C. to about 85° C.

In certain embodiments, the alkylating reagent used in step (d) is selected from the group consisting of 2,2,2-trifluoroethyl trifluoromethanesulfonate, 2,2,2-trifluoroethyl trichloromethanesulfonate, 1,1,1-trifluoro-2-iodoethane, 2-bromo-1,1,1-trifluoroethane, 1,1,1-trifluoro-2-chloroethane, 2,2,2-trifluoroethyl methanesulfonate, and 2,2,2-trifluoroethyl p-toluenesulfonate. In particular embodiments, the reagent used in step (d) is 2,2,2-trifluoroethyl trifluoromethanesulfonate.

In certain embodiments, step (d) comprises an alkylating additive. In certain embodiments, the alkylating additive used in step (d) is selected from the group consisting of symmetrical quaternary ammonium salts (e.g., tetrabutylammonium bromide, tetraethylammonium bromide, tetrabutylammonium hydrogen sulfate), non-symmetrical quaternary ammonium salts (e.g., benzyltrimethylammonium chloride, benzyltrimethylammonium bromide, benzyltrimethylammonium iodide, benzyltriethylammonium chloride, benzyltriethylammonium bromide, benzyltriethylammonium iodide, benzyltributylammonium chloride, benzyltributylammonium bromide, benzyltributylammonium iodide, phenyltrimethylammonium chloride, phenyltrimethylammonium bromide, phenyltrimethylammonium iodide, decyltrimethylammonium bromide), lithium chloride, and phosphonium salts (e.g., methyltriphenoxyphosphonium iodide, tetrabutylphosphonium bromide).

In certain embodiments, the base used in step (d) is selected from the group consisting of cesium carbonate, lithium bases (e.g., lithium hydroxide, lithium phosphate, lithium carbonate, lithium ethoxide, lithium methoxide, lithium trifluoromethanesulfonate), sodium bases (e.g., sodium hydroxide, sodium carbonate, sodium bicarbonate, sodium acetate, sodium tert-butoxide, sodium methoxide, sodium ethoxide, sodium pivalate, sodium propionate, sodium hydride), potassium bases (e.g., potassium phosphate, potassium hydroxide, potassium carbonate, potassium bicarbonate, potassium tert-butoxide, potassium phosphate dibasic, potassium phosphate monobasic, potassium acetate, potassium pivalate), calcium bases (e.g., calcium hydroxide, calcium carbonate), amine bases (e.g., triethylamine, N,N-diisopropylehtylamine, N-methylmorpholine, 1,8-diazabicyclo[5.4.0]undec-7-ene, lithium bis(trimethylsilyl)amide, sodium bis(trimethylsilyl)amide, potassium bis(trimethylsilyl)amide, lithium diisopropylamide, pyridine, 1-methylimidazole, imidazole, 2,6-lutidine, 4-methyl morpholine, 2,6-ditertbutylpyridine), and barium bases (e.g., barium hydroxide, barium carbonate,). In particular embodiments, the base used in step (d) is a potassium base. In particular embodiments, the base used in step (d) is potassium phosphate.

In certain embodiments, the solvent used in step (d) is selected from the group consisting of polar aprotic solvent (e.g., N,N-dimethylformamide, N-methyl-2-pyrrolidone, N,N-dimethylacetamide, pyridine, dimethyl sulfoxide, sulfolane), ketone solvents (e.g., acetone, methyl ethey ketone, methyl isobutyl ketone), hydrocarbon solvents (e.g., toluene, heptane, hexane), alcohol solvents (e.g., methanol, ethanol, isopropyl alcohol, tert-amyl alcohol, tert-butyl alcohol, 1-butanol, n-butanol), ether solvents (e.g., tetrahydrofuran, 2-methyltetrahydrofuran, methyl tert-butyl ether), acetate solvents (e.g., ethyl acetate, isopropyl acetate), acetonitrile, dichloromethane, and a combination thereof. In particular embodiments, the solvent used in step (d) is a polar aprotic solvent. In particular embodiments, the solvent used in step (d) is N,N-dimethylformamide.

In certain embodiments, step (d) is carried out in the temperature range of from about 60° C. or less. In certain embodiments, step (d) is carried out in the temperature range of from about −20° C. to about 60° C. In particular embodiments, step (d) is carried out in the temperature range of from about 0° C. to about 40° C. In particular embodiments, step (d) is carried out at about 20° C.

In certain embodiments, the boron coupling agent used in step (e) is selected from the group consisting of bis(pinacolato)diboron, bis(neopentyl glycolato)diboron, bisboronic acid, and bis(ethylene glycolato diboron). In particular embodiments, the boron coupling agent used in step (e) is bis(pinacolato)diboron.

In certain embodiments, the base used in step (e) is selected from the group consisting of cesium acetate, potassium propionate, sodium propionate, potassium acetate, sodium acetate, cesium acetate, potassium propionate, sodium propionate, potassium carbonate, sodium carbonate, cesium carbonate, potassium bicarbonate, sodium bicarbonate, sodium phosphate, sodium hydroxide, potassium hydroxide, potassium fluoride, potassium phosphate dibasic, potassium phosphate tribasic, sodium hydroxide, potassium hydroxide, dicyclohexylamine, N-methylmorpholine, triethylamine, and diisopropylethylamine. In particular embodiments, the base used in step (e) is potassium acetate.

In certain embodiments, the palladium catalyst used in step (e) is selected from the group consisting of bis(di-tert-butyl(4-dimethylaminophenyl)phosphine)dichloropalladium(II), bis[(dicyclohexyl)(4-dimethylaminophenyl)phosphine]palladium(II) chloride, dichlorobis(triphenylphosphine)palladium(II), [1,1'-bis(diphenylphosphino)ferrocene]dichloropalladium(II), [1,2-bis(diphenylphosphino)ethane]dichloropalladium(II), and dichloro[9,9-dimethyl-4,5-bis(diphenylphosphino)xanthene]palladium(II). In certain embodiments, the palladium catalyst used in step (e) is palladium(II) precatalyst (e.g., palladium(II) chloride, palladium(II) acetate, palladium(II) trifluoroacetate) or palladium(0) precatalyst (e.g., tetrakis(triphenylphosphine)palladium(0), bis(dibenzylideneacetone)palladium(0)) and further comprises a phosphine ligand (e.g., tricyclohexylphosphine, triphenylphosphine, cyclohexyldiphenylphosphine, dicyclohexylphenylphosphine). In particular embodiments, the palladium catalyst used in step (e) is bis(triphenylphosphine)palladium (II) dichloride.

In certain embodiments, the solvent used in step (e) is selected from the group consisting of ethers (e.g., 1,4-dioxane, 2-methyltetrahydrofuran, dimethoxyethane), aromatic hydrocarbon solvents (e.g., toluene, xylenes), esters (e.g., ethyl acetate, isopropyl acetate, propyl acetate, isobutyl acetate), alcohols (e.g., ethanol, isopropanol), and polar aprotic solvents (e.g., N,N-dimethylformamide, N,N-dimethylacetamide, N-methyl-2-pyrrolidine), and a combination thereof. In particular embodiments, the solvent used in step (e) is toluene and N,N-dimethylformamide.

In certain embodiments, step (e) is carried out in the temperature range of from about 120° C. or less. In certain embodiments, step (e) is carried out in the temperature range of from about 20° C. to about 120° C. In particular embodiments, step (e) is carried out in the temperature range of from about 95° C. to about 105° C.

In some embodiments, a process for preparing a compound of formula 1b-02:

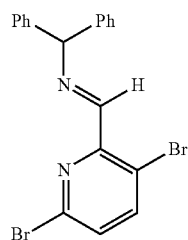

or a co-crystal, solvate, salt, or combination thereof is provided, comprising:

(a) combining the compound of formula 1j:

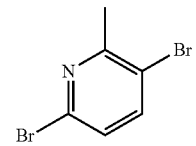

or a co-crystal, solvate, salt, or combination thereof, with an oxidant, a base, a solvent, and optionally a catalyst or optionally an additive, to provide a compound of formula 1h:

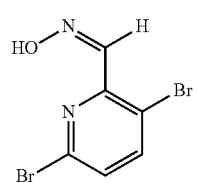

or a co-crystal, solvate, salt, or combination thereof;

(b) hydrolyzing the compound of formula 1h or a co-crystal, solvate, salt, or combination thereof, with a reagent and a solvent, to provide a compound of formula 1a:

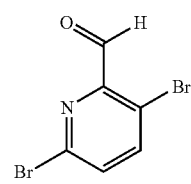

or a co-crystal, solvate, salt, or combination thereof;

(c) combining the compound of formula 1a or a co-crystal, solvate, salt, or combination thereof, with a bisulfite source and a solvent, to provide a compound of formula 1i:

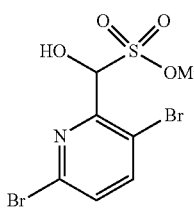

or a co-crystal, solvate, salt, or combination thereof, wherein $M^2$ is $K^+$ or $Na^+$; and (d) combining the compound of formula 1i or a co-crystal, solvate, salt, or combination thereof, with benzhyhydrylamine, a base, and a solvent, to provide the compound of formula 1b-02 or a co-crystal, solvate, salt, or combination thereof.

In certain embodiments, the oxidant used in step (a) is selected from the group consisting of alkyl nitrites (e.g. iso-amyl nitrite, n-butyl nitrite, n-propyl nitrite, tert-butyl nitrite). In particular embodiments, the oxidant used in step (a) is tert-butyl nitrite.

In certain embodiments, the base used in step (a) is selected from the group consisting of metal alkoxides (e.g., sodium tert-butoxide, sodium methoxide, sodium iso-propoxide, potassium tert-butoxide, potassium iso-propoxide, sodium ethoxide) and metal amides (e.g., potassium amide, sodium amide, LDA). In particular embodiments, the base used in step (a) is potassium tert-butoxide.

In certain embodiments, the solvent used in step (a) is selected from the group consisting of tetrahydrofuran, ethers (e.g., MTBE, diethyl ether, CPME), nitriles (e.g., acetonitrile), DMSO, and a combination thereof. In particular embodiments, the solvent used in step (a) is tetrahydrofuran.

In certain embodiments, step (a) comprises a catalyst or an additive. In certain embodiments, the catalyst or additive used in step (a) is selected from the group consisting of benzoic acid and copper salts (e.g. copper diacetate).

In certain embodiments, step (a) does not comprise a catalyst or an additive.

In certain embodiments, step (a) is carried out in the temperature range of from about 40° C. or less. In certain embodiments, step (a) is carried out in the temperature range of from about −20° C. to about 40° C. In particular embodiments, step (a) is carried out in the temperature range of from about 0° C. to about 10° C.

In certain embodiments, the reagent used in step (b) is selected from the group consisting of glyoxylic acid, pyruvic acid, sodium dithionite, sodium bisulfite, potassium metabisulfite, 3-methoxypropionic acid, sodium nitrite, nitrosyl chloride, tert-butyl nitrite, and potassium persulfate. In particular embodiments, the reagent used in step (b) is glyoxylic acid.

In certain embodiments, the solvent used in step (b) is selected from the group consisting of ketones (e.g. acetone, methyl ethyl ketone (MEK)) alcohols (e.g. methanol, ethanol), THF, water, and a combination thereof. In particular embodiments, the solvent used in step (b) is water.

In certain embodiments, step (b) is carried out in the temperature range of from about 100° C. or less. In certain embodiments, step (b) is carried out in the temperature range of from about 0° C. to about 100° C. In particular embodiments, step (b) is carried out in the temperature range of from about 50° C. to about 90° C.

In certain embodiments, the bisulfite source used in step (c) is selected from the group consisting of potassium metabisulfite and sodium bisulfite. In particular embodiments, the bisulfite source used in step (c) is potassium metabisulfite.

In certain embodiments, the solvent used in step (c) is selected from the group consisting of alcohols (e.g. methanol, ethanol, isopropanol, n-propanol, n-butanol, t-butanol), ethers (e.g. MTBE, THF, 2-methyltetrahydrofuran, CPME, diethylether, diisopropyl ether), water, and a combination thereof. In particular embodiments, the solvent used in step (c) is water and isopropanol.

In certain embodiments, step (c) is carried out in the temperature range of from about 60° C. or less. In certain embodiments, step (c) is carried out in the temperature range of from about 0° C. to about 60° C. In particular embodiments, step (c) is carried out in the temperature range of from about 20° C. to about 30° C.

In certain embodiments, the base used in step (d) is selected from the group consisting of hydroxides (e.g., potassium hydroxide, sodium hydroxide), bicarbonates (e.g., potassium or sodium bicarbonate), carbonates (e.g. potassium or sodium carbonates), and phosphates (e.g. potassium or sodium phosphate, mono- bi- or tribasic). In particular embodiments, the base used in step (d) is potassium hydroxide.

In certain embodiments, the solvent used in step (d) is selected from the group consisting of ethers (e.g., diethyl ether, methyl tert-butyl ether, tetrahydrofuran, 2-methyltetrahydrofuran, 1,4-dioxane), polar aprotic solvents (e.g., N,N-dimethylformamide, N,N-dimethylacetamide, N-methylpyrrolidinone), aromatic solvents (e.g., benzene, xylenes), chlorinated solvents (e.g., dichloromethane), water, and a combination thereof. In particular embodiments, the solvent used in step (d) is water and 2-methyltetrahydrofuran.

In certain embodiments, step (d) is carried out in the temperature range of from about 120° C. or less. In certain embodiments, step (d) is carried out in the temperature range of from about −20° C. to about 120° C. In particular embodiments, step (d) is carried out in the temperature range of from about 20° C. to about 80° C.

In some embodiments, a process for preparing a compound of formula IX:

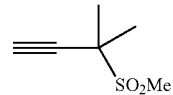

IX or a co-crystal, solvate, salt, or combination thereof is provided, comprising combining 3-Chloro-3-methylbut-1-yne (3-CMB):

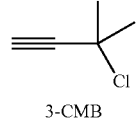

3-CMB with a reagent, a ligand, a solvent, an acid, and a catalyst, to provide the compound of formula IX or a co-crystal, solvate, salt, or combination thereof.

In certain embodiments, the reagent is selected from the group consisting of sodium methanesulfinate, lithium methanesulfinate, and potassium methanesulfinate. In particular embodiments, the reagent is sodium methanesulfinate.

In certain embodiments, the ligand is selected from the group consisting of N,N,N',N'-Tetramethylethylenediamine (TMEDA), L-proline, DMAP, 2,2'-bipyridine, TEA, DIPEA, pyridine, ethylenediamine, 1.2-diaminocyclohexane, and N, N'-dimethylcyclohexane-1,2-diamine. In particular embodiments, the ligand is N,N,N',N'-Tetramethylethylenediamine.

In certain embodiments, the catalyst is selected from the group consisting of CuCl, CuCl$_2$, CuBr, CuI, CuSO$_4$, CuO, Cu$_2$O, Cu(OAc), Cu(OAc)$_2$, FeCl$_2$, FeBr$_3$, CuBr$_2$, Cu(NO$_3$)$_2$, FeCl$_3$, and Fe(NO$_3$)$_3$.9H$_2$O. In particular embodiments, the catalyst is copper (II) acetate.

In certain embodiments, the solvent is selected from the group consisting of esters (e.g., ethyl acetate, isopropyl acetate, butyl acetate, isobutyl acetate), ethers (e.g., diethyl ether, methyl tert-butyl ether, tetrahydrofuran, 2-methyltetrahydrofuran, 1,4-dioxane), aromatic solvents (e.g., toluene, benzene, xylenes), polar aprotic solvents (e.g., N,N-dimethylformamide, N,N-dimethylacetamide, N-methylpyrrolidinone, dimethylsulfoxide), polar protic solvents (e.g., methanol, ethanol, 2-propanol, t-butyl alcohol, sec-butyl alcohol, t-amyl alcohol), chlorinated solvents (e.g., dichloromethane, dichloroethane, chloroform), nitriles (e.g., propionitrile, butyronitrile), ketones (e.g., acetone, 2-butanone, methyl isobutyl ketone), and a combination thereof. In particular embodiments, the solvent is isopropyl acetate.

In certain embodiments, the acid is selected from the group consisting of sulfuric acid, hydrochloric acid, ammonium chloride, ammonium hydroxide, phosphoric acid, acetic acid, and citric acid. In certain embodiments, the acid is an aqueous acid. In certain embodiments, the acid is selected from the group consisting of 5% aqueous sulfuric acid, 5% aqueous hydrochloric acid, 10% aqueous ammonium chloride, 10% aqueous ammonium hydroxide, 5% aqueous phosphoric acid, 5% aqueous acetic acid, and 5% aqueous citric acid. In particular embodiments, the acid is 5% aqueous sulfuric acid.

In certain embodiments, the process is carried out in the temperature range of from about 120° C. or less. In certain embodiments, the process is carried out in the temperature range of from about −20° C. to about 120° C. In particular embodiments, the process is carried out in the temperature range of from about 20° C. to about 60° C. In particular embodiments, the process is carried out at about 40° C.

In some embodiments, a process for preparing a compound of formula X:

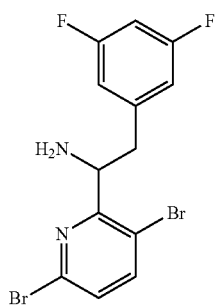

or a co-crystal, solvate, salt, or combination thereof is provided, comprising contacting a compound of formula VIII:

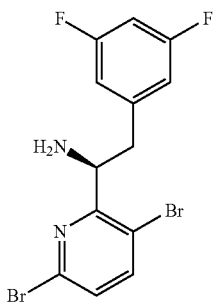

an enantiomer of the compound of formula VIII, or a mixture of the compound of formula VIII and the enantiomer of the compound of formula VIII, or a co-crystal, solvate, salt, or combination of any of the foregoing, with an aldehyde, a solvent, and one reagent selected from the group consisting of a metal catalyst and a base, to provide the compound of formula X, or a co-crystal, solvate, salt, or combination thereof.

In certain embodiments, the process comprises contacting the compound of formula VIII, the enantiomer of the compound of formula VIII, or a mixture of the compound of the compound of formula VIII and the enantiomer of the compound of formula VIII, or a co-crystal, solvate, salt, or combination of any of the foregoing, with an aldehyde, a solvent, and a metal catalyst to provide the compound of formula X. In certain embodiments, the process comprises contacting the compound of formula VIII, the enantiomer of the compound of formula VIII, or a mixture of the compound of formula VIII and the enantiomer of the compound of formula VIII, or a co-crystal, solvate, salt, or combination of any of the foregoing, with an aldehyde, a solvent, and a base to provide the compound of formula X.

In certain embodiments, the aldehyde is selected from the group consisting of aromatic aldehydes (e.g., benzaldehyde, 2,4-dichlorobenzaldehyde, 2-methoxybenzaldehyde, 4-(dimethylamino)benzaldehyde, 2-(dimethylamino)benzaldehyde, 2-hydroxy-5-methoxybenzaldehyde, 2-hydroxy-5-nitrobenzaldehyde, 5-chloro-2-hydroxybenzaldehyde, 4-hydroxybenzaldehyde, 2-hydroxybenzaldehyde, 3,5-dichloro-2-hydroxybenzaldehyde, 3-hydroxybenzaldehyde, 2-hydroxy-3-nitrobenzaldehyde); heteroaromatic aldehydes (e.g., 2-formylpyridine, 3-(trifluoromethyl)picolinaldehyde, 4-chloropicolinaldehyde, nicotinaldehyde, quinolone-4-carbaldehyde, quinolone-2-carbaldehyde); and aliphatic aldehydes (e.g., formaldehyde, ethyl glyoxylate, glyoxylic acid). In particular embodiments, the aldehyde is 2-formylpyridine.

In certain embodiments, the metal catalyst is selected from the group consisting of zinc salts (e.g., zinc(II) oxide, zinc(II) acetate, zinc(II) trifluoromethanesulfonate, zinc(II) trifluoroacetate, zinc(II) chloride, zinc (II) stearate, zinc (II) neodecanoate, zinc (II) tetrafluoroborate); nickel salts (e.g., nickel(II) acetate, nickel(II) chloride, nickel(II) triflate); indium salts (e.g., indium (III) acetate); copper salts (e.g., copper(II) acetate); cobalt salts (e.g., cobalt(II) acetate); and manganese salts (e.g., manganese(II) acetate). In particular embodiments, the metal catalyst is zinc(II) acetate.

In certain embodiments, the base is selected from the group consisting of lithium hydroxide, sodium hydroxide, potassium hydroxide, DBU, DBN, DABCO, tetramethylguanidine, BEMP, and 1-tert-Butyl-4,4,4-tris(dimethylamino)-2,2-bis[tris(dimethylamino)-phosphoranylidenamino]-2$\lambda^5$,4$\lambda^5$-catenadi(phosphazene) (t-Bu-P$_4$).

In certain embodiments, the solvent is selected from the group consisting of esters (e.g., ethyl acetate, isopropyl acetate), ethers (e.g., tetrahydrofuran, 2-methyl tertrahydrofuran, 1,4-dioxane), aprotic solvents (e.g., acetonitrile, N,N-dimethylformamide, N,N-dimethylacetamide, N-methylpyrrolidinone), aromatic solvents (e.g., benzene, toluene, xylenes), chlorinated solvents (e.g., dichloromethane), alcohols (e.g., methanol, ethanol, isopropanol) and a combination thereof. In particular embodiments, the solvent is toluene.

In certain embodiments, the process is carried out in the temperature range of from about 100° C. or less. In certain embodiments, the process is carried out in the temperature range of from about −20° C. to about 100° C. In particular embodiments, the process is carried out in the temperature range of from about 20° C. to about 80° C. In particular embodiments, the process is carried out at about 60° C.

Alternative reagents and reaction conditions to those disclosed above may also be employed. For example, alternative solvents may be used, such as other ethers (e.g., diethyl ether, methyl tert-butyl ether, cyclopentyl methyl ether, tetrahydrofuran, 2-methyltetrahydrofuran, 1,4-dioxane, dimethoxyethane), aromatic hydrocarbon solvents (e.g., toluene, benzene, xylenes), nitriles (e.g., propionitrile, butyronitrile, acetonitrile), esters (e.g., ethyl acetate, n-butyl acetate, isobutyl acetate, isopropyl acetate, propyl acetate), polar aprotic solvents (e.g., N,N-dimethylformamide, N,N-dimethylacetamide, N-methylpyrrolidinone, dimethylsulfoxide), alcohols (e.g., methanol, ethanol, 1-propanol, isopropanol, tert-amyl alcohol, n-butanol, sec-butanol), chlorinated solvents (e.g., dichloromethane, dichloroethane, chloroform), hydrocarbon solvents (e.g., n-hexane, cyclohexane, n-heptane), ketones (e.g., acetone, methyl ethyl ketone, methyl isobutylketone), and water. The reactions may also be performed with a combination of the aforementioned solvents or without solvent. Further, temperatures ranging from about −80° C. to about 130° C. may employed.

In some embodiments, a compound of formula VI:

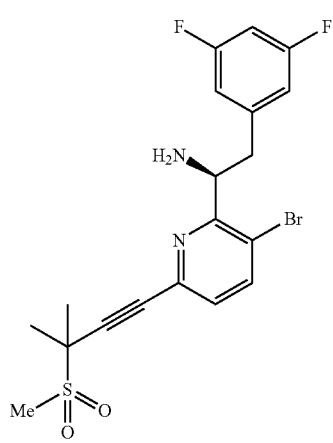

VI or a co-crystal, solvate, or combination thereof is provided.

In some embodiments, a compound of formula VIII:

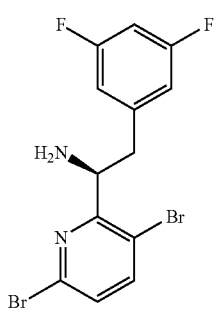

VIII or a co-crystal, solvate, salt or combination thereof is provided.

In certain embodiments, the compound of formula VIII is a compound of formula VIII-02:

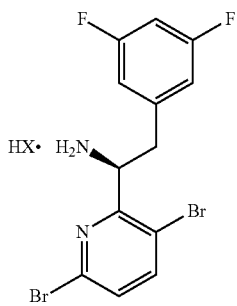

VIII-02 or a co-crystal, solvate, or combination thereof, wherein HX is a chiral or achiral acid.

In certain embodiments, HX is a chiral acid. In particular embodiments, HX is selected from the group consisting of L-lactic acid, L-(+)-tartaric acid, L-aspartic acid, L-glutamic acid, L-(−)-malic acid, D-glucuronic acid, (1R, 3S)-(+)-camphoric acid, (1S)-(+)-camphor-10-sulfonic acid, (R)-(+)-N-(1-phenylethyl)succinamic acid, carbobenzyloxy-L-proline, dibenzoyl-L-tartaric acid, (R)-(+)-3-methyladipic acid, (+)-menthyloxyacetic acid, (−)-pyroglutamic acid, (−)-n-acetyl-L-leucine, N-Boc-D-leucine, N-(+)-BOC-phenylalanine, (−)-quinic acid, (+)-n-acetyl-L-phenylalanine, (+)-N-BOC-isoleucine, L-(−)-acetyl glutamic acid, (−)-acetyl mandelic acid, (R)-(−)-citramalic acid, (−)-camphanic acid, and (R)-mandelic acid. In some embodiments, HX is (R)-mandelic acid. In some embodiments, HX is N-Boc-D-leucine.

In certain embodiments, HX is an achiral acid (i.e., a compound of formula VIII-04). In particular embodiments, HX is selected from the group consisting of sulfuric acid, methanesulfonic acid, p-toluenesulfonic acid, and phosphoric acid. In some embodiments, HX is methanesulfonic acid.

In some embodiments, a compound of formula IV:

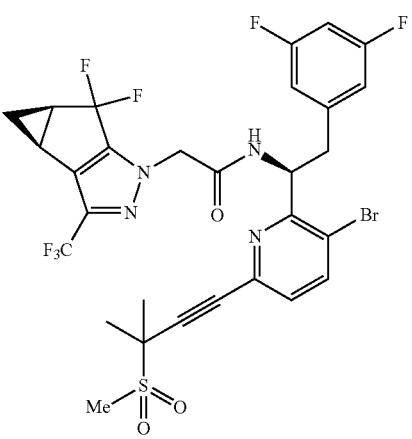

IV or a co-crystal, solvate, salt, or combination thereof is provided.

In certain embodiments, a compound of formula III:

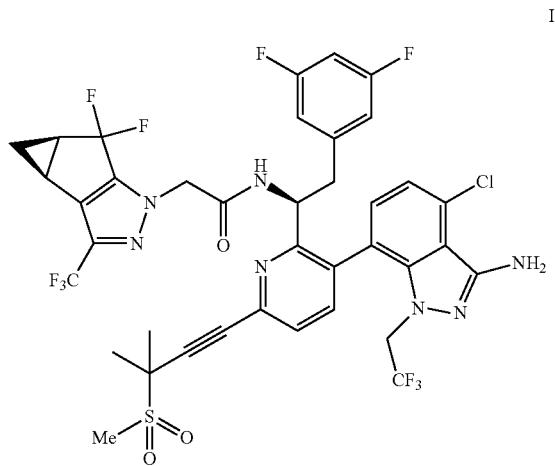

III or a co-crystal, solvate, salt, or combination thereof is provided.

In certain embodiments, the compound of formula III is:

III-03

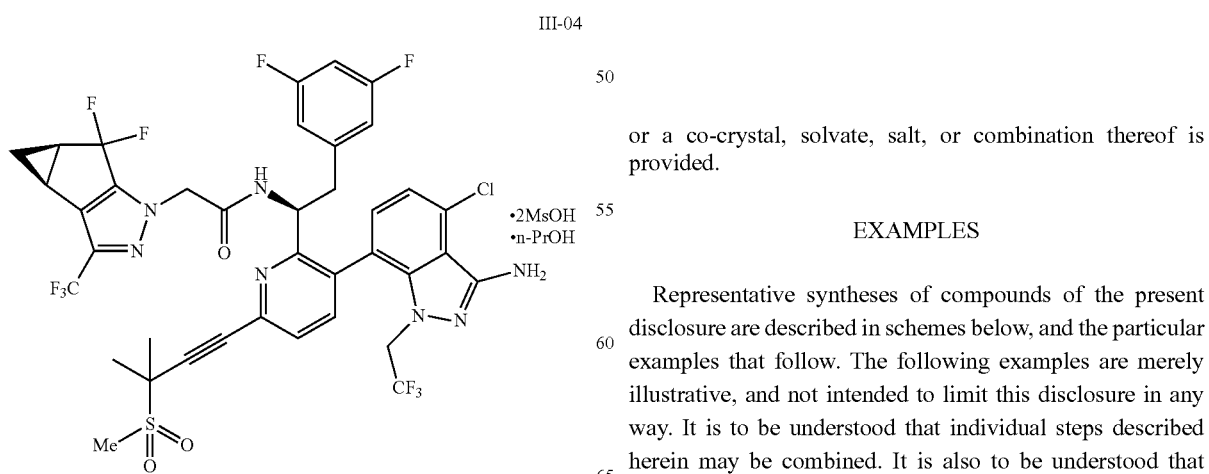

or a co-crystal or solvate or combination thereof.

In certain embodiments, the compound of formula III is:

III-04 or a co-crystal thereof.

In certain embodiments, the compound of formula III is:

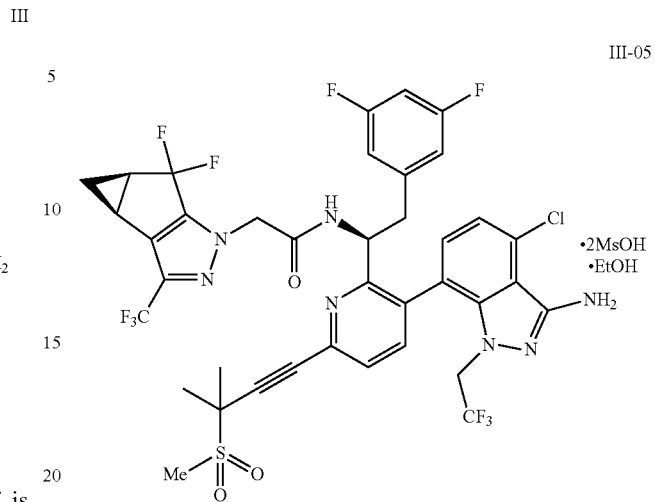

III-05 or a co-crystal thereof.

In certain embodiments, a compound of formula II:

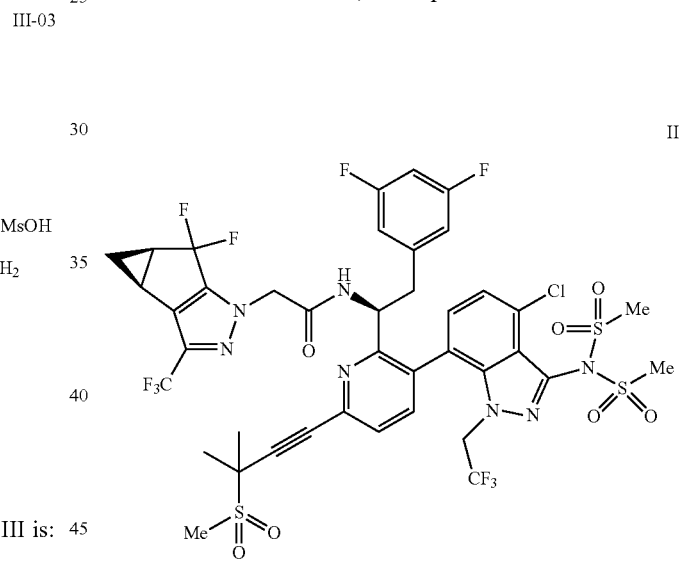

II or a co-crystal, solvate, salt, or combination thereof is provided.

EXAMPLES

Representative syntheses of compounds of the present disclosure are described in schemes below, and the particular examples that follow. The following examples are merely illustrative, and not intended to limit this disclosure in any way. It is to be understood that individual steps described herein may be combined. It is also to be understood that separate batches of a compound may be combined and carried forth in the next synthetic step.

I. Synthesis of Starting Materials and Intermediates

Example 1a: Preparation of (5)-1-(3,6-dibromopyridin-2-yl)-2-(3,5-difluorophenyl)ethan-1-amine (VIII-02), or a Co-Crystal, Solvate, Salt, or Combination Thereof, and Starting Materials and/or Intermediates Therein

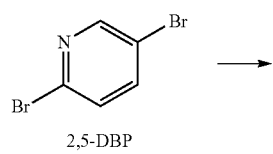

2,5-DBP

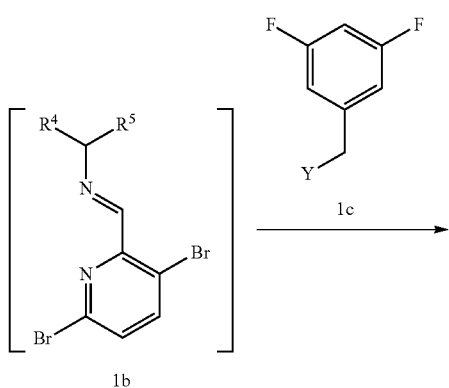

1a

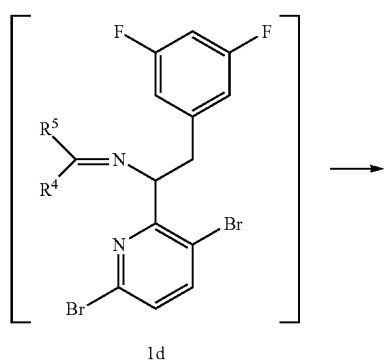

1b

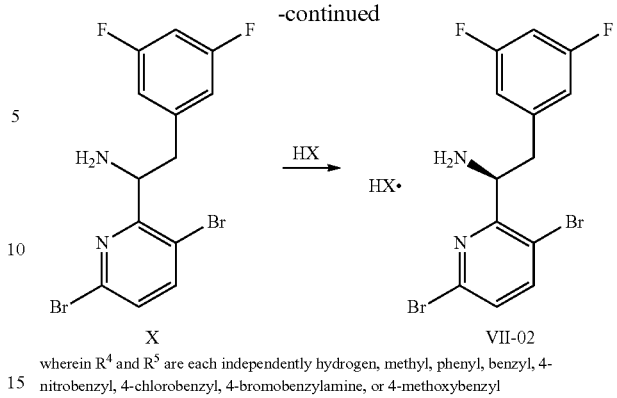

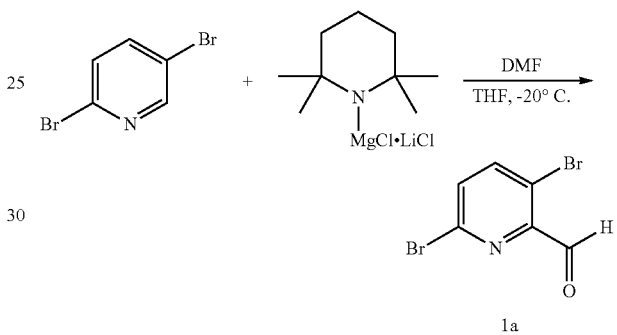

wherein R⁴ and R⁵ are each independently hydrogen, methyl, phenyl, benzyl, 4-nitrobenzyl, 4-chlorobenzyl, 4-bromobenzylamine, or 4-methoxybenzyl Synthesis of 3,6-dibromopicolinaldehyde (1a)

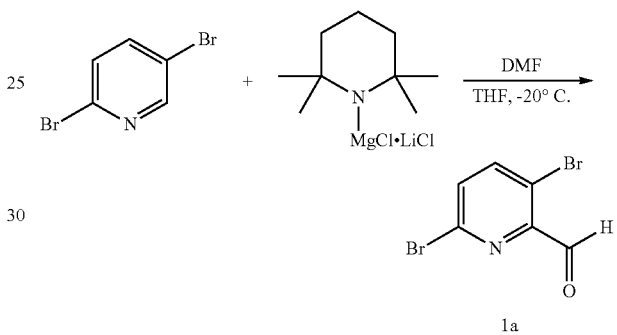

1a

A dry reaction flask with magnetic stir-bar was charged with 2,5-dibromopyridine (1.0 g). The flask was inerted under nitrogen, THF (4.2 mL) was added, and the thin slurry agitated. Separately, a dry glass reactor was charged with 2,2,6,6-tetramethylpiperidinylmagnesium chloride, lithium chloride complex (TMPMgCl.LiCl) (5.8 mL, 6.3 mmol). The TMPMgCl.LiCl solution was agitated and cooled to about −20° C. The 2,5-dibromopyridine solution was added to the TMPMgCl.LiCl solution over about 30 min, maintaining a temperature below about −18° C. Upon completing the addition, the flask was rinsed forward to the reactor with three additional portions of THF (1 mL×2), and aged at about −20 for about 1 hour. A solution of N,N-dimethylformamide (1.6 mL, 20 mmol) in THF (1.6 mL) was added to the reactor over about 15 min. The reaction mixture was aged for a further 15 min. and quenched by the addition of a solution of acetic acid (1.9 mL, 34 mmol) in water (10 mL) over about 20 minutes, maintaining a temperature of no more than about 0° C. To the reactor was added isopropyl acetate (10 mL) and the reaction mixture was warmed to about 20° C. After aging for 30 min, the mixture was filtered through diatomaceous earth and the reactor rinsed with a mixture of isopropyl acetate (10 mL), saturated aqueous ammonium chloride (10 mL) and 0.2 M aqueous hydrochloric acid (10 mL). The reactor rinse was filtered and the pH of the combined reaction mixture was adjusted to about 8-9 by the addition of a 10% aqueous sodium hydroxide solution (about 6 mL). The mixture was filtered a second time to remove magnesium salts and transferred to a separatory funnel. The phases were separated and the aqueous phase was extracted with isopropyl acetate (3×10 mL). The combined organic extracts were washed with 50% saturated aqueous sodium chloride (20 mL), dried over anhydrous sodium sulfate, and filtered. The solution was concentrated to dryness by rotary evaporation and purified by chromatography (eluting with 0-100% ethyl acetate in heptane) to afford 3,6-dibromopicolinaldehyde (1a) as a solid. $^1$H NMR (400 MHz, DMSO-d6) δ 9.94 (q, J=0.6 Hz, 1H), 8.19 (dq, J=8.4, 0.6 Hz, 1H), 7.82 (dt, J=8.4, 0.7 Hz, 1H). $^{13}$C NMR (101 MHz, DMSO-d$_6$) δ 189.33, 148.59, 145.66, 140.17, 133.19, 120.27.

Synthesis of 3,6-dibromopicolinaldehyde (1a)

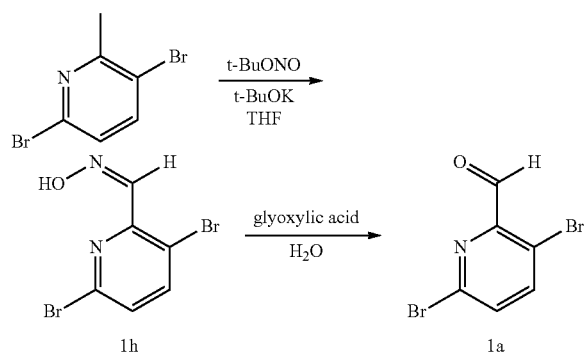

A solution of 2,5-dibromo-6-methylpyridine (8.03 g) in THF (81 mL) was cooled to about 0° C. To this solution was charged tert-butyl nitrite (4.33 g), followed by a dropwise addition of potassium tert-butoxide (28 mL, 1.5 equiv, 20 wt % solution in THF). The reaction mixture was agitated at about 0° C. until the reaction was complete. The reaction mixture was diluted with THF (24 mL), and quenched with ammonium chloride (6.38 g, 119 mmol) in water (43 mL). The reaction mixture was distilled under vacuum to approximately 55 mL to afford a slurry, which was filtered and washed twice with water (2×24 mL) to afford 1h. $^1$H NMR (400 MHz, DMSO-d$_6$) δ 11.69 (s, 1H), 8.08 (d, J=8.4 Hz, 1H), 7.67 (s, 1H), 7.61 (d, J=8.5 Hz, 1H).

A solution of glyoxylic acid (407 L, 50 wt % in water) was heated to about 80° C. and in portions was charged with 1h (40.69 kg, 145.4 mol). Reaction mixture was held at this temperature until the reaction was complete. The reaction mixture was cooled to about 20° C., filtered, and the filter cake was washed with water until the filtrate had a pH≥5, to afford 1a. $^1$H NMR (400 MHz, DMSO-d$_6$) δ 9.95 (s, 1H), 8.22 (d, J=8.4 Hz, 2H), 7.85 (d, J=8.4 Hz, 1H).

Synthesis of (E)-N-benzhydryl-1-(3,6-dibromopyridin-2-yl)methanimine (1b-02)

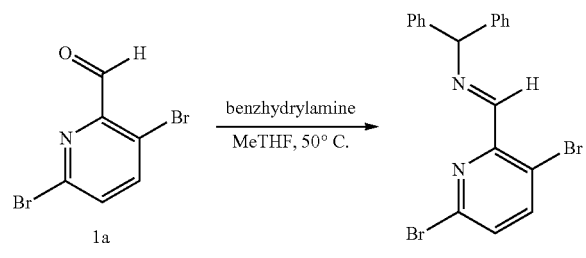

Compound 1a (5.0 g, 18.0 mmol) in toluene (20 mL) was heated to about 50° C. and benzhydrylamine (3.47 g, 18.9 mmol) was charged in one portion and agitated at this temperature until the reaction was deemed complete. Methanol (61 mL) was charged and the reaction mixture was distilled to a volume of approximately 25 mL. Methanol (40 mL) was charged and the reaction mixture was distilled to a volume of approximately 30 mL. The resulting slurry was filtered and rinsed with two portions of methanol (15 mL each) and dried under vacuum to afford 1b-02.

Alternatively, compound 1a (10.0 g, 37.8 mmol) in 2-methyltetrahydrofuran (50 mL) was heated to about 50° C. and benzhydrylamine (7.28 g, 39.7 mmol) was charged dropwise. The reaction was agitated at this temperature until it was deemed complete. The reaction mixture was distilled to a volume of approximately 30 mL. To the reaction mixture was charged heptane (100 mL) and 1b-02 seed (59.3 mg, 0.138 mmol). The resulting slurry was filtered, rinsed with two portions of heptane (2×20 mL), and dried under vacuum to afford 1b-02. $^1$H NMR (400 MHz, DMSO-d$_6$) δ 8.73 (s, 1H), 8.12 (d, J=8.4 Hz, 1H), 7.67 (d, J=8.4 Hz, 1H), 7.44-7.40 (m, 4H), 7.38-7.32 (m, 4H), 7.28-7.22 (m, 2H), 5.88 (s, 1H).

Synthesis of (E)-N-benzhydryl-1-(3,6-dibromopyridin-2-yl)methanimine (1b-02)

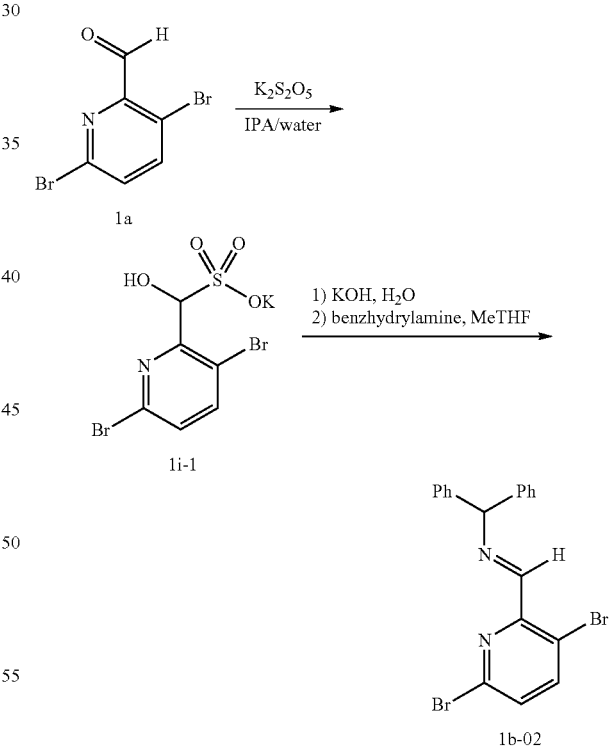

1a (2.00 g) was combined with isopropanol (7.6 mL) and agitated at ambient temperature. To this mixture was added potassium metabisulfite (0.96 g) in water (3.8 mL), dropwise. This mixture was agitated for at least 90 minutes and the resulting slurry was filtered. The filter cake was rinsed twice with isopropanol (6 mL then 12 mL) to afford 1i-1. $^1$H NMR (400 MHz, DMSO-d$_6$) δ 7.92 (d, J=8.3 Hz, 1H), 7.47 (d, J=8.3 Hz, 1H), 5.48-5.38 (m, 2H).

1i-1 (1.00 g) was combined with 2-methyltetrahydrofuran (3.5 mL) and agitated at ambient temperature. To this slurry was charged potassium hydroxide (443.8 mg, 7.91 mmol) in water (4 mL) and the biphasic mixture was agitated for 2 hours. The layers were separated and the aqueous layer was extracted with an additional portion of 2-methyltetrahydrofuran (3.5 mL). To the combined organics was charged benzhydrylamine (0.47 mL, 2.7 mmol). The reaction mixture was concentrated in vacuo (~300 mbar, 45° C. bath) to a volume of approximately 3 mL. Heptane (7 mL) was charged and the mixture was agitated. The resulting slurry was filtered to afford 1b-02. $^1$H NMR (400 MHz, DMSO-d$_6$) δ 8.73 (s, 1H), 8.12 (d, J=8.4 Hz, 1H), 7.67 (d, J=8.4 Hz, 1H), 7.44-7.40 (m, 4H), 7.38-7.32 (m, 4H), 7.28-7.22 (m, 2H), 5.88 (s, 1H).

Synthesis of (E)-N-benzhydryl-1-(3,6-dibromopyridin-2-yl)methanimine (1b-02)

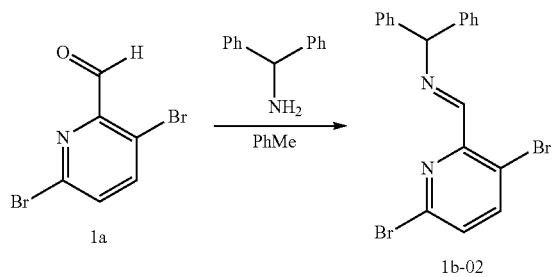

Compound 1a (1.0 g) was added to a reactor, and toluene (6.0 mL) was added to the reactor. The mixture was agitated. Aminodiphenylmethane (0.73 g, 1.05 equiv.) was added to the reaction mixture. The jacket was heated to about 60° C., and the mixture was allowed to age for about 1 hour. After about one hour, the mixture was carried forward to the next step. $^1$H NMR (400 MHz, DMSO-d$_6$) δ 8.68 (s, 1H), 8.05 (d, J=8.4 Hz, 1H), 7.60 (d, J=8.4 Hz, 4H), 7.40-7.34 (m, 7H), 7.29 (td, J=6.9, 6.5, 1.7 Hz, 5H), 7.22-7.16 (m, 3H), 5.81 (s, 1H).

Synthesis of N-(1-(3,6-dibromopyridin-2-yl)-2-(3,5-difluorophenyl)ethyl)-1,1-diphenylmethanimine (1d-02)

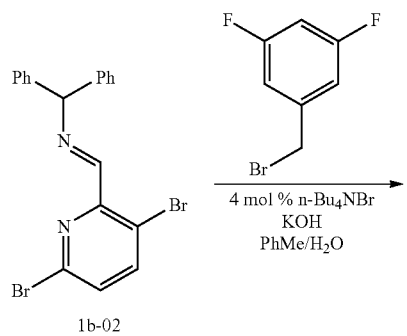

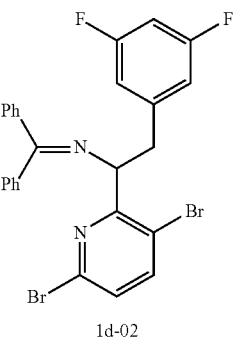

A solution of 1b-02 in toluene (1.0 g in 3.8 mL) was stirred in a reactor at about 60° C. Tetrabutylammonium bromide (0.08 g, 0.10 equiv.) was added, 3,5-difluorobenzylbromide (0.60 g, 1.20 equiv.) was added, and potassium hydroxide (50% in water, 1.3 g, 5 equiv.) was added. The mixture was aged for about 4 hours and sampled for conversion. When the reaction was complete, the aqueous phase was removed, and water (3.1 mL) was added to the reactor. Contents were agitated and phases were allowed to settle. The aqueous phase was removed, and the toluene solution of 1d-02 was carried forward to the next step. $^1$H NMR (400 MHz, Chloroform-d) δ 7.78 (dd, J=8.6, 1.0 Hz, 1H), 7.64-7.60 (m, 2H), 7.59-7.53 (m, 1H), 7.49 (d, J=8.3 Hz, 1H), 7.47 (s, 0H), 7.45 (s, 0H), 7.43 (d, J=0.7 Hz, 0H), 7.41-7.34 (m, 3H), 7.33 (t, J=1.4 Hz, 1H), 7.28 (t, J=7.3 Hz, 2H), 7.22 (s, 0H), 7.18 (d, J=8.3 Hz, 1H), 6.87 (dd, J=7.7, 1.7 Hz, 2H), 6.55 (dt, J=9.0, 2.3 Hz, 1H), 6.50 (dd, J=7.0, 4.9 Hz, 3H), 5.26 (s, 0H), 5.16 (t, J=6.9 Hz, 1H), 3.32 (dd, J=13.2, 6.6 Hz, 1H), 3.16 (dd, J=13.1, 7.2 Hz, 1H).

Synthesis of 1-(3,6-dibromopyridin-2-yl)-2-(3,5-difluorophenyl)ethan-1-amine (X) from N-(1-(3,6-dibromopyridin-2-yl)-2-(3,5-difluorophenyl)ethyl)-1,1-diphenylmethanimine (1d-02)

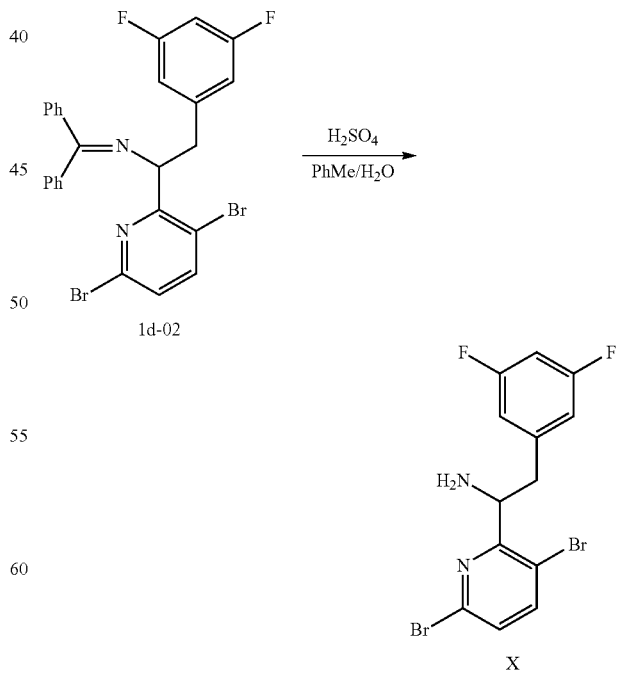

A solution of 1d-02 in toluene (1.0 g in 3.0 mL) was stirred in a reactor at about 60° C. Sulfuric acid (0.93 g, 5 equiv.) was diluted into water (3.5 mL), and added to the reactor. The mixture was aged for about 4 hours. When the reaction was complete, the aqueous phase was removed. The aqueous phase was recharged to the reactor, and heptane (2.5 mL) was added. The mixture was agitated and agitation stopped and layers allowed to settle. The aqueous phase was removed, and heptane was discharged to waste. Toluene (5.0 mL) and potassium hydroxide (50% in water, 2.1 g, 10 equiv.) was added to the reactor. The aqueous acidic solution was added to the reactor. The mixture was agitated for about 10 minutes, and agitation stopped and phases allowed to settle. The aqueous phase was discharged to waste. Water (2.5 mL) was added to the reactor, and the mixture was agitated for about 5 minutes, and agitation was stopped and the phases were allowed to settle. The aqueous phase was discharged to waste. The toluene solution of 1-(3,6-dibromopyridin-2-yl)-2-(3,5-difluorophenyl)ethan-1-amine (X) was carried forward to the next step. $^1$H NMR (400 MHz, Chloroform-d) δ 7.60 (d, J=8.3 Hz, 1H), 7.21 (d, J=8.3 Hz, 1H), 6.74-6.67 (m, 2H), 6.66-6.58 (m, 1H), 4.57-4.45 (m, 1H), 3.02 (dd, J=13.5, 5.2 Hz, 1H), 2.72 (dd, J=13.5, 8.6 Hz, 1H), 1.77 (s, 3H).

Synthesis of (S)-1-(3,6-dibromopyridin-2-yl)-2-(3,5-difluorophenyl)ethan-1-amine (R)-2-hydroxy-2-phenylacetate (VIII-03)

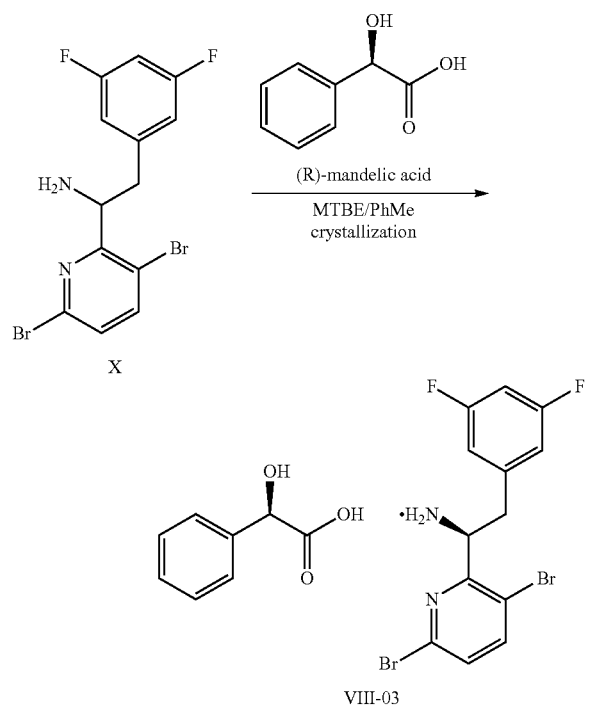

VIII-03

A solution of X in toluene (1.0 g in 7.1 mL) was stirred in a reactor at about 60° C. The mixture was distilled to minimum volumes (2.9 mL), and methyl tert-butyl ether was added (7.1 mL). (R)-(−)-Mandelic acid (0.41 g, 1 equiv.) was added, and the mixture was cooled to about 0° C. The newly formed slurry was filtered, providing (S)-1-(3,6-dibromopyridin-2-yl)-2-(3,5-difluorophenyl)ethan-1-amine (R)-2-hydroxy-2-phenylacetate (VIII-03). $^1$H NMR (400 MHz, DMSO-d$_6$) δ 7.93 (d, J=8.4 Hz, 1H), 7.49 (d, J=8.4 Hz, 1H), 7.34 (d, J=7.3 Hz, 2H), 7.28-7.14 (m, 4H), 7.01 (tt, J=9.4, 2.3 Hz, 1H), 6.79 (d, J=7.4 Hz, 3H), 4.77 (s, 1H), 4.55 (d, J=6.6 Hz, 1H), 3.02 (s, 1H), 2.92 (d, J=6.7 Hz, 2H), 1.05 (s, 2H).

Synthesis of (S)-1-(3,6-dibromopyridin-2-yl)-2-(3,5-difluorophenyl)ethan-1-amine N-acetyl-D-Leucine (VIII-04)

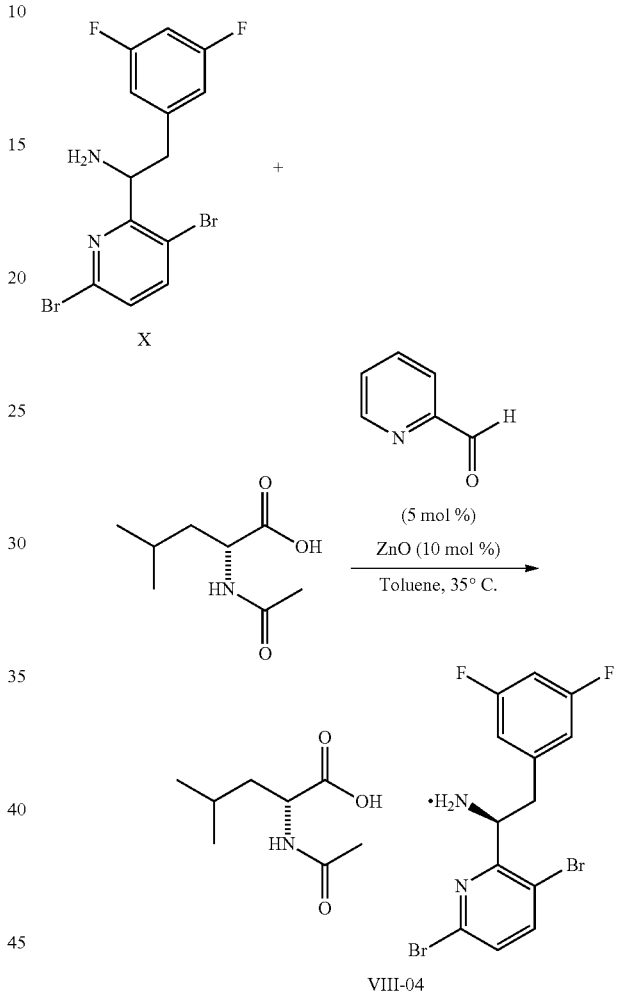

VIII-04

A reactor was charged with X (15.0 g), N-acetyl-D-leucine (8.28 g) and zinc oxide (0.311 g). Toluene (375 mL) was charged to the reactor followed by 2-pyridinecarboxaldehyde (183 μL). The mixture was aged at about 55° C. for about 6 hrs. and then held at about 35° C. for about 4 days. The mixture was cooled to about 0° C. and held for about 17 hrs. The product was isolated by filtration and the filter cake was washed with cold toluene (2×75 mL). The filter cake was re-charged to the reactor. Ethanol (150 mL) was added and the mixture distilled to remove residual toluene. Once the toluene was removed, the reactor volume was adjusted with ethanol to about 90 mL and the mixture was cooled to about 25° C. Water (210 mL) was added over approximately 10 min. and the mixture aged for approximately 12 hrs. The slurry was filtered and the solids were dried to afford VIII-04. $^1$H NMR (400 MHz, DMSO-d$_6$) δ 8.03 (d, J=8.0 Hz, 1H), 7.95 (d, J=8.3 Hz, 1H), 7.49 (d, J=8.3 Hz, 1H), 7.03 (tt, J=9.5, 2.4 Hz, 1H), 6.87 (dtd, J=8.4, 6.2, 2.2 Hz, 2H), 5.49 (s, 3H), 4.42 (dd, J=7.9, 5.9 Hz, 1H), 4.18 (q, J=7.8 Hz, 1H), 2.93 (dd, J=13.3, 5.9 Hz, 1H), 2.85 (dd, J=13.2, 8.0 Hz, 1H), 1.83 (s, 3H), 1.71-1.54 (m, 1H), 1.47 (dd, J=8.4, 6.2 Hz, 2H), 0.88 (d, J=6.6 Hz, 3H), 0.83 (d, J=6.5 Hz, 3H). $^{13}$C NMR (101 MHz, DMSO-d$_6$) δ 174.72, 169.03, 162.07 (dd, J=245.5, 13.3 Hz), 161.79, 143.51, 142.82 (t, J=9.4 Hz), 139.72, 128.39, 119.30, 113.36-111.39 (m), 101.73 (t, J=25.7 Hz), 55.19, 50.69, 41.74 (d, J=2.3 Hz), 40.51, 24.36, 22.91, 22.44, 21.46.

Example 1b: Preparation of Alternative Starting Materials and Intermediates for Use in the Formation of (S)-1-(3,6-dibromopyridin-2-yl)-2-(3,5-difluorophenyl)ethan-1-amine (VIII), or a Co-Crystal, Solvate, Salt, or Combination Thereof Synthesis of (R)-1-(3,6-dibromopyridin-2-yl)-2-(3, 5-difluorophenyl)ethan-1-ol (XII)

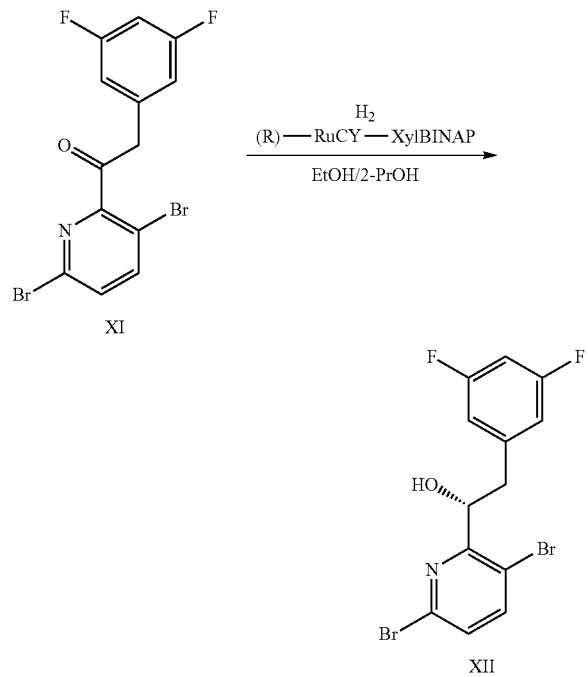

A stainless steel autoclave equipped with a glass inner tube was charged with compound XI (1.00 g) and (R)—RuCY-XylBINAP (16 mg, 0.05 equiv.). EtOH (1.0 mL) and IPA (1.0 mL) followed by tert-BuOK (1.0 M solution in THF, 0.51 mL, 0.2 equiv.) were added to the autoclave. After being purged by H$_2$, the autoclave was charged with 3 MPa (≅435 psi) of H$_2$. The mixture was stirred at about 20° C. for about 10 h. To the mixture, conc. HCl aqueous solution was added and pH was adjusted to 2. $^1$H NMR (400 MHz, CDCl3): δ 7.72 (d, J=8.2 Hz, 1H), 7.33 (d, J=8.2 Hz, 1H), 6.80-6.72 (m, 2H), 6.68 (tt, J=9.2, 2.4 Hz, 1H), 5.16 (dd, J=8.2, 3.4 Hz, 1H), 3.60 (br, 1H), 3.12 (dd, J=13.8, 3.4 Hz, 1H), 2.81 (dd, J=13.8, 8.2 Hz, 1H). 13C NMR (100 MHz, CDCl3): δ 162.8 (dd, J=246.4, 12.9 Hz), 160.1, 143.0, 141.3 (t, J=9.1 Hz), 139.8, 128.7 (t, J=35.7 Hz), 117.9, 112.3 (m), 102.1 (t, J=25.0 Hz), 72.0, 43.0. 19F NMR (376 MHz, CDCl3): δ −112.1 (m).

Synthesis of N-(1-(3,6-dibromopyridin-2-yl)-2-(3,5-difluorophenyl)ethyl)-15-chloranimine (X-02)

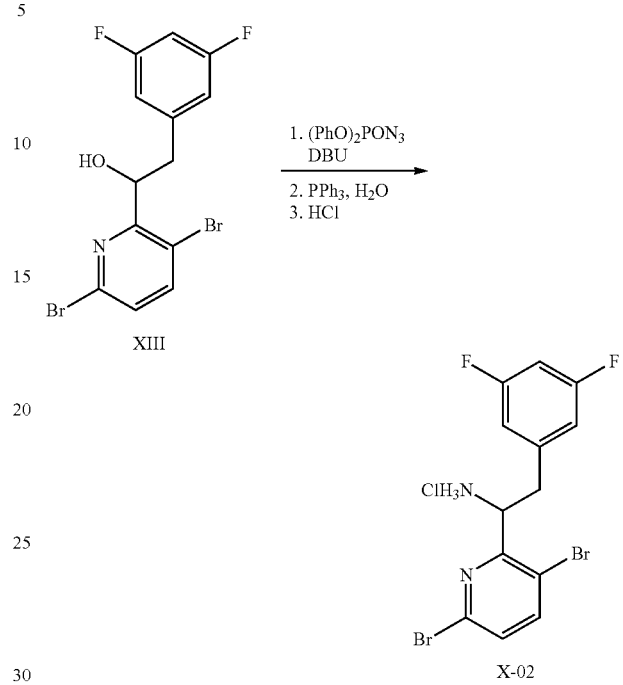

Compound XIII (0.0 g) was dissolved in THF (4.2 mL) and was cooled over an ice bath. Diphenylphosphoryl azide (0.66 mL, 1.2 equiv.) was added followed by DBU (0.46 mL, 1.2 equiv.) over about 25 min at below about 4° C. The dark mixture was aged about 1 hour, and the cooling bath was removed. After about 2.5 hours age at RT, some starting material was still present so more diphenylphosphoryl azide (0.15 equiv.) and DBU (0.15 equiv.) were added after cooling over an ice bath. After about 2 hours, more diphenylphosphoryl azide (0.08 equiv.) and DBU (0.08 equiv.) were added. The reaction mixture was allowed to age overnight for about 16 h to allow the conversion to azide intermediate complete. The reaction mixture was cooled over an ice bath and triphenylphosphine (1.0 g, 1.5 equiv.) was added over about 15 min at about 6° C.). The cooling bath was removed after about 10 min and the reaction mixture was agitated for additional about 2.5 hours. To this reaction mixture was added water (0.18 mL, 4 equivalents) and the resulting mixture was aged for about 15 hours at room temperature. The mixture was diluted with EtOAc (5.0 mL) and was washed with water (4.2 mL+2.0 mL). The aqueous layer was back extracted with EtOAc (4.0 mL) and the EtOAc layer was washed with water (1.0 mL). The organic layers were combined, concentrated via rotary evaporation and evaporated with EtOAc (4×4.0 mL) to dry. The residue was dissolved to a 50 ml solution in EtOAc, and cooled over an ice bath to become slurry. To the cold slurry 4N HCl/dioxane (0.76 mL, 1.2 equiv.) was added and the slurry was aged about 2 hours at room temperature. The solid product was filtered and the filter cake was rinsed with EtOAc and dried at about 35 to 50° C. under vacuum to give X-02.

Recrystallization: A portion of the above obtained X-02 (1.0 g) was mixed with EtOAc (10 mL) and was heated to 65° C. to afford thick slurry. The slurry was aged at about 65° C. for about 2 hours, and overnight at room temperature. The solids were filtered with recycling the mother liquor to help transfer the solids. The filter cake was rinsed with EtOAc, and dried overnight at about 50° C. vacuum to afford X-02. $^1$H NMR (300 MHz, DMSO-d) δ 8.78 (br s, 3H), 8.06-8.02 (m, 1H), 7.64-7.61 (m, 1H), 7.15-7.08 (m, 1H), 6.83-6.78 (m, 2H), 4.87-4.82 (m, 1H), 3.35-3.25 (m, 1H), 3.17-3.05 (m, 1H). $^{19}$F NMR (282.2 MHz, Chloroform-d) δ −109.9-110.1 (m).

Synthesis of 1-(3,6-dibromopyridin-2-yl)-2-(3,5-difluorophenyl)ethyl Methanesulfonate (XIII-A)

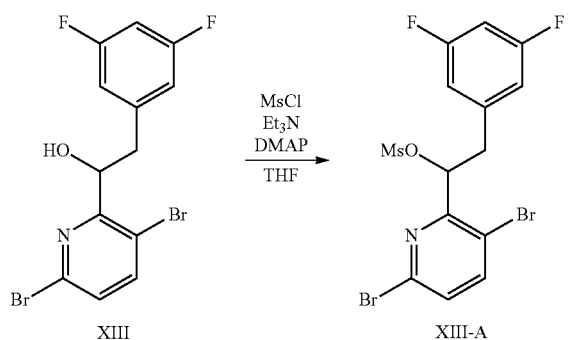

Compound XIII (1.0 g) and DMAP (0.1 equiv.) were dissolved in THF (4.5 mL) and cooled over an ice bath. Triethylamine (Et$_3$N) (0.39 mL, 1.1 equiv.) was added followed by methanesulfonyl chloride (218 μL, 1.1 equiv.). The cooling bath was removed, and the mixture was aged about 1.5 hours at room temperature. The reaction mixture was cooled over an ice bath and quenched with water (10 mL). The mixture was diluted with EtOAc and the phases were separated. The aqueous phase was extracted with EtOAc, and the combined organic phase was dried (Na$_2$SO$_4$) and was passed through silica gel with EtOAc. The filtrate was concentrated to afford the mesylate (XIII-A). $^1$H NMR (300 MHz, Chloroform-d) δ 7.72-7.66 (m, 1H), 7.38-7.32 (m, 1H), 6.78-6.63 (m, 3H), 6.17-6.13 (m, 1H), 3.40-3.25 (m, 2H), 2.87 (s, 3H). $^{19}$F NMR (282.2 MHz, Chloroform-d) δ −109.3-109.5 (m).

Synthesis of 1-(3,6-dibromopyridin-2-yl)-2-(3,5-difluorophenyl)ethan-1-amine (X) from 1-(3,6-dibromopyridin-2-yl)-2-(3,5-difluorophenyl)ethyl Methanesulfonate

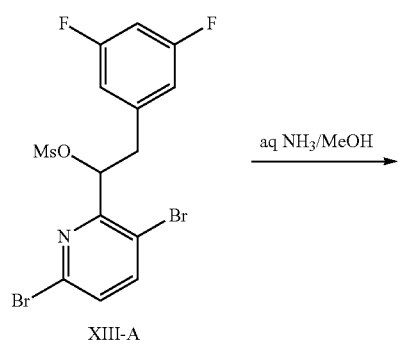

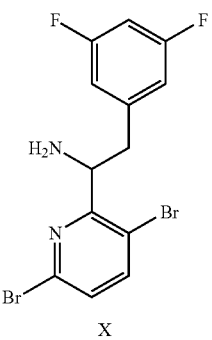

A glass pressure bottle was charged with the mesylate (XIII-A) (1.0 g), 28-30% ammonium hydroxide (19 mL) and MeOH (4.7 mL). The mixture was sealed and heated at about 70° C. for about 16 hours, and extracted with 2-MeTHF/EtOAc. The organic layer was dried (Na$_2$SO$_4$) and purified by silica gel chromatography (10-60% EtOAc/hexanes) to afford racemic amine X. $^1$H NMR (300 MHz, Chloroform-d) δ 7.70-7.60 (m, 1H), 7.30-7.20 (m, 1H), 6.78-6.60 (m, 3H), 4.46-4.58 (m, 1H), 3.00-3.16 (m, 1H), 2.70-2.80 (m, 1H). $^{19}$F NMR (282.2 MHz, Chloroform-d) δ −110.3-110.4 (m).

Synthesis of (Z)—N-(1-(3,6-dibromopyridin-2-yl)-2-(3,5-difluorophenyl)vinyl)acetamide (1f)

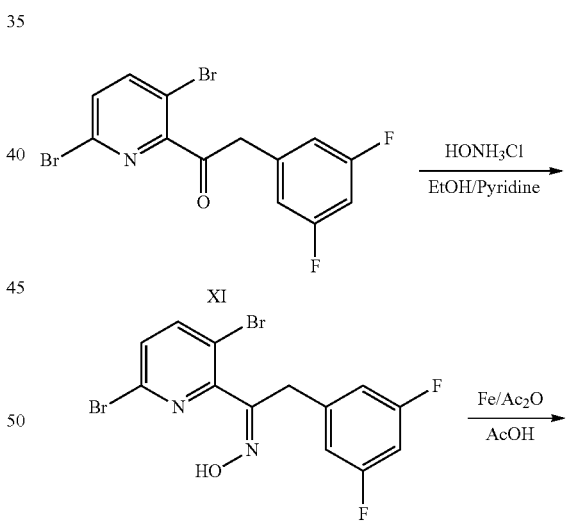

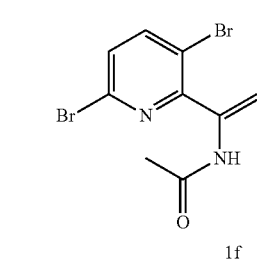

A glass reactor was charged with XI (1.0 g). Ethanol (5.0 mL) was added, and the slurry was agitated while hydroxylamine hydrochloride (0.88 g) was charged. Pyridine (1.0 mL) was added and the mixture heated at about 55-65° C. for about two hours. The mixture was cooled to about 20° C., transferred to a flask, and concentrated to approximately 75 mL by rotary evaporation. The concentrate was returned to the reactor, rinsing through with isopropyl acetate (5.0 mL). Residue remaining in the flask was carefully (gas evolution) rinsed into the reactor with saturated aqueous sodium bicarbonate (5.0 mL). The bi-phasic mixture was agitated, the phases separated, and the organic extract washed with water (3.2 mL) and saturated sodium chloride (3.2 mL). The organic extract was dried over anhydrous sodium sulfate, filtered, and concentrated to dryness by rotary evaporation to yield 1e which was used without further purification.

A glass reactor was charged with iron powder (<10 micron, 0.30 g mmol) followed by acetic acid (1.6 mL) and acetic anhydride (0.72 mL). The slurry was de-gassed by holding the reactor contents under vacuum until bubbling was observed, and back-filled with nitrogen (3 cycles). The mixture was heated at 115-120° C. for 2 hours and cooled to 40° C. Compound 1e from the previous step in isopropyl acetate (2.0 mL) was added over 30 min. Upon completing the addition, the temperature was raised to 45-65° C. and the mixture aged for about 2 hours. A slurry of diatomaceous earth (1.0 g) in isopropyl acetate (2.0 mL) was added, followed by toluene (2.0 mL). The slurry was filtered, hot, through a Buchner funnel and the reactor and filter cake were washed with warm isopropyl acetate (3×1.8 mL). The filtrate was transferred to a reactor and the solution washed with 0.5% aqueous sodium chloride (4.2 mL). Water (3.1 mL) was added to the reactor and the mixture was cooled to about 5° C. The pH was adjusted to 7-9 with the addition of 50 wt % aqueous sodium hydroxide; following separation, the organic extract was warmed to room temperature and washed with aqueous 1% (w/w) sodium chloride NaCl (3.6 mL). The organic extract was discharged to a flask and dried over anhydrous sodium sulfate (ca. 0.8 g), filtered through diatomaceous earth, and concentrated to approximately 4 mL at 100 mmHg and 45° C. water bath. The warm solution was returned to the reactor, rinsing forward with isopropyl acetate to a produce a total volume of approximately 5.2 mL. This solution was heated further to 50° C. with agitation, cooled to about 35° C., and seeded with pure 1f (0.006 g). Heptane (9.6 mL) was added over a period of about 4 hours, the solution was cooled to about 10° C., and the product was isolated by filtration. The filter cake was washed with 33.3% iPAc in heptane (4.0 mL) and dried in a vacuum oven at 40° C. with nitrogen sweep for approximately 24 hours. Compound 1f, a mixture of geometric isomers (approximately 94:6 ratio) was isolated. Major isomer: $^1$H NMR (400 MHz, DMSO-$d_6$) δ 9.96 (s, 1H), 8.04 (d, J=8.4 Hz, 1H), 7.66 (d, J=8.4 Hz, 1H), 7.05 (s, 1H), 6.97 (tt, J=9.2, 2.2 Hz, 1H), 6.40-6.31 (m, 2H), 1.97 (s, 3H). $^{13}$C NMR (101 MHz, DMSO-$d_6$) δ 168.37, 162.04 (dd, J=245.1, 13.9 Hz), 154.47, 143.63, 139.45, 139.40-139.18 (m), 135.99, 129.44, 120.66, 113.80, 111.23-109.68 (m), 101.77 (t, J=26.0 Hz), 23.49.

Synthesis of (S)—N-(1-(3,6-dibromopyridin-2-yl)-2-(3,5-difluorophenyl)ethyl)acetamide (1g)

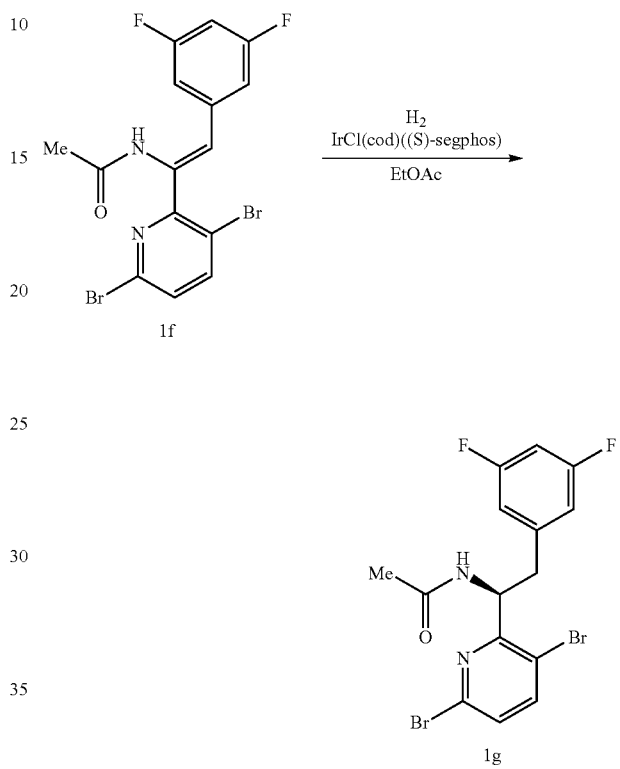

Preparation of catalyst solution: A flask was charged with [IrCl(cod)((S)-segphos)] (110 mg) and the internal atmosphere was replaced with $N_2$. EtOAc (200 mL) was added to the flask and the mixture was stirred until the catalyst solid was dissolved.

A stainless steel autoclave was charged with compound 1f (1.0 mg). EtOAc (16 mL) and followed by the catalyst solution prepared above (4.0 mL, 0.001 equiv.) were added to the autoclave. After being purged by Hz, the autoclave was charged with 3 MPa (≅435 psi) of Hz. The mixture was stirred at about 130° C. for about 6 hours and cooled to room temperature and $H_2$ was vented out. The reaction mixture was purified by silica gel column chromatography (EtOAc/Hexane=1/4 to 1/1) to afford 1g. 1H NMR (400 MHz, CD2Cl2): δ 7.70 (d, J=8.0 Hz, 1H), 7.30 (d, J=8.0 Hz, 1H), 6.68 (tt, J=9.2, 2.4 Hz, 1H), 6.64-6.58 (m, 2H), 6.49 (brd, J=8.0 Hz, 1H), 5.74 (ddt, J=8.0, 7.2, 6.4 Hz, 1H), 3.10 (dd, J=13.6, 6.4 Hz, 1H), 2.99 (dd, J=13.6, 7.2 Hz), 1.95 (s, 3H). 13C NMR (100 MHz, CD2Cl2): δ 169.5, 163.3 (dd, J=246.0, 12.9 Hz), 159.1, 143.6, 141.4 (t, J=9.1 Hz), 140.7, 129.1, 119.9, 112.9 (m), 102.6 (t, J=25.1 Hz), 53.0, 41.3, 23.6. 19F NMR (376 MHz, CD2Cl2): δ −111.3 (m).

Synthesis of (S)-1-(3,6-dibromopyridin-2-yl)-2-(3,5-difluorophenyl)ethan-1-amine (VIII) from 1-(3,6-dibromopyridin-2-yl)-2-(3,5-difluorophenyl)ethan-1-one (XI), Method 1

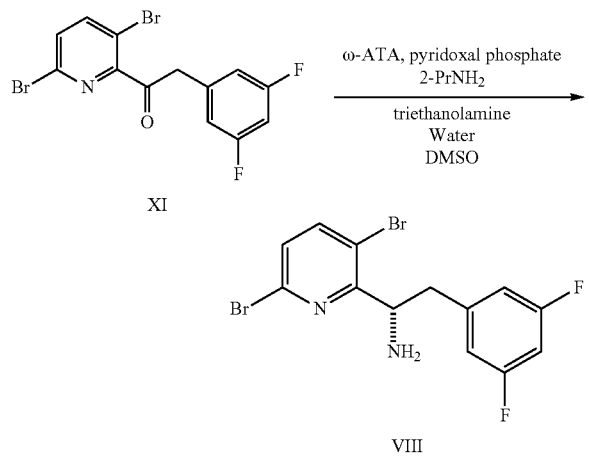

A glass-lined reactor was charged with isopropylamine (about 18 g) and triethanolamine (3.8 g). Water (231 mL) was added and the pH was adjusted to about 7.5 by the addition of concentrated hydrochloric acid. A portion of the buffer solution (23 mL) was removed. The transaminase enzyme (2.5 g) was added to the reactor as a suspension in buffer solution (12 mL), followed by addition of pyridoxal phosphate monohydrate (50 mg) as a solution in buffer solution (12 mL). A solution of XI (1.0 g) in dimethylsulfoxide (23 mL) was added to the reactor and the mixture was heated at about 35° C. for about 48 hours with constant nitrogen sparging of the solution. The reaction mixture was cooled to about 20° C. the unpurified amine was removed by filtration. The filter cake was washed with water (3×7.7 mL) and the product was dried at about 60° C. under vacuum with nitrogen sweep to afford VIII.

Synthesis of (S)-1-(3,6-dibromopyridin-2-yl)-2-(3,5-difluorophenyl)ethan-1-amine (VIII) from 1-(3,6-dibromopyridin-2-yl)-2-(3,5-difluorophenyl)ethan-1-one (XI), Method 2

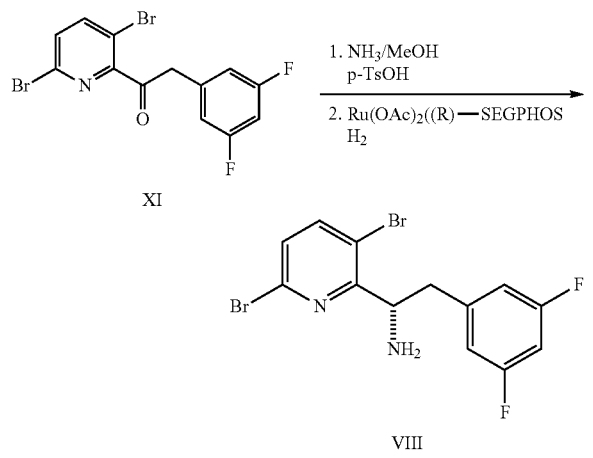

A stainless steel reactor was charged with XI (1.0 g) and p-toluenesulfonic acid (0.49 g). Ammonia (7 M in methanol, 3.7 mL) was added and the vessel was sealed and heated at about 60° C. for about 18 hours. The mixture was cooled to about 20° C. and sparged for about 30 min to remove excess ammonia. A solution of diacetato[(R)-5,5'-bis(diphenylphosphino)-4,4'-bi-1,3-benzodioxole]ruthenium(II) (0.10 g) in methanol (0.5 mL) was added to the reactor, which was sealed and heated at about 60° C. under a hydrogen atmosphere (400 psi) for a further about 6-10 hours. Upon cooling to about 20° C. the mixture was filtered through a plug of silica, rinsing with additional methanol (5.0 mL). Concentration of the filtrate by rotary evaporation affords VIII.

Example 1c: Preparation of 1-(3,6-dibromopyridin-2-yl)-2-(3,5-difluorophenyl)ethan-1-amine (X) by racemization of (S)-1-(3,6-dibromopyridin-2-yl)-2-(3,5-difluorophenyl)ethan-1-amine (VIII)

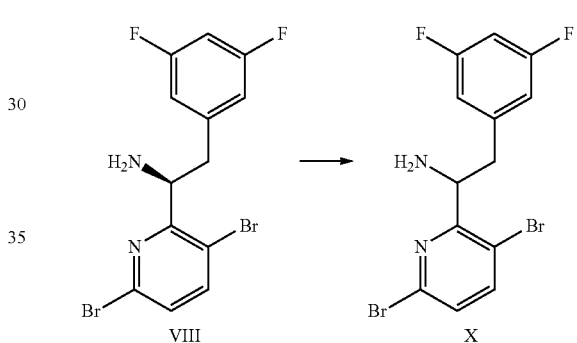

A vial was charged with zinc acetate (25 mol %), enantioenriched VIII (1.0 g, 92:8 enantiomer ratio), toluene (10 mL), and 2-formylpyridine (5 mol %). The vial was warmed to about 60° C. and stirred for about 4 h.

Example 2: Preparation of (S)-1-(3-bromo-6-(3-methyl-3-(methylsulfonyl)but-1-yn-1-yl)pyridin-2-yl)-2-(3,5-difluorophenyl)ethan-1-amine (VI)

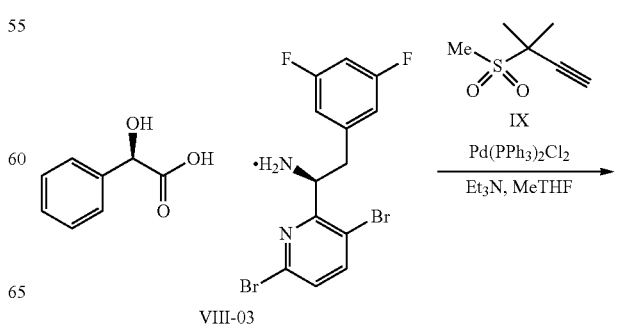

147
-continued

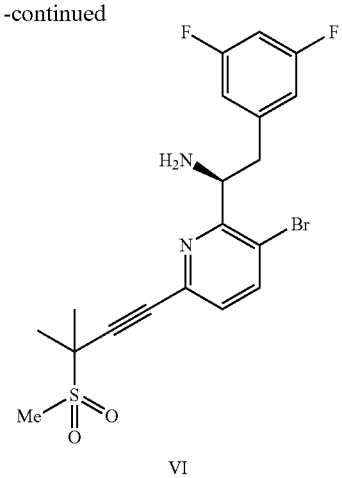

VI

A glass-lined reactor was charged with (S)-1-(3,6-dibromopyridin-2-yl)-2-(3,5-difluorophenyl)ethan-1-amine (R)-mandelic acid salt (VIII-03) (1.0 g), 3-methyl-3-(methylsulfonyl)but-1-yne (IX) (about 0.3 g), and dichlorobis(triphenylphosphine)palladium(II) (about 0.39 g). The reactor was evacuated and purged with nitrogen to inert. To this reactor was added 2-methyltetrahydrofuran (6.4 kg) and triethylamine (0.92 kg 5.0 equiv.). The reaction mixture was agitated at about 65-75° C. until the reaction was deemed complete by HPLC analysis. Upon cooling to about 30-40° C. the reaction mixture was discharged to another reactor and the parent reactor was rinsed with 2-methyltetrahydrofuran (4.6 g) and the resulting solution transferred to the receiving reactor. To the reactor was added water (5.0 g) and the biphasic mixture agitated at about 30-40° C. for about 30 min. Agitation was ceased and the mixture was allowed to layer for 30 min. The lower aqueous layer was discharged and the remaining organic solution held for about 15 hours. A solution of N-acetyl-L-cysteine (196 g) and sodium hydroxide (0.80 g) in water (11.8 g) was prepared. To the reactor was added approximately half of the N-acetyl-L-cysteine solution (6.7 g). The mixture was agitated at about 55-65° C. for about 30 min. The temperature was adjusted to about 30-40° C. and agitation was ceased. After about 30 min had elapsed, the lower aqueous phase was discharged. The remaining alkaline N-acetyl-L-cysteine solution (5.4 kg) was added and the mixture was heated, with agitation, to about 55-65° C. and held for about 30 min. The temperature was adjusted to about 30-40° C. and agitation was ceased. After about 30 min had elapsed, the lower aqueous phase was discharged. To the reactor was added a solution of sodium chloride (0.26 g) in water (4.9 g) and the mixture agitated at about 30-40° C. for about 30 min. Agitation was ceased and the biphasic mixture allowed to layer for about 30 min. The lower aqueous layer was discharged and the contents cooled to about 15-25° C. and held for about 16 hours. The mixture was concentrated at about 55-65° C. The concentrated solution was cooled to about 30-40° C. and heptane (3.4 kg) was added over about 2 hours. The resulting slurry was cooled to about 20° C. and aged for about 20 h, and filtered. The filter cake was washed with 2-methyltetrahydrofuran/heptane (1:1 v/v, 2 mL) and the solids dried in a vacuum oven at about 40° C. to yield (S)-1-(3-bromo-6-(3-methyl-3-(methylsulfonyl)but-1-yn-1-yl)pyridin-2-yl)-2-(3,5-difluorophenyl)ethan-1-amine (VI)). $^1$H NMR (400 MHz, DMSO-d$_6$) δ 8.05 (d, J=8.2 Hz, 1H), 7.42 (d, J=8.2 Hz, 1H), 7.01 (tt, J=9.5, 2.4 Hz, 1H), 6.97-6.84 (m, 2H), 4.41

148
(dd, J=8.5, 5.2 Hz, 1H), 3.20 (s, 3H), 2.93 (dd, J=13.3, 5.2 Hz, 1H), 2.79 (dd, J=13.3, 8.5 Hz, 1H), 1.99 (s, 2H), 1.68 (s, 6H). $^{13}$C NMR (101 MHz, DMSO-d$_6$) δ 162.25, 162.00 (dd, J=245.2, 13.4 Hz), 143.88 (t, J=9.4 Hz), 141.09, 139.72, 127.51, 120.08, 112.58-112.12 (m), 101.45 (t, J=25.7 Hz), 87.94, 84.25, 57.24, 55.90, 42.57, 34.99, 22.19.

Example 2a: Preparation of 3-methyl-3-(methylsulfonyl)but-1-yne (IX)

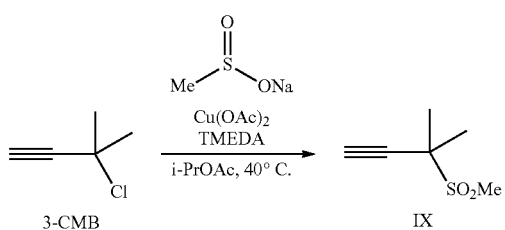

Sodium methansulfinate (418.1 g), copper (II) acetate (26.6 g), N,N,N',N'-Tetramethylethylenediamine (TMEDA, 34.0 g), and isopropyl acetate (2100 mL) were added to a reactor and the suspension was agitated at 20-25° C. 3-Chloro-3-methylbut-1-yne (3-CMB, 300 g) was added slowly to maintain a constant temperature of about 20-25° C. The reaction mixture was then heated to about 30° C. until the reaction was complete. The mixture was cooled to about 20° C. and washed twice with 5% aqueous sulfuric acid (600 mL). The combined aqueous layers were then extracted with isopropyl acetate (600 mL). The combined organic layers were then washed with water (600 mL). The product was then isolated by crystallization from isopropyl acetate (900 mL) and n-heptane (1.8 kg) at about 0° C. The wet cake was then washed with cold n-heptane to afford IX. $^1$H NMR (400 MHz, DMSO-d$_6$) δ 3.61 (s, 1H), 3.07 (s, 3H), 1.55 (s, 6H); $^{13}$C NMR (100 MHz, DMSO) δ 82.59, 77.76, 56.95, 34.95, 22.77.

Example 3a: Preparation of (3bS,4aR)-3-(trifluoromethyl)-1,3b,4,4a-tetrahydro-5H-cyclopropa[3,4]cyclopenta[1,2-c]pyrazol-5-one (XV) from lithium (Z)-2,2,2-trifluoro-1-(3-oxobicyclo[3.1.0]hexan-2-ylidene)ethan-1-olate (3a)

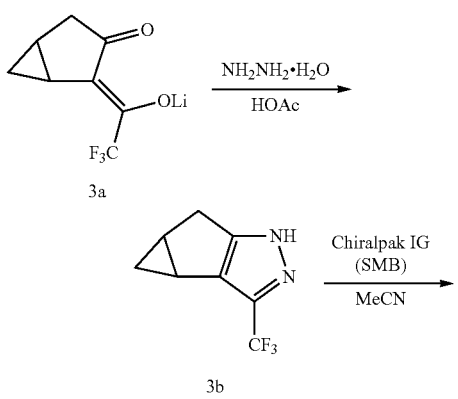

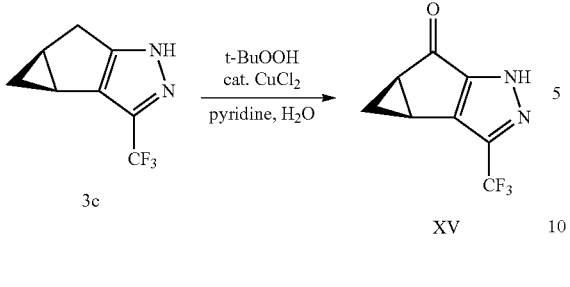

Synthesis of 3-(trifluoromethyl)-3b,4,4a,5-tetrahydro-1H-cyclopropa[3,4]cyclopenta[1,2-c]pyrazole (3b)

A reactor was charged with 3a (1.0 g) and AcOH (4.2 ml) and the resulting solution was adjusted to about 20° C. Hydrazine hydrate (0.29 g, 1.4 equiv.) was added over about 60 min at about 17-25° C. and the reaction mixture was stirred for about 2 hours at about 20-25° C., warmed up to about 45 to 50° C. over about 30 min, and aged at about 50° C. overnight. Water was slowly (5 mL) added at about 50° C. and product started to crystallize after addition of 5 mL of water. Another 5 mL of water was added at about 50° C., and the slurry was cooled down to about 20° C. in about one hour and held overnight at about 20° C. The solids were filtered, washed with water (4×3 mL), and dried under vacuum at about 30° C. to yield 3b. $^1$H NMR (400 MHz, Chloroform-d) δ 2.99 (dd, J=17.0, 6.1 Hz, 1H), 2.89-2.78 (m, 1H), 2.14 (dddd, J=9.1, 7.9, 3.6, 2.5 Hz, 2H), 1.13 (td, J=7.8, 5.1 Hz, 1H), 0.36-0.26 (m, 1H).

Isolation of (3bS,4aS)-3-(trifluoromethyl)-3b,4,4a,5-tetrahydro-1H-cyclopropa[3,4]cyclopenta[1,2-c]pyrazole (3c)

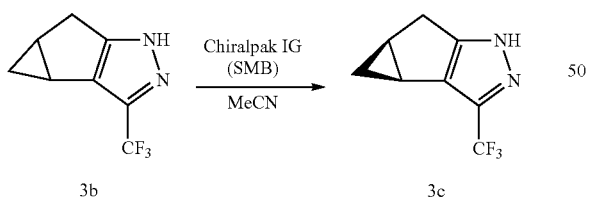

Chiral purification of 3b (1.0 g) was achieved using a 8×50 mm simulated moving bed (SMB) chromatography system and Chiralpak IG (20μ particle size) stationary phase using acetonitrile as a mobile phase to afford 3c. $^1$H NMR (400 MHz, Chloroform-d) δ 3.00 (dd, J=17.0, 5.7 Hz, 1H), 2.90-2.77 (m, 1H), 2.21-2.05 (m, 2H), 1.13 (td, J=7.8, 5.1 Hz, 1H), 0.35-0.27 (m, 1H).

Synthesis of (3bS,4aR)-3-(trifluoromethyl)-1,3b,4,4a-tetrahydro-5H-cyclopropa[3,4]cyclopenta[1,2-c]pyrazol-5-one (XV)

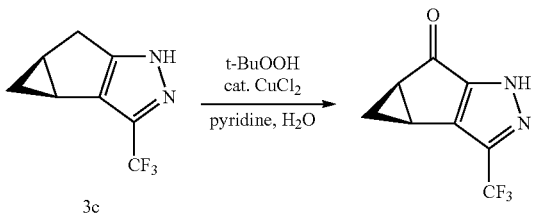

A reactor was charged with water (7 mL) and CuCl$_2$·2H$_2$O (0.09 g, 0.1 equiv). To the reactor was added pyridine (0.42 g, 1 equiv.) and 3c. tert-Butylhydroperoxide (70% in water, 5.5 g, 8 equiv.) was added over about 0.5 hour. The reaction mixture was stirred at about 20° C. for about 2.5 days and quenched with aqueous sodium metabisulfite solution (0.73 g in 2.5 mL water). The quenched reaction mixture was extracted with isopropyl acetate (20 mL), and the aqueous layer was back extracted with isopropyl acetate (2.0 ml). The organic layers were combined and washed with aqueous ethylenediaminetetraacetic acid (EDTA) solution 0.16 g EDTA 10 ml in water), the aqueous layer was dropped, and the organic layer was further washed with aqueous EDTA solution (0.015 g EDTA in 20 ml water). The washed organic layer was concentrated to dryness. To the residue was added isopropyl acetate (2.0 ml) and heptane (2.0 mL). The solution was seeded and stirred overnight at about 20° C., further diluted with heptane (2.0 mL), and the mixture was concentrated to dryness. The residue was suspended in heptane (4.0 mL) at about 40° C. The solid was filtered and the filter cake was washed with heptane (1.0 mL) and dried at about 40° C. to yield XV. $^1$H NMR (400 MHz, Chloroform-d) δ 2.84 (dt, J=6.8, 4.2 Hz, 1H), 2.71-2.64 (m, 1H), 1.79-1.67 (m, 2H).

Example 3b: Preparation of (3bS,4aR)-3-(trifluoromethyl)-1,3b,4,4a-tetrahydro-5H-cyclopropa[3,4]cyclopenta[1,2-c]pyrazol-5-one (XV) from lithium (Z)-1-((1S,5R)-4,4-dimethoxy-3-oxobicyclo[3.1.0]hexan-2-ylidene)-2,2,2-trifluoroethan-1-olate (3d-02)

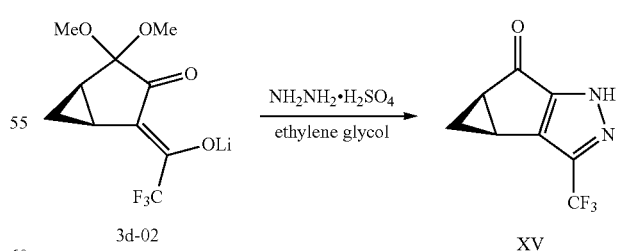

Hydrazine sulfate (0.45 g, 0.95 equiv.) and ketal lithium salt 3d-02 (1.0 g) were dissolved in ethylene glycol (9.5 mL), and the solution was heated to about 40° C. for about 16 hours. Reaction was cooled to room temperature and water (9.0 mL) was added. Reaction was polish filtered and The filtrate was collected and to this receiving flask was added water (10 mL, 2×). Slurry was cooled in ice water bath for about five hours, and filtered. Solids were washed with ice water (10 mL, 2×), deliquored, and dried to afford XV. $^1$H NMR (400 MHz, CDCl3) δ 11.83 (bs, 1H), 2.93-2.77 (m, 1H), 2.77-2.58 (m, 1H), 1.86-1.57 (m, 2H). $^{19}$F NMR (376 MHz, CDCl$_3$) δ −61.69. $^{13}$C NMR (101 MHz, CDCl$_3$) δ 188.56, 144.08, 142.92, 121.82, 119.15, 36.28, 31.87, 14.15.

Example 3c: Preparation of (3bS,4aR)-3-(trifluoromethyl)-1,3b,4,4a-tetrahydro-5H-cyclopropa[3,4]cyclopenta[1,2-c]pyrazol-5-one (XV) from (1S,2S)-2-iodo-N-methoxy-N-methylcyclopropane-1-carboxamide (3f) and 1-(4-methoxybenzyl)-4-(4,4,5,5-tetramethyl-1,3,2-dioxaborolan-2-yl)-3-(trifluoromethyl)-1H-pyrazole (3i) and Preparation of Starting Materials and/or Intermediates Therein Synthesis of (1S,2S)-2-iodo-N-methoxy-N-methyl-cyclopropane-1-carboxamide (3f)

Starting material iodoacid 3e is a mixture of 3e and cyclopropane carboxylic acid (des-iodo 3e) with mole ratio of 3e to des-iodo 3e of 2:1 by NMR. A mixture of 3e (1.0 g), N,O-dimethyl hydroxylamine-HCl (0.46 g) and carbonyl diimidazole (1.72 g) in THF was stirred overnight at room temperature. The reaction mixture was diluted with water, extracted with CH$_2$Cl$_2$, and concentrated to afford unpurified 3f (1.8 g). The unpurified 3f was purified by column chromatography to afford 3f which was a mixture of Weinreb amide 3f and des-iodo-3f (about 80:20 by HPLC).

Synthesis of 1-(4-methoxybenzyl)-4-(4,4,5,5-tetramethyl-1,3,2-dioxaborolan-2-yl)-3-(trifluoromethyl)-1H-pyrazole (3i)

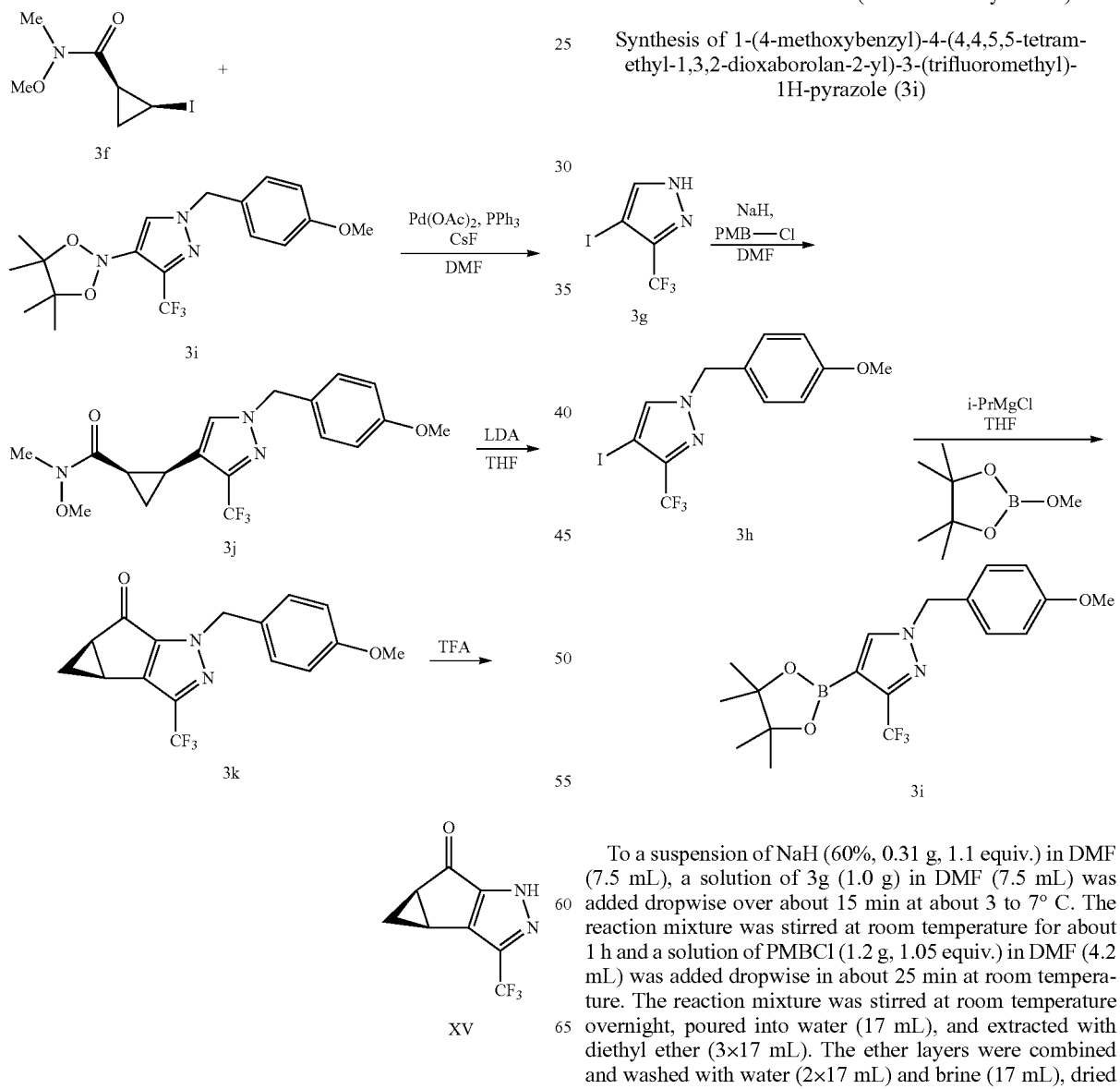

To a suspension of NaH (60%, 0.31 g, 1.1 equiv.) in DMF (7.5 mL), a solution of 3g (1.0 g) in DMF (7.5 mL) was added dropwise over about 15 min at about 3 to 7° C. The reaction mixture was stirred at room temperature for about 1 h and a solution of PMBCl (1.2 g, 1.05 equiv.) in DMF (4.2 mL) was added dropwise in about 25 min at room temperature. The reaction mixture was stirred at room temperature overnight, poured into water (17 mL), and extracted with diethyl ether (3×17 mL). The ether layers were combined and washed with water (2×17 mL) and brine (17 mL), dried over Na₂SO₄, and concentrated in vacuo to give unpurified 3h. Unpurified 3h was absorbed in silica gel (4.3 g) and purified by silica gel chromatography (eluting with 5-25% EtOAc in hexanes) to give 3h (1.5 g).

To solution of iodopyrazole 3h (1.0 g) in THF (8 mL) i-PrMgCl (2M in ether, 1.8 mL, 1.1 equiv.) was added dropwise over about 10 min at below about 5° C. The resulting solution was stirred at about 0° C. for about 70 min and 2-methoxy-4,4,5,5-tetramethyl-1,3,2-dioxaborolane (970 mg, 1.81 equiv.) was added at below about 6° C. The reaction mixture was warmed up to room temperature, quenched by addition of saturated NH₄Cl (20 mL), and extracted with EtOAc (2×20 mL). The combined organic layer was washed with saturated NH₄Cl (10 mL) and concentrated to unpurified oil, which was combined with the unpurified oil from a previous batch (prepared using 1.1 g of 3h), absorbed on silica gel (6 g), and purified via silica gel chromatography (eluting with 5-40% EtOAc/Hexanes,). Boronate 3i was obtained. ¹H NMR (300 MHz, Chloroform-d) δ 7.60 (s, 1H), 7.23-7.19 (m, 2H), 6.90-6.85 (m, 2H), 5.25 (s, 2H), 3.81 (m, 3H), 1.29 (s, 12H).

Synthesis of (1R,2S)—N-methoxy-2-(1-(4-methoxybenzyl)-3-(trifluoromethyl)-1H-pyrazol-4-yl)-N-methylcyclopropane-1-carboxamide (3j)

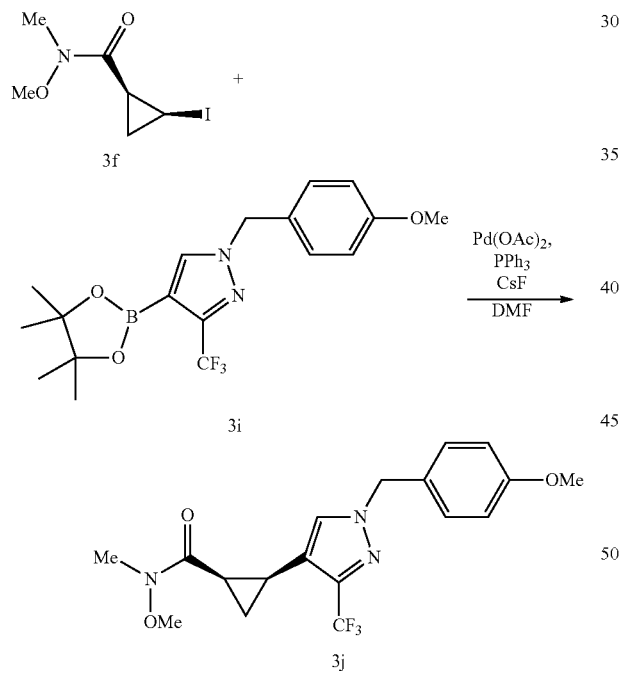

A mixture of unpurified iodide 3f (1.0 g), boronate 3i (about 2.2 g), CsF (4.5 equiv.), Pd(OAc)₂ (0.1 equiv.), and PPh₃ (0.5 equiv.) in DMF (58 mL) was degassed by bubbling N₂ and heated at about 87° C. for about 15 hours. The reaction mixture was diluted with water, extracted with MTBE, concentrated and the unpurified product was purified by column chromatography to give 3j. ¹H NMR (300 MHz, Chloroform-d) δ 7.18-7.14 (m, 3H), 6.86-6.82 (m, 2H), 5.24-5.08 (m, 2H), 3.77 (s, 3H), 3.63 (s, 3H), 3.05 (s, 3H), 2.37-2.32 (m, 1H), 1.50-1.42 (m, 1H), 1.32-1.21 (m, 2H).

Synthesis of (3bS,4aR)-1-(4-methoxybenzyl)-3-(trifluoromethyl)-1,3b,4,4a-tetrahydro-5H-cyclopropa[3,4]cyclopenta[1,2-c]pyrazol-5-one (3k)

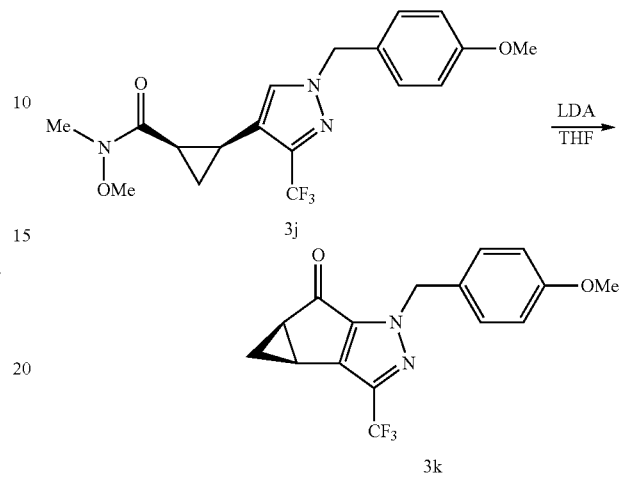

Compound 3j (1.0 g) was treated with freshly prepared LDA (3.3 eq then 0.7 equiv.) at about −67° C. for about 2.5 hours. The reaction mixture was quenched with saturated NH₄Cl (12.5 mL) and diluted with MTBE (63 mL). The organic layer was washed with brine, concentrated, and purified by column chromatography to give 3k. ¹H NMR (300 MHz, Chloroform-d) δ 7.36-7.33 (m, 2H), 6.86-6.83 (m, 2H), 5.28 (s, 2H), 3.78 (s, 3H), 2.73-2.65 (m, 1H), 2.60-2.53 (1H), 1.70-1.61 (m, 2H).

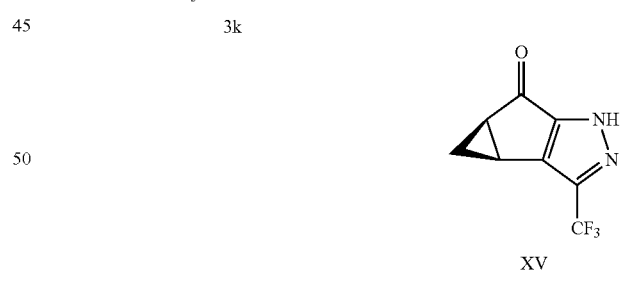

Synthesis of (3bS,4aR)-3-(trifluoromethyl)-1,3b,4,4a-tetrahydro-5H-cyclopropa[3,4]cyclopenta[1,2-c]pyrazol-5-one (XV)

A mixture of 3k (1.0 g) and TFA (5 mL) was heated at about 75° C. for about 3 hours and concentrated. The residue was dissolved in DCM (50 mL), washed with saturated NaHCO₃ and brine, concentrated, and purified by column chromatography to give XV. ¹H NMR (300 MHz, Chloroform-d) δ 2.86-2.80 (m, 1H), 2.68-2.63 (m, 1H), 1.77-1.65 (m, 2H).

Example 3d: Resolution of 2-(2,2,2-trifluoroacetyl)bicyclo[3.1.0]hexan-3-one (31) with quinine

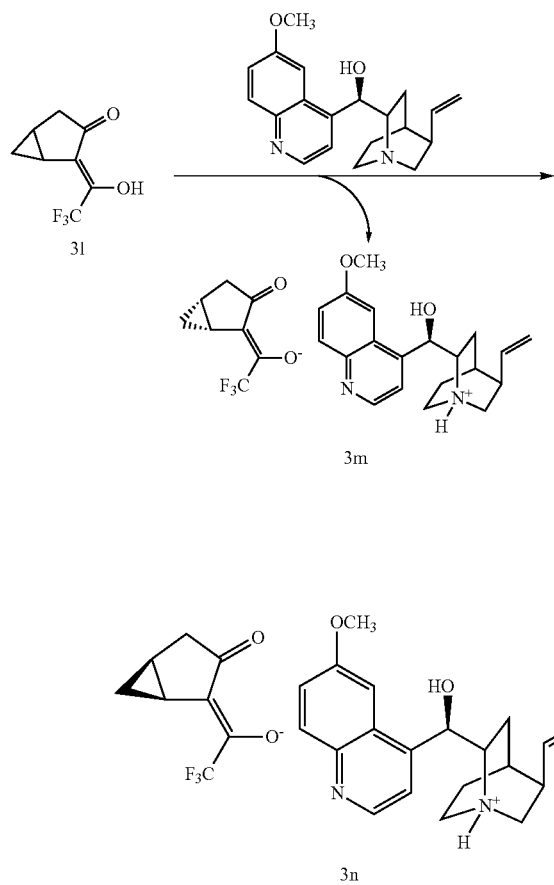

A flask was charged with 31 (1.0 g), acetone (2.5 ml), and quinine (1.7 g, 0.65 equiv). The mixture was stirred at about 15 to 25° C. for about 18 hours and the solids were isolated by filtration and washed with acetone to provide the quinine salt 3n.

Example 4a: Preparation of ethyl 2-((3bS,4aR)-5-oxo-3-(trifluoromethyl)-3b,4,4a,5-tetrahydro-1H-cyclopropa[3,4]cyclopenta[1,2-c]pyrazol-1-yl)acetate (XIV) from (3bS,4aR)-3-(trifluoromethyl)-1,3b,4,4a-tetrahydro-5H-cyclopropa[3,4]cyclopenta[1,2-c]pyrazol-5-one (XV)

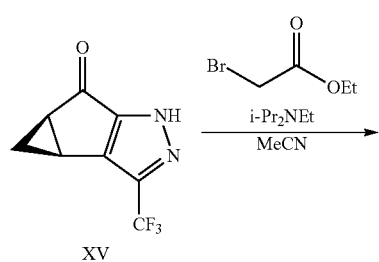

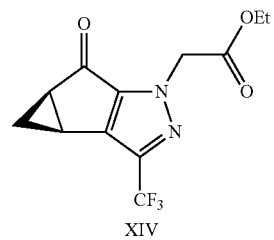

Acetonitrile (5 vol.) was added to a reactor containing XV (1.0 g). N,N-Diisopropylethylamine (0.80 g, 1.25 equiv.) was added at about 0° C. Ethyl bromoacetate (0.91 g, 1.1 equiv.) was added over about 1 hour at about 0° C. The reaction was stirred at about 5° C. for about 30 minutes and warmed to about 10° C. The reaction was stirred until complete as determined by HPLC, warmed to about 20° C., and extracted with MTBE (2 vol.) and saturated NaCl (6 vol.). The aqueous layer was removed and the organic phase was concentrated and diluted with EtOH (3 vol.). The reaction was crystallized by the addition of $H_2O$ (7.8 vol.) at about 20° C. The mixture was cooled to about 5° C. over about 2 hours and maintained at about 5° C. for about 0.5 hour. The mixture was filtered at about 5° C. and washed with cold water (4 vol). The product was dried at about 40° C. under vacuum to give XIV. $^1$H NMR (400 MHz, Chloroform-d) δ 4.97 (s, 2H), 4.31-4.17 (m, 2H), 2.77 (dddd, J=6.4, 5.2, 2.9, 2.3 Hz, 1H), 2.65-2.55 (m, 1H), 1.74-1.64 (m, 2H), 1.34-1.19 (m, 5H), 0.94-0.84 (m, 1H).

Example 4b: Preparation of ethyl 2-((3bS,4aR)-5-oxo-3-(trifluoromethyl)-3b,4,4a,5-tetrahydro-1H-cyclopropa[3,4]cyclopenta[1,2-c]pyrazol-1-yl)acetate (XIV) from (1R,5S)-bicyclo[3.1.0]hexan-2-one (4a)

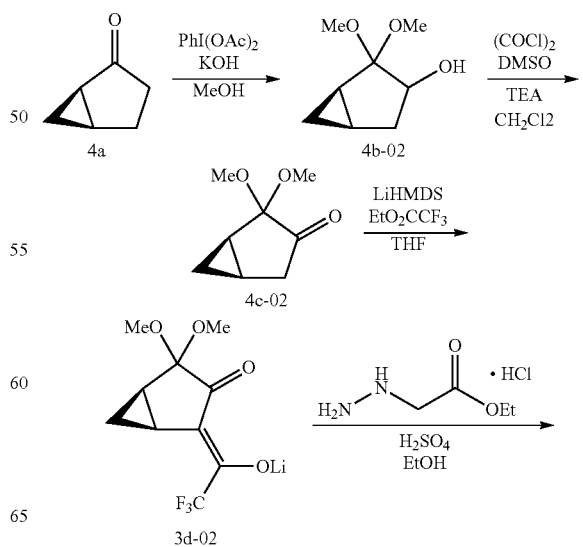

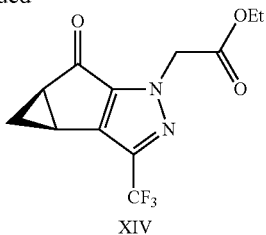

XIV

Synthesis of (1R,5R)-2,2-dimethoxybicyclo[3.1.0]hexan-3-ol (4b-02)

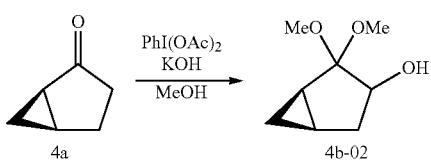 [SMILES: "MeOH" ; O=C1CC[C@H]2C[C@@H]12 ; COC1(OC)C(O)C[C@H]2C[C@H]21]

Potassium hydroxide (KOH) (2.2 g, 3.50 equiv.) and anhydrous methanol (13 mL) were added to a reactor and the reaction mixture was warmed to about 55° C. and agitated until KOH solids were dissolved completely. The mixture was adjusted to about 0 to 6° C. and compound 4a (1.0 g) was slowly added while maintaining the internal temperature at NMT 6° C. The reaction mixture was agitated for about 45 min at about 0 to 6° C. Diacetoxy iodobenzene (PhI(OAc)$_2$, 5.0 g, 1.5 equiv.) was added over about 2 hours while maintaining the internal temperature at NMT 6° C. The reaction mixture was agitated for NLT 1 hour at about 0 to 6° C. Water (10 g) and heptane (10 mL) were added to the reaction mixture and the biphasic was agitated for NLT 30 min at about 19 to 25° C. The aqueous layer was separated and washed with heptane (10 mL). The combined organic layer was extracted twice with aqueous solution of methanol (MeOH, 10 mL) and water (5 g). The combined aqueous layer was concentrated under vacuum. The aqueous layer was extracted twice with DCM (15 mL and 5 mL). The combined organic layer was concentrated and dried under vacuum. The unpurified compound 4b-02 was obtained. $^1$H NMR (600 MHz, CDCl$_3$): δ 3.98 (d, 1H), 3.45 (s, 3H), 3.25 (s, 3H), 2.40 (s, 1H), 2.21 (m, 1H), 1.78 (d, 1H), 1.48 (m, 1H), 1.38 (m, 1H), 0.83 (q, 1H), 0.58 (m, 1H). $^{13}$C NMR (150 MHz, CDCl$_3$): δ 110.91, 72.19, 51.18, 49.02, 34.08, 21.66, 14.75, 8.37.

Synthesis of (1R,5R)-2,2-dimethoxybicyclo[3.1.0]hexan-3-one (4c-02)

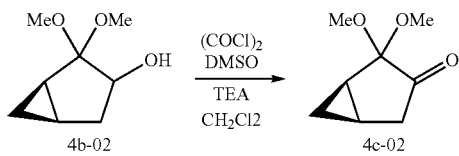 [SMILES: COC1(OC)C(O)C[C@H]2C[C@H]21 ; COC1(OC)C(=O)C[C@H]2C[C@H]21]

Oxalyl chloride (0.96 g, 1.20 equiv.) and dichloromethane (10 mL) were added to a reactor and the mixture was cooled to about −78° C. Dimethyl sulfoxide (DMSO, 1.2 g, 2.4 equiv.) was added over about 30 min while maintaining the internal temperature below about −60° C. After agitation for about 5 min, the solution of compound 4b-02 (1.0 g) in dichloromethane (6 mL) was added over about 30 min while maintaining the internal temperature below about −60° C. and the reaction mixture was agitated for about 20 min at about −60° C. Triethylamine (TEA, 3.1 g, 4.8 equiv.) was added over about 40 min at about −60° C., and the reaction mixture was warmed to about 10 to 20° C. Water (15 g) was added and the biphasic was agitated about 30 min at about 10 to 20° C. After phase separation, the aqueous layer was back-extracted with dichloromethane (10 mL). Combined organic layer was concentrated until no distillate was observed. To the residue was added MTBE (1 mL), filtered and evaporated to afford unpurified compound 4c-02. $^1$H NMR (600 MHz, CDCl$_3$): δ 3.45 (s, 3H), 3.27 (s, 3H), 2.79 (ddd, 1H), 2.30 (d, 1H), 1.73 (td, 1H), 1.63 (m, 1H), 0.96 (m, 1H), 0.25 (td, 1H). $^{13}$C NMR (150 MHz, CDCl$_3$): δ 207.75, 102.13, 50.93, 50.50, 38.87, 19.15, 9.30, 8.56.

Synthesis of lithium (Z)-1-((1S,5R)-4,4-dimethoxy-3-oxobicyclo[3.1.0]hexan-2-ylidene)-2,2,2-trifluoroethan-1-olate (3d-02)

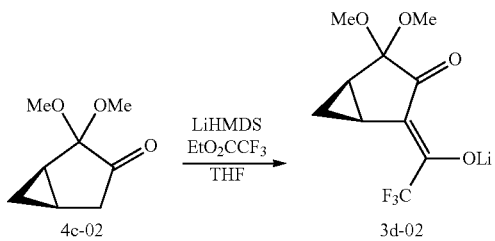

A reactor was charged with compound 4c-02 (1.0 g), ethyl trifluoroacetate (CF$_3$COOEt, 0.91 g, 1.0 equiv.) and tetrahydrofuran (THF, 0.5 mL) and the reaction mixture was cooled to about −10 to 0° C. The 1M solution of lithium bis(trimethylsilyl)amide (LiHMDS, 7.0 mL, 1.10 equiv.) was added over about 40 min while maintaining the internal temperature below about 0° C. The reaction mixture was agitated for about 2 hours at about −10 to 0° C. until the reaction was complete. After then, the reaction mixture was warmed to about 20° C. followed by charging tert-butyl methyl ether (MTBE, 10 mL) and water (10 g). After agitating for about 30 min, the organic layer was separated and the aqueous layer was back-extracted twice with mixture of MTBE (6 mL) and THF (4 mL). The combined organic layer was concentrated until no distillate was observed. To the unpurified solids, THF (3 mL) and heptane (15 mL) were added at about 20° C., and the reaction mixture was cooled to about 0° C. and agitated about 1 hour. The resulting slurry was filtered and wet cake was washed with heptane (7 g) and dried under vacuum at about 40° C. to afford compound 3d-02. $^1$H NMR (600 MHz, DMSO-d$_6$): δ 3.31 (s, 3H), 3.27 (s, 3H) 2.01 (m, 1H), 1.42 (td, 1H), 0.96 (m, 1H), 0.08 (q, 1H). (600 MHz, CDCl$_3$ with THF) δ 3.44 (s, 3H), 3.24 (s, 3H), 2.26 (m, 1H), 1.48 (m, 1H), 1.04 (q, 1H), 0.25 (m, 1H). $^{13}$C NMR (150 MHz, DMSO-d$_6$): 193.20, 120.78, 118.86, 105.53, 104.04, 50.66, 49.86, 17.34, 16.20, 13.78.

Synthesis of ethyl 2-((3bS,4aR)-5-oxo-3-(trifluoromethyl)-3b,4,4a,5-tetrahydro-1H-cyclopropa[3,4]cyclopenta[1,2-c]pyrazol-1-yl)acetate (XIV)

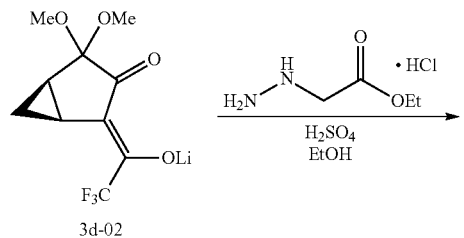

3d-02

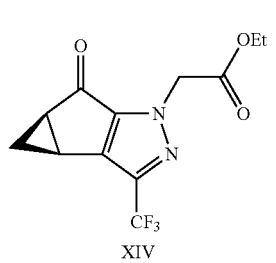

XIV

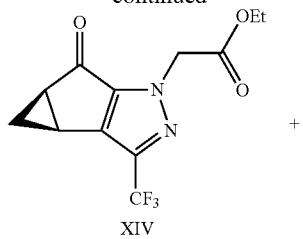

XIV

+

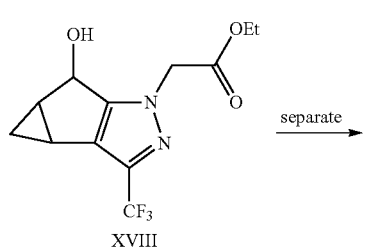

XVIII separate →

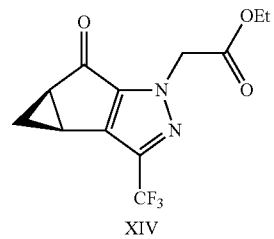

XIV

Compound 3d-02 (1.0 g), ethyl hydrazinoacetate hydrochloride (EHA.HCl, 0.60 g, 1.0 equiv.) and absolute ethanol (EtOH, 15 mL) were added to a reactor and the reaction mixture was cooled to about 0-5° C. Sulfuric acid (H₂SO₄, 0.19 g, 0.50 equiv.) was added while maintaining the internal temperature below about 5° C. Triethyl orthoformate (0.86 g, 1.50 equiv.) was added and the reaction mixture was agitated at about 0 to 5° C. for about 15 hours. The reaction mixture was warmed to about 20 to 25° C. and water (30 g) was added over about 15 minutes. The content was cooled to about 0 to 5° C. and agitated for about 1 hour. The slurry was filtered and wet cake was washed with water (5 g) and dried under vacuum at about 45° C. to afford XIV. $^1$H NMR (600 MHz, CDCl₃): δ 4.97 (s, 1H), 4.23 (qd, 2H), 2.77 (quint, 1H), 2.60 (quint, 1H), 1.69 (m, 2H), 1.28 (t, 3H). $^{13}$C NMR (150 MHz, CDCl₃): δ 187.14, 165.98, 143.35, 143.12, 121.37, 119.59, 62.34, 51.83, 35.35, 31.72, 14.00, 13.73.

Example 4c: Kinetic resolution of ethyl 2-(5-oxo-3-(trifluoromethyl)-3b,4,4a,5-tetrahydro-1H-cyclopropa[3,4]cyclopenta[1,2-c]pyrazol-1-yl)acetate (XVII) to form ethyl 2-((3bS,4aR)-5-oxo-3-(trifluoromethyl)-3b,4,4a,5-tetrahydro-1H-cyclopropa[3,4]cyclopenta[1,2-c]pyrazol-1-yl)acetate (XIV)

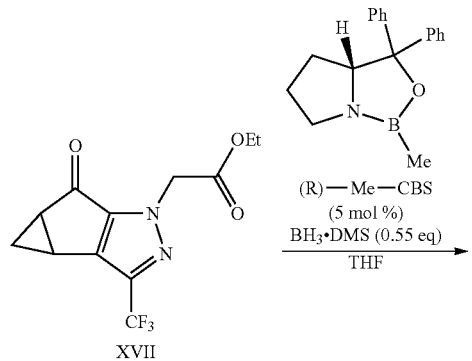

XVII

Compound XVII (1.0 g), (R)-2-methyl-CBS-oxazaborolidine (0.0.05 g, 0.05 equiv.), and tetrahydrofuran (11.9 g) were combined and cooled to about 0 to 5° C. A solution of borane dimethyl sulfide complex (0.14 g, 0.55 equiv.) in tetrahydrofuran (0.67 g) was added to the mixture, and the mixture was agitated at about 0 to 5° C. until the reaction was deemed complete. Methanol (1 mL) was added to the mixture at about 0 to 5° C. over about 1 h, and the mixture was adjusted to about 15 to 25° C. The mixture was concentrated under vacuum and combined with tetrahydrofuran (2.7 g). The mixture was combined with 4-dimethylaminopyridine (0.18, 0.44 equiv.) and succinic anhydride (0.30 g, 0.87 equiv.) and agitated at about 15 to 25° C. until the reaction was deemed complete. The mixture was combined with tert-butyl methyl ether (5.2 g) and washed with 1 M aqueous HCl (6.7 g), twice with 5 wt % aqueous potassium carbonate (6.7 g each), and 5 wt % aq. sodium chloride (6.7 g). The organics were concentrated under reduced pressure to an oil which was dissolved in dichloromethane (0.1 g) and purified by flash column chromatography (2.0 g silica gel, 20:80 to 80:20 gradient of ethyl acetate:hexanes). The combined fractions were concentrated under vacuum to give XIV.

Example 4d: Preparation of (1R,5S)-bicyclo[3.1.0]hexan-2-one (4a)

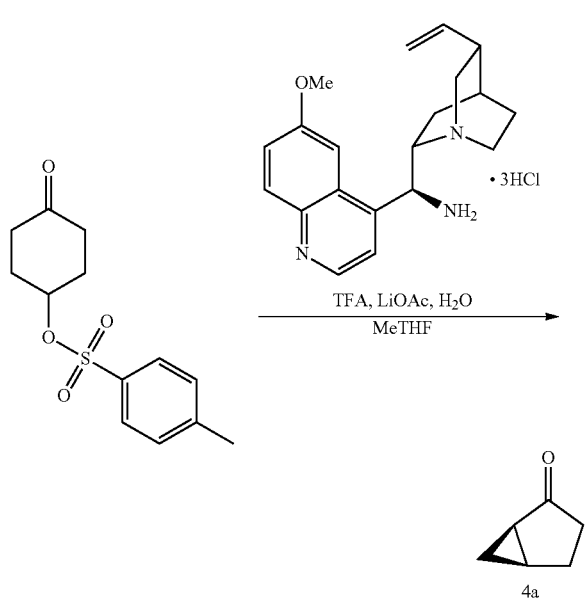

4-Tosyloxycyclohexanone (50 mg), (8α,9S)-6'-methoxycinchonan-9-amine trihydrochloride (16 mg), trifluoroacetic acid (28 µL), lithium acetate (49 mg), water (3.4 µL), and 2-methyltetrahydrofuran (0.75 mL) were combined in a vial. The mixture was agitated at about 20° C. until the reaction was complete. 4a was isolated by vacuum distillation. $^1$H NMR (400 MHz, CDCl$_3$) δ 2.05 (m, 5H), 1.74 (m, 1H), 1.18 (m, 1H), 0.91 (m, 1H).

Example 5: Synthesis of ethyl 2-((3bS,4aR)-3-(trifluoromethyl)-4,4a-dihydrospiro[cyclopropa[3,4]cyclopenta[1,2-c]pyrazole-5,2'-[1,3]dithiolane]-1(3bH)-yl)acetate (5h) from (1R,5R)-2,2-dimethoxybicyclo[3.1.0]hexan-3-ol (4b-02)

Synthesis of (1R,5R)-spiro[bicyclo[3.1.0]hexane-2,2'-[1,3]dithiolan]-3-ol (5d)

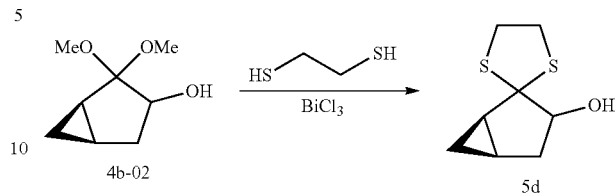

A mixture of ketal alcohol 4b-02 (1.0 g), ethanedithiol (0.91 g), MeCN (7.5 ml) and BiCl$_3$ (0.30 g) was agitated at r.t. overnight. The solids were removed by filtration and the filtrate was concentrated and the residue was further purified by flash column on silica gel to obtain the two isomers. Major product: $^1$H NMR (400 MHz, Chloroform-d) δ 3.82 (ddt, J=6.1, 1.3, 0.6 Hz, 1H), 3.41-3.32 (m, 2H), 3.31-3.23 (m, 1H), 3.14-3.06 (m, 1H), 2.71 (s, 1H), 2.33 (dddd, J=14.0, 6.2, 4.8, 1.4 Hz, 1H), 2.00 (d, J=13.9 Hz, 1H), 1.79-1.72 (m, 1H), 1.54-1.46 (m, 1H), 1.04 (dt, J=5.1, 3.9 Hz, 1H), 0.63-0.54 (m, 1H). Minor product: $^1$H NMR (400 MHz, Chloroform-d) δ 3.83 (q, J=9.1 Hz, 1H), 3.43-3.34 (m, 2H), 3.33-3.25 (m, 2H), 2.35 (d, J=11.2 Hz, 1H), 2.18 (ddd, J=12.7, 6.7, 0.4 Hz, 1H), 1.84 (ddd, J=8.1, 6.3, 3.7 Hz, 1H), 1.60-1.51 (m, 1H), 1.43-1.35 (m, 1H), 0.65 (tdt, J=8.1, 5.9, 0.8 Hz, 1H), 0.57 (dddd, J=5.9, 4.2, 3.7, 0.6 Hz, 1H).

Synthesis of (1R,5R)-spiro[bicyclo[3.1.0]hexane-2,2'-[1,3]dithiolan]-3-one (5e)

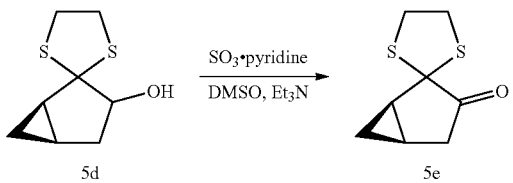

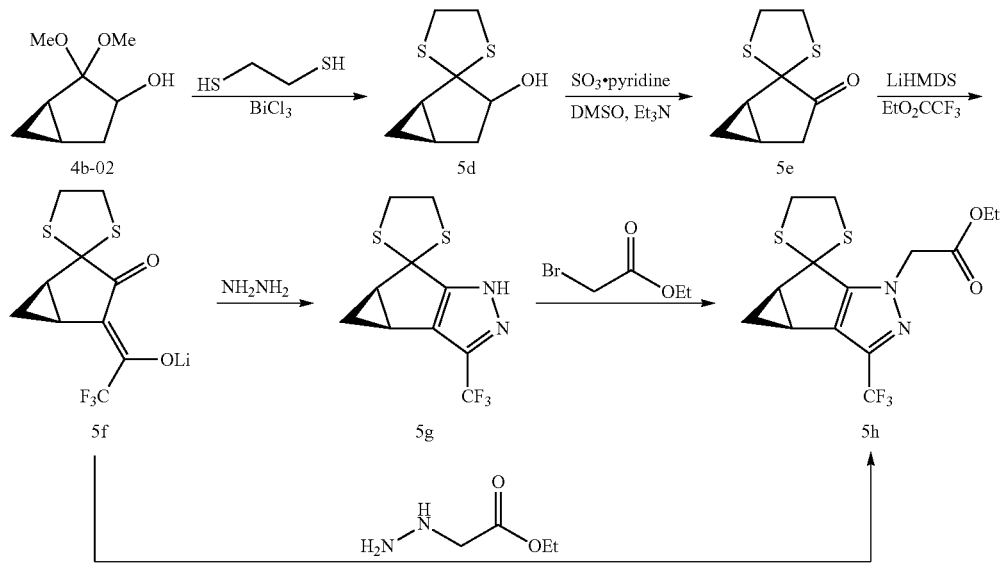

To a dried flask was sequentially added dithiolane alcohol 5d (1.0 g), CH$_2$Cl$_2$ (25 ml), anhydrous DMSO (8.5 ml), and triethylamine (3.5 ml) and the resulting mixture was aged at room temperature for about 21 hours. The reaction mixture was transferred to a separatory funnel, diluted with CH$_2$Cl$_2$ (30 ml), washed with 1 M HCl (25 ml), and water (25 ml). The CH$_2$Cl$_2$ layer was concentrated to a solid and further purify by flash column chromatography on silica gel eluted with gradient EtOAc/n-heptane (0-20%) to obtain 5e. $^1$H NMR (400 MHz, Chloroform-d) δ 3.57 (dddd, J=10.5, 5.6, 4.3, 0.5 Hz, 1H), 3.49-3.41 (m, 1H), 3.39-3.28 (m, 2H), 3.10 (ddd, J=18.3, 5.6, 2.2 Hz, 1H), 2.29 (d, J=18.3 Hz, 1H), 1.89 (ddd, J=8.0, 7.0, 3.9 Hz, 1H), 1.63 (tdd, J=7.3, 5.6, 4.1 Hz, 1H), 1.05 (tdd, J=8.0, 6.3, 2.2 Hz, 1H), 0.21 (dt, J=6.4, 4.0 Hz, 1H).

Synthesis of lithium (Z)-2,2,2-trifluoro-1-((1R,5S)-3-oxospiro[bicyclo[3.1.0]hexane-2,2'-[1,3]dithiolan]-4-ylidene)ethan-1-olate (5f)

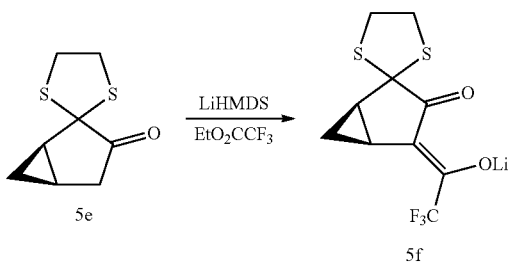

To a flask with dithiolane ketone 5e (1.0 g) under N$_2$ was added anhydrous THF (8.8 ml), and the mixture was cooled to about −78° C. and followed by addition of LiHMDS (1 M in THF, 7.4 ml) over about 5 min. The resulting mixture was agitated at about −78° C. for about 0.5 hours, and ethyl trifluoroacetate (0.88 ml) was added. The resulting mixture was agitated at about −78° C. for about 10 minutes, at about 0° C. for about 1 hour, and at room temperature overnight. THF was removed under reduced pressure and the residue was crystallized in n-heptane (about 18 ml). The solid product was isolated by filtration, and the filter cake was rinsed with n-heptane (4.1 ml), and dried at about 50° C. under vacuum to provide 5f. $^1$H NMR (400 MHz, Acetonitrile-d$_3$) δ 6.98 (s, 0H), 5.20 (s, 0H), 3.60-3.50 (m, 2H), 3.46-3.36 (m, 2H), 2.28-2.20 (m, 1H), 1.80 (ddd, J=8.3, 7.2, 4.1 Hz, 1H), 1.39 (s, 1H), 1.03 (ddd, J=8.3, 6.7, 4.8 Hz, 1H), 0.17 (ddd, J=4.7, 4.2, 3.6 Hz, 1H).

Synthesis of (3bS,4aR)-3-(trifluoromethyl)-1,3b,4,4a-tetrahydrospiro[cyclopropa[3,4]cyclopenta[1,2-c]pyrazole-5,2'-[1,3]dithiolane] (5g)

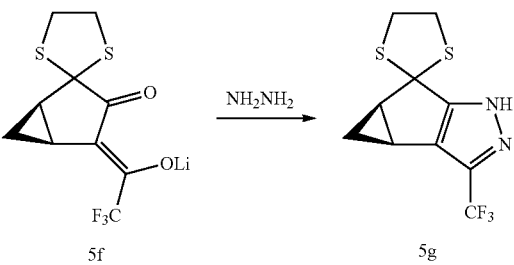

To flask containing the dithiolane lithium salt 5f (1.0 g) was added water (10 ml), hydrazine hydrate (0.88 ml) and acetic acid (10 ml). The reaction mixture was heated at about 35° C. for about 2 hours, and at about 55° C. for about 2 hours. Water was removed under reduced pressure and the residue was diluted with acetic acid (20 ml) and heated at about 55° C. for about 0.5 hour and held at room temperature overnight. The reaction mixture was further heated at about 65° C. for about 20 hours, and cooled down and concentrated to remove volatile components by rotavap. The residue was triturated with water (50 ml) at about 0° C. and the solid residue was isolated and further washed with ice-cold water (2×10 ml). The solids were further dried to afford unpurified 5g. $^1$H NMR (400 MHz, Chloroform-d) δ 3.65-3.46 (m, 4H), 2.60 (dddd, J=8.3, 5.6, 4.2, 0.7 Hz, 1H), 2.47-2.38 (m, 1H), 1.33 (dddd, J=8.2, 7.4, 5.7, 0.7 Hz, 1H), 0.66 (dddd, J=5.7, 4.3, 3.6, 0.7 Hz, 1H).

Synthesis of ethyl 2-((3bS,4aR)-3-(trifluoromethyl)-4,4a-dihydrospiro[cyclopropa[3,4]cyclopenta[1,2-c]pyrazole-5,2'-[1,3]dithiolane]-1(3bH)-yl)acetate (5h) from (3bS,4aR)-3-(trifluoromethyl)-1,3b,4,4a-tetrahydrospiro[cyclopropa[3,4]cyclopenta[1,2-c]pyrazole-5,2'-[1,3]dithiolane] (5g)

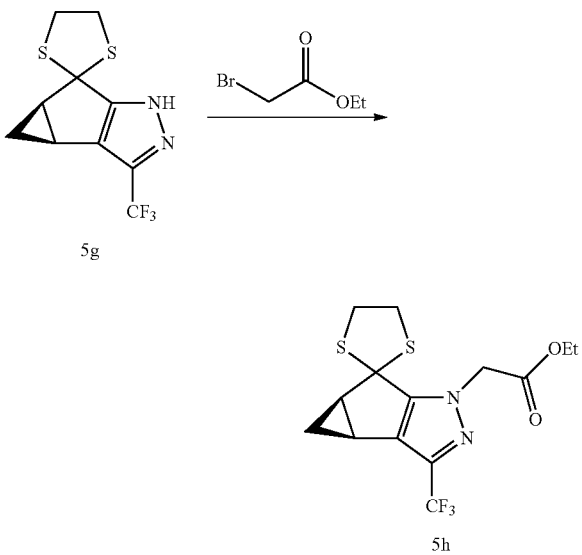

A reactor was charged with dithiolane pyrazole 5g (1.0 g) and THF (15 ml). The contents were adjusted to about 0 to −5° C. and followed by addition of ethyl bromoacetate (0.44 ml, 1.1 equiv.). To the resulting mixture NaHMDS (2 M, 2.0 ml, 1.1 equiv.) was added over about 10 min via syringe pump at about −2.5 to 0° C. and the mixture was held for about 3 hours, a second portion of ethyl bromoacetate (0.050 ml, 0.12 equiv.) was added, and the mixture was aged for about 1 hour. The reaction mixture was quenched by excess water (2 ml) to form 5h.

Synthesis of ethyl 2-((3bS,4aR)-3-(trifluoromethyl)-4,4a-dihydrospiro[cyclopropa[3,4]cyclopenta[1,2-c]pyrazole-5,2'-[1,3]dithiolane]-1(3bH)-yl)acetate (5h) from lithium (Z)-2,2,2-trifluoro-1-((1R,5S)-3-oxospiro[bicyclo[3.1.0]hexane-2,2'-[1,3]dithiolan]-4-ylidene)ethan-1-olate (5f)

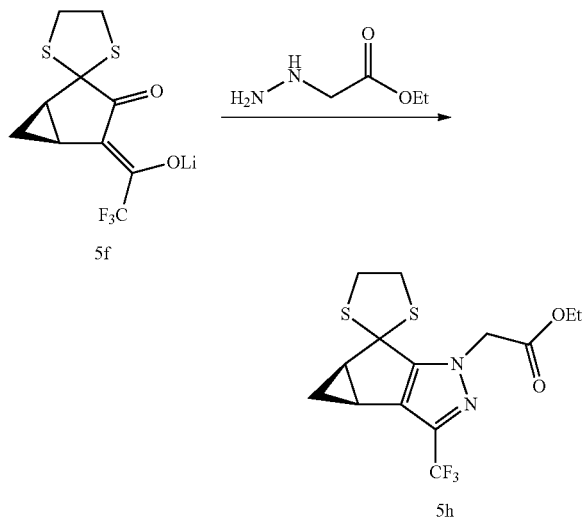

A 100 ml flask was charged with ethanol (5 ml). The contents were cooled to about 0° C. and acetyl chloride (1.1 g, 4.0 equiv.) was added over about 10 min. The mixture was agitated at about 0° C. for about 20 minutes and at room temperature for about 20 minutes. To the freshly prepared HCl ethanol solution was added EHA.HCl (0.68 g, 1.2 equiv.) and dithiolane lithium salt 5f (1.0 g). The reaction mixture was heated at about 40° C. for about 22 hours. Ethanol was removed under reduced pressure, and the residue was partitioned between ethyl acetate (5 ml) and water (5 ml). The aqueous layer was discarded, and the organic layer was sequentially washed with aqueous NaHCO$_3$(5%, 5 ml) and brine (5%, 5 ml) and 5h was obtained in the EtOAc layer. $^1$H NMR (400 MHz, DMSO-d$_6$) δ 5.14-4.97 (m, 2H), 4.14 (qd, J=7.1, 1.0 Hz, 2H), 3.67-3.35 (m, 4H), 2.69 (ddd, J=8.2, 5.6, 4.2 Hz, 1H), 2.44 (ddd, J=7.2, 5.5, 3.5 Hz, 1H), 1.37-1.29 (m, 1H), 1.21-1.14 (m, 3H), 0.44 (ddd, J=5.3, 4.2, 3.6 Hz, 1H).

Synthesis of ethyl 2-((3bS,4aR)-3-(trifluoromethyl)-4,4a-dihydrospiro[cyclopropa[3,4]cyclopenta[1,2-c]pyrazole-5,2'-[1,3]dithiolane]-1(3bH)-yl)acetate (5h) from (1R,5R)-spiro[bicyclo[3.1.0]hexane-2,2'-[1,3]dithiolan]-3-one (5e)

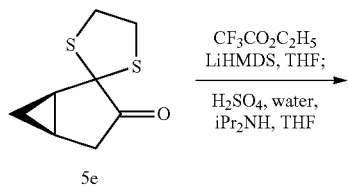

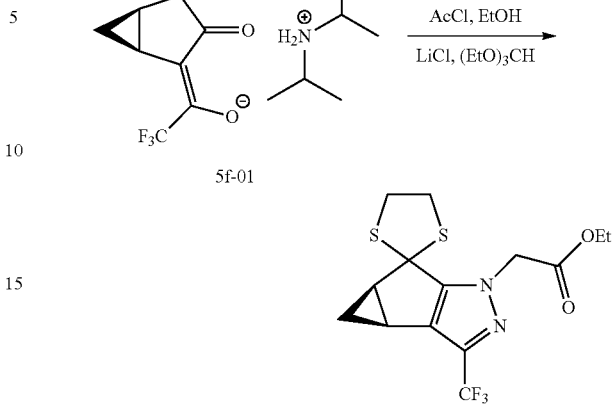

5e (756 mg) was charged to a vessel and dissolved in 2-methyltetrahydrofuran (7.6 mL). To this solution was charged ethyl trifluoroacetate (0.57 g) and the resulting solution was cooled to about 0° C. Lithium hexamethyldisilazide (1.0 M solution in THF, 4.5 g) was charged over about 60 minutes and reaction was agitated until complete. A solution of sulfuric acid (2.0 g) in water (5.6 mL) was charged, then the reaction was warmed to about 20° C. and agitated for about 20 minutes. Layers were separated and aqueous layer was extracted twice with 2-methyltetrahydrofuran (5.3 mL). Combined organic layer was concentrated to about 0.4 mL and N,N-diisopropylamine (0.5 g) was charged. The product was crystallized by the addition of heptane (11 ml). The slurry was filtered and the filter cake was washed with heptane, then deliquored thoroughly, and dried to afford 5f-01. $^1$H NMR (400 MHz, Acetonitrile-d$_3$) δ 7.84 (m, 2H), 3.58 (d, J=8.7 Hz, 2H), 3.47-3.27 (m, 4H), 2.20 (s, 1H), 1.81-1.68 (m, 1H), 1.24 (dd, J=6.5, 0.6 Hz, 12H), 0.99 (q, J=6.5 Hz, 1H), 0.13 (s, 1H).

Acetyl chloride (1.02 g) was charged to a cooled reaction vessel containing ethanol (5.0 mL) at about 0° C., then warmed to about 20° C. and agitated for about 30 minutes. In a separate vessel, 5f-01(1.00 g), ethyl hydrazinoacetate hydrochloride (0.48 g), and lithium chloride (0.39 g) were combined, and the acetyl chloride/ethanol solution was charged to this mixture, followed by triethylorthoformate (1.16 g). The mixture was heated to about 45° C. and agitated until reaction was complete. The reaction was then concentrated to 2 volumes and dichloromethane (5.0 mL) was added followed by water (5.0 mL). Layers were separated and organic layer was washed with 5 wt % aqueous sodium bicarbonate followed by 10 wt % aqueous sodium chloride to afford a solution of 5h in dichloromethane that was carried forward into the subsequent step. $^1$H NMR (400 MHz, DMSO-d$_6$) δ 5.27-4.79 (m, 2H), 4.14 (qd, J=7.1, 1.1 Hz, 2H), 3.70-3.42 (m, 4H), 2.68 (dtd, J=8.0, 6.4, 5.9, 4.4 Hz, 1H), 2.44 (ddd, J=7.2, 5.5, 3.6 Hz, 1H), 1.32 (ddd, J=8.2, 7.2, 5.4 Hz, 1H), 1.18 (t, J=7.1 Hz, 3H), 0.44 (dt, J=5.4, 3.9 Hz, 1H); $^{13}$C NMR (101 MHz, DMSO-d$_6$) δ 167.14, 148.36, 133.80 (q, J=38.3 Hz), 128.77 (m), 121.54 (q, J=268.4 Hz), 65.33, 61.79, 51.14, 41.30, 40.98, 40.49, 23.57, 15.52, 14.33; $^{19}$F NMR (376 MHz, DMSO-d$_6$) δ −60.31.

Synthesis of (1R,5R)-spiro[bicyclo[3.1.0]hexane-2,
2'-[1,3]dithiolan]-3-one (5e) from (1R,5R)-spiro
[bicyclo[3.1.0]hexane-2,2'-[1,3]dithiolan]-3-one (5e)
from (1R,5 S)-bicyclo[3.1.0]hexan-2-one (4a)

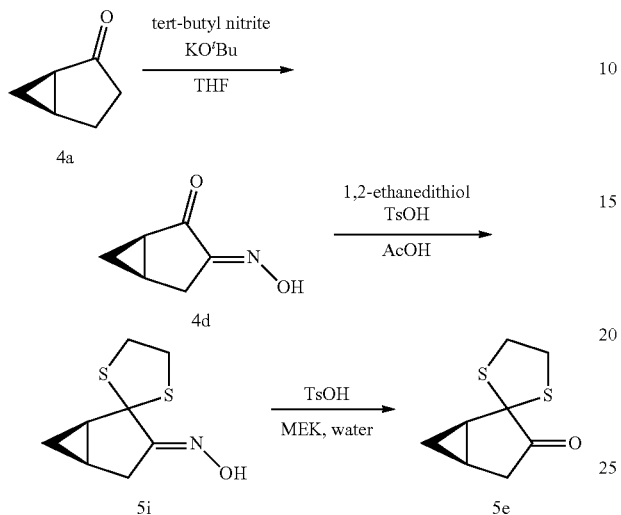

Tert-butyl nitrite (1.31 g) was charged to a vessel containing 4a (1.00 g, 1.0 equiv) and tetrahydrofuran (5.0 mL) at about 20° C. Potassium tert-butoxide (6.1 g, 1.7M in tetrahydrofuran) was charged over not less than 30 minutes. The mixture was then agitated until the reaction was complete. The reaction was quenched with aqueous citric acid (2.00 g in 10.00 g water) and extracted with dichloromethane (10.0 mL, 3×). This solution was partially concentrated and the product was isolated by the addition of heptane (6.0 mL). The slurry was filtered and the filter cake was washed with heptane (2.0 mL), then deliquored thoroughly to afford 4d. $^1$H NMR (400 MHz, DMSO-$d_6$) δ 12.26 (s, 1H), 2.73 (d, J=18.5 Hz, 1H), 2.63 (ddd, J=18.6, 5.3, 2.0 Hz, 1H), 2.17-2.01 (m, 2H), 1.34 (dddd, J=9.2, 7.1, 4.9, 2.0 Hz, 1H), 0.77 (td, J=4.6, 3.4 Hz, 1H).

1,2-Ethanedithiol (0.41 g) was charged to a vessel containing a solution of 4d (0.50 g, 4.0 mmol) in glacial acetic acid (2.5 mL) at about 20° C. Para-toluenesulfonic acid monohydrate (0.15 g) was added and the mixture was agitated until the reaction was complete. The product was isolated by the addition of water (2 mL). The slurry was filtered and the filter cake was washed with water, then deliquored thoroughly to afford 5i. $^1$H NMR (400 MHz, DMSO-$d_6$) δ 10.93 (s, 1H), 3.63-3.51 (m, 2H), 3.51-3.42 (m, 1H), 3.39-3.31 (m, 1H), 2.83 (d, J=17.4 Hz, 1H), 2.59-2.52 (m, 1H), 1.87 (ddd, J=8.0, 6.2, 3.7 Hz, 1H), 1.65 (dddd, J=7.7, 6.2, 5.2, 3.9 Hz, 1H), 0.93 (tdd, J=7.6, 5.5, 1.7 Hz, 1H), 0.02 (dt, J=5.5, 3.8 Hz, 1H).

Para-toluenesulfonic acid (0.90 g) was charged to a vessel containing a suspension of 5i (0.50 g, 2.5 mmol) in methyl ethyl ketone (2.5 mL) and water (2.5 mL). The mixture was agitated at about 85° C. until the reaction was complete. The product was isolated from the reaction mixture by cooling to about 20° C., adding water (2.50 mL), and cooling to about 0° C. The slurry was filtered and the filter cake was washed with water, then deliquored thoroughly to afford 5e. $^1$H NMR (400 MHz, DMSO-$d_6$) δ 3.55-3.37 (m, 3H), 3.28-3.13 (m, 1H), 3.03 (ddd, J=18.5, 5.6, 2.2 Hz, 1H), 2.20 (d, J=18.5 Hz, 1H), 1.84 (ddd, J=8.0, 7.0, 3.8 Hz, 1H), 1.66 (tdd, J=7.2, 5.6, 4.1 Hz, 1H), 1.03 (tdd, J=7.9, 5.9, 2.1 Hz, 1H), 0.06 (dt, J=6.0, 4.0 Hz, 1H).

Example 6: Preparation of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (VII) from ethyl 2-((3bS,4aR)-5-oxo-3-(trifluoromethyl)-3b,4,4a,5-tetrahydro-1H-cyclopropa[3,4]cyclopenta[1,2-c]pyrazol-1-yl)acetate (XIV)

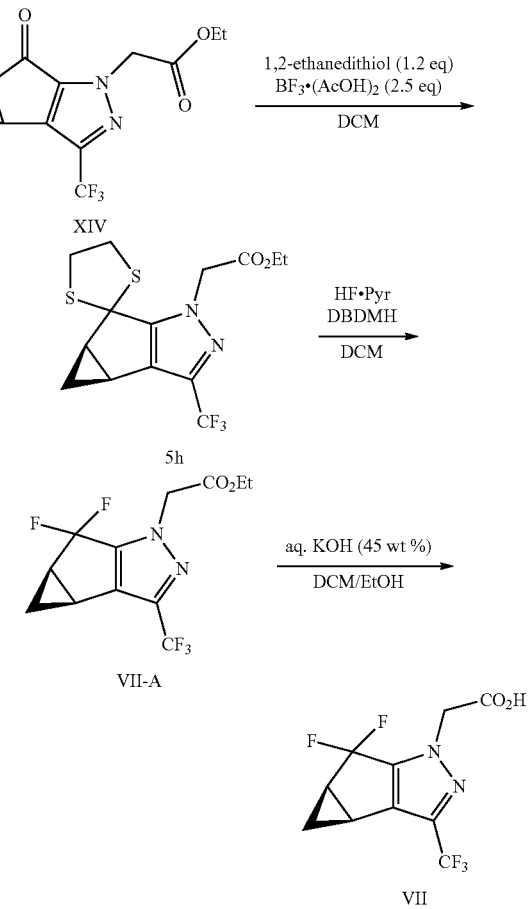

Synthesis of ethyl 2-((3bS,4aR)-3-(trifluoromethyl)-4,4a-dihydrospiro[cyclopropa[3,4]cyclopenta[1,2-c]pyrazole-5,2'-[1,3]dithiolane]-1(3bH)-yl)acetate (5h) from ethyl 2-((3bS,4aR)-5-oxo-3-(trifluoromethyl)-3b,4,4a,5-tetrahydro-1H-cyclopropa[3,4]cyclopenta[1,2-c]pyrazol-1-yl)acetate (XIV)

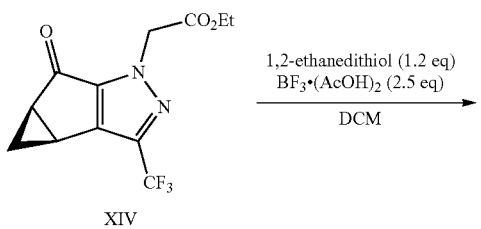

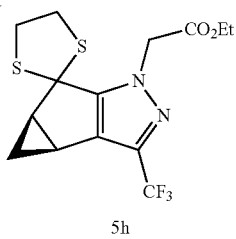

5h

Dichloromethane (27 g) was added to a reactor containing XIV (1.0 g) and cooled to about 10° C. To this was added 1,2-ethanedithiol (0.18 g, 1.2 equiv.). To this was added boron trifluoride acetic acid complex (3.3 g, 2.5 equivalents) over about 25 minutes, and the reaction mixture was agitated at about 20° C. until complete. A solution of calcium chloride dihydrate (0.80g, 0.78 equiv) in 0.10 N hydrochloric acid (16 g) was added over about 1 hour at about 10° C., and the mixture was agitated for about 90 minutes at about 20° C. The organic layer was washed successively with water (8 g) and sodium bicarbonate solution (5 wt/wt %). The organic layer was concentrated to afford 5h. $^1$H NMR (400 MHz, DMSO-$d_6$) δ 5.27-4.79 (m, 2H), 4.14 (qd, J=7.1, 1.1 Hz, 2H), 3.70-3.42 (m, 4H), 2.68 (dtd, J=8.0, 6.4, 5.9, 4.4 Hz, 1H), 2.44 (ddd, J=7.2, 5.5, 3.6 Hz, 1H), 1.32 (ddd, J=8.2, 7.2, 5.4 Hz, 1H), 1.18 (t, J=7.1 Hz, 3H), 0.44 (dt, J=5.4, 3.9 Hz, 1H). $^{13}$C NMR (101 MHz, DMSO-$d_6$) δ 167.14, 148.36, 133.80 (q, J=38.3 Hz), 128.77 (m), 121.54 (q, J=268.4 Hz), 65.33, 61.79, 51.14, 41.30, 40.98, 40.49, 23.57, 15.52, 14.33. $^{19}$F NMR (376 MHz, DMSO-$d_6$) δ -60.31.

Synthesis of ethyl 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetate (VII-A)

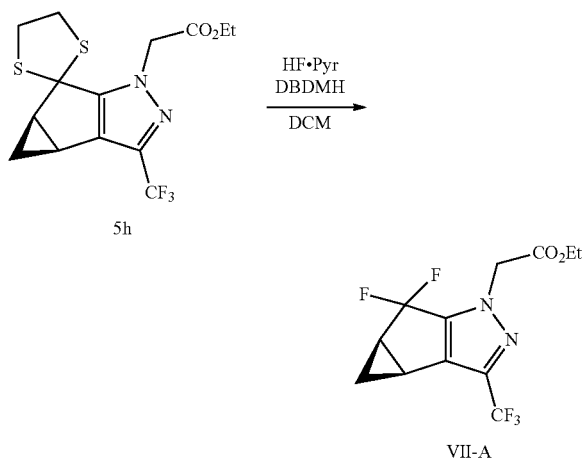

Dichloromethane (26 g) was added to a reactor containing 1,3-dibromo-5,5-dimethylhydantoin (DBDMH, 2.4 g, 3.1 equiv.) and cooled to about -10° C. To this was added 70% hydrofluoric acid/pyridine complex (1.3 g, 17 equiv.), followed by a solution of 5h (1.0 g) in dichloromethane (3 g). The reaction was agitated at about 0° C. until complete. A solution of potassium hydroxide (3.7 g, 25 equivalents) and potassium sulfite (1.9 g, 4 equiv.) in water (24 g) was added, maintaining an internal temperature of about 5° C., and agitated for about 30 minutes at about 20° C. Layers were separated and organic layer was washed with hydrochloric acid (1.1 g, 4 equiv.) in water (9.6 g). The organic layer was concentrated to afford VII-A. $^1$H NMR (400 MHz, DMSO-$d_6$) δ 5.31-5.04 (m, 2H), 4.17 (q, J=7.1 Hz, 2H), 2.78-2.57 (m, 2H), 1.47 (dddd, J=8.5, 7.1, 5.5, 1.4 Hz, 1H), 1.19 (t, J=7.1 Hz, 3H), 1.04 (tdt, J=5.3, 4.0, 1.8 Hz, 1H). NMR (101 MHz, DMSO-$d_6$) δ 166.79, 143.15 (t, J=29.4 Hz), 134.65 (q, J=39.0 Hz), 132.99, 121.05 (q, J=268.4 Hz), 120.52 (t, J=243.3 Hz), 62.09, 52.49, 27.95 (dd, J=34.7, 29.0 Hz), 23.82 (d, J=2.6 Hz), 14.25, 12.14 (t, J=3.1 Hz). $^{19}$F NMR (376 MHz, DMSO-$d_6$) δ -60.47, -79.68 (dd, J=253.5, 13.2 Hz), -103.09 (dd, J=253.3, 9.8 Hz).

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (VII)

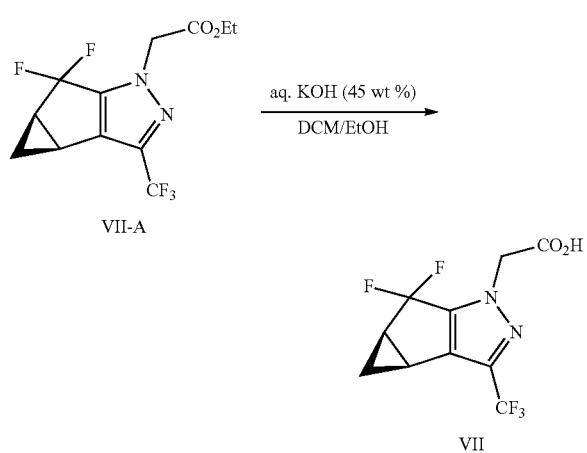

A reactor was charged with a solution of VII-A (1.0 g) in dichloromethane (18 g) and cooled to about 5° C. To this was added ethanol (1.5 g), followed by potassium hydroxide (45 wt/wt %, 0.74 g, 2.0 equiv.). The reaction mixture was agitated at about 20° C. until complete. Water (3.7 g) was added and the reaction mixture was agitated for about 30 minutes. Organic layer was removed and reaction was cooled to about 10° C. Dichloromethane (18 g) was added, followed by 2N hydrochloric acid (3.3 g, 2.2 equiv.). Reaction was warmed to about 20° C. and agitated for 10 minutes. Layers were separated and aqueous phase was washed with dichloromethane (18 g). Organic layers were combined and concentrated on rotary evaporator to afford VII. $^1$H NMR (400 MHz, DMSO-$d_6$) δ 13.50 (s, 1H), 5.14-4.81 (m, 2H), 2.82-2.56 (m, 2H), 1.46 (dddd, J=8.5, 7.1, 5.5, 1.4 Hz, 1H), 1.08-1.00 (m, 1H). $^{13}$C NMR (101 MHz, DMSO-$d_6$) δ 168.16, 143.05 (t, J=29.4 Hz), 134.40 (q, J=38.9 Hz), 132.80, 121.11 (q, J=268.4 Hz), 120.55 (t, J=243.3 Hz), 52.54, 27.97 (dd, J=34.7, 29.0 Hz), 23.81 (d, J=2.5 Hz), 12.13 (t, J=3.1 Hz). $^{19}$F NMR (376 MHz, DMSO-$d_6$) δ -60.39 (d, J=1.4 Hz), -79.83 (dd, J=253.2, 13.1 Hz), -102.97 (dd, J=253.2, 9.8 Hz).

Example 7: Preparation of 4-chloro-7-(4,4,5,5-tetramethyl-1,3,2-dioxaborolan-2-yl)-1-(2,2,2-trifluoroethyl)-1H-indazol-3-amine (V-02) and its Mesylated Derivatives Synthesis of 4-chloro-7-bromo-1-(2,2,2-trifluoroethyl)-1H-indazol-3-amine (V-A)

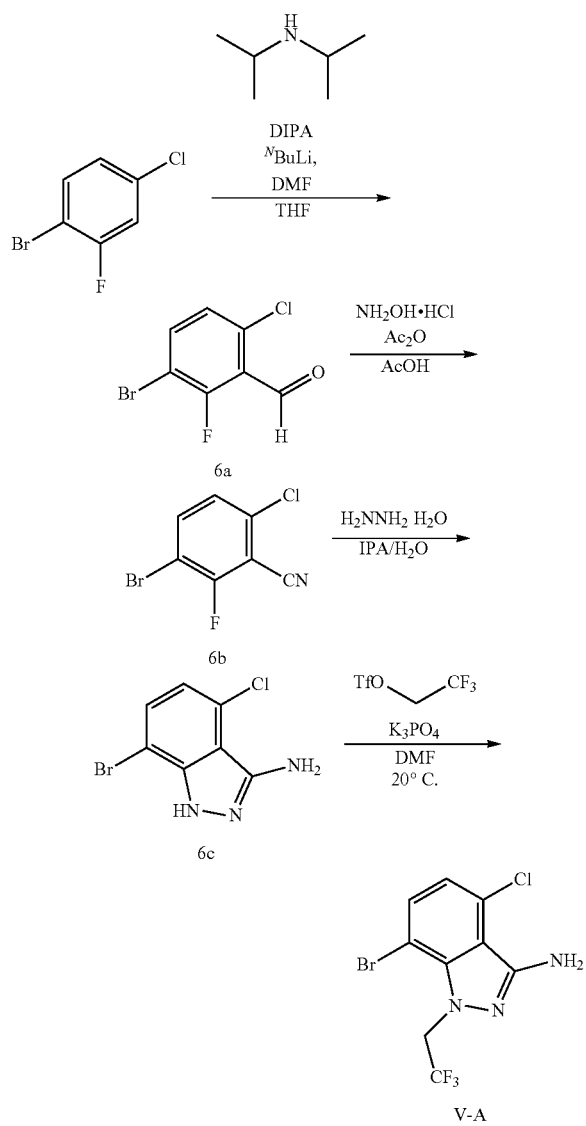

To a reactor was added tetrahydrofuran (THF, 275 kg) and diisopropylamine (DIPA, 30 kg) and the mixture was cooled to about −35° C. nButyl lithium (2.5 mol/L in hexanes, 74 kg) was charged slowly keeping the reaction temperature less than −30° C. The mixture was agitated at −35° C. until the reaction was complete. 1-bromo-4-chloro-2-fluorobenzene (52 kg) was charged keeping reaction temperature less than 30° C. and the mixture was agitated at −35° C. until reaction was complete. N,N-dimethylformamide (DMF, 36 kg) was charged keeping reaction temperature less than −30° C. and the mixture was agitated at about −35° C. until reaction was complete. Hydrochloric acid (HCl, 18 mass % in water, 147 kg) was charged keeping reaction temperature less than −5° C. The reaction was warmed to about 0° C., water (312 kg) was added, and the reaction was extracted with methyl tert-butyl ether (MTBE, 770 kg). The organic was warmed to about 20° C. and washed with brine (NaCl, 23.5 mass % in water, 1404 kg). The mixture was distilled to about 3-4 volumes and heptane was charged (354 kg). The product was isolated by distillation to 3-4 volumes. The slurry was filtered and washed with heptane (141 kg) and dried to afford 6a. $^1$H NMR (400 MHz, DMSO-d$_6$) δ 10.23 (d, J=1.2 Hz, 1H), 8.00 (dd, J=8.7, 1.4 Hz, 1H), 7.44 (dd, J=8.7, 1.4 Hz, 1H).

6a (98.5 kg) was charged to a reactor containing acetic anhydride (105 kg) and acetic acid (621 kg) at 20° C. The mixture was heated to about 45° C. and hydroxylamine hydrochloride (31.5 kg) was charged. The reaction was heated to about 75° C. and agitated until the reaction was complete. The product was isolated from the reaction mixture by adding water (788 kg) at about 45° C. The mixture was cooled to about 25° C. and then the slurry was filtered. The filtered cake was washed with water (197 kg,). The cake was dried to afford 6b. $^1$H NMR (400 MHz, DMSO-d$_6$) δ 8.11 (dd, J=8.8, 1.4 Hz, 1H), 7.58 (dd, J=8.8, 1.4 Hz, 1H).

To a reactor was charged 6b (84 kg), isopropanol (318 kg), and water (285 kg). Hydrazine hydrate (20 wt % in water, 178 kg) was charged and the mixture was heated to about 80° C. until the reaction was complete. The product was isolated by cooling the reaction to about 25° C. The slurry was filtered and the filtered cake was washed with a mixture of isopropanol (127 kg) and water (168 kg). The wet solids were recharged to the reactor and water (838 g) was added. The mixture was agitated at about 25° C. and then filtered and washed with water (168 g, 2 rel). The cake was dried to afford 6c. $^1$H NMR (400 MHz, DMSO-d$_6$) δ 12.20 (s, 1H), 7.41 (d, J=7.9 Hz, 1H), 6.84 (d, J=7.9 Hz, 1H), 5.31 (s, 2H).

6c (75 kg) was charged to a reactor containing N,N-dimethylformamide (75 kg). Potassium phosphate (99.8 kg) was charged to the reactor at about 25° C. and the mixture was agitated. 2,2,2-trifluoroethyl trifluoromethanesulfonate (74.3 kg) was charged at about 25° C. and the mixture was agitated until the reaction was complete. Water (375 kg) was charged and the mixture was agitated at about 20° C. The slurry was filtered and washed with water (150 kg). N,N-dimethylformamide (424 kg) and the wet solid were charged to a reactor at about 20° C. The mixture was agitated at about 45° C. 5% hydrochloric acid (450 kg) was charged dropwise to the mixture at about 45° C. The mixture was cooled to about 25° C. The slurry was filtered and washed with water (375 g). Water (375 kg) and the filtered solid were charged to a reactor at about 20° C. The mixture was agitated for about 1 hour at about 20° C. The slurry was filtered and washed with water (375 kg). The cake was dried to afford V-A. $^1$H NMR (400 MHz, DMSO-d$_6$) δ 7.57 (d, J=8.1 Hz, 1H), 6.98 (d, J=8.1 Hz, 1H), 5.70 (s, 2H), 5.32 (q, J=8.6 Hz, 2H).

Synthesis of 4-chloro-7-(4,4,5,5-tetramethyl-1,3,2-dioxaborolan-2-yl)-1-(2,2,2-trifluoroethyl)-1H-indazol-3-amine (V-02)

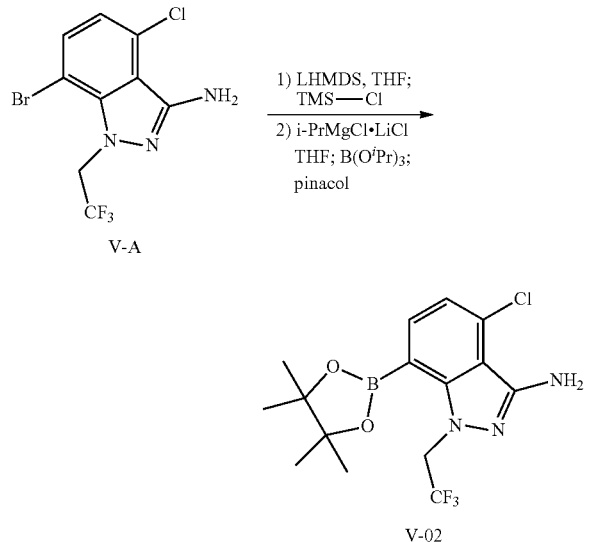

A reactor containing tetrahydrofuran (27 g) and V-A (1.0 g) was cooled to about 0° C. Chlorotrimethylsilane (7.6 g, 2.3 equiv) was added, followed by the slow addition of lithium bis(trimethylsilyl)amide (5.7 g, 1 M in THF, 2.1 equiv.). The mixture was stirred at about 0° C. until bistrimethylsilane protection was complete. The solution was washed with ammonium chloride in water (10 wt %, 52 g), toluene (44 g) was added, and the biphasic mixture was filtered through celite. The organic and aqueous phases were separated and the aqueous phase was washed with toluene (44 g). The organics were combined, washed with brine (58 g), and azeotropically distilled. The solution was cooled to about 0° C., isopropylmagnesium chloride lithium chloride complex (2.7 g, 1.3 M in THF, 1.2 equiv.) was added and the reaction was stirred at about 0° C. until lithium halogen exchange was complete. Isopropoxyboronic acid pinacol ester (6.8 g, 1.2 equiv.) was added and the reaction was stirred at about 0° C. until borylation was complete. At about 0° C., The reaction was quenched with aqueous hydrochloric acid (52 g, 1 M), acetonitrile (16 g) was added, and the mixture was stirred until trimethylsilane deprotection was complete. The solution was extracted with ethyl acetate (45 g) and the organic was washed twice with brine (2×58 g). The solution was concentrated to low volumes (26 g), dimethylformamide (47 g) was added, and the solution was concentrated again (51 g). The product was crystallized by the addition of water (50 g). The slurry was filtered and filter cake was washed with heptane (14 g). The solids were dried to afford V-02. $^1$H NMR (400 MHz, DMSO-$d_6$) δ 7.70 (dd, J=7.6, 1.0 Hz, 1H), 7.07 (dd, J=7.6, 1.0 Hz, 1H), 5.58 (s, 2H), 5.46 (q, J=9.1 Hz, 2H), 1.32 (s, 12H).

Synthesis of 4-chloro-7-(4,4,5,5-tetramethyl-1,3,2-dioxaborolan-2-yl)-1-(2,2,2-trifluoroethyl)-1H-indazol-3-amine (V-02)

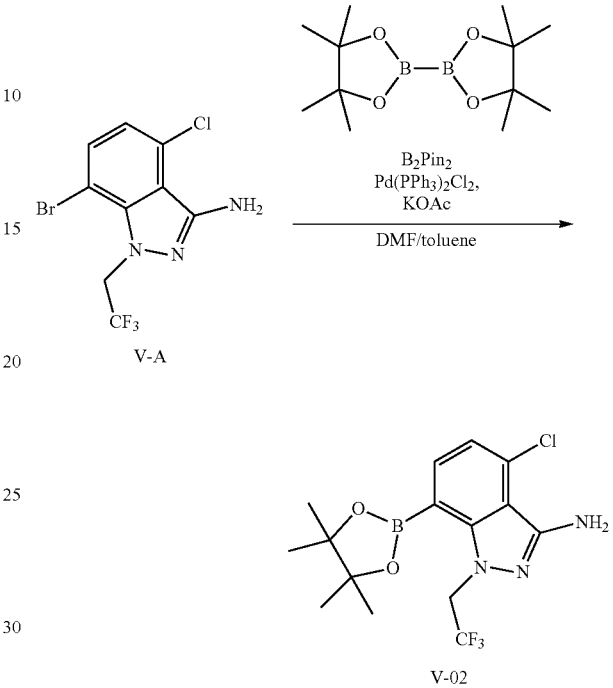

To a reactor was charged V-A (30 kg), bis(pinacolato)diboron (27.9 kg), bis(triphenylphosphine)palladium (II) dichloride (0.9 kg, 1.5 mol %), N,N-dimethylformamide (56 kg, 2 rel. vol.) and toluene (157 kg, 6 rel vol.). The mixture was heated to about 105° C. until the reaction was complete. The mixture was cooled to about 25° C., filtered through celite (15 kg, 0.5 rel. wt.) and rinsed forward with ethyl acetate (270 kg, 10 rel vol.). PSA-17 palladium scavenger (3 kg, 10 wt %) was added and the mixture was stirred at about 45° C. The mixture was filtered and the cake was washed with ethyl acetate (54 kg, 2 rel. vol.). The mixture was washed twice with lithium chloride (180 kg, 6 rel. vol.) and once with brine (NaCl, 23.5 mass % in water, 180 kg, 6 rel. vol.). The mixture was then concentrated to about 5-6 rel. vol. under vacuum, heated to about 45° C. then cooled to about 25° C. Heptane (102 kg, 5 rel. vol.) was charged and the mixture was concentrated to about 4-5 rel. vol. The product was isolated by charging heptane (41 kg, 2 rel. vol.) and cooling the mixture to about 0° C. The slurry was filtered and washed with heptane (41 kg, 2 rel. vol.). The wet solids were recharged to the reactor with ethyl acetate (27 kg, 1 rel. vol.) and heptane (82 kg, 4 rel. vol.), heated to about 65° C., and then cooled to about 5° C. The slurry was filtered and washed with heptane (41 kg, 2 rel. vol.). The cake was dried to afford V-02. $^1$H NMR (400 MHz, DMSO-$d_6$) δ 7.70 (dd, J=7.6, 1.0 Hz, 1H), 7.07 (dd, J=7.6, 1.0 Hz, 1H), 5.58 (s, 2H), 5.46 (q, J=9.1 Hz, 2H), 1.32 (s, 12h).

Synthesis of N-(4-chloro-7-(4,4,5,5-tetramethyl-1,3,2-dioxaborolan-2-yl)-1-(2,2,2-trifluoroethyl)-1H-indazol-3-yl)-N-(methylsulfonyl)methanesulfonamide (V-04)

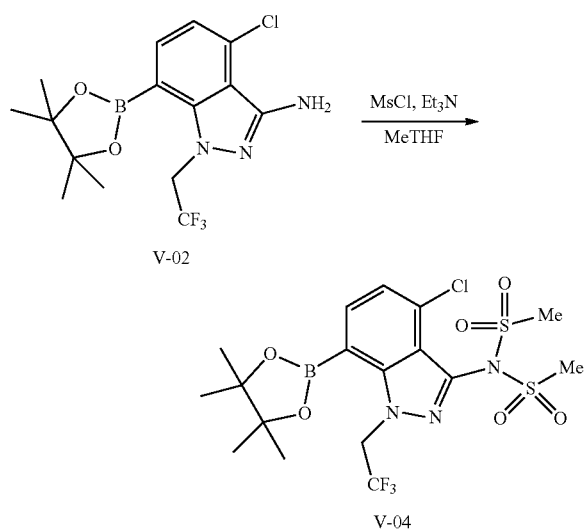

To a 100 mL reactor was added V-02 (5.00 g), 2-methyltetrahydrofuran (50 mL), and triethylamine (11.1 mL). The mixture was cooled to about 10° C. and methanesulfonyl chloride (2.58 mL, 33.3 mmol) was added to the mixture. The mixture was agitated at about 10° C. until reaction was complete. The mixture was concentrated to dryness and the residue was purified by column chromatography to afford V-04. $^1$H NMR (400 MHz, DMSO-d$_6$) δ 7.96 (d, J=7.7 Hz, 1H), 7.50 (d, J=7.6 Hz, 1H), 5.95 (q, J=8.8 Hz, 2H), 3.66 (s, 6H), 1.37 (s, 12H).

Synthesis of N-(4-chloro-7-(4,4,5,5-tetramethyl-1,3,2-dioxaborolan-2-yl)-1-(2,2,2-trifluoroethyl)-1H-indazol-3-yl)methanesulfonamide (V-03)

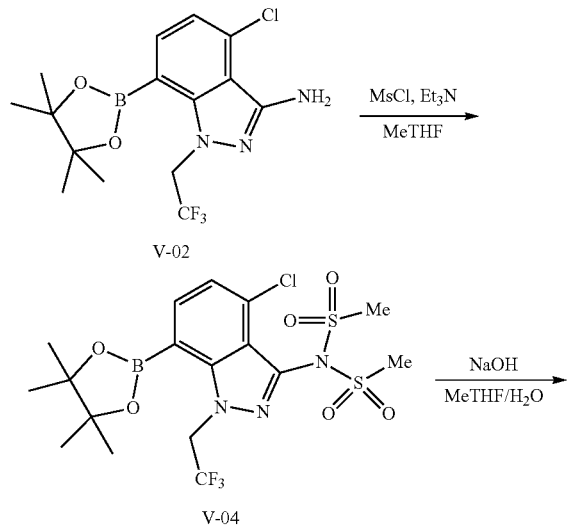

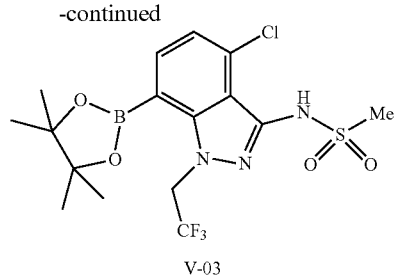

To a 100 mL reactor was added V-02 (5.00 g), 2-methyltetrahydrofuran (50 mL), and triethylamine (11.1 mL, 79.6 mmol). The mixture was cooled to about 10° C. and methanesulfonyl chloride (2.58 mL) was added to the mixture. The mixture was agitated at about 10° C. until reaction was complete. To the mixture was added 2-methyltetrahydrofuran (21.5 g) and sodium hydroxide (0.43 g) and the mixture was agitated at about 25° C. until the reaction was complete. To the resulting solution was added 2-methyltetrahydrofuran (21.5 g), water (25 g) and acetic acid to achieve a pH of less than 7. The lower aqueous layer was then removed and the organic layer was washed with brine (5 wt %, 7.8 g). The organic layer was then concentrated to dryness and the residue was purified by column chromatography to afford V-03. $^1$H NMR (400 MHz, DMSO-d$_6$) δ 9.96 (s, 1H), 7.86 (d, J=7.6 Hz, 1H), 7.34 (d, J=7.6 Hz, 1H), 5.80 (q, J=8.9 Hz, 2H), 3.22 (s, 3H), 1.36 (s, 12H).

Synthesis of N-(7-bromo-4-chloro-1-(2,2,2-trifluoroethyl)-1H-indazol-3-yl)-N-(methylsulfonyl)methanesulfonamide (V-06)

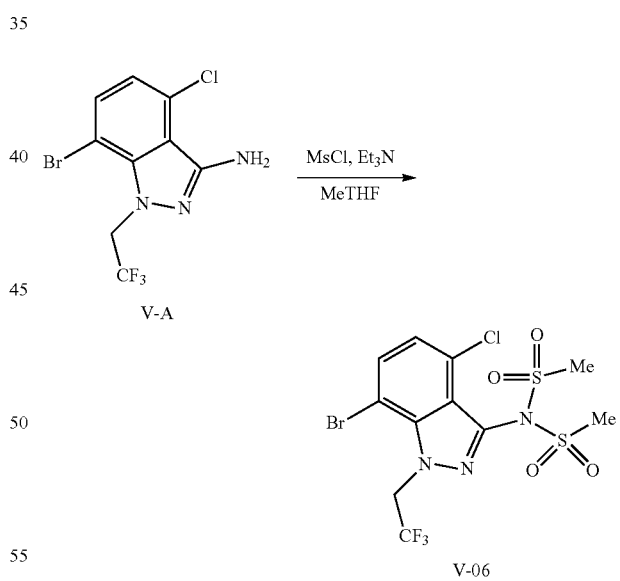

To a reactor was added V-A (3 g), 2-methyltetrahydrofuran (25.8 g), and triethylamine (7.6 mL). The mixture was cooled to about 10° C., methanesulfonyl chloride (1.8 mL) was added, and the mixture was stirred until reaction was complete. The reaction mixture was washed with aqueous sodium chloride (30 mL) and the organic layer was evaporated to dryness. The residue was purified by column chromatography to afford V-06. $^1$H NMR (400 MHz, DMSO-d$_6$) δ 7.83 (d, J=8.0 Hz, 1H), 7.35 (d, J=8.1 Hz, 1H), 5.79 (q, J=8.5 Hz, 2H), 3.62 (s, 6H).

Synthesis of N-(7-bromo-4-chloro-1-(2,2,2-trifluoroethyl)-1H-indazol-3-yl)methanesulfonamide (V-05)

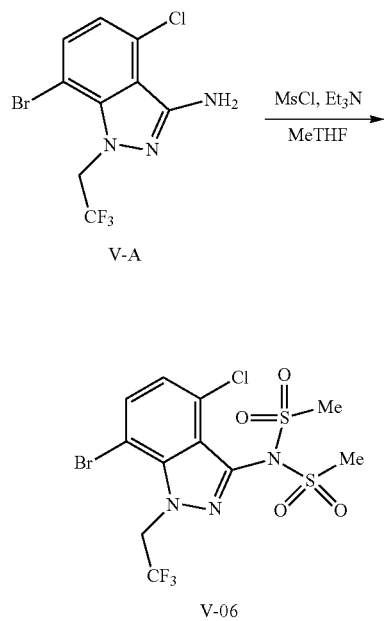

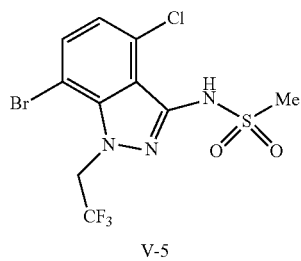

To a reactor was added V-02 (3 g), 2-methyltetrahydrofuran (30 mL), and triethylamine (7.6 mL). The mixture was cooled to about 10° C., methanesulfonyl chloride (1.8 mL) was added, and the mixture was stirred until reaction was complete. The reaction mixture was washed with aqueous sodium chloride (30 mL) and the organic portion was concentrated to dryness.

To the resulting mixture (2.7 g) was added 2-methyltetrahydrofuran (15 mL) and sodium hydroxide (1M in water, 15 mL). The mixture was stirred at about 20° C. until the reaction was complete. The aqueous layer was removed and the organic was washed with acetic acid (0.7M in water, 10 mL) and sodium chloride (5 wt % in water, 10 mL). The organic layer was then concentrated to dryness and the residue was purified by column chromatography to afford V-05. $^1$H NMR (400 MHz, DMSO-$d_6$) δ 10.03 (s, 1H), 7.71 (dd, J=8.0, 1.6 Hz, 1H), 7.20 (dd, J=8.1, 1.6 Hz, 1H), 5.64 (q, J=8.7 Hz, 3H), 3.19 (2, 3H).

Synthesis of N-(4-chloro-7-(4,4,5,5-tetramethyl-1,3,2-dioxaborolan-2-yl)-1-(2,2,2-trifluoroethyl)-1H-indazol-3-yl)-N-(methylsulfonyl)methanesulfonamide (V-04)

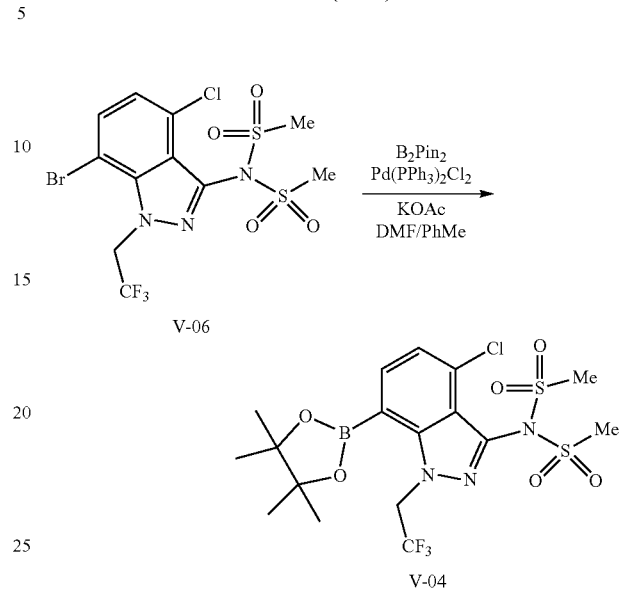

To a reactor was charged V-06 (148 mg), bis(pinacolato)diboron (93 mg), potassium acetate (90 mg) and bis(triphenylphosphine)palladium (II) chloride (4.3 mg, 1.5 mol %). N,N-dimethylformamide (0.2 mL) and toluene (0.6 mL) were added and the reaction was heated to about 105° C. until completion. V-04 was formed. $^1$H NMR (400 MHz, DMSO-$d_6$) δ 7.96 (d, J=7.7 Hz, 1H), 7.50 (d, J=7.6 Hz, 1H), 5.95 (q, J=8.8 Hz, 2H), 3.66 (s, 6H), 1.37 (s, 12H).

Synthesis of N-(4-chloro-7-(4,4,5,5-tetramethyl-1,3,2-dioxaborolan-2-yl)-1-(2,2,2-trifluoroethyl)-1H-indazol-3-yl)methanesulfonamide (V-03)

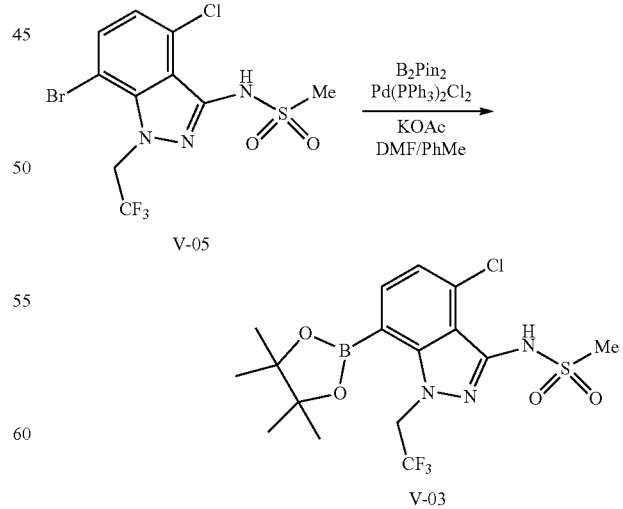

To a reactor was charged V-05 (124 mg), bis(pinacolato)diboron (93 mg), potassium acetate (90 mg) and bis(triphenylphosphine)palladium (II) chloride (4.3 mg, 1.5 mol %).

N,N-dimethylformamide (0.2 mL.) and toluene (0.6 mL, 6 rel. vol.) were added and the reaction was heated to about 105° C. until completion. V-03 was formed. ¹H NMR (400 MHz, DMSO-d₆) δ 9.96 (s, 1H), 7.86 (d, J=7.6 Hz, 1H), 7.34 (d, J=7.6 Hz, 1H), 5.80 (q, J=8.9 Hz, 2H), 3.22 (s, 3H), 1.36 (s, 12H).
II. Synthesis of the Compound of Formula I
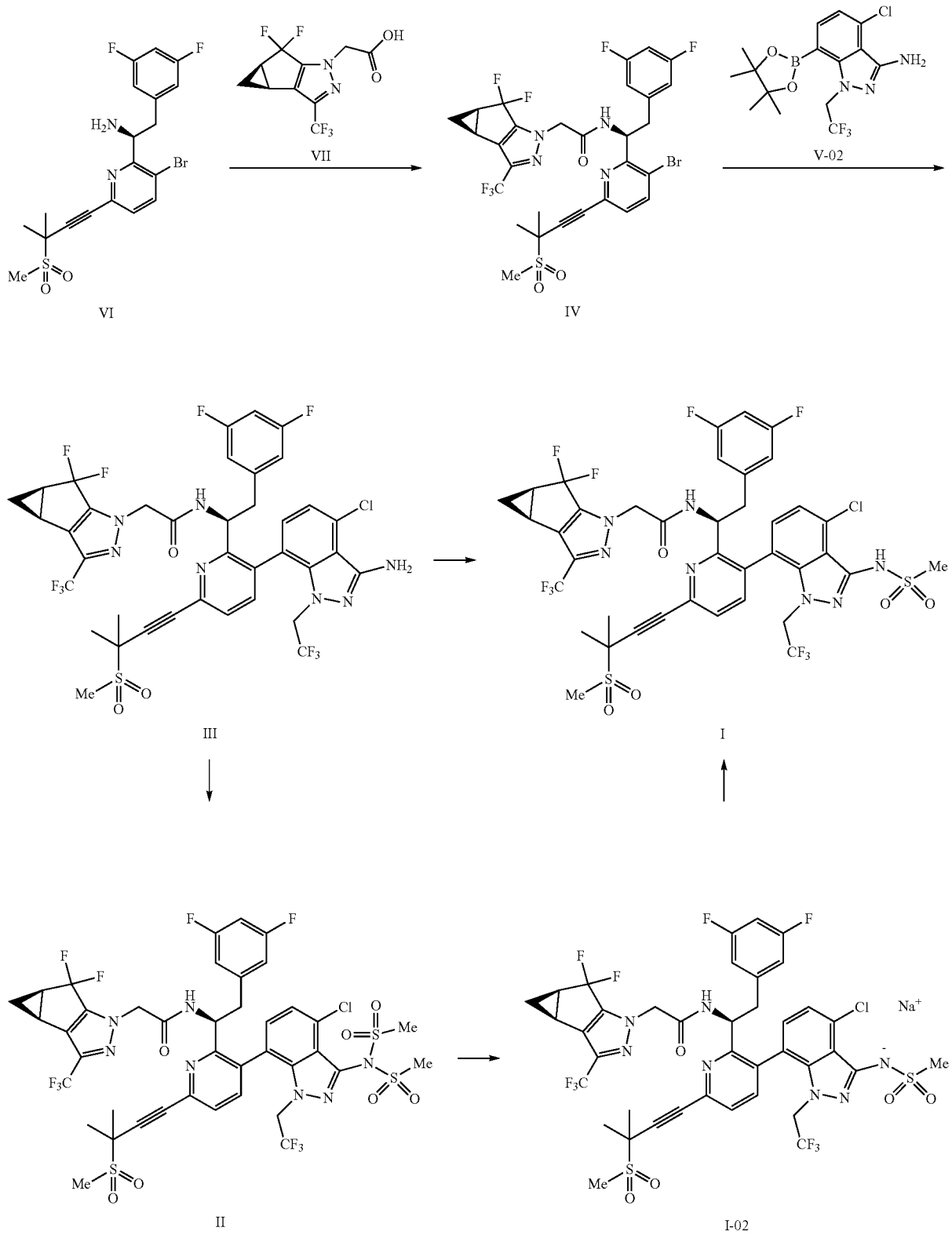

Example 8: Preparation of N—((S)-1-(3-bromo-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (IV)

Synthesis of N—((S)-1-(3-bromo-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (IV) from (S)-1-(3-bromo-6-(3-methyl-3-(methylsulfonyl)but-1-yn-1-yl)pyridin-2-yl)-2-(3,5-difluorophenyl)ethan-1-amine (VI)

Method 1

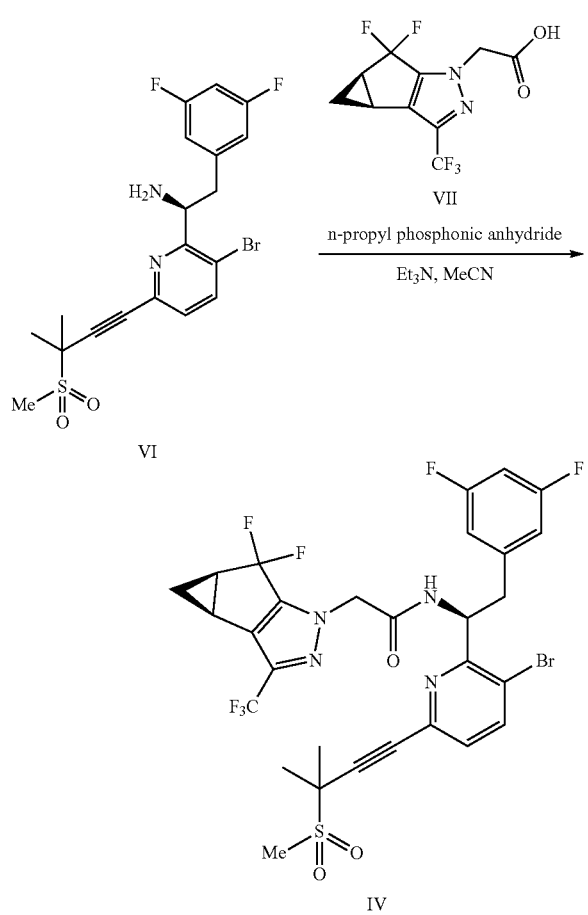

n-Propylphosphonic anhydride (T3P, 3.1 g, 1.5 equiv.) was slowly added to a reactor containing amine VI (1.5 g), acid VII (1.0 g, 1.1 equiv.), triethylamine (Et₃N, 0.5 g, 1.5 equiv.), and acetonitrile (MeCN, 8.0 g). The mixture was agitated at about 20° C. until the reaction was complete. The product was crystallized from the reaction mixture with DMF (0.63 g), and water (15 g). The slurry was filtered and the filter cake was washed with a mixture of acetonitrile and water (2×2.5 g). The cake was dried to afford IV. $^1$H NMR (400 MHz, DMSO-d₆) δ 9.19 (d, J=8.3 Hz, 1H), 8.12 (d, J=8.3 Hz, 1H), 7.50 (d, J=8.3 Hz, 1H), 7.07 (tt, J=9.4, 2.4 Hz, 1H), 6.96-6.87 (m, 2H), 5.52 (td), J=8.8, 5.3 Hz, 1H), 4.93-4.73 (m, 2H), 3.22 (s, 3H), 3.11-2.90 (m, 2H), 2.66-2.52 (m, 2H), 1.69 (s, 6H), 1.45-1.36 (m, 1H), 1.02-0.93 (m, 1H). $^{13}$C NMR (100 MHz, DMSO-d₆): δ 164.42, 163.62, 163.49, 161.17, 161.04, 158.19, 142.92, 142.20, 142.10, 142.01, 141.63, 140.23, 134.11, 133.73, 132.14, 128.66, 122.23, 120.49, 119.56, 112.49, 112.25, 104.75, 102.25, 88.62, 84.20, 57.44, 53.85, 53.03, 35.21, 23.41, 22.46, 22.40, 11.79.

Synthesis of N—((S)-1-(3-bromo-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (IV) from (5)-1-(3-bromo-6-(3-methyl-3-(methylsulfonyl)but-1-yn-1-yl)pyridin-2-yl)-2-(3,5-difluorophenyl)ethan-1-amine (VI)

Method 2

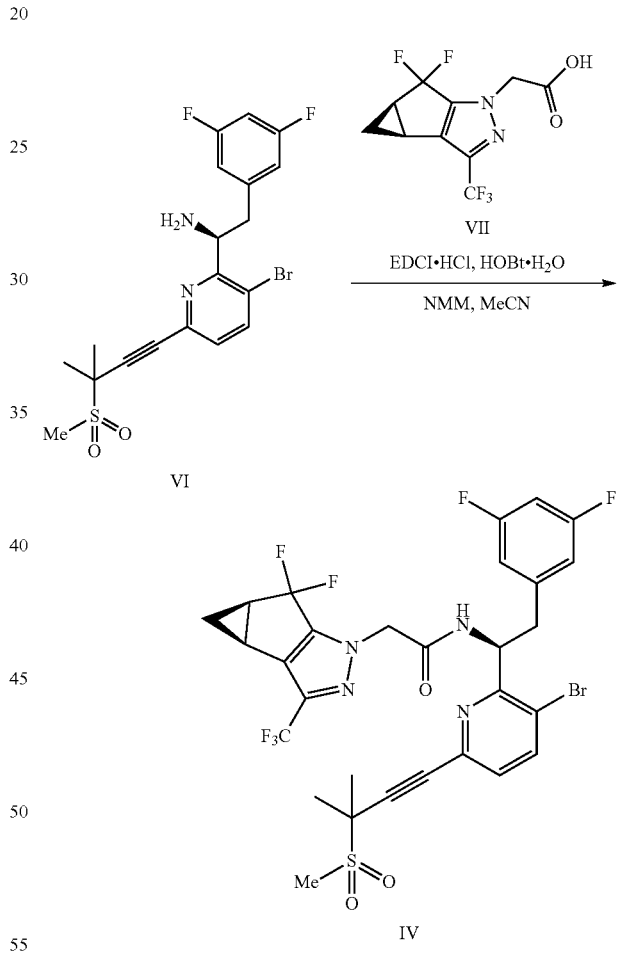

N-methylmorpholine (NMM, 0.51 g, 2.3 equiv.) was added to a vessel containing amine VI (1.0 g), acid VII (1.0 g), 1-hydroxybenzotriazole hydrate (HOBt.H₂O, 0.17 g, 0.5 equiv.), N-(3-dimethylaminopropyl)-N'-ethylcarbodiimide (EDCI.HCl, 0.52 g, 1.25 equiv.), and acetonitrile (MeCN, 7.8 g). The mixture was agitated at about 20° C. until the reaction was complete. The product was crystallized from the reaction mixture with DMF (2.8 g), and water (10 g). The slurry was filtered and the filter cake was washed with a mixture of acetonitrile and water. The cake was dried to afford IV. $^1$H NMR (400 MHz, DMSO-d₆) δ 9.19 (d, J=8.3

Hz, 1H), 8.12 (d, J=8.3 Hz, 1H), 7.50 (d, J=8.3 Hz, 1H), 7.07 (tt, J=9.4, 2.4 Hz, 1H), 6.96-6.87 (m, 2H), 5.52 (td, J=8.8, 5.3 Hz, 1H), 4.93-4.73 (m, 2H), 3.22 (s, 3H), 3.11-2.90 (m, 2H), 2.66-2.52 (m, 2H), 1.69 (s, 6H), 1.45-1.36 (m, 1H), 1.02-0.93 (m, 1H). $^{13}$C NMR (100 MHz, DMSO-$d_6$): δ 164.42, 163.62, 163.49, 161.17, 161.04, 158.19, 142.92, 142.20, 142.10, 142.01, 141.63, 140.23, 134.11, 133.73, 132.14, 128.66, 122.23, 120.49, 119.56, 112.49, 112.25, 104.75, 102.25, 88.62, 84.20, 57.44, 53.85, 53.03, 35.21, 23.41, 22.46, 22.40, 11.79.

Example 9: Preparation of N—((S)-1-(3-(3-amino-4-chloro-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (III)

Synthesis of Compound III-04 were washed twice with sodium chloride in water (5 wt %, 11 g). The solution was azeotropically distilled into 1-propanol (3.3 g). To the propanol solution at about 50° C. was added methanesulfonic acid (0.31 g, 2.25 equiv.) and the product was crystallized using dibutyl ether (5.1 g). The slurry was cooled to about 10° C., filtered, and the filter cake was washed with a 5:1 mixture of propanol in dibutyl ether (1.6 g). The solids were dried to afford III-04. $^1$H NMR (400 MHz, DMSO-$d_6$) δ 9.19 (d, J=8.3 Hz, 2H), 7.84-7.69 (m, 4H), 7.11 (d, J=7.7 Hz, 2H), 7.07-6.95 (m, 3H), 6.82 (d, J=7.7 Hz, 2H), 6.54-6.40 (m, 4H), 4.90 (d, J=16.4 Hz, 2H), 4.76-4.60 (m, 4H), 4.15 (dq, J=16.6, 8.4 Hz, 2H), 3.75 (dt, J=16.3, 8.7 Hz, 2H), 3.25 (s, 7H), 2.99-2.86 (m, 4H), 2.63-2.50 (m, 3H), 2.41 (s, 14H), 1.73 (d, J=2.1 Hz, 13H), 0.93 (dd, J=6.1, 3.9 Hz, 2H).

Synthesis of N—((S)-1-(3-(3-amino-4-chloro-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (III)

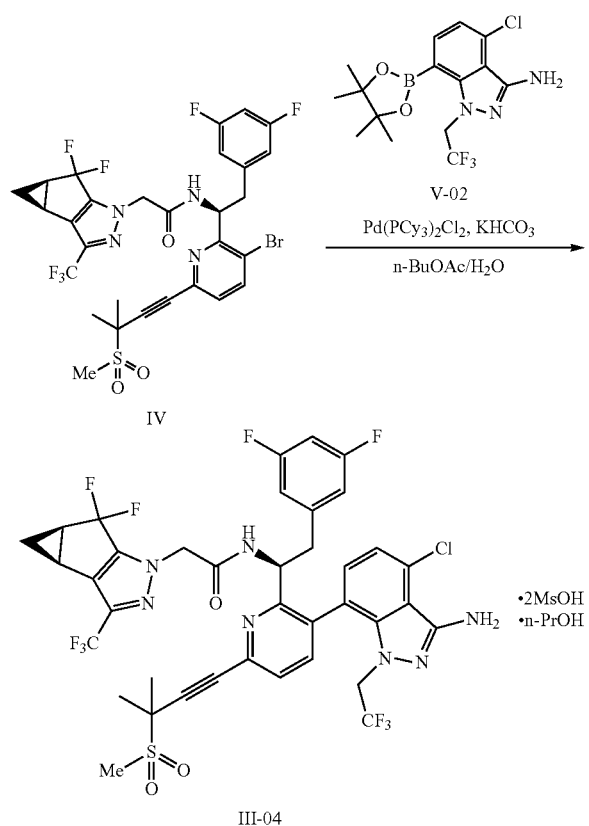

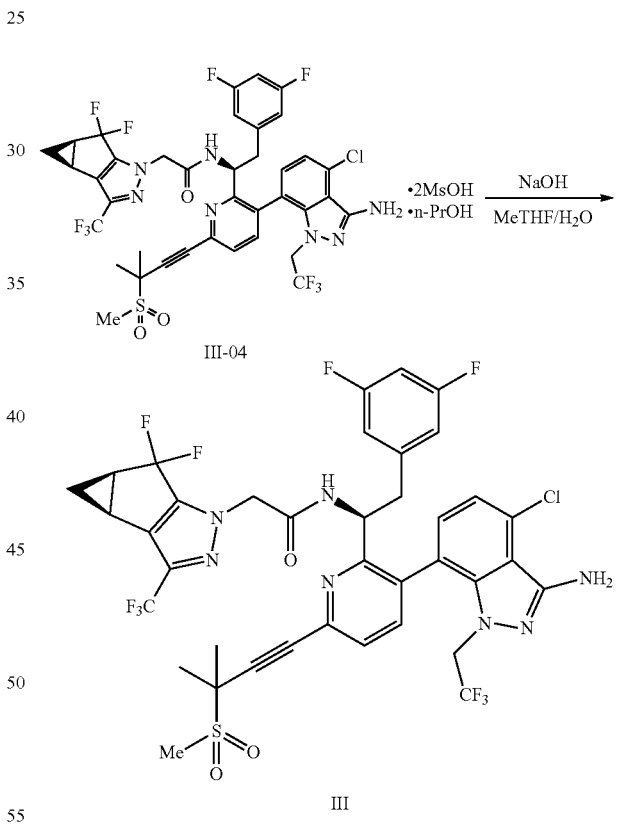

To a reactor was added IV (1.0 g), potassium bicarbonate (0.43 g, 1.3 equiv), dichlorobis(tricyclohexylphosphine)palladium(II) (28 mg, 2.5 mol %), V-02 (0.67 g), butyl acetate (7.3 g) and water (2.1 g). The reactor was inerted and the mixture was agitated at about 85° C. (75-90° C.) until the reaction was complete. The mixture was cooled to about 40° C. and passed through celite (0.52 g). The celite cake was rinsed with butyl acetate (1.8 g). The filtrate and rinse were combined and this solution was washed twice with a mixture of N-acetyl-L-cysteine (0.31 g) dissolved in water (5.2 g) and sodium hydroxide in water (5 wt %, 5.4 g). The organics Aqueous sodium hydroxide (0.2 M; 2.2 equivalents; 9.2 g) was added to a reactor containing III-04 (1.0 g) in MeTHF (8.3 g) at about 20° C. The biphasic mixture was agitated for about 15 min, and the aqueous layer was removed. The organic layer was washed four times with 2.0 wt % aqueous sodium chloride (9.8 g) and was distilled. The solution containing III was used directly in the II process below. A sample was concentrated to dryness for analysis. $^1$H NMR (400 MHz, CDCl$_3$): δ 7.44 (m, 1H), 7.39 (br, 1H), 7.18 (m, 1H), 6.90 (m, 1H), 6.65 (m 1H), 4.10 (m, 2H), 3.72 (m, 4H), 2.78 (m 2H), 2.56 (br, 4H), 1.31 (s, 9H). $^{13}$C NMR (100

MHz, DMSO-d₆): δ 176.88, 158.95, 141,06, 129.55, 112.79, 109.56, 106.83, 66.66, 65.73, 57.45, 54.12, 39.53, 27.63.

Example 10: Preparation of N—((S)-1-(3-(4-chloro-3-(N-(methylsulfonyl)methylsulfonamido)-1-(2,2,2-trifluoroethyl)-1H-indazol-7-yl)-6-(3-methyl-3-(methylsulfonyl) but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (II)

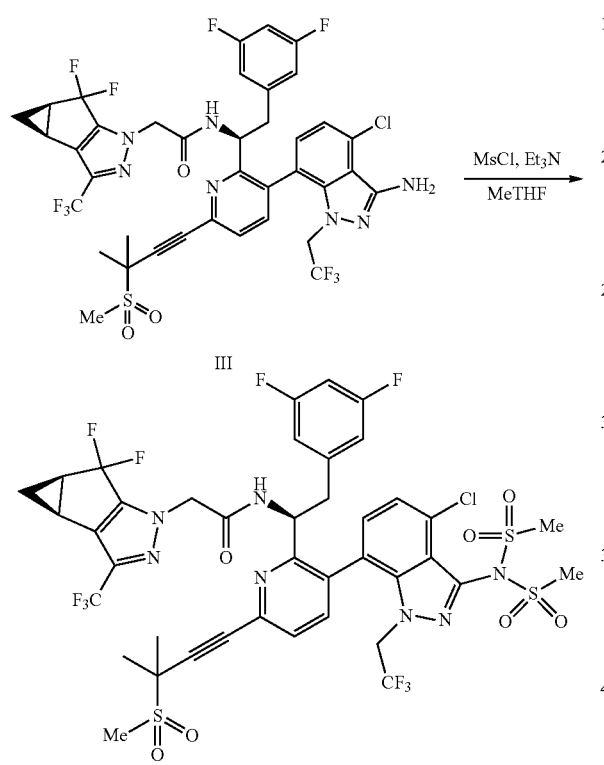

Methanesulfonyl chloride (0.32 g, 2.5 equivalents) was added to a reactor containing III (1.0 g), triethylamine (0.69 g, 6.0 equivalents), and MeTHF (11 g) at about 10° C. The mixture was agitated at about 10° C. until the reaction was complete. The reaction mixture was washed with water (6.4 g) for about 15 minutes, and warmed to about 20° C. The layers were separated and the organic layer was washed for about 15 minutes with 10 wt % aqueous sodium chloride (6.9 g). The layers were separated and the organic layer was used directly in the next step. An aliquot was concentrated to dryness for analysis. ¹H NMR (400 MHz, δ₆-DMSO; 9:1 mixture of atropisomers): δ 9.20 (d, J=7.9 Hz 1H), 8.99* (d, J=8.6 Hz, 1H), 7.96* (d, J=7.9 Hz, 1H), 7.83 (d, J=8.0 Hz, 1H), 7.80* (d, J=7.9 Hz, 1H), 7.76 (d, J=8.0 Hz, 1H), 7.45 (d, J=7.7 Hz, 1H), 7.41* (d, J=7.8 Hz, 1H), 7.31* (d, J=7.8 Hz, 1H), 7.02 (tt, J=9.4, 2.1 Hz, 1H), 6.92* (s, 1H), 6.91 (d, J=7.7 Hz, 1H), 6.48 (m, 2H), 4.92* (s, 1H), 4.88 (d, J=16.4 Hz, 1H), 4.79* (d, J=16.8 Hz, 1H), 4.73* (d, J=16.4 Hz, 1H), 4.71* (m, 1H), 4.69 (m, 1H), 4.62* (s, 1H), 4.60 (m, 1H), 4.38* (dq, J=16.4, 8.2 Hz, 1H), 4.12 (dq, J=16.7, 8.4 Hz, 1H), 3.68* (s, 3H), 3.66* (s, 3H), 3.63 (s, 3H), 3.58 (s, 3H), 3.26 (s, 3H), 3.12* (dd, J=13.8, 10.5 Hz, 1H), 3.05 (dd, J=13.5, 5.8 Hz, 1H), 2.97 (dd, J=13.5, 8.5 Hz, 1H), 2.78* (dd, J=13.7, 3.9 Hz, 1H), 2.59 (m, 1H), 2.53 (m, 1H), 1.75 (s), 1.75 (s, 6H), 1.39 (m, 1H), 0.98 (m, 1H). ¹³C NMR (100 MHz, DMSO-d₆, 9:1 mixture of atropisomers): δ 164.5, 163.6*, 162.1 (dd, J=246.3, 13.4 Hz), 162.0* (dd, J=246.1, 13.3 Hz), 158.7, 158.4*, 142.7 (t, J=29.3 Hz), 142.3, 142.0*, 141.8 (t, J=9.4 Hz), 140.6*, 139.9, 139.7*, 139.3, 135.8*, 135.0, 133.8 (q, J=39.0 Hz), 132.2*, 132.1 (m), 131.6, 129.6, 129.4*, 126.7, 125.3, 125.2*, 124.1*, 123.4, 122.8*, 122.7 (q, J=280.9 Hz), 120.7 (q, J=268.3 Hz), 119.9 (t, J=243.7 Hz), 119.8, 119.5*, 119.0*, 118.9, 112.0, 102.2 (t, J=225.7 Hz), 101.8*, 88.4, 84.5, 57.3, 52.93, 52.86, 52.7, 52.5*, 50.7 (q, J=33.8 Hz), 50.3*, 42.6*, 42.4, 42.3*, 42.2, 39.51, 39.5, 38.9*, 35.1, 27.5 (dd, J=35.0, 28.6 Hz), 23.1, 22.4, 22.3, 11.5. (*signals arising from minor atropisomer)

Example 11: Preparation of N—((S)-1-(3-(4-chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (I)

Synthesis of sodium (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)amide (I-02)

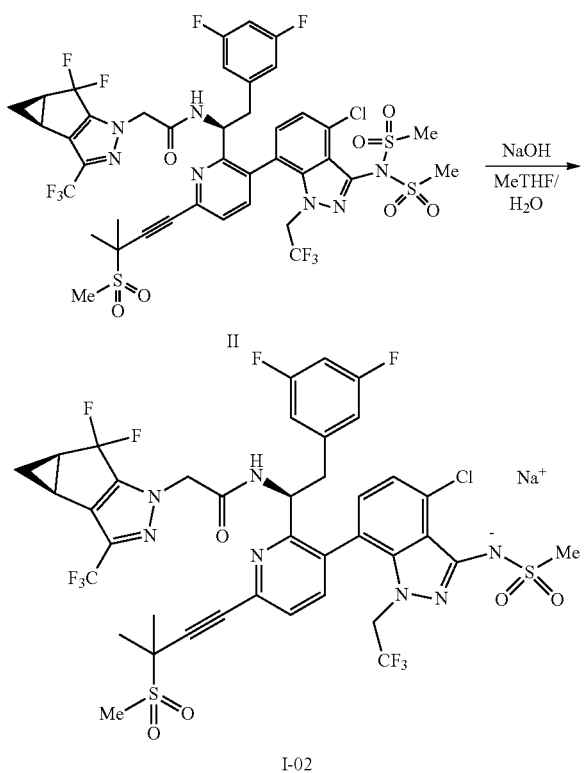

I-02

Sodium hydroxide (1 M, 2.9 g, 3.0 equiv.) was added to a reactor containing II (1.0 g) and 2-methyltetrahydrofuran (8.4 g) at about 35° C. The mixture was agitated until the reaction was deemed complete. The reaction mixture was adjusted to between about 20 and 40° C. and the bottom layer was removed. The organic layer was washed with water (2.9 g) for about 15 minutes, and the bottom layer was removed. The organic solvent was swapped for ethanol and the solution was concentrated to about 5 volumes and the temperature was adjusted to about 35° C. n-Heptane (3.4 g) was slowly added, and the mixture was aged for about 12 hours. The solids were collected by filtration, and the filter cake was washed with ethanol/n-heptane (1:1). The resultant wet cake was dried under vacuum to afford I-02. $^1$H NMR (400 MHz, DMSO-d$_6$) δ 9.09 (d, J=8.0 Hz, 1H), 8.93* (d, J=8.5 Hz), 7.80-7.72* (m), 7.71 (s, 2H), 6.99 (tt, J=9.5, 2.4 Hz, 1H), 6.94 (d, J=7.6 Hz, 1H), 6.90* (d, J=6.3 Hz), 6.69 (d, J=7.6 Hz, 1H), 6.57-6.51* (m), 6.48-6.40 (m, 2H), 4.90 (d, J=16.5 Hz, 1H), 4.77 (d, J=16.4 Hz, 1H), 4.70 (td, J=8.3, 5.2 Hz, 1H), 4.63* (d, J=16.5 Hz), 4.22 (dq, J=16.7, 8.4 Hz, 1H), 3.90-3.75 (m, 1H), 3.26 (s, 3H), 2.92 (td, J=13.8, 8.5 Hz, 2H), 2.83* (s), 2.80 (s, 3H), 2.64-2.51 (m, 2H), 1.74 (d, J=2.2 Hz, 6H), 1.44-1.34 (m, 1H), 0.94 (dq, J=6.0, 3.7 Hz, 1H); $^{13}$C NMR (100 MHz, dmso) δ 164.39, 163.43, 163.39, 163.25, 160.94, 160.91, 160.81, 158.93, 158.22, 152.64, 151.94, 142.92, 142.72, 142.63, 142.43, 142.34, 142.19, 142.10, 142.00, 141.43, 141.14, 139.55, 139.36, 133.95, 133.56, 133.17, 132.12, 131.93, 131.68, 129.66, 129.56, 128.17, 127.91, 126.86, 126.76, 125.02, 122.35, 122.21, 122.08, 122.05, 119.93, 119.88, 119.38, 118.88, 118.18, 117.54, 117.21, 117.04, 112.18, 112.02, 111.95, 111.84, 111.78, 102.28, 102.03, 101.81, 88.14, 88.00, 84.69, 84.65, 57.33, 53.22, 52.96, 52.76, 52.44, 40.15, 39.94, 39.73, 39.52, 39.31, 39.10, 38.97, 38.89, 38.65, 35.10, 35.08, 27.86, 27.56, 27.52, 27.23, 23.19, 22.42, 22.41, 22.30, 22.28, 11.63. * Signals arising from minor atropisomer. $^{13}$C NMR data is reported for the mixture of atropisomers.

Synthesis of N—((S)-1-(3-(4-chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (I) from sodium (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)amide (I-02)

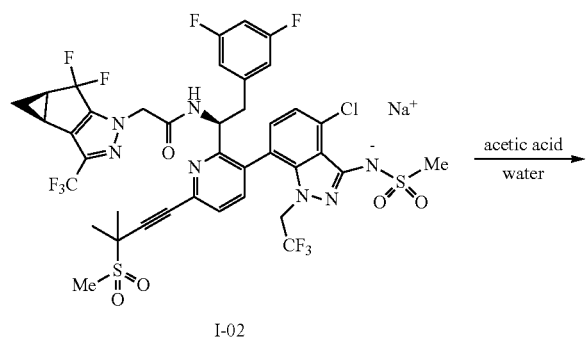

I-02

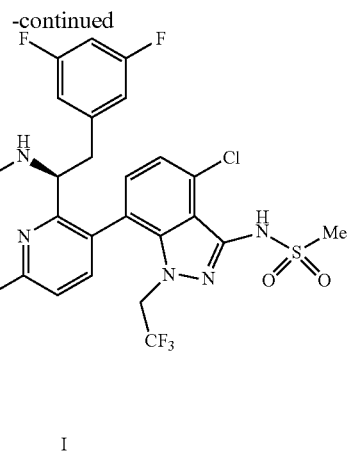

I

Compound I-02 (1.0 g) and glacial acetic acid (2.1 g) were combined at about 20° C. and were agitated until dissolved. The resultant solution was transferred to a reactor containing water (15 g) over about 1 hour. The resultant slurry was further agitated for about one hour, and was filtered. The wet cake was washed with water (2×5 g), deliquored, and dried at about 60° C. under vacuum to provide I. $^1$H NMR (400 MHz, δ$_6$-DMSO; 5:1 mixture of atropisomers) δ 10.11* (s), 10.00 (s, 1H), 9.25 (d, J=8.0 Hz, 1H), 8.92* (d, J=8.4 Hz), 7.90* (d, J=7.6 Hz), 7.81 (d, J=8.0 Hz, 1H), 7.76 (d, J=8.0 Hz, 1H), 7.32 (d, J=7.6 Hz, 1H), 7.23* (d, J=8.0 Hz), 7.19* (d, J=8.0 Hz), 7.02 (tt, J=9.4, 2.4 Hz, 1H), 6.94* (m), 6.86 (d, J=7.6 Hz, 1H), 6.54* (m), 6.48 (m, 2H), 4.92 (d, J=16.4 Hz, 1H), 4.77* (d, J=16.4 Hz), 4.71 (d, J=16.4 Hz, 1H), 4.68* (m), 4.51 (dq, J=16.4, 8.3 Hz, 1H), 4.19* (dq, J=16.4, 8.2 Hz), 3.96 (dq, J=16.8, 8.4 Hz, 1H), 3.27 (s, 3H), 3.24* (s), 3.17 (s, 3H), 3.11* (dd, J=13.0, 3.4 Hz), 3.02 (dd, J=13.6, 5.6 Hz, 1H), 2.95 (dd, J=13.8, 8.6 Hz, 1H), 2.92* (m), 2.60 (m, 1H), 2.55 (m, 1H), 1.74 (s, 6H), 1.40 (m, 1H), 0.96 (m, 1H); $^{13}$C NMR (100 MHz, δ$_6$-DMSO; 5:1 mixture of atropisomers) δ 164.5, 163.4*, 162.1 (dd, J=246.0, 13.4 Hz), 162.0* (dd, J=246.1, 13.4 Hz), 158.8, 158.1*, 142.7 (t, J=29.3 Hz), 142.3, 142.1* (m), 141.9 (t, J=9.5 Hz), 141.7*, 140.2*, 140.0*, 139.8*, 139.5, 139.3, 139.2, 133.8 (q, J=38.7 Hz), 132.0 (m), 131.7*, 131.1, 130.3*, 130.0, 126.8, 126.4, 126.2*, 123.0* (m), 122.9 (q, J=281.7 Hz), 122.7*, 122.1, 120.7 (q, J=268.3 Hz), 119.9 (t, J=243.4 Hz), 119.0, 118.7*, 117.5*, 117.4, 112.0 (m), 102.1 (t, J=25.6 Hz), 101.9* (m), 88.5*, 88.4, 84.5, 57.3, 52.8, 52.7, 52.4*, 50.2 (q, J=33.3 Hz), 50.0 (m), 41.4*, 41.2, 39.8, 38.7, 35.1, 27.5 (dd, J=35.1, 29.0 Hz), 23.2, 22.4, 22.3, 22.2*, 11.6. * Signals arising from the minor atropisomer.

Alternatively, a premixed solution of acetic acid (1.5 g), ethanol (12 g), and water (0.3 g) were combined with Compound I-02 at 20° C. and were agitated until dissolved. The resultant solution was transferred to a reactor containing water (100 g) over about 30 minutes. The resultant slurry was further agitated for about one hour, and was filtered. The wet cake was washed with water (2×25 g), deliquored, and dried at about 60° C. under vacuum to provide I.

189

Synthesis of N—((S)-1-(3-(4-chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (I) from N—((S)-1-(3-(3-amino-4-chloro-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (III)

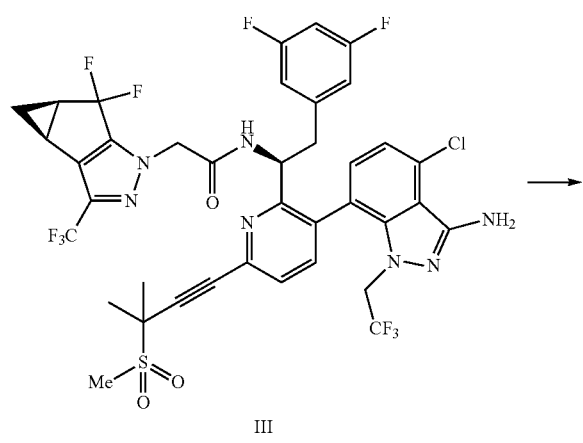

III

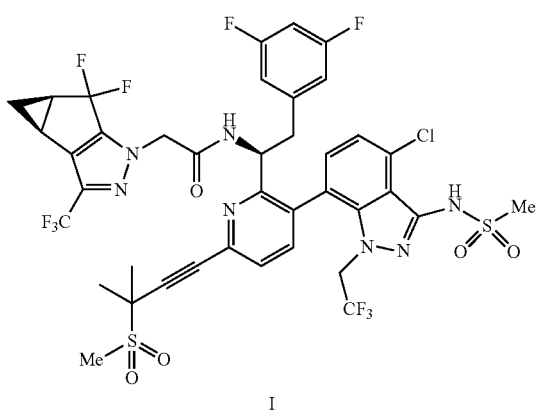

I

A reactor was charged with III (1.0 g) followed by cyclopentyl methyl ether (2.0 mL). The contents were adjusted to about 80° C. In a separate reactor, methanesulfonic acid anhydride (0.3 g, 1.5 equiv.) was dissolved in cyclopentyl methyl ether (6 mL). The solution was added to the first reactor via a syringe pump over 5 h. Following addition, the reaction mixture was aged for 16 h. The reaction mixture was quenched with water (10 mL). UPLC analysis of the organic phase showed I with 94.8% purity.

190

Synthesis of N—((S)-1-(3-(4-chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (I) from N—((S)-1-(3-bromo-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (IV)

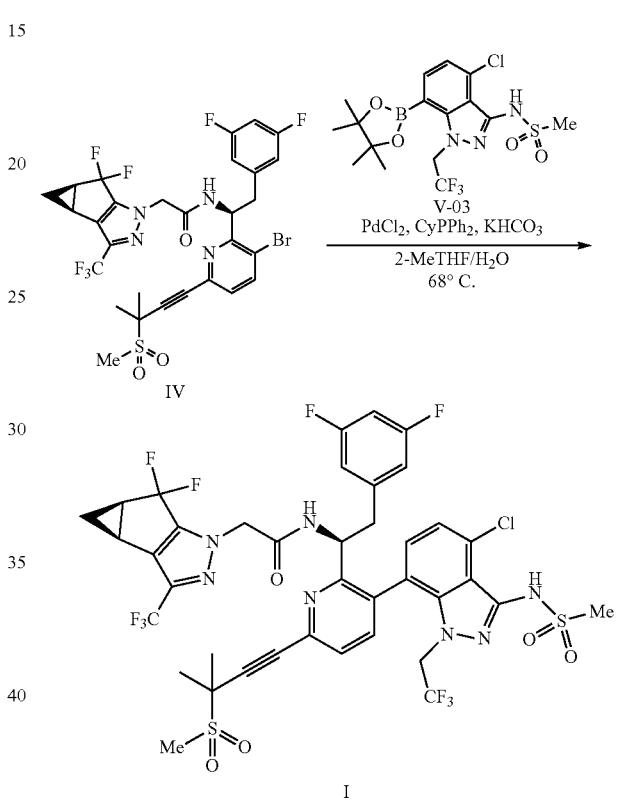

To a 40 mL vial was added IV (1.00 g), potassium bicarbonate (420 mg), palladium(II) chloride (4.9 mg, 2.0 mol %), cyclohexyldiphenylphosphine (13.4 mg, 3.6 mol %), V-03 (849 mg), 2-methyltetrahydrofuran (8.0 mL) and water (2.0 mL). The vial was inerted and the mixture was agitated at about 68° C. (65-73° C.) until the reaction was complete. The mixture was cooled to about 40° C. and the aqueous layer was removed. The organic layer was washed with aqueous acetic acid (5% w/v, 5.1 g). The organic was then concentrated to dryness and the residue was purified by column chromatography to afford I. $^1$H NMR (400 MHz, DMSO-d$_6$) δ 10.12 (s, 0.2H), 10.00 (s, 1H), 9.25 (d, J=8.2 Hz, 1H), 8.92 (d, J=8.6 Hz, 0H), 7.90 (d, J=7.9 Hz, 0.1H), 7.85-7.71 (m, 2H), 7.52-7.50 (m, 0.1H), 7.32 (d, J=7.7 Hz, 1H), 7.21 (q, J=9.6 Hz, 0.4H), 7.11-6.97 (m, 1H), 6.94-6.89 (m, 0.2H), 6.86 (d, J=7.7 Hz, 1H), 6.55 (d, J=7.4 Hz, 0.4H), 6.52-6.43 (m, 2H), 4.92 (d, J=16.4 Hz, 1H), 4.81-4.66 (m, 1.5H), 4.64-4.45 (m, 2.4H), 4.28-4.13 (m, 0.2H), 4.08-3.92 (m, 1.6H), 3.32 (s, 0.7H), 3.30-3.22 (m, 4.4H), 3.17 (s, 3H), 3.08-2.89 (m, 2.2H), 2.69-2.53 (m, 2.2H), 2.12 (s, 0.2H), 1.99 (s, 1H), 1.91 (s, 0.3H), 1.80-1.70 (m, 6H), 1.48-1.36 (m, 1.2H), 1.23-1.12 (m, 1.3H), 0.96 (s, 1.2H).

Synthesis of N—((S)-1-(3-(4-chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (I) from N—((S)-1-(3-bromo-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (IV)

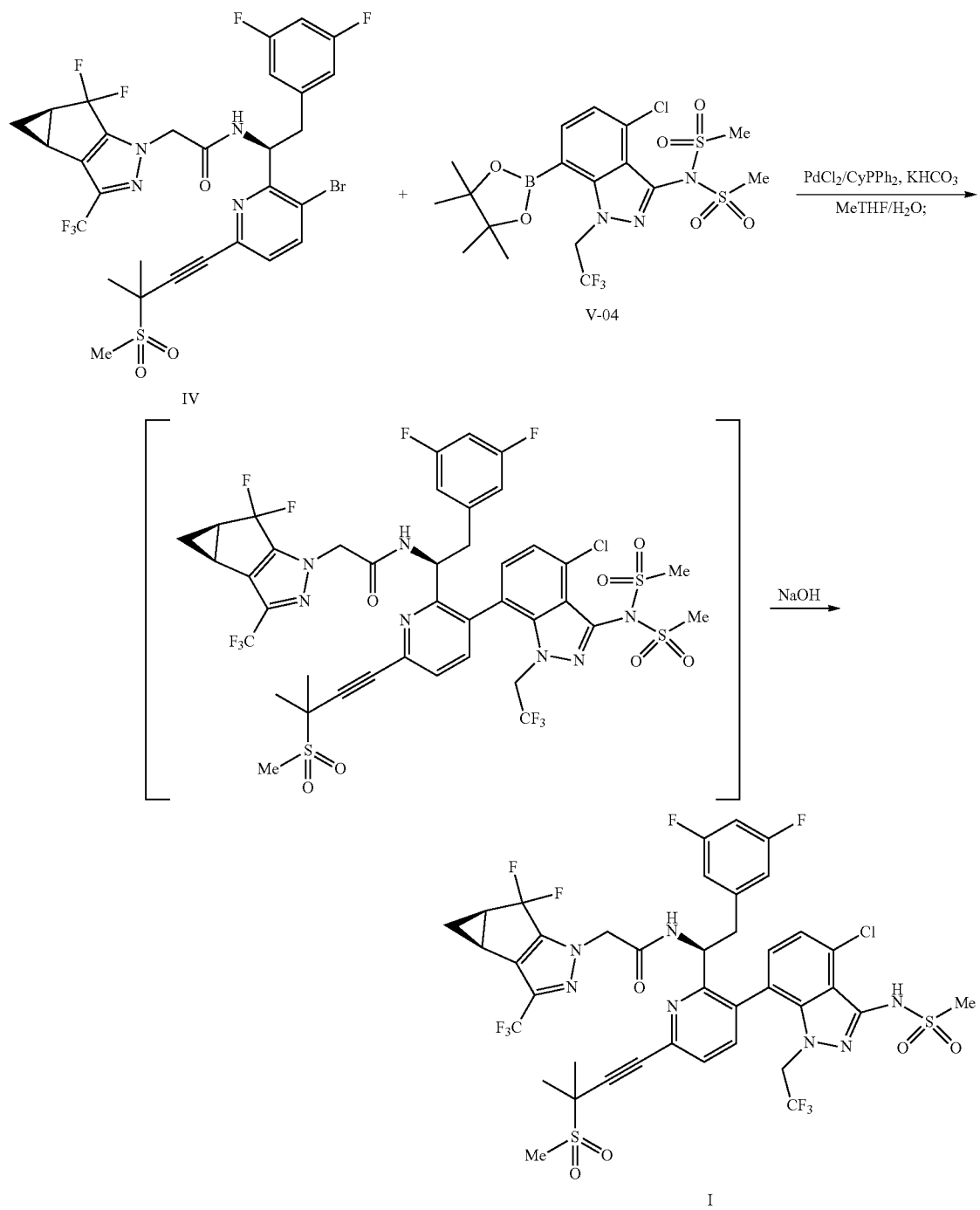

To a 40 mL vial was added IV (1.00 g), potassium bicarbonate (420 mg), palladium(II) chloride (4.9 mg, 2.0 mol %), cyclohexyldiphenylphosphine (13.4 mg, 3.6 mol %), V-04 (923 mg), 2-methyltetrahydrofuran (8.0 mL) and water (2.0 mL). The vial was inerted and the mixture was agitated at about 68° C. (65-73° C.) until the reaction was complete. The mixture was cooled to about 40° C. and the aqueous layer was removed. The organic was stirred with aqueous sodium hydroxide (5% w/w, 6.3 g) at 40° C. until reaction was complete. The organic was washed with aqueous acetic acid (5% w/v, 5.1 g). The organic was then concentrated to dryness and the residue was purified by column chromatography to afford I. $^1$H NMR (400 MHz, DMSO-$d_6$) δ 10.12 (s, 0.2H), 10.00 (s, 1H), 9.25 (d, J=8.2 Hz, 1H), 8.92 (d, J=8.6 Hz, 0H), 7.90 (d, J=7.9 Hz, 0.1H), 7.85-7.71 (m, 2H), 7.52-7.50 (m, 0.1H), 7.32 (d, J=7.7 Hz, 1H), 7.21 (q, J=9.6 Hz, 0.4H), 7.11-6.97 (m, 1H), 6.94-6.89 (m, 0.2H), 6.86 (d, J=7.7 Hz, 1H), 6.55 (d, J=7.4 Hz, 0.4H), 6.52-6.43 (m, 2H), 4.92 (d, J=16.4 Hz, 1H), 4.81-4.66 (m, 1.5H), 4.64-4.45 (m, 2.4H), 4.28-4.13 (m, 0.2H), 4.08-3.92 (m, 1.6H), 3.32 (s, 0.7H), 3.30-3.22 (m, 4.4H), 3.17 (s, 3H), 3.08-2.89 (m, 2.2H), 2.69-2.53 (m, 2.2H), 2.12 (s, 0.2H), 1.99 (s, 1H), 1.91 (s, 0.3H), 1.80-1.70 (m, 6H), 1.48-1.36 (m, 1.2H), 1.23-1.12 (m, 1.3H), 0.96 (s, 1.2H).

All references, including publications, patents, and patent documents were incorporated by reference herein, as though individually incorporated by reference. The present disclosure provides reference to various embodiments and techniques. However, it should be understood that many variations and modifications may be made while remaining within the spirit and scope of the present disclosure.

What was claimed is:

1. A process for preparing a compound of formula III:

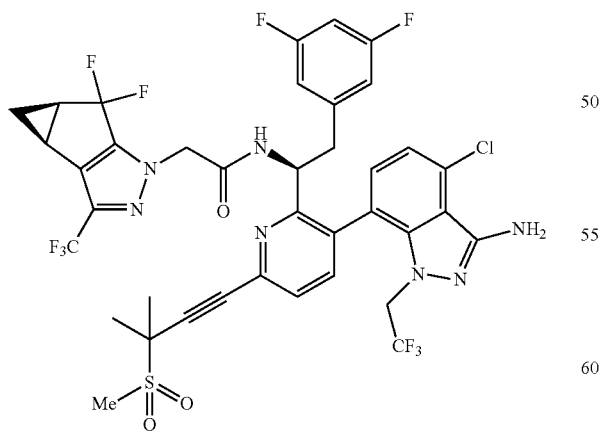

III or a co-crystal, solvate, salt, or combination thereof, comprising:

combining a compound of formula IV:

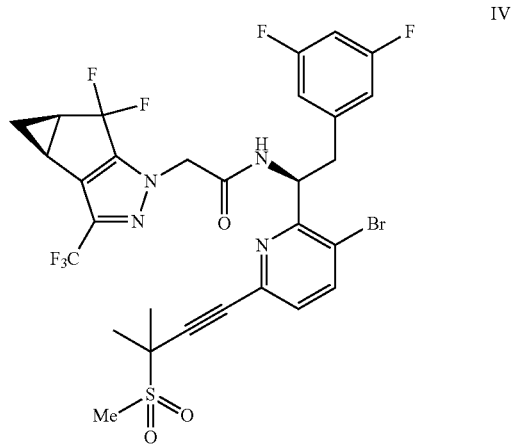 [SMILES: CC(C)(C#Cc1ccc(Br)c([C@H](Cc2cc(F)cc(F)c2)NC(=O)Cn2nc(C(F)(F)F)c3c2C(F)(F)[C@@H]2C[C@H]32)n1)S(C)(=O)=O]

IV or a co-crystal, solvate, salt, or combination thereof, with a compound of formula V:

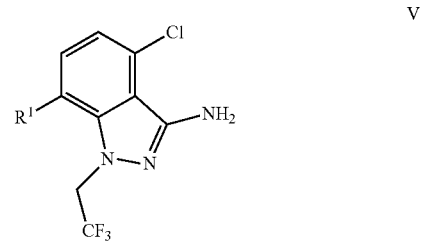

V or a co-crystal, solvate, salt, or combination thereof, wherein $R^1$ is B(OH)$_2$, B(OCH(Me)CH$_2$C(Me)$_2$O), B((1,2-di-O)C$_6$H$_4$), B(OCH$_2$C(Me)$_2$CH$_2$O), BF$_3$K, B(O$_2$CCH$_2$N(Me)CH$_2$CO$_2$), or B(OC(Me)$_2$C(Me)$_2$O), a palladium catalyst selected from the group consisting of palladium(II) chloride, palladium acetate, palladium trifluoroacetate, dichloro(1,5-cyclooctadiene) palladium(II), allylpalladium(II) chloride dimer, palladium(II) acetylacetonate, (tetrakis (triphenylphosphine)palladium(0) and bis (dibenzylideneacetone)palladium(0), a base selected from the group consisting of potassium bicarbonate, sodium bicarbonate, sodium carbonate, potassium carbonate, cesium carbonate, potassium fluoride, potassium phosphate dibasic, potassium phosphate tribasic, sodium hydroxide, potassium hydroxide, dicyclohexylamine, N-methylmorpholine, and triethylamine, and a solvent selected from the group consisting of n-butyl acetate, water, di-n-butyl ether, 1,4-dioxane, 2-methyltetrahydrofuran, dimethoxyethane, toluene, xylenes, ethyl acetate, isopropyl acetate, propyl acetate, isobutyl acetate, ethanol, isopropanol, N,N-dimethylformamide, N,N-dimethylacetamide, N-methyl-2-pyrrolidine, and combinations thereof, to provide the compound of formula III or a co-crystal, solvate, salt, or combination thereof.

2. The process of claim 1, wherein $R^1$ is B(OC(Me)$_2$C (Me)$_2$O).

3. The process of claim 1, wherein the palladium catalyst is palladium(II) chloride and the process further comprises a phosphine ligand which is cyclohexyldiphenylphosphine.

4. The process of claim 1, wherein the base is potassium bicarbonate.

5. The process of claim 1, wherein the solvent is a mixture of 2-methyltetrahydrofuran and water.

6. The process of claim 1, further comprising combining a compound of formula VI:

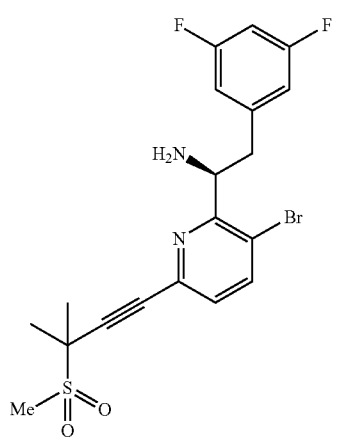

or a co-crystal, solvate, salt, or combination thereof, with a compound of formula VII:

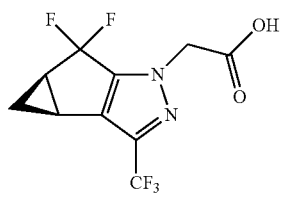

or a co-crystal, solvate, salt, or combination thereof,
a base selected from the group consisting of triethylamine, tributylamine, ethyldiisopropylamine, N-methylmorpholine, pyridine, 2,6-lutidine, and N-methylimidazole,
a solvent selected from the group consisting of acetonitrile, ethyl acetate, n-butyl acetate, isopropyl acetate, diethyl ether, methyl tert-butyl ether, tetrahydrofuran, 2-methyltetrahydrofuran, 1,4-dioxane, toluene, benzene, xylenes, N,N-dimethylformamide, N,N-dimethylacetamide, N-methylpyrrolidinone, dimethylsulfoxide, dichloromethane, dichloroethane, chloroform, propionitrile, butyronitrile, and combinations thereof, and
optionally a coupling reagent selected from the group consisting of n-propylphosphonic anhydride, 2-chloro-4,6-dimethoxy-1,3,5-triazine, 4-(4,6-dimethoxy-1,3,5-triazin-2-yl)-4-methylmorpholinium chloride, 2-chloro-1-methylpyridinium iodide, boric acid, tetramethyl orthosilicate, trimethoxysilane, dicyclohexylcarbodiimide, diisopropylcarbodiimide, 1-ethyl-3-(3-dimethylaminopropyl)carbodiimide, carbonyl diimidazole, isobutyl chloroformate, diphenylphosphinic chloride, 2-(7-aza-1H-benzotriazole-1-yl)-1,1,3,3-tetramethyluronium hexafluorophosphate, O-benzotriazole-N,N,N',N'-tetramethyluronium-hexafluorophosphate, O-(7-azabenzotriazole-1-yl)-N,N,N',N'-tetramethyluronium tetrafluoroborate, O-(benzotriazol-1-yl)-N,N,N',N'-tetramethyluronium tetrafluoroborate, O-(6-chlorobenzotriazol-1-yl)-N,N,N',N'-tetramethyluronium hexafluorophosphate, (benzotriazol-1-yloxy)tris(dimethylamino)phosphonium hexafluorophosphate, chloro-N,N,N',N'-tetramethylformamidinium hexafluorophosphate, (benzotriazol-1-yloxy)tripyrrolidinophosphonium hexafluorophosphate, 4-(4,6-dimethoxy-1,3,5-triazin-2-yl)-4-methylmorphonium chloride, and (1-cyano-2-ethoxy-2-oxoethylidenaminooxy) dimethylamino-morpholino-carbenium hexafluorophosphate,
in the temperature range of from about 0° C. to about 40° C.,
to provide a compound of formula IV:

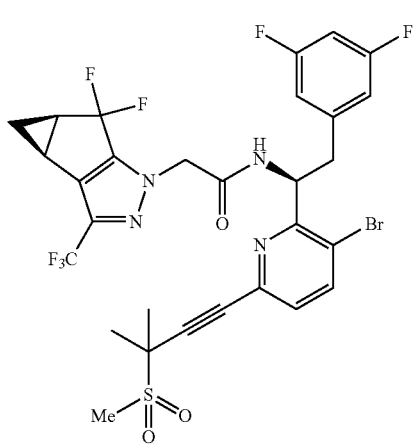

or a co-crystal, solvate, salt, or combination thereof.

7. The process of claim 6, wherein the coupling reagent is n-propylphosphonic cyclic anhydride.

8. The process of claim 6, wherein the base is triethylamine.

9. The process of claim 6, wherein the solvent is acetonitrile.

10. The process of claim 6, further comprising combining a compound of formula VIII-02:

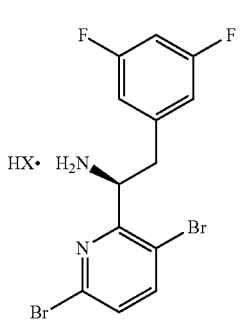

or a co-crystal, solvate, salt, or combination thereof, wherein HX is a chiral or achiral acid selected from the group consisting of L-lactic acid, L-(+)-tartaric acid, L-aspartic acid, L-glutamic acid, L-(−)-malic acid, D-glucuronic acid, (1R, 3S)-(+)-camphoric acid, (1S)-(+)-camphor-10-sulfonic acid, (R)-(+)-N-(1-phenylethyl)succinamic acid, carbobenzyloxy-L-proline, dibenzoyl-L-tartaric acid, (R)-(+)-3-methyladipic acid, (+)-menthyloxyacetic acid, (−)-pyroglutamic acid, (−)-n-acetyl-L-leucine, (−)-N-acetyl-D-leucine, N-Boc-D-leucine, N-(+)-BOC-phenylalanine, (−)-quinic acid, (+)-n-acetyl-L-phenylalanine, (+)-N-BOC-isoleucine, L-(−)-acetyl glutamic acid, (−)-acetyl mandelic acid, (R)-(−)-citramalic acid, (−)-camphanic acid, and (R)-mandelic acid, with a compound of formula IX:

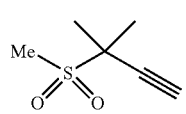

IX or a co-crystal, solvate, or combination thereof,
a base selected from the group consisting of triethylamine, diisopropylamine, ethyldiisopropylamine, pyrrolidine, 1,4-diazabicylo[2.2.2]-octane, 1,8-diazabicyclo[5.4.0]undec-7-ene, 1,5-diazabicyclo-4.3.0]non-5-ene, pyridine, cesium carbonate, potassium carbonate, sodium carbonate, piperidine, potassium phosphate, and tetrabutylammonium fluoride,
a solvent selected from the group consisting of diethyl ether, methyl tert-butyl ether, tetrahydrofuran, 2-methyltetrahydrofuran, 1,4-dioxane, benzene, toluene, xylenes, N,N-dimethylformamide, N,N-dimethylacetamide, N-methylpyrrolidinone, acetonitrile, water, and combinations thereof, and
a palladium catalyst selected from the group consisting of [(π-allyl)PdCl]$_2$, Pd(acac)$_2$, (SIPr)PdCl$_2$, PdCl$_2$(PPh$_3$)$_2$, PdCl$_2$, Pd(OAc)$_2$, PdCl$_2$(CH$_3$CN)$_2$, and Pd$_2$(dba)$_3$, optionally, in combination with a tertiary phosphine, selected from the group consisting of triphenylphosphine, tri-cyclohexylphosphine, tri-tert-butylphosphine, 1,2-bis(diphenylphosphino)ethane, 1,3-bis(diphenylphosphino)propane, and 1,1'-bis(diphenylphosphino)ferrocene,
wherein the process is carried out in the temperature range of from about 50° C. to about 80° C., to provide a compound of formula VI:

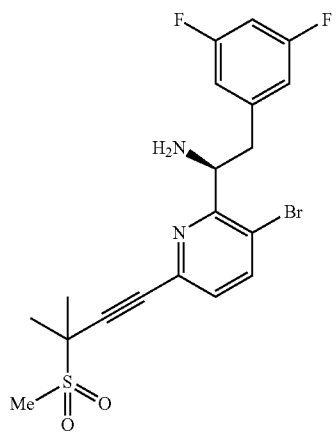

VI or a co-crystal, solvate, salt, or combination thereof.

11. The process of claim 10, wherein HX is N-Boc-D-leucine or (−)-N-acetyl-D-leucine.

12. The process of claim 10, wherein the palladium catalyst is PdCl$_2$(PPh$_3$)$_2$.

13. The process of claim 10, wherein the base is triethylamine.

14. The process of claim 10, wherein the solvent is acetonitrile.

15. The process of claim 1, further comprising:
(a) combining the compound of formula III, or a co-crystal, solvate, salt, or combination thereof, with a second solvent and an acid to provide a compound of formula III-02:

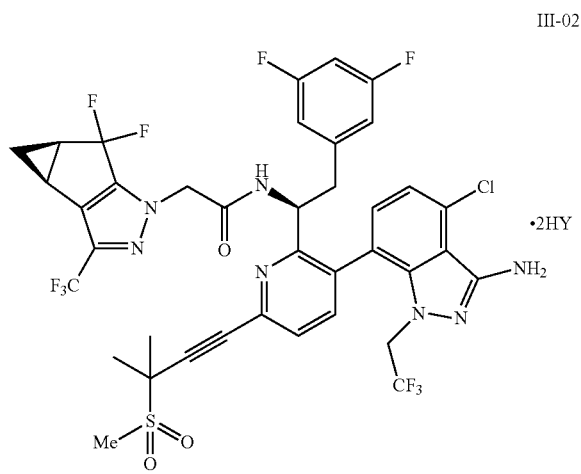 [SMILES: CC(C)(C#Cc1ccc(-c2ccc(Cl)c3c(N)nn(CC(F)(F)F)c23)c([C@H](Cc2cc(F)cc(F)c2)NC(=O)Cn2nc(C(F)(F)F)c3c2C(F)(F)[C@@H]2C[C@H]32)n1)S(C)(=O)=O]

III-02 or a co-crystal, solvate, or combination thereof, wherein HY is selected from the group consisting of acetic acid, oxalic acid, sulfuric acid, hydrochloric acid, phosphoric acid, chloroacetic acid, citric acid, nitric acid, formic acid, lactic acid, ascorbic acid, benzoic acid, propionic acid, ethanesulfonic acid, p-toluenesulfonic acid, benzenesulfonic acid, and methanesulfonic acid; and
(b) free-basing the compound of formula III-02 or a co-crystal, solvate, or combination thereof, by combining it with a second base and a third solvent in the temperature range of from about 0° C. to about 50° C. to provide the compound of formula III or a co-crystal, or solvate, or combination thereof.

16. The process of claim 15, wherein HY is methanesulfonic acid.

17. The process of claim 15, wherein the second solvent is selected from the group consisting of 1-propanol, isopropanol, ethanol, methanol, tert-amyl alcohol, acetonitrile, methyl isobutyl ketone, dichloromethane, 2-methyl tetrahydrofuran, ethyl acetate, isopropyl acetate, n-butyl ether, methyl tert-butyl ether, toluene, and cyclopentyl methyl ether, and combinations thereof.

18. The process of claim 15, wherein the compound of formula III-02 is produced as an ethanol solvate.

19. The process of claim 15, wherein the second base is selected from the group consisting of sodium hydroxide, lithium hydroxide, potassium hydroxide, sodium carbonate, potassium carbonate, sodium bicarbonate, potassium bicarbonate, benzyltrimethylammonium hydroxide, choline hydroxide, sodium or potassium methoxide, sodium or potassium ethoxide, triethylamine, 1,4-diazabicyclo[2.2.2] octane, 1,8-diazabicyclo[5.4.0]undec-7-ene, ammonium hydroxide, and diethylamine.

20. The process of claim 19, wherein the second base is sodium hydroxide.

21. The process of claim 15, wherein the third solvent is selected from the group consisting of water, diethyl ether, 1,4-dioxane, 2-methyltetrahydrofuran, dimethoxyethane, methyl tert-butyl ether, toluene, xylenes, ethyl acetate, isopropyl acetate, and combinations thereof.

22. The process of claim 21, wherein the third solvent is 2-methyltetrahydrofuran and water.

\* \* \* \* \*

UNITED STATES PATENT AND TRADEMARK OFFICE
CERTIFICATE OF CORRECTION

PATENT NO. : 11,117,886 B2  
APPLICATION NO. : 16/869653  
DATED : September 14, 2021  
INVENTOR(S) : Amanda Lynn Vandehey et al.

Page 1 of 1

It is certified that error appears in the above-identified patent and that said Letters Patent is hereby corrected as shown below:

On the Title Page

Column 1 (Item (72), Inventors), Line 9, delete "Redwood," and insert -- Redwood City, --;

Column 2 (Item (56), Other Publications), delete "diazatricylo" and insert -- diazatricyclo --;

In the Claims

Column 196, Line 9, Claim 6, delete "methylmorphonium" and insert -- methylmorpholinium --;

Column 197, Line 21, Claim 10, delete "1,4-diazabicylo" and insert -- 1,4-diazabicyclo --;

Column 197, Line 22, Claim 10, delete "1,5-diazabicyclo-4.3.0]" and insert -- 1,5-diazabicyclo[4.3.0] --.

Signed and Sealed this  
Eighteenth Day of January, 2022

Drew Hirshfeld  
*Performing the Functions and Duties of the*  
*Under Secretary of Commerce for Intellectual Property and*  
*Director of the United States Patent and Trademark Office*